(12) United States Patent
Elokdah et al.

(10) Patent No.: US 7,723,329 B2
(45) Date of Patent: May 25, 2010

(54) SUBSTITUTED-3-SULFONYLINDAZOLE DERIVATIVES AS 5-HYDROXYTRYPTAMINE-6 LIGANDS

(75) Inventors: Hassan Mahmoud Elokdah, North Wales, PA (US); Alexander Alexei Greenfield, West Windsor, NJ (US); Kevin Liu, West Windsor, NJ (US); Robert Emmett McDevitt, Freehold, NJ (US); Geraldine Ruth McFarlane, Monmouth Junction, NJ (US); Cristina Grosanu, Keansburg, NJ (US); Jennifer Rebecca Lo, Plainsboro, NJ (US); Yanfang Li, Lawrenceville, NJ (US); Albert Jean Robichaud, Ringoes, NJ (US); Ronald Charles Bernotas, Royersford, PA (US)

(73) Assignee: Wyeth LLC, Madison, NJ (US)

( * ) Notice: Subject to any disclaimer, the term of this patent is extended or adjusted under 35 U.S.C. 154(b) by 756 days.

(21) Appl. No.: 11/504,350

(22) Filed: Aug. 14, 2006

(65) Prior Publication Data

US 2007/0037802 A1    Feb. 15, 2007

Related U.S. Application Data

(60) Provisional application No. 60/708,315, filed on Aug. 15, 2005.

(51) Int. Cl.
| A61K 31/5377 | (2006.01) |
| A61K 31/496 | (2006.01) |
| A61K 31/416 | (2006.01) |
| C07D 413/02 | (2006.01) |
| C07D 231/56 | (2006.01) |

(52) U.S. Cl. .............. 514/232.8; 514/254.06; 514/322; 514/406; 544/140; 544/371; 546/199; 548/361.5

(58) Field of Classification Search ............... None
See application file for complete search history.

(56) References Cited

U.S. PATENT DOCUMENTS

| 6,391,872 | B1 | 5/2002 | Marfat |
| 6,509,357 | B1 | 1/2003 | Zhou et al. |
| 6,613,781 | B2 | 9/2003 | Zhou et al. |
| 6,716,837 | B1 | 4/2004 | Edwards et al. |
| 6,727,246 | B2 | 4/2004 | Bernotas et al. |
| 6,767,912 | B2 | 7/2004 | Zhou et al. |
| 6,815,456 | B2 | 11/2004 | Zhou et al. |
| 6,831,094 | B2 | 12/2004 | Li et al. |
| 6,995,176 | B2 | 2/2006 | Bernotas et al. |
| 2002/0115670 | A1 | 8/2002 | Kelly et al. |
| 2004/0023970 | A1 | 2/2004 | Bernotas et al. |
| 2004/0024023 | A1 | 2/2004 | Bernotas et al. |
| 2004/0024210 | A1 | 2/2004 | Johansson et al. |
| 2004/0138286 | A1 | 7/2004 | Imazaki et al. |
| 2004/0167030 | A1 | 8/2004 | Bernotas et al. |
| 2004/0167122 | A1 | 8/2004 | Bernotas et al. |
| 2005/0113283 | A1 | 5/2005 | Solow-Cordero et al. |
| 2005/0215595 | A1 | 9/2005 | Arora et al. |
| 2007/0054896 | A1 | 3/2007 | Elokdah et al. |

FOREIGN PATENT DOCUMENTS

| WO | WO 03/101962 A | 12/2003 |
| WO | WO 2004/009548 A | 1/2004 |
| WO | WO 2004/074243 A2 | 9/2004 |

*Primary Examiner*—Kamal A Saeed
(74) *Attorney, Agent, or Firm*—Thomas C. McKenzie

(57) ABSTRACT

The present invention provides a compound of formula I and the use thereof for the treatment of a central nervous system disorder related to or affected by the 5-HT6 receptor.

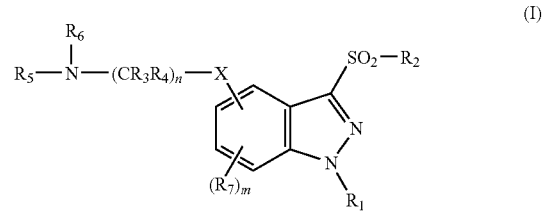

22 Claims, No Drawings

SUBSTITUTED-3-SULFONYLINDAZOLE DERIVATIVES AS 5-HYDROXYTRYPTAMINE-6 LIGANDS

BACKGROUND OF THE INVENTION

This application claims the benefit under 35 U.S.C. §119 (e) to co-pending U.S. provisional application No. 60/708315, filed Aug. 15, 2005, which is hereby incorporated by reference in its entirety.

Serotonin (5-hydroxytryptamine) (5-HT) receptors play a critical role in many physiological and behavioral functions in humans and animals. These functions are mediated through various 5-HT receptors distributed throughout the body. There are now approximately fifteen different human 5-HT receptor subtypes that have been cloned, many with well-defined roles in humans. One of the most recently identified 5-HT receptor subtypes is the 5-HT6 receptor, first cloned from rat tissue in 1993 (Monsma, F. J.; Shen, Y.; Ward, R. P.; Hamblin, M. W. *Molecular Pharmacology* 1993, 43, 320-327) and subsequently from human tissue (Kohen, R.; Metcalf, M. A.; Khan, N.; Druck, T.; Huebner, K.; Sibley, D. R. *Journal of Neurochemistry* 1996, 66, 47-56). The receptor is a G-protein coupled receptor (GPCR) positively coupled to adenylate cyclase (Ruat, M.; Traiffort, E.; Arrang, J-M.; Tardivel-Lacombe, L.; Diaz, L.; Leurs, R.; Schwartz, J-C. *Biochemical Biophysical Research Communications* 1993, 193, 268-276). The receptor is found almost exclusively in the central nervous system (CNS) areas both in rat and in human. In situ hybridization studies of the 5-HT6 receptor in rat brain using mRNA indicate principal localization in the areas of 5-HT projection including striatum, nucleus accumbens, olfactory tubercle, and hippocampal formation (Ward, R. P.; Hamblin, M. W.; Lachowicz, J. E.; Hoffman, B. J.; Sibley, D. R.; Dorsa, D. M. *Neuroscience* 1995, 64, 1105-1111).

There are many potential therapeutic uses for 5-HT6 ligands in humans based on direct effects and on indications from available scientific studies. These studies provided information including the localization of the receptor, the affinity of ligands with known in vivo activity, and results obtained from various animal studies conducted so far (Woolley, M. L.; Marsden, C. A.; Fone, K. C. F. *Current Drug Targets: CNS & Neurological Disorders* 2004, 3(1), 59-79).

One therapeutic use of modulators of 5-HT6 receptor function is in the enhancement of cognition and memory in human diseases such as Alzheimer's. The high levels of receptor found in important structures in the forebrain, including the caudate/putamen, hippocampus, nucleus accumbens, and cortex indicate a role for the receptor in memory and cognition since these areas are known to play a vital role in memory (Gerard, C.; Martres, M.-P.; Lefevre, K.; Miquel, M. C.; Verge, D.; Lanfumey, R.; Doucet, E.; Hamon, M.; El Mestikawy, S. *Brain Research,* 1997, 746, 207-219). The ability of known 5-HT6 receptor ligands to enhance cholinergic transmission also supported the cognition use (Bentley, J. C.; Boursson, A.; Boess, F. G.; Kone, F. C.; Marsden, C. A.; Petit, N.; Sleight, A. J. *British Journal of Pharmacology,* 1999, 126(7), 1537-1542). Studies have demonstrated that a known 5-HT6 selective antagonist significantly increased glutamate and aspartate levels in the frontal cortex without elevating levels of noradrenaline, dopamine, or 5-HT. This selective elevation of neurochemicals known to be involved in memory and cognition indicates the role 5-HT6 ligands play in cognition (Dawson, L. A.; Nguyen, H. Q.; Li, P. British Journal of Pharmacology, 2000, 130(1), 23-26). Animal studies of memory and learning with a known selective 5-HT6 antagonist found positive effects (Rogers, D. C.; Hatcher, P. D.; Hagan, J. J. *Society of Neuroscience, Abstracts* 2000, 26, 680). More recent studies have supported this finding in several additional animal models of cognition and memory including in a novel object discrimination model (King, M. V.; Sleight, A. J.; Wooley, M. L.; Topham, I. A.; Marsden, C. A.; Fone, K. C. F. *Neuropharmacology* 2004, 47(2), 195-204 and Wooley, M. L.; Marsden, C. A.; Sleight, A. J.; Fone, K. C. F. *Psychopharmacology,* 2003, 170(4), 358-367) and in a water maze model (Rogers, D. C.; Hagan, J. J. *Psychopharmacology,* 2001, 158(2), 114-119 and Foley, A. G.; Murphy, K. J.; Hirst, W. D.; Gallagher, H. C.; Hagan, J. J.; Upton, N.; Walsh, F. S.; Regan, C. M. *Neuropsychopharmacology* 2004, 29(1), 93-100).

A related therapeutic use for 5-HT6 ligands is the treatment of attention deficit disorders (ADD, also known as Attention Deficit Hyperactivity Disorder or ADHD) in both children and adults. Because 5-HT6 antagonists enhance the activity of the nigrostriatal dopamine pathway and because ADHD has been linked to abnormalities in the caudate (Ernst, M; Zametkin, A. J.; Matochik, J. H.; Jons, P. A.; Cohen, R. M. *Journal of Neuroscience* 1998, 18(15), 5901-5907), 5-HT6 antagonists attenuate attention deficit disorders.

Early studies examining the affinity of various CNS ligands with known therapeutic utility or a strong structural resemblance to known drugs implicates 5-HT6 ligands in the treatment of schizophrenia and depression. For example, clozapine (an effective clinical antipsychotic) has high affinity for the 5-HT6 receptor subtype. Also, several clinical antidepressants have high affinity for the receptor as well and act as antagonists at this site (Branchek, T. A.; Blackburn, T. P. *Annual Reviews in Pharmacology and Toxicology* 2000, 40, 319-334).

Further, recent in vivo studies in rats indicate that 5-HT6 modulators are useful in the treatment of movement disorders including epilepsy (Stean, T.; Routledge, C.; Upton, N. British Journal of Pharmacology 1999, 127 Proc. Supplement 131P and Routledge, C.; Bromidge, S. M.; Moss, S. F.; Price, G. W.; Hirst, W.; Newman, H.; Riley, G.; Gager, T.; Stean, T.; Upton, N.; Clarke, S. E.; Brown, A. M. *British Journal of Pharmacology* 2000, 130(7), 1606-1612).

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

SUMMARY OF THE INVENTION

The present invention provides a 3-sulfonylindazole compound of formula I

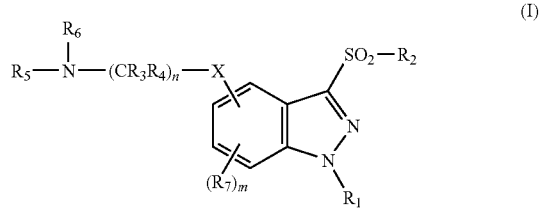

wherein
  X is O, S, NR, $CH_2$, $CH_2Y$, $CH_2Z$, CO, CONR or NRCO;
  Y is O, S or NR;
  Z is CO;
  n is 0 or an integer of 1, 2, 3, 4, 5 or 6 when X is $CH_2$;
  n is an integer of 1, 2, 3, 4, 5 or 6 when X is $CH_2Z$, CO or NRCO;

n is an integer of 2, 3, 4, 5 or 6 when X is O, S, NR, $CH_2Y$ or CONR;

R is H or an optionally substituted alkyl group;

$R_1$ is H or an alkyl, cycloalkyl, aryl or heteroaryl group each optionally substituted;

$R_2$ is an optionally substituted alkyl, cycloalkyl, aryl or heteroaryl group or an optionally substituted 8- to 13-membered bicyclic or tricyclic ring system having a N atom at the bridgehead and optionally containing 1, 2 or 3 additional heteroatoms selected from N, O or S;

$R_3$ and $R_4$ are each independently H, or an optionally substituted alkyl group;

$R_5$ and $R_6$ are each independently H, or an alkyl, alkenyl, alkynyl, cycloalkyl, cycloheteroalkyl, aryl or heteroaryl group each optionally substituted, or $R_5$ and $R_6$ may be taken together with the atom to which they are attached to form an optionally substituted 3- to 7-membered ring optionally containing an additional heteroatom selected from O, N or S;

$R_7$ is H, halogen, CN, $OR_8$, $CO_2R_9$, $CONR_1OR_1$, or an alkyl, alkenyl, alkynyl, cycloalkyl, cycloheteroalkyl, aryl or heteroaryl group each optionally substituted;

m is an integer of 1, 2 or 3;

$R_8$ is H, $COR_{12}$ or an alkyl, alkenyl, alkynyl, aryl or heteroaryl group each optionally substituted;

$R_9$ is H or a $C_1$-$C_6$alkyl, aryl or heteroaryl group each optionally substituted;

$R_{10}$ and $R_{11}$ are each independently H or an optionally substituted alkyl group; and $R_{12}$ is an optionally substituted $C_1$-$C_6$alkyl, cycloalkyl, cycloheteroalkyl, aryl or heteroaryl group; or a stereoisomer thereof or a pharmaceutically acceptable salt thereof.

The present invention also provides methods and compositions useful for the therapeutic treatment of central nervous system disorders related to or affected by the 5-HT6 receptor.

DETAILED DESCRIPTION OF THE INVENTION

The 5-hydroxytryptamine-6 (5-HT6) receptor has been identified by molecular cloning. Its ability to bind a wide range of therapeutic compounds used in psychiatry, coupled with its intriguing distribution in the brain has stimulated significant interest in new compounds which are capable of interacting with or affecting said receptor. Significant efforts are being made to understand the role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders, for example see C. Reavill and D. C. Rogers, Current Opinion in Investigational Drugs, 2001, 2(1):104-109, Pharma Press Ltd and Woolley, M. L.; Marsden, C. A.; Fone, K. C. F. *Current Drug Targets: CNS & Neurological Disorders* 2004, 3(1), 59-79.

Surprisingly, it has now been found that 3-sulfonylindazole compounds of formula I demonstrate 5-HT6 affinity along with significant sub-type selectivity. Advantageously, said formula I compounds are effective therapeutic agents for the treatment of central nervous system (CNS) disorders associated with or affected by the 5-HT6 receptor. Accordingly, the present invention provides a 3-sulfonylindazole compound of formula I

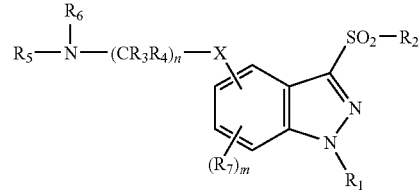

(I)

wherein
X is O, S, NR, $CH_2$, $CH_2Y$, $CH_2Z$, CO, CONR or NRCO;
Y is O, S or NR;
Z is CO;
n is 0 or an integer of 1, 2, 3, 4, 5 or 6 when X is $CH_2$;
n is an integer of 1, 2, 3, 4, 5 or 6 when X is $CH_2Z$, CO or NRCO;
n is an integer of 2, 3, 4, 5 or 6 when X is O, S, NR, $CH_2Y$ or CONR;
R is H or an optionally substituted alkyl group;
$R_1$ is H or an alkyl, cycloalkyl, aryl or heteroaryl group each optionally substituted;
$R_2$ is an optionally substituted alkyl, cycloalkyl, aryl or heteroaryl group or an optionally substituted 8- to 13-membered bicyclic or tricyclic ring system having a N atom at the bridgehead and optionally containing 1, 2 or 3 additional heteroatoms selected from N, O or S;
$R_3$ and $R_4$ are each independently H, or an optionally substituted alkyl group;
$R_5$ and $R_6$ are each independently H, or an alkyl, alkenyl, alkynyl, cycloalkyl, cycloheteroalkyl, aryl or heteroaryl group each optionally substituted, or $R_5$ and $R_6$ may be taken together with the atom to which they are attached to form an optionally substituted 3- to 7-membered ring optionally containing an additional heteroatom selected from O, N or S;
$R_7$ is H, halogen, CN, $OR_8$, $CO_2R_9$, $CONR_{10}R_{11}$, or an alkyl, alkenyl, alkynyl, cycloalkyl, cycloheteroalkyl, aryl or heteroaryl group each optionally substituted;
m is an integer of 1, 2 or 3;
$R_8$ is H, $COR_{12}$ or an alkyl, alkenyl, alkynyl, aryl or heteroaryl group each optionally substituted;
$R_9$ is H or a $C_1$-$C_6$alkyl, aryl or heteroaryl group each optionally substituted;
$R_{10}$ and $R_{11}$ are each independently H or an optionally substituted alkyl group; and
$R_{12}$ is an optionally substituted $C_1$-$C_6$alkyl, cycloalkyl, cycloheteroalkyl, aryl or heteroaryl group; or a stereoisomer thereof or a pharmaceutically acceptable salt thereof.

It is understood that the claims encompass all possible stereoisomers and prodrugs. Moreover, unless stated otherwise, each alkyl, alkenyl, alkynyl, cycloalkyl cycloheteroalkyl, aryl or heteroaryl group is contemplated as being optionally substituted.

An optionally substituted moiety may be substituted with one or more substituents. The substituent groups, which are optionally present, may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl or lower alkoxy groups. Unless otherwise specified, typically, 0-4 substituents may be present. When any of the foregoing substituents represents or contains an alkyl substituent group, this may be linear or branched and may contain up to 12 carbon atoms, preferably up to 6 carbon atoms, more preferably up to 4 carbon atoms.

As used herein, the term "alkyl" includes both ($C_1$-$C_{10}$) straight chain and ($C_3$-$C_{12}$) branched-chain (unless defined otherwise) monovalent saturated hydrocarbon moiety. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, and the like. Specifically included within the definition of "alkyl" are those alkyl groups that are optionally substituted. Suitable alkyl substitutions include, but are not limited to, CN, OH, $NR_{10}R_{11}$, halogen, phenyl, carbamoyl, carbonyl, alkoxy or aryloxy.

As used herein the term "haloalkyl" designates a $C_nH_{2n+1}$ group having from one to 2n+1 halogen atoms which may be the same or different. Examples of haloalkyl groups include $CF_3$, $CH_2Cl$, $C_2H_3BrCl$, $C_3H_5F_2$, or the like.

The term "halogen", as used herein, designates fluorine, chlorine, bromine, and iodine.

The term "alkenyl", as used herein, refers to either a ($C_2$-$C_8$) straight chain or ($C_3$-$C_{10}$) branched-chain monovalent hydrocarbon moiety containing at least one double bond. Such hydrocarbon alkenyl moieties may be mono or polyunsaturated, and may exist in the E or Z configurations. The compounds of this invention are meant to include all possible E and Z configurations. Examples of mono or polyunsaturated hydrocarbon alkenyl moieties include, but are not limited to, chemical groups such as vinyl, 2-propenyl, isopropenyl, crotyl, 2-isopentenyl, butadienyl, 2-(butadienyl), 2,4-pentadienyl, 3-(1,4-pentadienyl), and higher homologs, isomers, or the like.

The term "alkynyl", as used herein, refers to an alkyl group having one or more triple carbon-carbon bonds. Alkynyl groups preferably contain 2 to 6 carbon atoms. Examples of alkynyl groups include, but are not limited to, ethynyl, propynyl, butynyl, pentynyl, and the like. In some embodiments, alkynyl groups can be substituted with up to four substituent groups, as described below.

The term "cycloalkyl", as used herein, refers to a monocyclic, bicyclic, tricyclic, fused, bridged, or spiro monovalent saturated hydrocarbon moiety of 3-10 carbon atoms, unless otherwise specified, wherein the carbon atoms are located inside or outside of the ring system. Any suitable ring position of the cycloalkyl moiety may be covalently linked to the defined chemical structure. Examples of cycloalkyl moieties include, but are not limited to, chemical groups such as cyclopropyl, cyclopropyl methyl, cyclobutyl, cyclopentyl, cyclohexyl, cyclohexyl methyl, cyclohexylethyl, cycloheptyl, norbornyl, adamantyl, spiro[4.5]decanyl, and homologs, isomers, or the like.

The term "cycloheteroalkyl" as used herein designates a $C_5$-$C_7$ cycloalkyl ring system containing 1, 2 or 3 heteroatoms, which may be the same or different, selected from N, O or S and optionally containing one double bond. Exemplary of the cycloheteroalkyl ring systems included in the term as designated herein are the following rings wherein $X_1$ is NR', O or S and R is H or an optional substituent as defined hereinbelow.

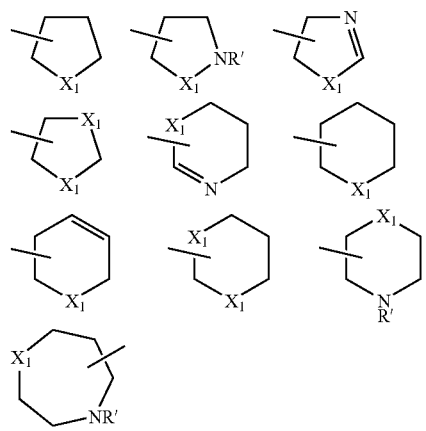

The term "aryl", as used herein, refers to an aromatic carbocyclic moiety of up to 20 carbon atoms, which may be a single ring (monocyclic) or multiple rings (bicyclic, up to three rings) fused together or linked covalently. Any suitable ring position of the aryl moiety may be covalently linked to the defined chemical structure. Examples of aryl moieties include, but are not limited to, chemical groups such as phenyl, 1-naphthyl, 2-naphthyl, biphenyl, anthryl, phenanthryl, fluorenyl, indanyl, biphenylenyl, acenaphthenyl, acenaphthylenyl, and the like.

The term "heteroaryl" as used herein designates an aromatic heterocyclic ring system, which may be a single ring (monocyclic) or multiple rings (bicyclic, up to three rings) fused together or linked covalently. Preferably, heteroaryl is a 5- to 6-membered ring. The rings may contain from one to four hetero atoms selected from nitrogen, oxygen, or sulfur, wherein the nitrogen or sulfur atom(s) are optionally oxidized, or the nitrogen atom(s) are optionally quarternized. Any suitable ring position of the heteroaryl moiety may be covalently linked to the defined chemical structure. Examples of heteroaryl moieties include, but are not limited to, heterocycles such as furan, thiophene, pyrrole, pyrazole, imidazole, oxazole, isoxazole, thiazole, isothiazole, oxadiazole, triazole, pyridine, pyrimidine, pyrazine, pyridazine, benzimidazole, benzoxazole, benzisoxazole, benzothiazole, benzofuran, benzothiophene, thianthrene, dibenzofuran, dibenzothiophene, indole, indazole, quinoline, isoquinoline, quinazoline, quinoxaline, purine, or the like.

Exemplary of the 8- to 13-membered bicyclic or tricyclic ring systems having a N atom at the bridgehead and optionally containing 1, 2 or 3 additional heteroatoms selected from N, O or S included in the term as designated herein are the following ring systems wherein W is NR', O or S; and R' is H or an optional substituent as described hereinbelow:

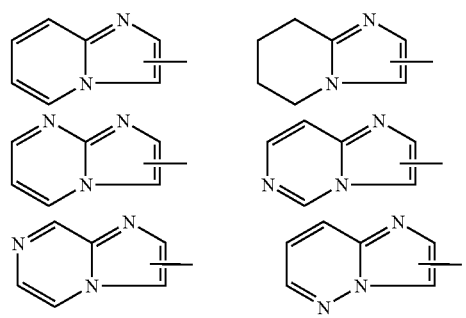

-continued

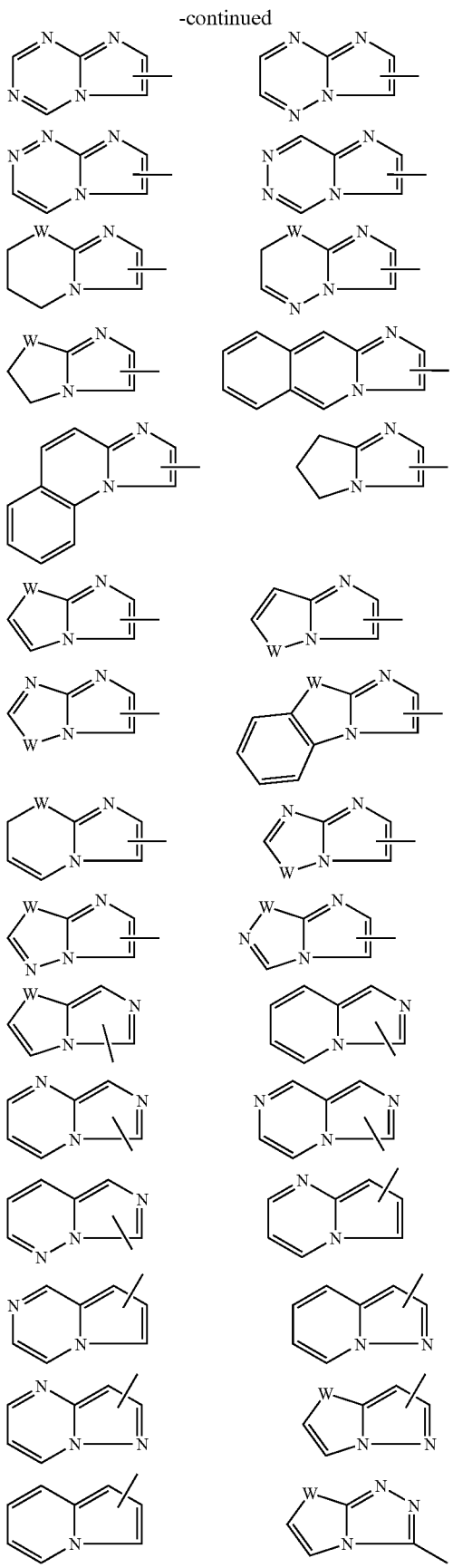

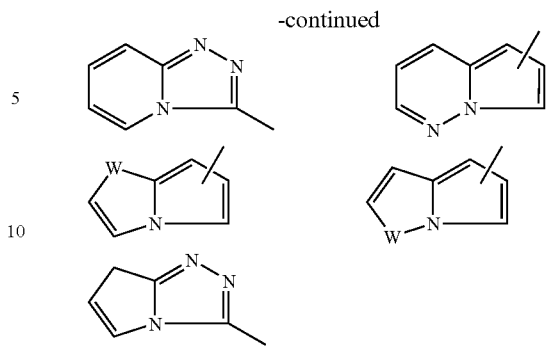

The compounds of this invention are limited to those that are chemically feasible and stable. Therefore, a combination of substituents or variables in the compounds described above is permissible only if such a combination results in a stable or chemically feasible compound.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon are within the scope of this invention.

The compounds of the present invention may be converted to salts, in particular pharmaceutically acceptable salts using art recognized procedures. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethyl-propylamine, or a mono-, di-, or trihydroxy lower alkylamine, for example mono-, di- or triethanolamine. Internal salts may furthermore be formed. Salts which are unsuitable for pharmaceutical uses but which can be employed, for example, for the isolation or purification of free compounds or their pharmaceutically acceptable salts, are also included. The term "pharmaceutically acceptable salt", as used herein, refers to salts derived from organic and inorganic acids such as, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Preferred compounds of the invention are those compounds of formula I wherein X is O, NR or $CH_2$. Another group of preferred compounds is those formula I compounds wherein n is 2 or 3. Also preferred are those formula I compounds wherein $R_2$ is an optionally substituted aryl or heteroaryl group or an optionally subtituted 8- to 13-membered bicyclic or tricyclic ring system having a N atom at the bridgehead and optionally containing 1, 2 or 3 additional heteroatoms selected from N, O or S.

More preferred compounds of the invention are those compounds of formula I wherein X is O and $R_5$ and $R_6$ are each independently H or $C_1$-$C_4$ alkyl. Another group of more preferred compounds is those compounds of formula I wherein X is O and n is 3. A further group of more preferred compounds are those compounds of formula I wherein X is O; n is 3 and $R_2$ is naphthyl.

Among the preferred compounds of the invention are:

N,N-Dimethyl-3-{[3-(1-naphthylsulfonyl)-1H-indazol-5-yl]oxy}propan-1-amine;
N-Methyl-N-{2-[3-(phenylsulfonyl)-1H-indazol-5-yl]ethyl}amine;
N,N-Dimethyl-N-{2-[3-(phenylsulfonyl)-1H-indazol-5-yl]ethyl}amine;
{2-[3-(Phenylsulfonyl)-1H-indazol-7-yl]ethyl}amine;
N,N-Dimethyl-N-{2-[3-(phenylsulfonyl)-1H-indazol-7-yl]ethyl}amine;
N-{2-[3-(Phenylsulfonyl)-1H-indazol-7-yl]ethyl}cyclopropanamine;
N,N-Dimethyl-N-{3-[3-(phenylsulfonyl)-1H-indazol-5-yl]propyl}amine;
N-{3-[3-(Phenylsulfonyl)-1H-indazol-5-yl]propyl}cyclopropanamine;
{3-[3-(Phenylsulfonyl)-1H-indazol-5-yl]propyl}amine;
{4-[3-(Phenylsulfonyl)-1H-indazol-5-yl]butyl}amine;
N-Methyl-N-{2-[3-(phenylsulfonyl)-1H-indazol-7-yl]ethyl}amine;
N-[3-(1-Naphthylsulfonyl)-1H-indazol-5-yl]ethane-1,2-diamine;
N,N-Dimethyl-2-{[3-(phenylsulfonyl)-1H-indazol-5-yl]oxy}ethanamine;
3-(Phenylsulfonyl)-5-(2-piperidin-1-ylethoxy)-1H-indazole;
3-(1-Naphthylsulfonyl)-5-(2-pyrrolidin-1-ylethoxy)-1H-indazole;
N,N-Dimethyl-2-{[3-(1-naphthylsulfonyl)-1H-indazol-5-yl]oxy}ethanamine;
N-(2-{[3-(1-Naphthylsulfonyl)-1H-indazol-5-yl]oxy}ethyl)cyclopentanamine;
5-(2-Morpholin-4-ylethoxy)-3-(1-naphthylsulfonyl)-1H-indazole;
N-Ethyl-N-methyl-2-{[3-(1-naphthylsulfonyl)-1H-indazol-5-yl]oxy}ethanamine;
N-(2-{[3-(1-Naphthylsulfonyl)-1H-indazol-5-yl]oxy}ethyl)butan-1-amine;
N~1~-[3-(1-Naphthylsulfonyl)-1H-indazol-5-yl]-beta-alaninamide;
N-Ethyl-2-{[3-(phenylsulfonyl)-1H-indazol-5-yl]oxy}ethanamine;
N-(2-{[3-(Phenylsulfonyl)-1H-indazol-5-yl]oxy}ethyl)propan-2-amine;
N-(2-{[3-(1-Naphthylsulfonyl)-1H-indazol-5-yl]oxy}ethyl)propan-2-amine;
N-Ethyl-2-{[3-(1-naphthylsulfonyl)-1H-indazol-5-yl]oxy}ethanamine;
N-Methyl-2-{[3-(1-naphthylsulfonyl)-1H-indazol-5-yl]oxy}ethanamine;
1-Methyl-3-(1-naphthylsulfonyl)-7-(2-piperidin-1-ylethoxy)-1H-indazole;
3-(1-Naphthylsulfonyl)-5-(2-piperidin-1-ylethoxy)-1H-indazole;
3-(2-Aminoethyl)-1-[(2,5-dimethoxyphenyl)sulfonyl]-1,3-dihydro-2H-imidazo[4,5-b]pyridin-2-one;
N,N-Diethyl-2-{[3-(1-naphthylsulfonyl)-1H-indazol-5-yl]oxy}ethanamine;
N-(2-{[3-(1-Naphthylsulfonyl)-1H-indazol-5-yl]oxy}ethyl)cyclopropanamine;
1-(3-Chlorobenzyl)-3-(1-naphthylsulfonyl)-7-(2-piperidin-1-ylethoxy)-1H-indazole;
1-(3-Chlorobenzyl)-3-(1-naphthylsulfonyl)-7-(2-pyrrolidin-1-ylethoxy)-1H-indazole;
(2S)-3-Methyl-N~1~-[3-(1-naphthylsulfonyl)-1H-indazol-5-yl]butane-1,2-diamine;
(2-{[1-(3-Chlorobenzyl)-3-(1-naphthylsulfonyl)-1H-indazol-7-yl]oxy}ethyl)amine;
N-(2-{[3-(Phenylsulfonyl)-1H-indazol-5-yl]oxy}ethyl)cyclopentanamine;
3-(Phenylsulfonyl)-5-(2-pyrrolidin-1-ylethoxy)-1H-indazole;
N-Methyl-2-{[3-(phenylsulfonyl)-1H-indazol-5-yl]oxy}ethanamine;
N-Methyl-2-{[1-methyl-3-(phenylsulfonyl)-1H-indazol-7-yl]oxy}ethanamine;
1-Methyl-3-(phenylsulfonyl)-7-(2-pyrrolidin-1-ylethoxy)-1H-indazole;
(2-{[1-(3-Chlorobenzyl)-3-(phenylsulfonyl)-1H-indazol-7-yl]oxy}ethyl)methylamine;
(2-{[1-(3-Chlorobenzyl)-3-(phenylsulfonyl)-1H-indazol-7-yl]oxy}ethyl)ethylamine;
1-(3-Chlorobenzyl)-3-(phenylsulfonyl)-7-(2-pyrrolidin-1-ylethoxy)-1H-indazole;
1-(3-Chlorobenzyl)-5-methoxy-3-(1-naphthylsulfonyl)-7-(2-piperidin-1-ylethoxy)-1H-indazole;
N-Methyl-2-{[3-(phenylsulfonyl)-1H-indazol-7-yl]oxy}ethanamine;
(2-{[1-(3-Chlorobenzyl)-3-(1-naphthylsulfonyl)-1H-indazol-7-yl]oxy}ethyl)ethylamine;
(2-{[1-(3-Chlorobenzyl)-3-(1-naphthylsulfonyl)-1H-indazol-7-yl]oxy}ethyl)methylamine;
N-Ethyl-2-{[3-(phenylsulfonyl)-1H-indazol-7-yl]oxy}ethanamine;
N,N-Diethyl-2-{[3-(phenylsulfonyl)-1H-indazol-7-yl]oxy}ethanamine;
N-(2-{[3-(Phenylsulfonyl)-1H-indazol-7-yl]oxy}ethyl)butan-1-amine;
3-(Phenylsulfonyl)-7-(2-pyrrolidin-1-ylethoxy)-1H-indazole;
3-(Phenylsulfonyl)-7-(2-piperidin-1-ylethoxy)-1H-indazole;
N,N-Diethyl-2-{[1-methyl-3-(1-naphthylsulfonyl)-1H-indazol-7-yl]oxy}ethanamine;
1-Methyl-3-(1-naphthylsulfonyl)-7-(2-pyrrolidin-1-ylethoxy)-1H-indazole;
N-Ethyl-2-{[1-methyl-3-(1-naphthylsulfonyl)-1H-indazol-7-yl]oxy}ethanamine;
3-(1-Naphthylsulfonyl)-7-(2-piperidin-1-ylethoxy)-1H-indazole;
3-(1-Naphthylsulfonyl)-7-(2-pyrrolidin-1-ylethoxy)-1H-indazole;
N-Ethyl-2-{[3-(1-naphthylsulfonyl)-1H-indazol-7-yl]oxy}ethanamine;
(2-{[3-(1-Naphthylsulfonyl)-1H-indazol-7-yl]oxy}ethyl)amine;
(2-{[1-(3-Chlorobenzyl)-5-fluoro-3-(1-naphthylsulfonyl)-1H-indazol-7-yl]oxy}ethyl)-dimethylamine;
(2-{[1-Benzyl-3-(1-naphthylsulfonyl)-1H-indazol-5-yl]oxy}ethyl)methylamine;

(2-{[1-Benzyl-3-(1-naphthylsulfonyl)-1H-indazol-5-yl]oxy}ethyl)dimethylamine;
(2-{[1-Benzyl-3-(1-naphthylsulfonyl)-1H-indazol-5-yl]oxy}ethyl)ethylamine;
N-Methyl-2-{[3-(1-naphthylsulfonyl)-1H-indazol-7-yl]oxy}ethanamine;
N,N-Dimethyl-2-{[3-(1-naphthylsulfonyl)-1H-indazol-7-yl]oxy}ethanamine;
5-Fluoro-3-(1-naphthylsulfonyl)-7-(2-pyrrolidin-1-ylethoxy)-1H-indazole;
5-Fluoro-3-(1-naphthylsulfonyl)-7-(2-piperidin-1-ylethoxy)-1H-indazole;
N,N-Diethyl-2-{[5-fluoro-3-(1-naphthylsulfonyl)-1H-indazol-7-yl]oxy}ethanamine;
(2-{[5-Fluoro-3-(1-naphthylsulfonyl)-1H-indazol-7-yl]oxy}ethyl)dimethylamine;
N-Ethyl-2-{[5-fluoro-3-(1-naphthylsulfonyl)-1H-indazol-7-yl]oxy}ethanamine;
(2-{[1-(3-Chlorobenzyl)-3-(1-naphthylsulfonyl)-1H-indazol-5-yl]oxy}ethyl)-dimethylamine;
N-Methyl-3-{[3-(1-naphthylsulfonyl)-1H-indazol-5-yl]oxy}propan-1-amine;
N-Ethyl-N-methyl-3-{[3-(1-naphthylsulfonyl)-1H-indazol-5-yl]oxy}propan-1-amine;
3-(1-Naphthylsulfonyl)-5-(3-piperidin-1-ylpropoxy)-1H-indazole;
N,N-Dimethyl-3-{[3-(1-naphthylsulfonyl)-1H-indazol-5-yl]oxy}propan-1-amine;
N,N-Diethyl-3-{[3-(1-naphthylsulfonyl)-1H-indazol-5-yl]oxy}propan-1-amine;
N-(3-{[3-(1-Naphthylsulfonyl)-1H-indazol-5-yl]oxy}propyl)butan-1-amine;
3-(1-Naphthylsulfonyl)-5-(3-pyrrolidin-1-ylpropoxy)-1H-indazole;
(2-{[5-Methoxy-3-(1-naphthylsulfonyl)-1H-indazol-7-yl]oxy}ethyl)methylamine;
(2-{[5-Methoxy-3-(1-naphthylsulfonyl)-1H-indazol-7-yl]oxy}ethyl)dimethylamine;
5-Methoxy-3-(1-naphthylsulfonyl)-7-(2-pyrrolidin-1-ylethoxy)-1H-indazole;
5-Methoxy-3-(1-naphthylsulfonyl)-7-(2-piperidin-1-ylethoxy)-1H-indazole;
(2-{[1-(3-Chlorobenzyl)-3-(1-naphthylsulfonyl)-1H-indazol-5-yl]oxy}ethyl)ethylamine;
(3-{[1-(3-Chlorobenzyl)-3-(1-naphthylsulfonyl)-1H-indazol-7-yl]oxy}propyl)-diethylamine;
1-(3-Chlorobenzyl)-3-(1-naphthylsulfonyl)-7-(3-pyrrolidin-1-ylpropoxy)-1H-indazole;
N-Methyl-3-{[3-(1-naphthylsulfonyl)-1H-indazol-7-yl]oxy}propan-1-amine;
N,N-Diethyl-3-{[3-(1-naphthylsulfonyl)-1H-indazol-7-yl]oxy}propan-1-amine;
N-Methyl-2-{[1-methyl-3-(1-naphthylsulfonyl)-1H-indazol-5-yl]oxy}ethanamine;
N,N-Dimethyl-2-{[1-methyl-3-(1-naphthylsulfonyl)-1H-indazol-5-yl]oxy}ethanamine;
N-Ethyl-N-methyl-2-{[1-methyl-3-(1-naphthylsulfonyl)-1H-indazol-5-yl]oxy}ethanamine;
N-Ethyl-2-{[1-methyl-3-(1-naphthylsulfonyl)-1H-indazol-5-yl]oxy}ethanamine;
N,N-Diethyl-2-{[1-methyl-3-(1-naphthylsulfonyl)-1H-indazol-5-yl]oxy}ethanamine;
N-(2-{[1-Methyl-3-(1-naphthylsulfonyl)-1H-indazol-5-yl]oxy}ethyl)propan-2-amine;
1-Methyl-3-(1-naphthylsulfonyl)-5-(2-pyrrolidin-1-ylethoxy)-1H-indazole;
{3-[3-(1-Naphthylsulfonyl)-1H-indazol-5-yl]propyl}amine;
(2-{[1-Methyl-3-(1-naphthylsulfonyl)-1H-indazol-7-yl]oxy}ethyl)amine;
N-Ethyl-3-{[3-(1-naphthylsulfonyl)-1H-indazol-5-yl]oxy}propan-1-amine;

N-Isopropyl-3-{[3-(1-naphthylsulfonyl)-1H-indazol-5-yl]oxy}propan-1-amine;
N-(3-{[3-(1-Naphthylsulfonyl)-1H-indazol-5-yl]oxy}propyl)cyclopentanamine;
5-(3-Morpholin-4-ylpropoxy)-3-(1-naphthylsulfonyl)-1H-indazole;
N-(3-{[3-(1-Naphthylsulfonyl)-1H-indazol-5-yl]oxy}propyl)cyclopropanamine;
(3-{[3-(1-Naphthylsulfonyl)-1H-indazol-5-yl]oxy}propyl)amine;
N-Methyl-4-{[3-(1-naphthylsulfonyl)-1H-indazol-5-yl]oxy}butan-1-amine
N,N-Dimethyl-4-{[(3-(1-naphthylsulfonyl)-1H-indazol-5-yl]oxy}butan-1-amine;
N-Ethyl-4-{[3-(1-naphthylsulfonyl)-1H-indazol-5-yl]oxy}butan-1-amine;
N,N-Diethyl-4-{[3-(1-naphthylsulfonyl)-1H-indazol-5-yl]oxy}butan-1-amine;
N-Methyl-4-{[3-(1-naphthylsulfonyl)-1H-indazol-5-yl]oxy}-N-propylbutan-1-amine;
3-(1-Naphthylsulfonyl)-5-(4-pyrrolidin-1-ylbutoxy)-1H-indazole;
3-(1-Naphthylsulfonyl)-5-(4-piperidin-1-ylbutoxy)-1H-indazole;
(4-{[3-(1-Naphthylsulfonyl)-1H-indazol-5-yl]oxy}butyl)amine;
(2-{[5-Fluoro-3-(1-naphthylsulfonyl)-1H-indazol-7-yl]oxy}ethyl)methylamine;
5-[(4-Methylpiperazin-1-yl)methyl]-3-(1-naphthylsulfonyl)-1H-indazole;
3-(1-Naphthylsulfonyl)-5-(piperazin-1-ylmethyl)-1H-indazole;
N-{[3-(1-Naphthylsulfonyl)-1H-indazol-5-yl]methyl}ethane-1,2-diamine;
N-Methyl-3-[3-(1-naphthylsulfonyl)-1H-indazol-5-yl]propan-1-amine;
N,N-Dimethyl-4-[3-(1-naphthylsulfonyl)-1H-indazol-5-yl]butan-1-amine;
N,N-Dimethyl-3-[3-(1-naphthylsulfonyl)-1H-indazol-5-yl]propan-1-amine;
N-Ethyl-N-methyl-3-[3-(1-naphthylsulfonyl)-1H-indazol-5-yl]propan-1-amine;
N-Isopropyl-3-[3-(1-naphthylsulfonyl)-1H-indazol-5-yl]propan-1-amine;
N-Ethyl-N-methyl-4-[3-(1-naphthylsulfonyl)-1H-indazol-5-yl]butan-1-amine;
(2-{[3-(1-Naphthylsulfonyl)-1H-indazol-5-yl]oxy}ethyl)amine;
3-(1-Naphthylsulfonyl)-5-(3-pyrrolidin-1-ylpropyl)-1H-indazole;
N-Isopropyl-4-[3-(1-naphthylsulfonyl)-1H-indazol-5-yl]butan-1-amine;
3-(1-Naphthylsulfonyl)-5-(4-pyrrolidin-1-ylbutyl)-1H-indazole;
N-Ethyl-4-[3-(1-naphthylsulfonyl)-1H-indazol-5-yl]butan-1-amine;
5-[(3-Methylpiperazin-1-yl)methyl]-3-(1-naphthylsulfonyl)-1H-indazole;
5-[(3,5-Dimethylpiperazin-1-yl)methyl]-3-(1-naphthylsulfonyl)-1H-indazole;
N-Ethyl-3-[3-(1-naphthylsulfonyl)-1H-indazol-5-yl]propan-1-amine;
{4-[3-(1-Naphthylsulfonyl)-1H-indazol-5-yl]butyl}amine;
5-[1-(4-Methylpiperazin-1-yl)ethyl]-3-(1-naphthylsulfonyl)-1H-indazole;
N,N,N'-Trimethyl-N'-{[3-(1-naphthylsulfonyl)-1H-indazol-5-yl]methyl}ethane-1,2-diamine;
N,N-Dimethyl-2-{[3-(1-naphthylsulfonyl)-1H-indazol-5-yl]methoxy}ethanamine;
5-{[(3R)-3-Methylpiperazin-1-yl]methyl}-3-(1-naphthylsulfonyl)-1H-indazole;

5-{[(3S)-3-Methylpiperazin-1-yl]methyl}-3-(1-naphthylsulfonyl)-1H-indazole;
(3S)—N-{[3-(1-Naphthylsulfonyl)-1H-indazol-5-yl]methyl}pyrrolidin-3-amine;
(3R)-1-{[3-(1-Naphthylsulfonyl)-1H-indazol-5-yl]methyl}pyrrolidin-3-amine;
N-[2-(Dimethylamino)ethyl]-3-(1-naphthylsulfonyl)-1H-indazole-5-carboxamide;
2-{[5-Fluoro-3-(phenylsulfonyl)-1H-indazol-7-yl]oxy}ethanamine;
N-[3-(1-Naphthylsulfonyl)-1H-indazol-6-yl]-beta-alaninamide;
N-[3-(1-Naphthylsulfonyl)-1H-indazol-7-yl]-3-piperidin-1-ylpropanamide;
$N^3$~,$N^3$~-Dimethyl-N-[3-(1-naphthylsulfonyl)-1H-indazol-7-yl]-beta-alaninamide;
2-{[3-(Phenylsulfonyl)-1H-indazol-7-yl]oxy}ethanamine;
N-[3-(1-Naphthylsulfonyl)-1H-indazol-7-yl]-beta-alaninamide;
N-[3-(1-Naphthylsulfonyl)-1H-indazol-7-yl]ethane-1,2-diamine;
N-[3-(1-Naphthylsulfonyl)-1H-indazol-6-yl]-3-piperidin-1-ylpropanamide;
N-[3-(1-Naphthylsulfonyl)-1H-indazol-6-yl]ethane-1,2-diamine;
$N^3$,$N^3$-diethyl-N-[3-(1-naphthylsulfonyl)-1H-indazol-7-yl]-beta-alaninamide;
N,N-Dimethyl-2-{[3-(1-naphthylsulfonyl)-1H-indazol-4-yl]oxy}ethanamine;
3-(1-Naphthylsulfonyl)-4-(2-piperidin-1-ylethoxy)-1H-indazole;
3-(1-Naphthylsulfonyl)-4-(2-pyrrolidin-1-ylethoxy)-1H-indazole;
2-{[3-(1-Naphthylsulfonyl)-1H-indazol-4-yl]oxy}ethanamine;
N-Methyl-2-{[3-(1-naphthylsulfonyl)-1H-indazol-6-yl]oxy}ethanamine;
2-{[3-(1-Naphthylsulfonyl)-1H-indazol-6-yl]oxy}ethanamine;

a stereoisomer thereof; or a pharmaceutically acceptable salt thereof.

Compounds of the invention may be prepared using conventional synthetic methods and, if required, standard isolation or separation techniques In Schemes I through VII below, Z represents the group $(CR_3R_4)_n$ wherein $R_3$, $R_4$ and n are as defined hereinabove for formula I.

Compounds of formula I wherein X is O (Ia) may be prepared as illustrated in Scheme I below wherein the chloromethylsulfone 2 is either commercially available or readily prepared using methods as described by M. Makosza and J. Golinski in J. Org. Chem., 1984, 49, 1488-1494; or by Antane, S.; Bernotas, R., Li, Y.; McDevitt, R.; Yan, Y. Synthetic Communications 2004, 34(13), 2443-2449 or by other known methods. Reaction of a sulfonylchloride 1 with sodium sulfite under basic conditions followed by reaction with chloro-bromo-methane affords the chloromethylsulfone 2. Reaction of 2 with a fluoronitrobenzene 3 under basic conditions gives the benzylsulfonyl derivative 4. Compound 4 is reacted with the diol, HO—$(CR_3R_4)_n$—OH, under basic conditions to give 5. Tosylation, followed by hydrogenation, of 5 gives the aniline 6. Compound 6 is reacted with sodium nitrite in the presence of an acid to give the indazole 7. Alkylation of the indazole 7 yields the alkylated tosylate compound 8. Displacement of the tosyl groups of either of compounds 7 or 8 with the appropriate amine then gives the desired compound of formula Ia. The reaction is shown in Scheme I wherein Ts represents p-toluenesulfonyl and Hal represents Cl, Br or I.

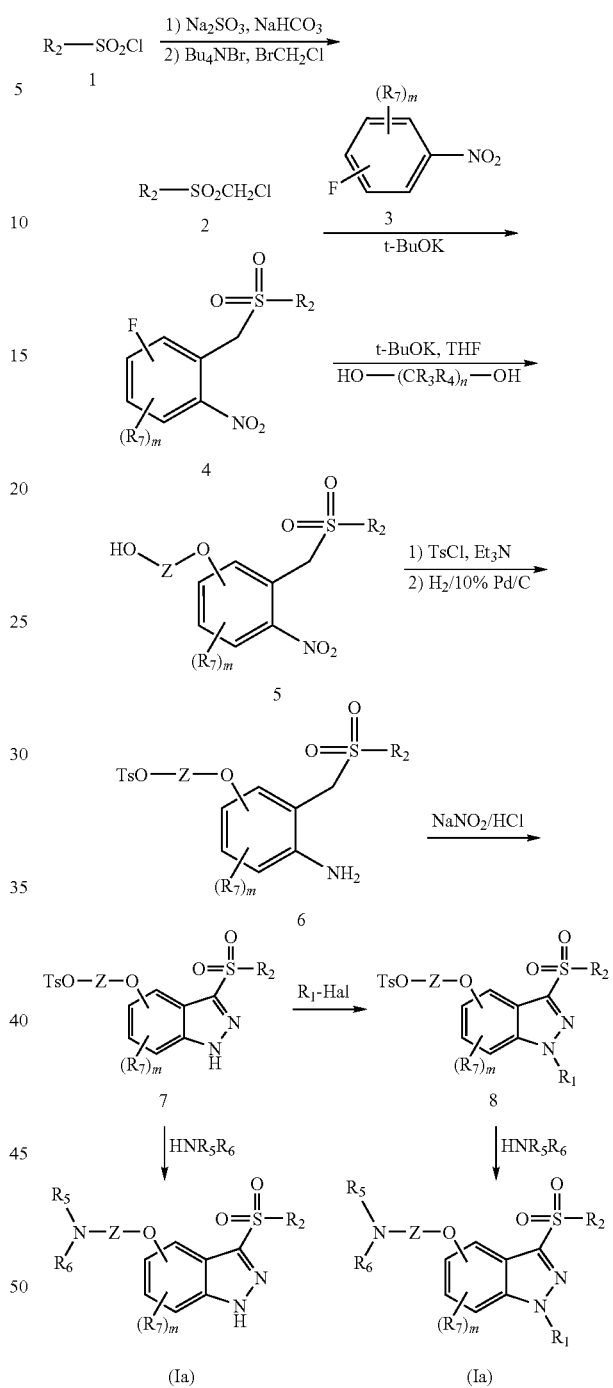

SCHEME I

Similarly, compounds of formula I wherein X is O and $R_5$ and $R_6$ are H (Ib), or compounds of formula Ia, may be prepared by reacting the nitrobenzene derivative 9 with chloromethylsulfone 2, followed by hydrogenation to give the aniline 10. The aniline 10 is converted to the indazole derivative 11, as described hereinabove in Scheme I. Alkylation or protection of the indazole 11 gives compound 12. Reaction of 12 with sodium azide followed by reduction of the azido group yields the desired primary amine Ib. Alternatively, reaction of 11 or 12 with an amine, $HNR_5R_6$, gives the compound of Ia. The reaction is shown in Scheme II wherein Hal represents Cl, Br or I.

SCHEME II

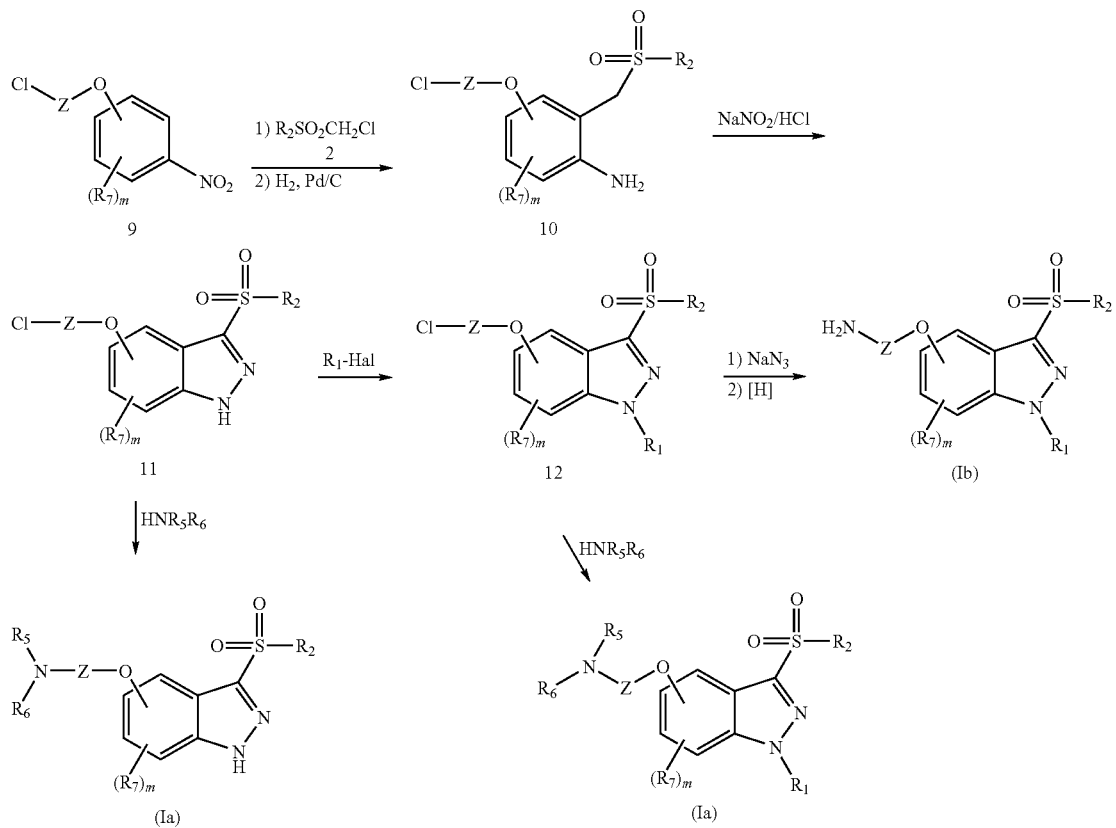

Alternatively, formula Ia compounds may be prepared by the reaction of an amino alcohol 14 with either a fluoronitrobenzene 13 under basic conditions, or a nitrophenol 15 under Mitsunobu conditions, to give the compound 16. Compound 16 is reacted with a chlorosulfone 2, followed by hydrogenation, to give the aniline 17. Subsequent formation of the desired formula Ia indazoles is carried out as described hereinabove in Schemes I and II. The reaction is shown in Scheme III wherein Hal represents Cl, Br or I.

SCHEME III

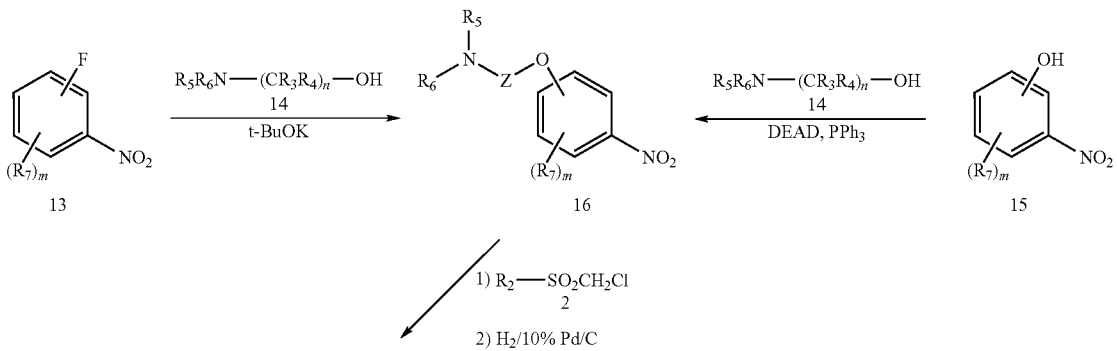

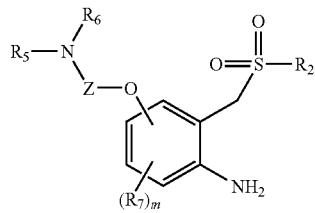

17

↓ NaNO₂/HCl
Na₂CO₃

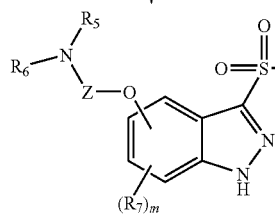

(Ia)

R₁-Hal

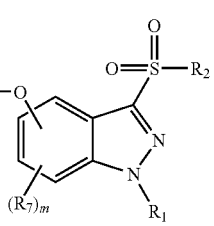

(Ia)

Compounds of formula I wherein X is NR and R and R₁ are H (Ib) or X is NRCO and R and R₁ are H (Ic) may be prepared by reacting a nitroindazole 18 with iodine to give the corresponding 3-iodoindazole 19; coupling 19 with a thiol 20, followed by oxidation with a suitable oxidizing agent such as m-chloroperbenzoic acid (mCPBA) to give the sulfone 21; reducing the nitro group of 21 with Sn/HCl or SnCl₂/HCl to obtain the corresponding amine 22; and either reacting 22 with the amino aldehyde 23 under reductive amination conditions to afford the desired compound of formula Ib, or coupling 22 with an amino acid 24 to give the desired compound of formula Ic. The reactions are shown in Scheme IV hereinbelow, wherein Ac represents COCH₃.

SCHEME IV

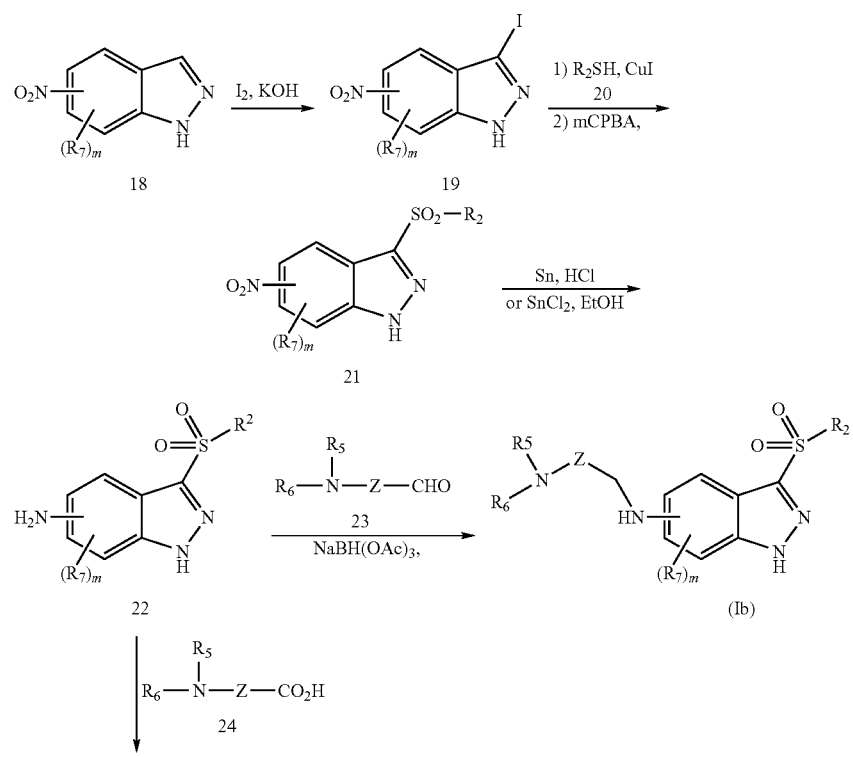

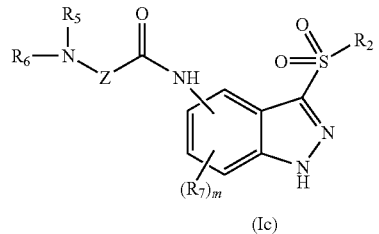

(Ic)

Compounds of formula I wherein X is CH$_2$ and R$_5$ and R$_6$ are other than H (Id) may be prepared by reacting the nitrobenzene compound 25 with the chloromethylsulfonyl compound 2 to obtain the intermediate 26; reducing the nitro group of compound 26 to the corresponding amine and nitrosating said amine, as described in Schemes II and III, to form the desired compound of formula Id wherein R$_1$ is H and optionally alkylating said compound to obtain the desired compound of formula Id wherein R$_1$ is other than H. The reactions are shown in Scheme V hereinbelow, wherein Hal represents Cl, Br or I.

SCHEME V

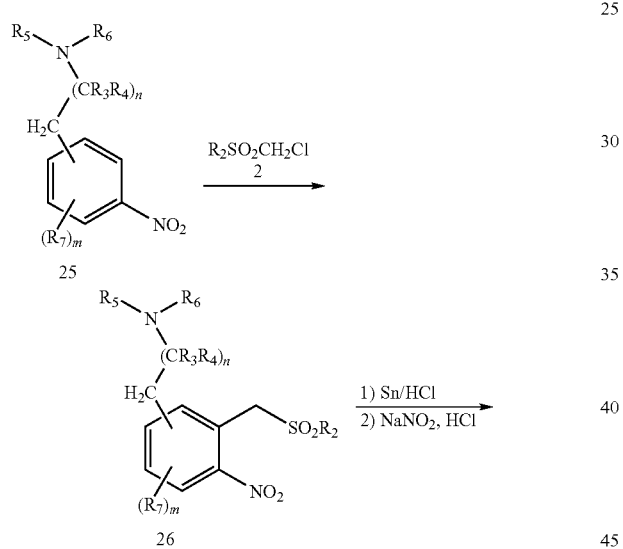

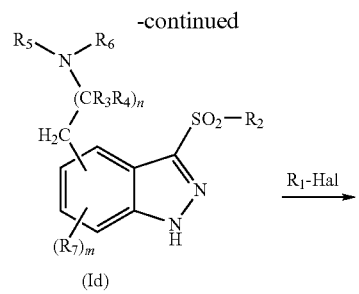

Compounds of formula Id wherein R$_5$ is H (Ie) may be prepared in a similar manner by protecting the compound 27 with a suitable protecting group such as t-butyloxycarbonyl (BOC), ethyloxycarbonyl, methyloxycarbonyl, benzyl (Bn), phthalimide, fluorenylmethylcarbonyl (Fmoc), acetyl, benzoyl, or the like to give the protected amine 28; reacting compound 28 with the chloromethylsulfonyl 2, followed by reduction and nitrosation as shown hereinabove in Scheme V to obtain the protected compound 29 and deprotecting to give the desired compound of formula Ie. The reaction is shown in Scheme VI hereinbelow, wherein Hal represents Cl, Br or I.

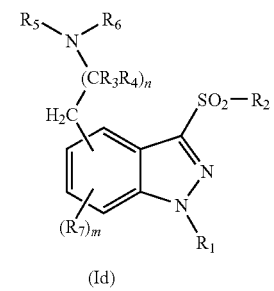

SCHEME VI

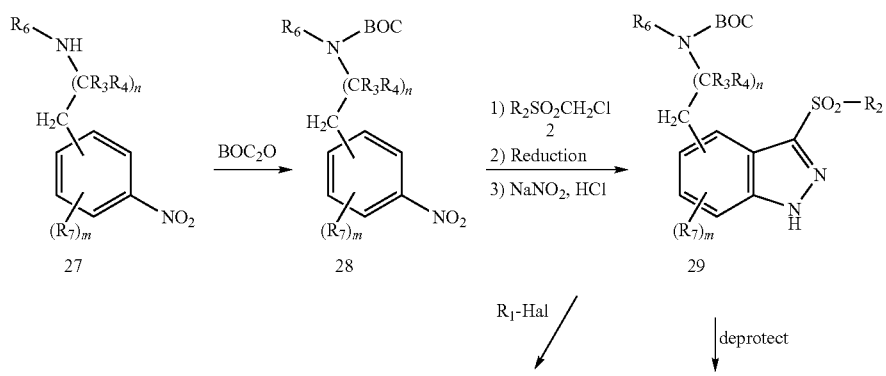

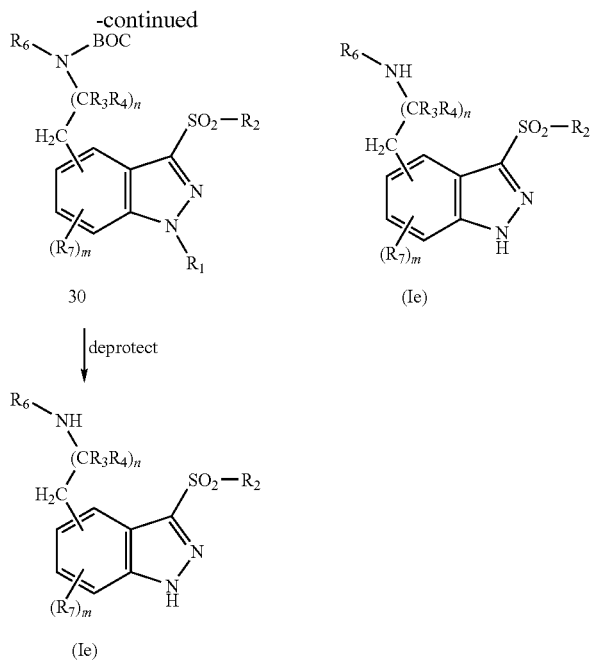

Compounds of formula Id may also be prepared by coupling the compound 31 with an alkyne 32 using Sonagashira conditions to give the compound 33; reducing 33 to the fully saturated amine 34; reacting 34 with NaNO$_2$ to give the indazole 35 and converting the hydroxyl group to a leaving group and displacing the leaving group with an amine, HNR$_5$R$_6$, optionally alkylating the resultant product to give the desired compound of formula Id. The reactions are shown in Scheme VII hereinbelow wherein TsCl represents tosyl chloride and Hal represents Cl, Br or I.

SCHEME VII

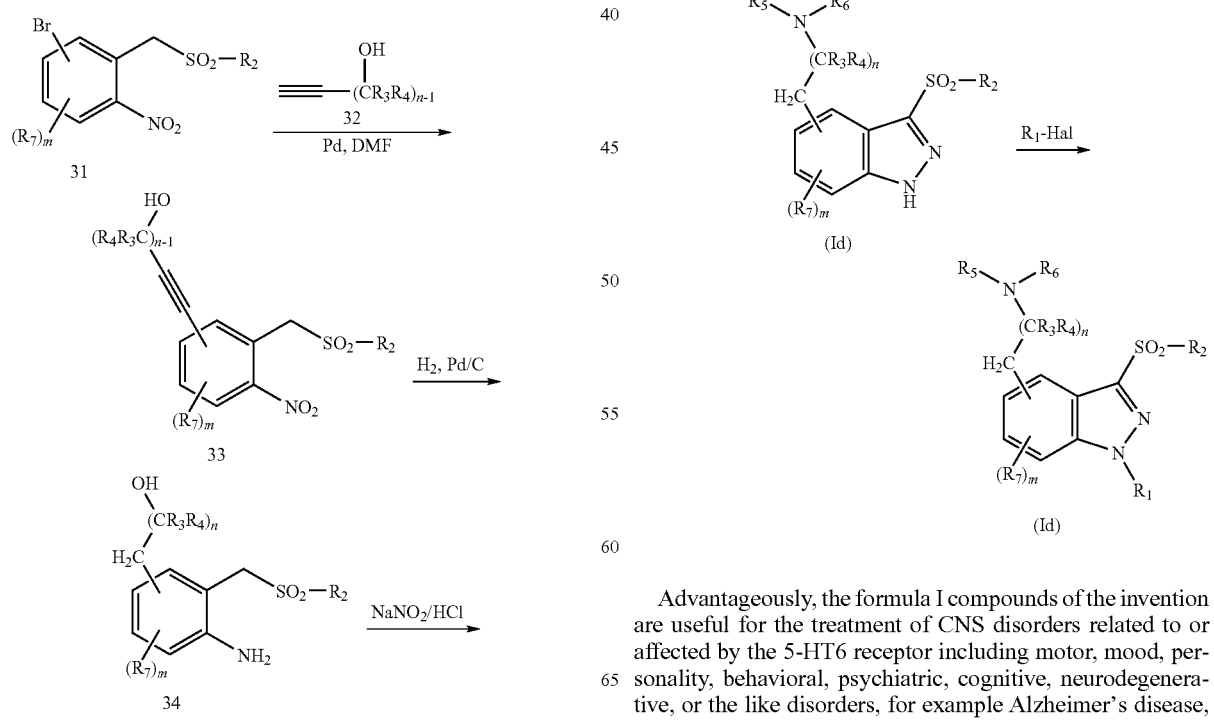

Advantageously, the formula I compounds of the invention are useful for the treatment of CNS disorders related to or affected by the 5-HT6 receptor including motor, mood, personality, behavioral, psychiatric, cognitive, neurodegenerative, or the like disorders, for example Alzheimer's disease, Parkinson's disease, attention deficit disorder, anxiety, epilepsy, depression, obsessive compulsive disorder, sleep disorders, neurodegenerative disorders (such as head trauma or stroke), feeding disorders (such as anorexia or bulimia), schizophrenia, memory loss, disorders associated with withdrawal from drug or nicotine abuse, or the like or certain gastrointestinal disorders such as irritable bowel syndrome. Accordingly, the present invention provides a method for the treatment of a disorder of the central nervous system related to or affected by the 5-HT6 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The term "providing" as used herein with respect to providing a compound or substance embraced by the invention, designates either directly administering such a compound or substance, or administering a prodrug, derivative or analog which forms an equivalent amount of the compound or substance within the body.

The inventive method includes: a method for the treatment of schizophrenia; a method for the treatment of a disease associated with a deficit in memory, cognition, and/or learning or a cognitive disorder such as Alzheimer's disease or attention deficit disorder; a method for the treatment of developmental disorders such as schizophrenia; Down's syndrome, Fragile X syndrome, autism or the like; a method for the treatment of behavioral disorders, e.g., anxiety, depression, or obsessive compulsive disorder; a method for the treatment of motion or motor disorders such as Parkinson's disease or epilepsy; a method for the treatment of a neurodegenerative disorder such as stroke or head trauma or withdrawal from drug addiction including addiction to nicotine, alcohol, or other substances of abuse, or any other CNS disease or disorder associated with or related to the 5-HT6 receptor.

In one embodiment, the present invention provides a method for treating attention deficit disorders (ADD, also known as Attention Deficit Hyperactivity Disorder or ADHD) in both children and adults. Accordingly, in this embodiment, the present invention provides a method for treating attention deficit disorders in a pediatric patient.

The present invention therefore provides a method for the treatment of each of the conditions listed above in a patient, preferably in a human, said method comprises providing said patient a therapeutically effective amount of a compound of formula I as described hereinabove. The compounds may be provided by oral or parenteral administration or in any common manner known to be an effective administration of a therapeutic agent to a patient in need thereof.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove. In one embodiment, the invention relates to compositions comprising at least one compound of formula I, or a pharmaceutically acceptable salt thereof, and one or more pharmaceutically acceptable carriers, excipients, or diluents. Such compositions include pharmaceutical compositions for treating or controlling disease states or conditions of the central nervous system. In certain embodiments, the compositions comprise mixtures of one or more compounds of formula I.

In certain embodiments, the invention relates to compositions comprising at least one compound of formula I, or a pharmaceutically acceptable salt thereof, and one or more pharmaceutically acceptable carriers, excipients, or diluents. Such compositions are prepared in accordance with acceptable pharmaceutical procedures. Pharmaceutically acceptable carriers are those carriers that are compatible with the other ingredients in the formulation and are biologically acceptable.

The compounds of formula I may be administered orally or parenterally, neat, or in combination with conventional pharmaceutical carriers. Applicable solid carriers can include one or more substances that can also act as flavoring agents, lubricants, solubilizers, suspending agents, fillers, glidants, compression aids, binders, tablet-disintegrating agents, or encapsulating materials. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

In certain embodiments, a compound of formula I is provided in a disintegrating tablet formulation suitable for pediatric administration.

Liquid carriers can be used in preparing solutions, suspensions, emulsions, syrups and elixirs. The active ingredient can be dissolved or suspended in a pharmaceutically acceptable liquid carrier such as water, an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

In certain embodiments, a liquid pharmaceutical composition is provided wherein said composition is suitable for pediatric administration. In other embodiments, the liquid composition is a syrup or suspension.

Liquid pharmaceutical compositions that are sterile solutions or suspensions can be administered by, for example, intramuscular, intraperitoneal or subcutaneous injection.

Sterile solutions can also be administered intravenously. Compositions for oral administration can be in either liquid or solid form.

The compounds of formula I may be administered rectally or vaginally in the form of a conventional suppository. For administration by intranasal or intrabronchial inhalation or insufflation, the compounds of formula I can be formulated into an aqueous or partially aqueous solution, which can then be utilized in the form of an aerosol. The compounds of formula I can also be administered transdermally through the use of a transdermal patch containing the active compound and a carrier that is inert to the active compound, is non-toxic to the skin, and allows delivery of the agent for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable. A variety of occlusive devices can be used to release the active ingredient into the blood stream such as a semipermeable membrane covering a reservoir containing the active ingredient with or without a carrier, or a matrix containing the active ingredient. Other occlusive devices are known in the literature.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The therapeutically effective amount of a compound of formula I provided to a patient will vary depending upon what is being administered, the purpose of the administration, such as prophylaxis or therapy, the state of the patient, the manner of administration, and the like. In therapeutic applications, compounds of formula I are provided to a patient suffering from a condition in an amount sufficient to treat or at least partially treat the symptoms of the condition and its complications. An amount adequate to accomplish this is a "therapeutically effective amount" as described previously herein. The dosage to be used in the treatment of a specific case must be subjectively determined by the attending physician. The variables involved include the specific condition and the size, age, and response pattern of the patient. The treatment of substance abuse follows the same method of subjective drug administration under the guidance of the attending physician. Generally, a starting dose is about 5 mg per day with gradual increase in the daily dose to about 150 mg per day, to provide the desired dosage level in the patient.

In certain embodiments, the present invention is directed to prodrugs of compounds of formula I. The term "prodrug," as used herein, means a compound that is convertible in vivo by metabolic means (e.g. by hydrolysis) to a compound of formula I. Various forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991), Bundgaard, et al., Journal of Drug Delivery Reviews, 8:1-38(1992), Bundgaard, J. of Pharmaceutical Sciences, 77:285 et seq. (1988); and Higuchi and Stella (eds.) Prodrugs as Novel Drug Delivery Systems, American Chemical Society (1975).

For a more clear understanding, and in order to illustrate the invention more clearly, specific examples thereof are set forth hereinbelow. The following examples are merely illustrative and are not to be understood as limiting the scope and underlying principles of the invention in any way. The terms HNMR, MS and HPLC designate mass spectrum, high performance liquid chromatography and proton nuclear magnetic resonance, respectively. The terms THF, DMF and DMSO designate tetrahydrofuran, dimethyl formamide and dimethylsulfoxide, respectively. All column chromatography is performed using $SiO_2$ as support. Unless otherwise noted, all parts are parts by weight.

EXAMPLE 1

[2-(3-Benzenesulfonyl-1H-indazol-5-yloxy)-ethyl]-dimethyl-amine

Step 1

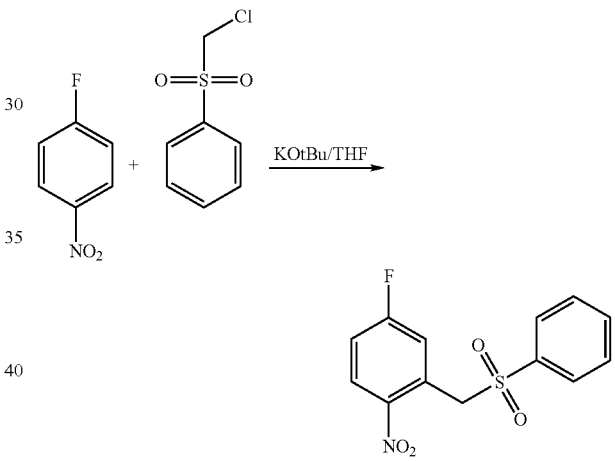

2-Benzenesulfonylmethyl-4-fluoro-1-nitro-benzene

To a solution of chloromethylphenyl sulfone (10.51 g, 55.13 mmol) in THF (110 mL) was added 5.9 mL (56 mmol) of 1-fluoro-4-nitrobenzene. The reaction mixture was chilled to 0° C., and 1.0 M potassium tert-butoxide in THF (145 mL, 145 mmol) was added dropwise. The reaction mixture was stirred under nitrogen at ambient temperature for one hour. Acetic acid (9 mL, 160 mmol) was then added. The reaction mixture was solvent evaporated and partitioned in brine and ethyl acetate. The organic phase was then dried with anhydrous magnesium sulfate, filtered and concentrated. The residue was stirred in diethyl ether, filtered and dried in vacuo at 73° C. for 12 hours. 2-Benzenesulfonylmethyl-4-fluoro-1-nitrobenzene as a light brown-yellow solid was obtained (10.24 g, 62.8%): MP: 169-171° C.; Mass spectrum (−EI, [M−H]$^-$) m/z 294. $^1$HNMR (500 MHz, DMSO-$d_6$): δ8.10-8.14 (m, 1H), 7.70-7.75 (m, 1H), 7.56-7.63 (m, 4H), 7.45-7.50 (m, 1H), 7.20 (dd, 1H, J=9.27 Hz and 2.81 Hz), 5.12 ppm (s, 2H). Elemental Analysis for $C_{13}H_{10}FNO_4S$: Calcd: C, 52.88; H, 3.41; N, 4.74; Found: C, 52.63; H, 3.14; N, 4.66;

Step 2

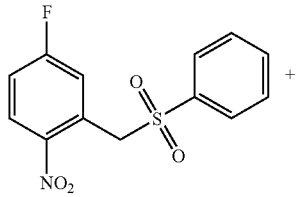

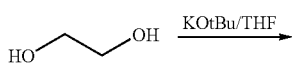

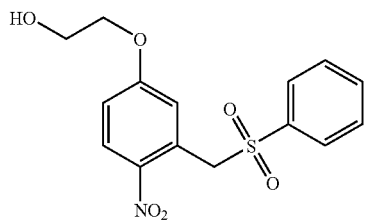

2-(3-Benzenesulfonylmethyl-4-nitro-phenoxy)-ethanol

A mixture of 2-benzenesulfonylmethyl-4-fluoro-1-nitrobenzene (10.2 g, 34.7 mmol), ethylene glycol (80 mL, 1.4 mol), and 1 M potassium tert-butoxide in THF (78 mL, 78 mmol) in THF (50 mL) was refluxed under nitrogen for 30 minutes. After cooling to about ambient temperature, the reaction mixture was solvent evaporated. Water was added to the residue, and it was poured into 2.0 N hydrochloric acid and ice. The mixture was then extracted with ethyl acetate and washed with water and brine. The organic phase was dried with anhydrous magnesium sulfate, filtered, concentrated and dried in vacuo at 74° C. for 20 minutes. 2-(3-Benzenesulfonylmethyl-4-nitro-phenoxy)-ethanol as a dark brown gum (11.7 g, 100% yield) was obtained; Mass spectrum (-EI, [M–H]$^-$) m/z 336. $^1$HNMR (500 MHz, DMSO-d$_6$): δ8.01 (d, 1H, J=9.15 Hz), 7.67-7.73 (m, 1H), 7.54-7.63 (m, 4H), 7.10 (dd, 1H, J=9.51 Hz and 2.93 Hz), 6.85 (d, 1H, J=2.81 Hz), 5.12 (s, 2H), 4.88-4.90 (m, 1H), 3.93-3.96 (m, 2H), 3.65 ppm (d, 2H, J=4.51 Hz). Elemental Analysis for C$_{15}$H$_{15}$NO$_6$S: Calcd: C, 53.41; H, 4.48; N, 4.15; Found: C, 53.47; H, 4.69; N, 4.04;

Step 3

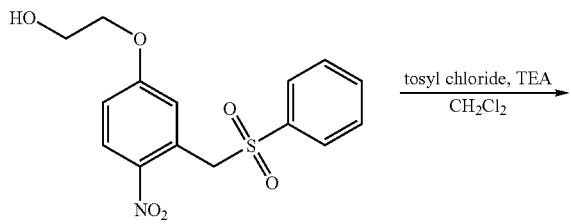

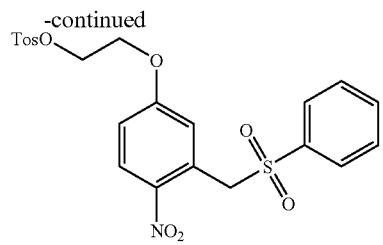

Toluene-4-sulfonic acid 2-(3-benzenesulfonylmethyl-4-nitro-phenoxy)-ethyl ester

A mixture of 2-(3-benzenesulfonylmethyl-4-nitro-phenoxy)-ethanol (8.2 g, 24 mmol), p-toluenesulfonyl chloride (9.39 g, 49.3 mmol) and triethylamine (19 mL, 140 mmol) in methylene chloride (85 mL) was stirred at ambient temperature under nitrogen for 4.5 hours. It then was solvent evaporated and partitioned in methylene chloride and aqueous sodium bicarbonate. The organic phase was then washed with brine, dried with anhydrous magnesium sulfate, filtered, concentrated and dried in vacuo at 63° C. for 30 minutes. The residue was purified by flash chromatography with 100% chloroform and 5% methanol in chloroform. It was dried in vacuo at 65° C. for 20 minutes to yield toluene-4-sulfonic acid 2-(3-benzenesulfonylmethyl-4-nitro-phenoxy)-ethyl ester as a yellow solid (8.1 g, 69%); Mass spectrum (-EI, [M–H]$^-$) m/z 490. $^1$HNMR (300 MHz, DMSO-d$_6$): δ7.99 (d, 1H, J=9.02 Hz), 7.67-7.75 (m, 3H), 7.54-7.62 (m, 4H), 7.43 (d, 2H, J=7.93 Hz), 7.00 (dd, 1H, J=9.15 Hz and 2.80 Hz), 6.78 (d, 1H, J=2.81 Hz), 5.09 (s, 2H), 4.29-4.31 (m, 2H), 4.13-4.15 (m, 2H), 2.37 ppm (s, 3H). Elemental Analysis for C$_{22}$H$_{21}$NO$_8$S 0.40 mol H$_2$O: Calcd: C, 52.98; H, 4.41; N, 2.81; Found: C, 52.67; H, 4.26; N, 2.61.

Step 4

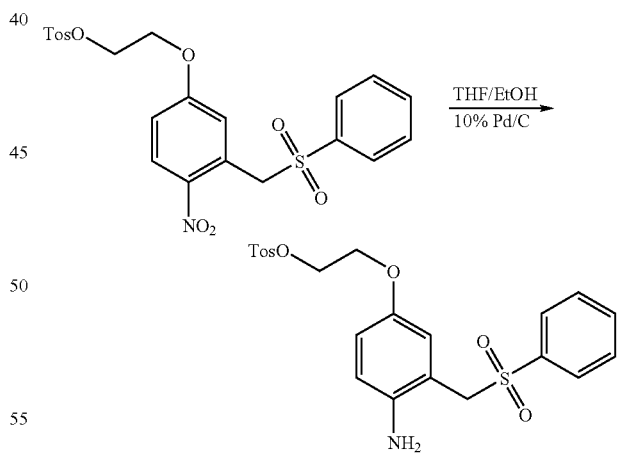

Toluene-4-sulfonic acid 2-(4-amino-3-benzenesulfonylmethyl-phenoxy)-ethyl ester

A solution of toluene-4-sulfonic acid 2-(3-benzenesulfonylmethyl-4-nitro-phenoxy)-ethyl ester (13.1 g, 26.7 mmol) in THF (350 mL) and ethanol (250 mL) was added to 10% palladium on carbon (5.8 g) and hydrogenated on the Parr apparatus with for one hour (starting pressure of 30-40 psi.).

The mixture was filtered over Celite, concentrated and dried in vacuo at 80° C. for 30 minutes to yield toluene-4-sulfonic acid 2-(4-amino-3-benzenesulfonylmethyl-phenoxy)-ethyl ester as a light yellow solid (11.7 g, 95.1%): MP: 144-6° C.; Mass spectrum (+EI, [M+H]+) m/z 462.

$^1$HNMR (500 MHz, DMSO-d$_6$): δ7.72-7.75 (m, 4H), 7.63-7.66 (m, 1H), 7.52-7.56 (m, 2H), 7.44 (d, 2H, J=8.05 Hz), 6.52 (d, 2H, J=1.58 Hz), 6.29-6.30 (m, 1H), 4.65 (s, 2H), 4.46 (s, 2H), 4.16-4.18 (m, 2H), 3.79-3.82 (m, 2H), 2.38 ppm (s, 3H). Elemental Analysis for C$_{22}$H$_{23}$NO$_6$S: Calcd: C, 57.25; H, 5.02; N, 3.03; Found: C, 57.60; H, 4.98; N, 3.10.

Step 5

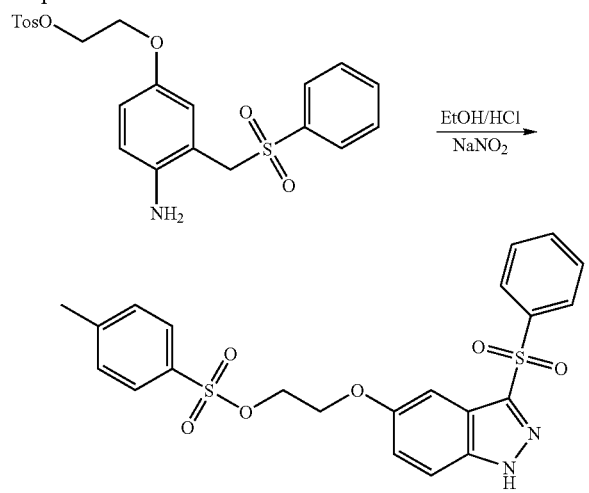

Toluene-4-sulfonic acid 2-(3-benzenesulfonyl-1H-indazol-5-yloxy)-ethyl ester

To a mixture of toluene-4-sulfonic acid 2-(4-amino-3-benzenesulfonylmethyl-phenoxy)-ethyl ester (11.7 g, 25.3 mmol) of in ethanol (350 mL) and 1.0 N hydrochloric acid (425 mL) was dropwise added sodium nitrite (2.67 g, 38.7 mmol) in water (50 mL). After stirring at ambient temperature for 1.5 hours, solid sodium carbonate was added to basic pH. The reaction mixture was stirred for an additional 2 hours. It was then solvent evaporated and extracted with warm ethyl acetate. The organic phase was washed with water and brine, dried with anhydrous magnesium sulfate, filtered and concentrated. The residue was purified by flash chromatography with 2% methanol in chloroform to yield toluene-4-sulfonic acid 2-(3-benzenesulfonyl-1H-indazol-5-yloxy)-ethyl ester as an orange solid (9.54 g, 79.5%): MP: 174-7° C.; Mass Spectrum (−EI, [M−H]−) m/z 471. $^1$HNMR (500 MHz, DMSO-d$_6$): δ14.11 (s, 1H), 7.96-7.98 (m, 2H), 7.74-7.77 (m, 2H), 7.62-7.66 (m, 1H), 7.53-7.59 (m, 3H), 7.39 (d, 2H, J=8.05 Hz), 7.24 (d, 1H, J=2.32 Hz), 6.97-7.00 (m, 1H), 4.35-4.37 (m, 2H), 4.21-4.23 (m, 2H), 2.33 ppm (s, 3H).

Step 6

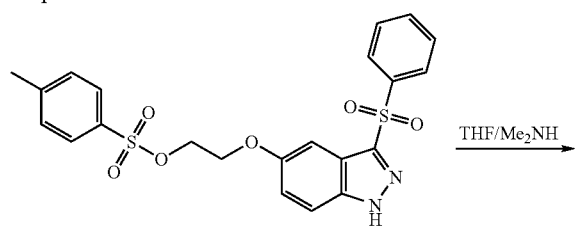

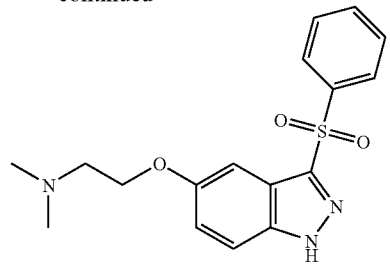

[2-(3-Benzenesulfonyl-1H-indazol-5-yloxy)-ethyl]-dimethyl-amine

A solution of toluene-4-sulfonic acid 2-(3-benzenesulfonyl-1H-indazol-5-yloxy)-ethyl ester (0.341 g, 0.722 mmol) in 2.0 N dimethylamine in THF (9 mL, 18 mmol) of was stirred at 70° C. for 6 hours in a sealed tube. After cooling somewhat, the reaction mixture was solvent evaporated and partitioned in ethyl acetate and aqueous sodium bicarbonate. The organic phase was washed with water and brine. It was dried with anhydrous magnesium sulfate, filtered and concentrated. The residue was partitioned in ethyl acetate/aqueous potassium carbonate. The organic phase was washed with water and brine, dried with anhydrous magnesium sulfate, filtered and concentrated. [2-(3-Benzenesulfonyl-1H-indazol-5-yloxy)-ethyl]-dimethyl-amine as a light yellow-brown solid (0.167 g, 67.1%) resulted. The compound was dissolved in methanol, and ethereal hydrochloride was added. After concentrating and drying in vacuo for 12 hours at 70° C., the hydrochloride as a light orange foam (94.0 mg) was obtained; Mass Spectrum (+EI, [M+H]+) m/z 346. $^1$HNMR (500 MHz, DMSO-d$_6$): δ14.22 (s, 1H), 10.00 (br, 1H), 7.97-7.99 (m, 2H), 7.56-7.68 (m, 4H), 7.42 (d, 1H, J=2.20 Hz), 7.17-7.20 (m, 1H), 4.39-4.42 (m, 2H), 3.52-3.53 (m, 2H), 2.84 ppm (s, 6H).

EXAMPLE 2

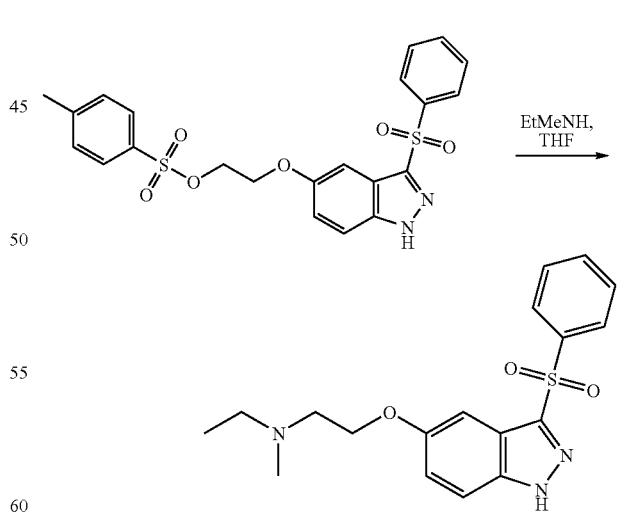

[2-(3-Benzenesulfonyl-1H-indazol-5-yloxy)-ethyl]-ethyl-methyl-amine

A solution of toluene-4-sulfonic acid 2-(3-benzenesulfonyl-1H-indazol-5-yloxy)-ethyl ester (0.364 g, 0.770 mmol)

and N-ethylmethylamine (0.95 mL, 11 mmol) in THF (8 mL) was stirred for 6 hours at 70° C. in a sealed tube. After cooling somewhat to ambient temperature, the reaction mixture was solvent evaporated and partitioned in ethyl acetate and aqueous sodium bicarbonate. The organic phase was washed with water and brine, dried with anhydrous magnesium sulfate, filtered and concentrated. After drying in vacuo at ambient temperature for 1.5 hours, the resulting buff solid (0.249 g, 89.9%), [2-(3-benzenesulfonyl-1H-indazol-5-yloxy)-ethyl]-ethyl-methyl-amine, was dissolved in methanol and methylene chloride, and ethereal hydrochloride was added. Concentration and drying at 80° C. for 12 hours yielded the hydrochloride as a light orange foam (0.253 g); Mass Spectrum (+EI, [M+H]$^+$) m/z 360. $^1$HNMR (500 MHz, DMSO-d$_6$): δ14.23 (s, 1H), 9.95 (br, s, 1H), 7.97-7.99 (m, 2H), 7.56-7.68 (m, 4H), 7.42 (d, 1H, J=2.32 Hz), 7.19 (dd, 1H, J=9.15 Hz and 2.32 Hz), 4.41-4.43 (m, 2H), 3.55-3.60 (m, 1H), 3.43-3.49 (m, 1H), 3.11-3.17 (m, 1H), 2.82 (d, 3H, J=4.63 Hz), 1.22-1.25 ppm (m, 3H).

EXAMPLE 3

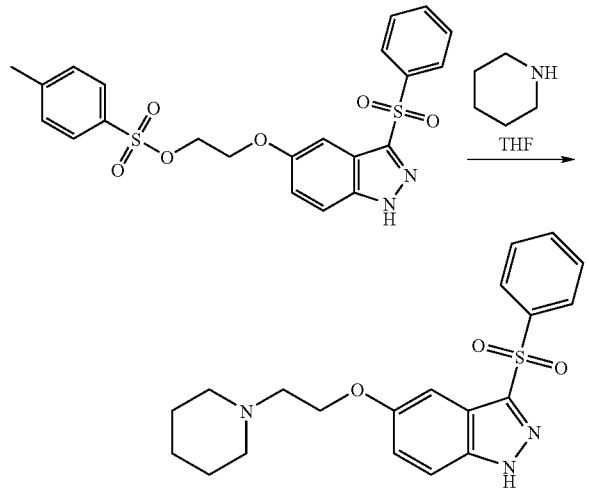

3-Benzenesulfonyl-5-(2-piperidin-1-yl-ethoxy)-1H-indazole

A solution of toluene-4-sulfonic acid 2-(3-benzenesulfonyl-1H-indazol-5-yloxy)-ethyl ester (0.386 g, 0.817 mmol) and piperidine (1.0 mL, 10 mmol) in THF (8 mL) was stirred at 70° C. for 6 hours in a sealed tube. After cooling somewhat to ambient temperature, the reaction mixture was solvent evaporated and partitioned in ethyl acetate and aqueous sodium bicarbonate. The organic phase was washed with water and brine. It was dried with anhydrous magnesium sulfate, filtered and concentrated. Drying in vacuo at 80° C. for 20 minutes resulted in 3-benzenesulfonyl-5-(2-piperidin-1-yl-ethoxy)-1H-indazole as a light yellow solid (0.275 g, 87.3%). This was dissolved in methanol, and ethereal hydrochloride was added. This mixture was concentrated and dried in vacuo at 70° C. for about 12 hours to yield the hydrochloride as a yellow solid (0.268 g): MP: 249-250° C.; Mass Spectrum (+EI, [M+H]$^+$) m/z 386.

$^1$HNMR (500 MHz, DMSO-d$_6$): δ14.24 (s, 1H), 10.02-10.03 (br, 1H), 7.97-7.99 (m, 2H), 7.56-7.68 (m, 4H), 7.41 (d, 1H, J=2.32 Hz), 7.18 (dd, 1H, J=9.15 Hz and 2.33 Hz), 4.44-4.46 (m, 2H), 3.48-3.51 (m, 4H), 2.94-3.04 (m, 2H), 1.65-1.77 (m, 5H), 1.31-1.42 ppm (m, 1H). Elemental Analysis for C$_{20}$H$_{23}$N$_3$O$_3$S.1.00 mol HCl.0.15 mol H$_2$O: Calcd: C, 56.57; H, 5.77; N, 9.90; Found: C, 56.34; H, 5.88; N, 9.57.

EXAMPLE 4

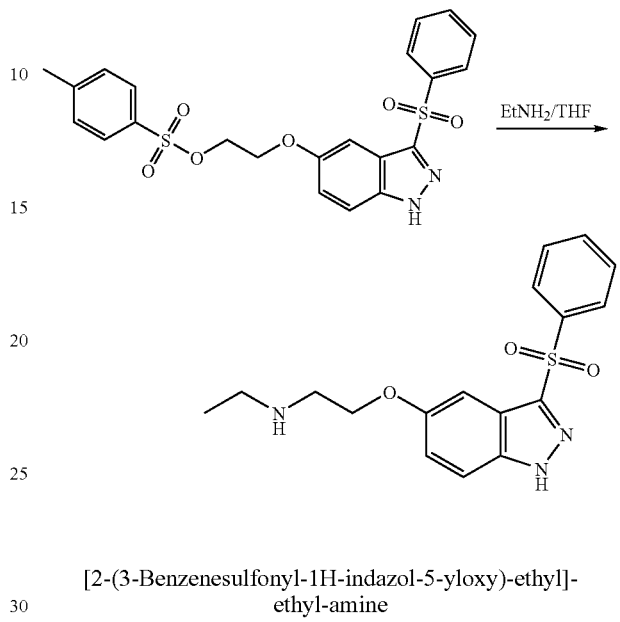

[2-(3-Benzenesulfonyl-1H-indazol-5-yloxy)-ethyl]-ethyl-amine

A solution of toluene-4-sulfonic acid 2-(3-benzenesulfonyl-1H-indazol-5-yloxy)-ethyl ester (0.361 g, 0.764 mmol) in 2.0 N ethylamine in THF (9 mL, 18 mmol) was stirred at 70° C. for 6 hours in a sealed tube. After cooling somewhat, the reaction mixture was solvent evaporated and partitioned in ethyl acetate and aqueous sodium bicarbonate. The organic phase was then washed with water and brine, dried with anhydrous magnesium sulfate, filtered and concentrated. The residue was purified by flash chromatography using 10% methanol in chloroform. After drying in vacuo at 68° C. for 20 minutes, [2-(3-benzenesulfonyl-1H-indazol-5-yloxy)-ethyl]-ethyl-amine as a light brown gum (0.116 g, 43.9%) was obtained. This was dissolved in chloroform and methanol, and ethereal hydrochloride was added. Concentrating and drying at 74° C. for 13.5 hours in vacuo yielded the hydrochloride as a buff solid (0.113 g): MP: 248-50° C. (dec). Mass Spectrum (+EI, [M+H]$^+$) m/z 346. $^1$HNMR (500 MHz, DMSO-d$_6$): δ14.23 (s, 1H), 8.81 (br, 2H), 7.96-7.98 (m, 2H), 7.56-7.68 (m, 4H), 7.40 (d, 1H, J=2.07 Hz), 7.19 (dd, 1H, J=9.15 Hz and 2.32 Hz), 4.31 (t, 2H, J=5.00 Hz), 3.35 (br, 2H), 3.00-3.05 (m, 2H), 1.18-1.22 ppm (m, 3H).

EXAMPLE 5

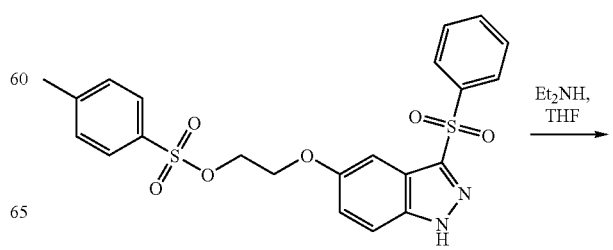

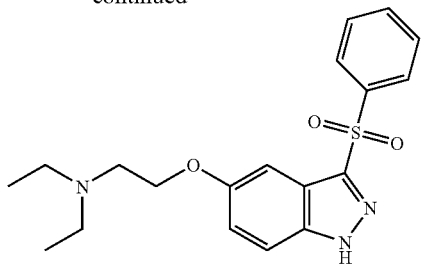

[2-(3-Benzenesulfonyl-1H-indazol-5-yloxy)-ethyl]-
diethyl-amine

A solution of toluene-4-sulfonic acid 2-(3-benzenesulfonyl-1H-indazol-5-yloxy)-ethyl ester (0.420 g, 0.889 mmol) and diethylamine (1.0 mL, 9.7 mmol) in THF (8 mL) was stirred at 70° C. for 6 hours in a sealed tube. Additional diethylamine (1.0 mL, 9.7 mmol) was added, and the reaction mixture was stirred at 80° C. in a sealed tube for an 6 hours. After cooling somewhat, the reaction mixture was solvent evaporated and partitioned in ethyl acetate and aqueous sodium bicarbonate. The organic phase was then washed with water and brine, dried with anhydrous magnesium sulfate, filtered and concentrated. The residue was purified by flash chromatography using 7.5% methanol in chloroform. After drying in vacuo at 80° C. for 20 minutes, [2-(3-benzenesulfonyl-1H-indazol-5-yloxy)-ethyl]-diethyl-amine as a pale yellow solid (0.155 g, 46.6%) was obtained. This was dissolved in methanol and chloroform and ethereal hydrochloride was added. The mixture was concentrated and dried in vacuo at 74° C. for 13.5 hours to yield the hydrochloride as a light orange foam (0.163 g); Mass Spectrum (+EI, [M+H]$^+$) m/z 374. $^1$HNMR (500 MHz, DMSO-d$_6$): δ14.24 (s, 1H), 9.94 (br, 1H), 7.96-7.99 (m, 2H), 7.56-7.68 (m, 4H), 7.41 (d, 1H, J=2.20 Hz), 7.16-7.19 (m, 1H), 4.40-4.43 (m, 2H), 3.52 (br, 2H), 3.19-3.23 (m, 4H), 1.23 ppm (t, 6H, J=7.20 Hz). Elemental Analysis for $C_{19}H_{23}N_3O_3S.1.00$ mol HCl.0.20 mol $H_2O$: Calcd: C, 55.18; H, 5.95; N, 10.16; Found: C, 54.85; H, 5.85; N, 10.02.

EXAMPLE 6

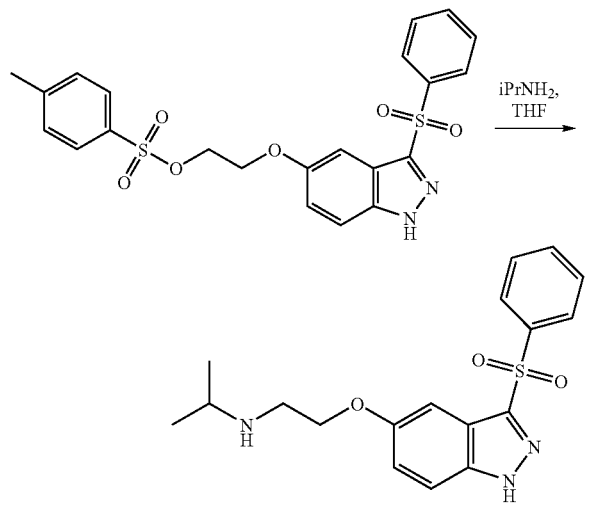

[2-(3-Benzenesulfonyl-1H-indazol-5-yloxy)-ethyl]-
isopropyl-amine

A solution of toluene-4-sulfonic acid 2-(3-benzenesulfonyl-1H-indazol-5-yloxy)-ethyl ester (0.378 g, 0.800 mmol) and isopropylamine (1.0 mL, 12 mmol) in THF (8 mL) was stirred at 70° C. for 6 hours in a sealed tube. Additional isopropyl amine (1.0 mL, 12 mmol) was added, and the reaction mixture was stirred at 80° C. for 6 hours in a sealed tube. After cooling somewhat, the reaction mixture was solvent evaporated and partitioned in ethyl acetate and aqueous sodium bicarbonate. The organic phase was then washed with water and brine, dried with anhydrous magnesium sulfate, filtered and concentrated. The residue was purified by flash chromatography using 10% methanol in chloroform. After drying in vacuo at 80° C. for 30 minutes, [2-(3-benzenesulfonyl-1H-indazol-5-yloxy)-ethyl]-isopropyl-amine as a pale yellow solid was obtained (0.110 g, 38.2%). This was dissolved in methanol and chloroform, and ethereal hydrochloride was added. The mixture was concentrated and dried in vacuo at 74° C. for 13.5 hours to yield the hydrochloride as an off-white solid (0.117 g): MP: 275-7° C. (dec); Mass Spectrum (+EI, [M+H]$^+$) m/z 360. $^1$HNMR (500 MHz, DMSO-d$_6$): δ14.22 (br, 1H), 8.75 (br, 2H), 7.96-7.98 (m, 2H), 7.56-7.68 (m, 4H), 7.41 (d, 1H, J=2.08 Hz), 7.19 (dd, 1H, J=9.15 Hz and 2.32 Hz), 4.30-4.33 (m, 2H), 3.34-3.40 (m, 3H), 1.25 ppm (d, 6H, J=6.59 Hz). Elemental Analysis for $C_{18}H_{21}N_3O_3S.1.00$ mol HCl.0.10 mol $H_2O$: Calcd: C, 54.36; H, 5.36; N, 10.57; Found: C, 54.02; H, 5.42; N, 10.22.

EXAMPLE 7

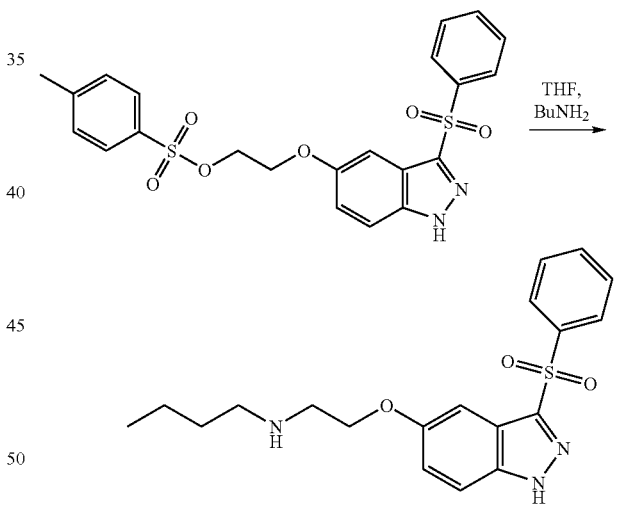

[2-(3-Benzenesulfonyl-1H-indazol-5-yloxy)-ethyl]-
butyl-amine

A solution of toluene-4-sulfonic acid 2-(3-benzenesulfonyl-1H-indazol-5-yloxy)-ethyl ester (0.348 g, 0.736 mmol) and n-butylamine (1.0 mL, 10 mmol) in THF (8 mL) was stirred at 70° C. for 6 hours in a sealed tube. After cooling somewhat, the reaction mixture was solvent evaporated and partitioned in ethyl acetate and aqueous sodium bicarbonate. The organic phase was then washed with water and brine, dried with anhydrous magnesium sulfate, filtered and concentrated. The residue was purified by flash chromatography using 7.5-10% methanol in chloroform. After drying in vacuo at 55° C. for 40 minutes, [2-(3-benzenesulfonyl-1H-indazol-5-yloxy)-ethyl]-butyl-amine as a light beige semi-solid (0.105 g, 38.2%) was obtained. This was dissolved in chloroform, and ethereal hydrochloride was added. The resulting solid was filtered and dried in vacuo at 75° C. for 16.5 hours to yield the hydrochloride as a white solid (0.0813 g): MP: 271-3° C. dec; Mass Spectrum (+EI, [M+H]$^+$) m/z 374. $^1$HNMR (300 MHz, DMSO-d$_6$): δ14.27-14.35 (br, 1H), 8.98-9.00 (br, 2H), 8.03-8.06 (m, 2H), 7.62-7.76 (m, 4H), 7.46 (d, 1H, J=2.19 Hz) 7.25 (dd, 1H, J=9.15 Hz and 2.29 Hz), 4.38-4.41 (m, 2H), 3.41-3.44 (m, 2H), 3.03 (t, 2H, J=7.87 Hz), 1.62-1.72 (m, 2H), 1.33-1.45 (m, 2H), 0.94 ppm (t, 3H, J=7.32 Hz). Elemental Analysis for $C_{19}H_{23}N_3O_3S.1.00$ mol HCl.0.05 mol H$_2$O: Calcd: C, 55.55; H, 5.91; N, 10.23; Found: C, 55.23; H, 5.87; N, 10.09.

EXAMPLE 8

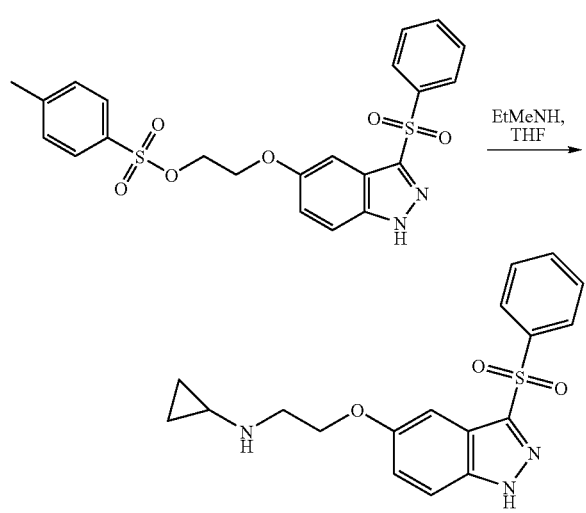

[2-(3-Benzenesulfonyl-1H-indazol-5-yloxy)-ethyl]-cyclopropyl-amine

A solution of toluene-4-sulfonic acid 2-(3-benzenesulfonyl-1H-indazol-5-yloxy)-ethyl ester (0.336 g, 0.711 mmol) and cyclopropylamine (1.0 mL, 14 mmol) in THF (8 mL) was stirred at 70° C. for 6 hours in a sealed tube. Additional cyclopropylamine (1.0 mL, 14 mmol) was added, and the reaction mixture was stirred for 6 hours at 80° C. in a sealed tube. After cooling somewhat, the reaction mixture was solvent evaporated and partitioned in ethyl acetate and aqueous sodium bicarbonate. The organic phase was then washed with water and brine, dried with anhydrous magnesium sulfate, filtered and concentrated. The residue was purified by flash chromatography using 5% methanol in chloroform. After drying in vacuo at 55° C. temperature for 25 minutes, [2-(3-benzenesulfonyl-1H-indazol-5-yloxy)-ethyl]-cyclopropyl-amine as a light yellow foam (0.127 g, 50.0%) was obtained. This was dissolved in chloroform, and ethereal hydrochloride was added. The mixture was concentrated and dried in vacuo at 75° C. for 16.5 hours to yield the hydrochloride as a buff solid (0.131 g): MP: 184-5° C. dec.; Mass Spectrum (+EI, [M+H]$^+$) m/z 358.

$^1$HNMR (300 MHz, DMSO-d$_6$): δ14.33 (s, 1H), 9.33 (br, 2H), 8.03-8.06 (m, 2H), 7.60-7.76 (m, 4H), 7.47 (d, 1H, J=2.11 Hz), 7.25 (dd, 1H, J=9.15 Hz and 2.38 Hz), 4.40-4.43 (m, 2H), 3.49-3.52 (m, 2H), 2.81-2.88 (m, 1H), 1.62-1.72 (m, 2H), 0.92-0.97 (m, 2H), 0.77-0.87 ppm (m, 2H).

EXAMPLE 9

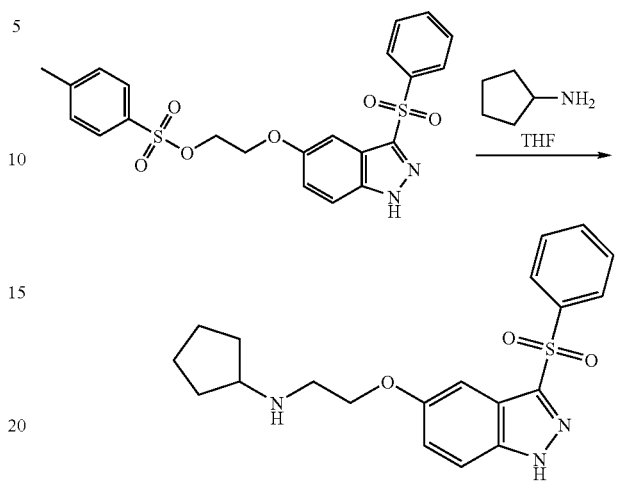

3-Benzenesulfonyl-5-(2-cyclopentyl-1-yl-ethoxy)-1H-indazole

A solution of toluene-4-sulfonic acid 2-(3-benzenesulfonyl-1H-indazol-5-yloxy)-ethyl ester (0.345 g, 0.730 mmol) and cyclopentylamine (1.0 mL, 10 mmol) in THF (8 mL) was stirred in a sealed tube at 70° C. for 6 hours and 80° C. for 6 hours. After cooling somewhat, the reaction mixture was solvent evaporated and partitioned in ethyl acetate and aqueous sodium bicarbonate. The organic phase was then washed with water and brine, dried with anhydrous magnesium sulfate, filtered and concentrated. The residue was purified by flash chromatography using 7.5% methanol in chloroform. After drying in vacuo at 57° C. for 25 minutes, benzenesulfonyl-5-(2-cyclopentyl-1-yl-ethoxy)-1H-indazole as a yellow foam (0.137 g, 48.8%) was obtained. This was dissolved in methanol and chloroform, and ethereal hydrochloride was added. The mixture was concentrated and dried in vacuo at 75° C. for 16.5 hours to yield the hydrochloride as a white solid (0.0956 g): MP: 255-8° C. (dec.); Mass Spectrum (+EI, [M+H]$^+$) m/z 386. $^1$HNMR (300 MHz, DMSO-d$_6$): δ14.31-14.41 (br, 1H), 9.13-9.14 (br, 2H), 8.03-8.06 (m, 2H), 7.62-7.76 (m, 4H), 7.46 (d, 1H, J=2.10 Hz) 7.25 (dd, 1H, J=9.15 Hz and 2.29 Hz), 4.39-4.42 (m, 2H), 3.58-3.63 (m, 1H), 3.41 (s, 2H), 1.99-2.05 (m, 2H), 1.67-1.82 (m, 4H), 1.53-1.62 ppm (m, 2H). Elemental Analysis for $C_{20}H_{23}N_3O_3S.1.00$ mol HCl.0.50 mol H$_2$O: Calcd: C, 55.74; H, 5.85; N, 9.75; Found: C, 55.39; H, 5.74; N, 9.62.

EXAMPLE 10

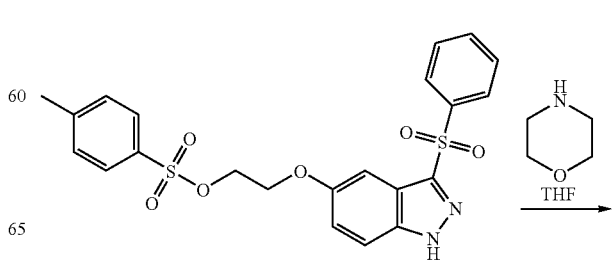

-continued

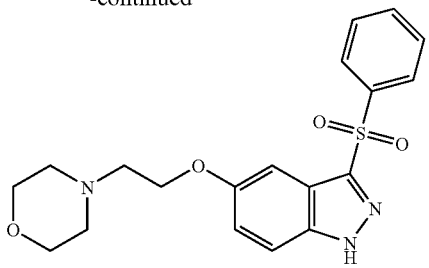

3-Benzenesulfonyl-5-(2-morpholin-4-yl-ethoxy)-1H-indazole

A solution of toluene-4-sulfonic acid 2-(3-benzenesulfonyl-1H-indazol-5-yloxy)-ethyl ester (0.359 g, 0.760 mmol) and morpholine (1.0 mL, 11 mmol) in THF (8 mL) was stirred at 70° C. for 6 hours in a sealed tube. After cooling somewhat, the reaction mixture was solvent evaporated and partitioned in ethyl acetate and aqueous sodium bicarbonate. The organic phase was then washed with water and brine, dried with anhydrous magnesium sulfate, filtered and concentrated. The residue was purified by flash chromatography using 5% methanol in chloroform. After drying in vacuo at 57° C. for 20 minutes, 3-benzenesulfonyl-5-(2-morpholin-4-yl-ethoxy)-1H-indazole as an off-white foam (0.0443 g, 15.1%) was obtained. This was dissolved in methanol and chloroform, and ethereal hydrochloride was added. The mixture was concentrated and dried in vacuo at 75° C. for 16.5 hours to yield the hydrochloride as a light orange foam (0.0411 g). Mass Spectrum (+EI, [M+H]$^+$) m/z 388. $^1$HNMR (300 MHz, DMSO-d$_6$): δ14.31 (s, 1H), 10.82-88 (br, 1H), 8.03-8.07 (m, 2H), 7.62-7.76 (m, 4H), 7.49 (d, 1H, J=2.10 Hz), 7.26 (dd, 1H, J=9.14 Hz and 2.28 Hz), 4.54 (s, 2H), 4.02 (d, 2H, J=11.71 Hz), 3.80-3.87 (m, 2H), 3.51-3.73 (m, 4H), 3.19-3.31 ppm (m, 2H).

EXAMPLE 11

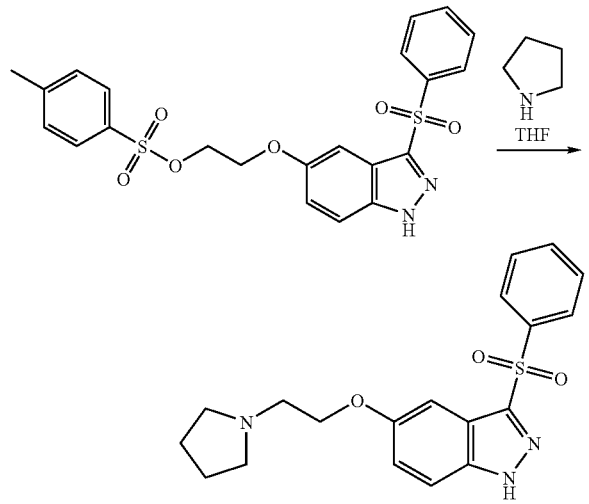

3-Benzenesulfonyl-5-(2-pyrrolidin-1-yl-ethoxy)-1H-indazole

A solution of toluene-4-sulfonic acid 2-(3-benzenesulfonyl-1H-indazol-5-yloxy)-ethyl ester (0.347 g, 0.734 mmol) and pyrrolidine (1.0 mL, 12 mmol) in THF (8 mL) was stirred at 70° C. in a sealed tube for 6 hours. After cooling somewhat, the reaction mixture was solvent evaporated and partitioned in ethyl acetate and aqueous sodium bicarbonate. The organic phase was then washed with water and brine, dried with anhydrous magnesium sulfate, filtered and concentrated. The residue was purified by flash chromatography using 7.5% methanol in chloroform. After drying at 55° C. in vacuo, 3-benzenesulfonyl-5-(2-pyrrolidin-1-yl-ethoxy)-1H-indazole as a pale yellow solid (0.0595 g, 21.8%) was obtained. This was dissolved in methanol and chloroform, and ethereal hydrochloride was added. The mixture was concentrated and dried in vacuo at 75° C. for 16.5 hours to yield the hydrochloride as a yellow foam (0.0598 g). Mass Spectrum (+EI, [M+H]$^+$) m/z 372.
$^1$HNMR (300 MHz, DMSO-d$_6$): δ14.30 (s, 1H), 10.35 (br, 1H), 8.05 (d, 2H, J=7.04 Hz), 7.63-7.75 (m, 4H), 7.48 (d, 1H, J=1.83 Hz) 7.25-7.29 (m, 1H), 4.45-4.48 (m, 2H), 3.66 (s, br, 4H), 3.18-3.19 (m, 2H), 1.94-2.06 ppm (m, 4H).

EXAMPLE 12

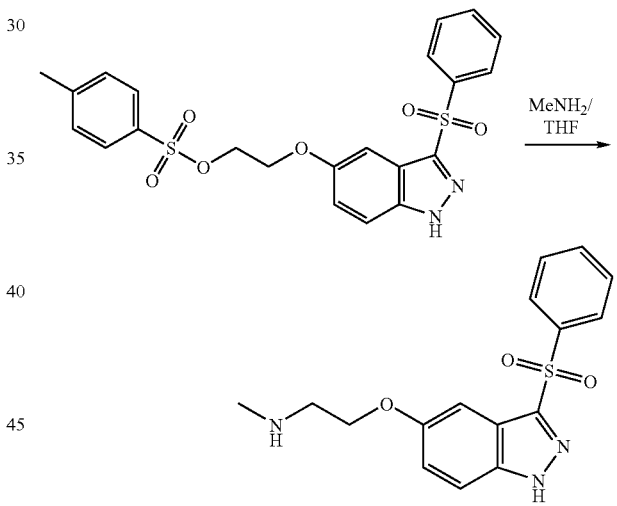

[2-(3-Benzenesulfonyl-1H-indazol-5-yloxy)-ethyl]-methyl-amine

A solution of toluene-4-sulfonic acid 2-(3-benzenesulfonyl-1H-indazol-5-yloxy)-ethyl ester (0.340 g, 0.720 mmol) in 2.0 M methylamine in THF (8 mL, 16 mmol) was stirred at 70° C. in a sealed tube for about 15.5 hours. After cooling somewhat, the reaction mixture was solvent evaporated and partitioned in chloroform and aqueous sodium bicarbonate. The organic phase was then washed with brine, dried with anhydrous magnesium sulfate, filtered and concentrated. The residue was purified by flash chromatography using 10% methanol in chloroform and 1.0% ammonium hydroxide/10% methanol in chloroform. After drying at 57° C. in vacuo for 20 minutes, [2-(3-benzenesulfonyl-1H-indazol-5-yloxy)-ethyl]-methyl-amine as a light yellow semi-solid (0.0461 g, 19.4%) was obtained. This was dissolved in methanol and chloroform, and ethereal hydrochloride was added. The mixture was concentrated and dried in vacuo at 73° C. for 20 hours to yield the hydrochloride as a tan foam (0.0422 g). Mass Spectrum (+EI, [M+H]$^+$) m/z 332. $^1$HNMR (500 MHz, DMSO-d$_6$): δ14.24 (s, 1H), 8.89 (s, 2H), 7.96-7.99 (m, 2H), 7.53-7.68 (m, 4H), 7.40 (d, 1H, J=2.19 Hz), 7.25 (dd, 1H, J=9.15 Hz and 2.32 Hz), 4.30-4.32 (m, 2H), 3.33-3.35 (m, 2H), 2.60-2.63 ppm (m, 3H).

EXAMPLE 13

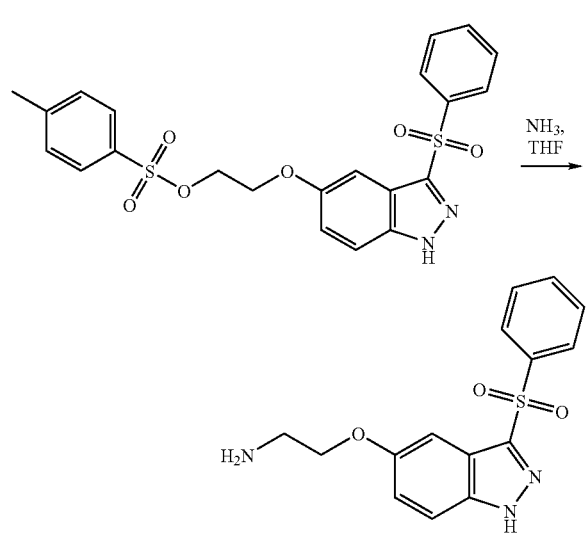

2-(3-Benzenesulfonyl-1H-indazol-5-yloxy)-ethylamine

Over five different reactions, liquid ammonia (about 10 mL) was added to a −78° C. solution of toluene-4-sulfonic acid 2-(3-benzenesulfonyl-1H-indazol-5-yloxy)-ethyl ester (1.72 g, 3.63 mmol) in THF (48 mL). This was usually allowed to warm to ambient temperature. This was heated in sealed tube for about 16-35 hours at 70-100° C. After cooling to about ambient temperature, the combined reaction mixtures were then poured into excess sodium bicarbonate solution and extracted with chloroform or methylene chloride. The organic phase was washed with brine, dried with anhydrous magnesium sulfate, filtered and concentrated. The residue was purified by flash chlormatography with 0.75% ammonium hydroxide/7.5% methanol in chloroform. The residue was further purified by HPLC using 30-80% (chloroform/methanol(8:2)/TEA) in heptane/TEA. Concentrating and drying yielded 2-(3-benzenesulfonyl-1H-indazol-5-yloxy)-ethylamine as a white solid to which was added methanol and ethereal hydrochloride. Concentration and drying for 30 hours in vacuo at 83° C. yielded the hydrochloride as a cream-colored solid (0.0951 g, 7.4%): MP: >300° C.; Mass Spectrum (−EI, [M−H]$^−$) m/z 316. $^1$HNMR (500 MHz, DMSO-d$_6$): δ14.24(s, 1H), 8.09 (br,s, 3H), 7.96-7.98 (m, 2H), 7.56-7.68 (m, 4H), 7.39 (d, 1H, J=2.20 Hz), 7.17 (dd, 1H, J=9.15 Hz and 2.32 Hz), 4.22-4.25 (m, 2H), 3.20-3.24 ppm (m, 2H). Elemental Analysis for C$_{15}$H$_{15}$N$_3$O$_3$S.1.00 mol HCl.0.85 mol H$_2$O: Calcd: C, 48.81; H, 4.83; N, 11.38; Found: C, 48.65; H, 4.77; N, 11.00.

EXAMPLE 14

Dimethyl-{3-[3-(naphthalene-1-sulfonyl)-1H-indazol-5-yloxy]-propyl}-amine

Step 1

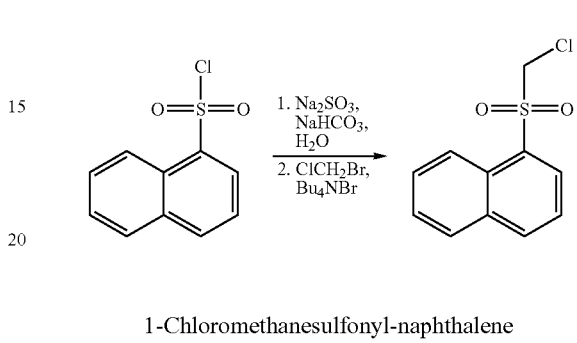

1-Chloromethanesulfonyl-naphthalene

A mixture of 1-naphthalene sulfonyl chloride (20.2 g, 89.1 mmol), sodium sulfite (22.5 g, 178 mmol) and sodium bicarbonate (15.1 g, 180 mmol) in water (125 mL) was stirred at 100° C. for one hour. After cooling to ambient temperature for 40 minutes, bromochloromethane (90 mL, 1.4 mol) and tetrabutylammonium bromide (2.87 g, 8.91 mmol) were added. The reaction mixture was then stirred at 75° C. for 14.5 hours. After cooling to ambient temperature, the layers of the reaction mixture were separated, and the organic phase was concentrated. The residue was purified by flash chromatography with 100% ethyl acetate. Hexane was added after concentration to help solidify, and the mixture was again concentrated. Drying at 80° C. in vacuo for 20 minutes yielded 1-chloromethanesulfonyl-naphthalene as a pale yellow solid (19.0 g, 88.8%). MP 103-5° C. Mass Spectrum (+EI, M$^+$) m/z 240.

$^1$HNMR (500 MHz, DMSO-d$_6$): δ8.64-5 (m, 1H), 8.41 (d, 1H, J=8.23 Hz), 8.27 (dd, 1H, J=7.33 Hz and 1.22 Hz), 8.16-8.18 (m, 1H), 7.71-7.81 (m, 3H), 5.40 ppm, (s, 2H). Elemental Analysis for C$_{11}$H$_9$ClO$_2$S: Calcd: C, 54.89; H, 3.77; N, 0.00; Found: C, 54.98; H, 3.81; N, 0.00.

Step 2

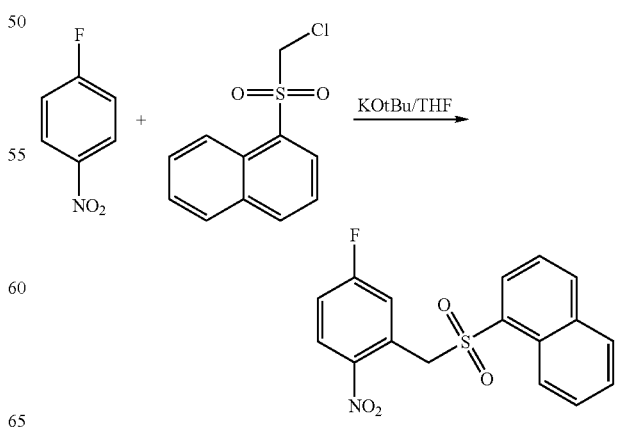

1-(5-Fluoro-2-nitro-phenylmethanesulfonyl)-naphthalene

To a chilled mixture of 1-chloromethanesulfonyl-naphthalene (19.7 g, 81.8 mmol) and 1-fluoro-4-nitrobenzene (8.7 mL, 82 mmol) in dry THF (197 mL) was dropwise added 1.0M potassium t-butoxide in THF (205 mL, 205 mmol). The reaction mixture was stirred at ambient temperature under nitrogen for 1.5 hours. Glacial acetic acid (16 mL, 280 mmol) was then added. After stirring at ambient temperature for 1 hour, 40 minutes, the reaction mixture was concentrated and partitioned in warm ethyl acetate and brine. The organic phase was dried with anhydrous magnesium sulfate, filtered and concentrated. The solid residue was stirred in ether, filtered and dried at 82° C. in vacuo for 1 hour. This yielded 1-(5-fluoro-2-nitro-phenylmethanesulfonyl)-naphthalene as a brown/rust-colored solid (19.9 g, 70.6%): MP: 155-160° C.; Mass Spectrum (−EI, [M−H]−) m/z 344. $^1$HNMR (300 MHz, DMSO-$d_6$): δ8.50-8.52 (m, 1H), 8.33 (d, 1H, J=8.30 Hz), 8.06-8.14 (m, 2H), 7.97 (dd, 1H, J=7.32 Hz and 1.22 Hz), 7.62-7.74 (m, 3H), 7.44-7.48 (m, 1H), 7.23-7.26 (m, 1H), 5.23 ppm (s, 2H). Elemental Analysis for $C_{17}H_{12}FNO_4S$: Calcd: C, 59.12; H, 3.50; N, 4.06; Found: C, 58.77; H, 3.30; N, 3.92.

Step 3:

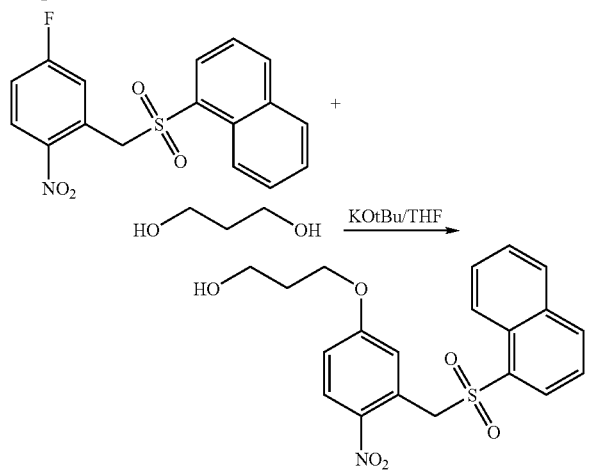

3-[3-(Naphthalene-1-sulfonylmethyl)-4-nitro-phenoxy]-propan-1-ol

To a mixture of 1-(5-fluoro-2-nitro-phenylmethanesulfonyl)-naphthalene (19.9 g, 57.6 mmol) and 1,3-propanediol (49 mL, 680 mmol) in dry THF (17 mL) was dropwise added 1.0M potassium tert-butoxide in THF (123 mL, 123 mmol). The reaction mixture was refluxed under nitrogen for 1 hour. It was allowed to cool to ambient temperature. Water was added to the reaction mixture, and it was poured into a mixture of ice and 2.0N hydrochloric acid. It was then extracted with ethyl acetate. The organic phase was washed with brine, dried with anhydrous magnesium sulfate, filtered and concentrated. The residue was purified by flash chromatography using 60% ethyl acetate in hexane and 100% ethyl acetate. The resulting yellow solid (12.9 g, 55.8% yield), 3-[3-(naphthalene-1-sulfonylmethyl)-4-nitro-phenoxy]-propan-1-ol, was obtained: MP: 134-5° C.; Mass Spectrum (−EI, [M−H]−) m/z 400. $^1$HNMR (500 MHz, DMSO-$d_6$): δ8.50-8.53 (m, 1H), 8.31 (d, 1H, J=8.17 Hz), 8.10-8.12 (m, 1H), 7.95-7.99 (m, 2H), 7.61-7.71 (m, 3H), 7.06 (dd, 1H, J=9.15 Hz and 2.80 Hz), 6.78 (d, 1H, J=2.81 Hz), 5.23 (s, 2H), 4.52-4.55 (m, 1H), 3.91-3.94 (m, 2H), 3.43-3.47 (m, 2H), 1.71-1.78 ppm (m, 2H). Elemental Analysis for $C_{20}H_{19}NO_6S$: Calcd: C, 59.84; H, 4.77; N, 3.49; Found: C, 59.78; H, 4.41; N, 3.43.

Step 4

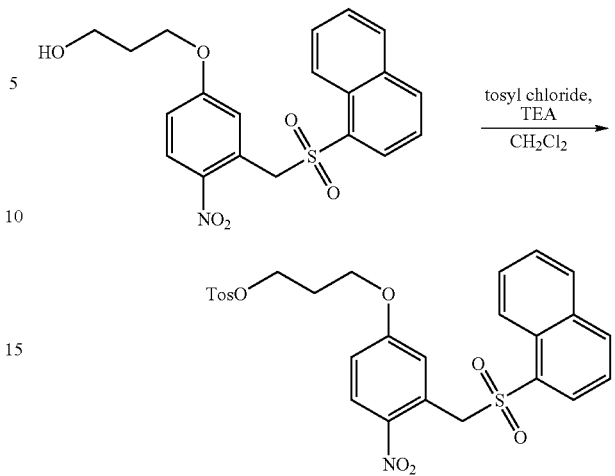

Toluene-4-sulfonic acid 3-[3-(naphthalene-1-sulfonylmethyl)-4-nitro-phenoxy]-propyl ester A solution of 3-[3-(naphthalene-1-sulfonylmethyl)-4-nitro-phenoxy]-propan-1-ol (12.9 g, 32.1 mmol), p-toluenesulfonyl chloride (24.6 g, 129 mmol) and triethylamine (37 mL, 270 mmol) in methylene chloride (300 mL) was stirred at ambient temperature under nitrogen. After 2 hours, a second portion of p-toluenesulfonyl chloride (12.1 g, 63.5 mmol) was added. The reaction was stirred for 2 more hours and then concentrated. The residue was partitioned in methylene chloride and aqueous sodium bicarbonate. The organic phase was washed with brine, dried with anhydrous magnesium sulfate, filtered and concentrated. The residue was purified by flash chromatography with 20-50% ethyl acetate in hexane, 100% ethyl acetate and then 100% methylene chloride (due to limited solubility). A yellow solid (13.0 g, 73.0%) was obtained as toluene-4-sulfonic acid 2-[3-(naphthalene-1-sulfonylmethyl)-4-nitro-phenoxy]-propyl ester: MP: 162-4° C.; Mass Spectrum (−EI, [M−H]−) m/z 554. $^1$HNMR (500 MHz, DMSO-$d_6$): δ8.52-8.54 (m, 1H), 8.31 (d, 1H, J=8.18 Hz), 8.09-8.11 (m, 1H), 7.97-8.00 (m, 2H), 7.62-7.73 (m, 5H), 7.35 (d, 2H, J=7.93 Hz), 6.92 (dd, 1H, J=9.15 Hz and 2.81 Hz), 6.73 (d, 1H, J=2.80 Hz), 5.22 (s, 2H), 4.09 (t, 2H, J=5.98 Hz), 3.79-3.82 (m, 2H), 2.29 (s, 3H), 1.91-1.97 ppm (m, 2H). Elemental Analysis for $C_{27}H_{25}NO_8S_2$: Calcd: C, 58.37; H, 4.54; N, 2.52; Found: C, 58.13; H, 4.43; N, 2.41.

Step 5

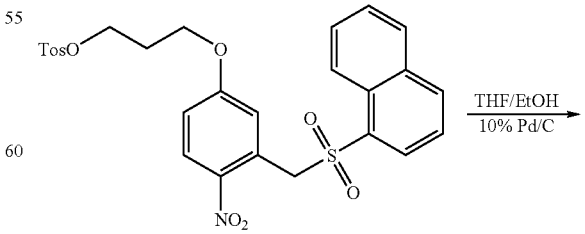

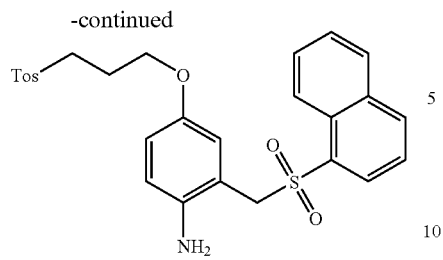

Toluene-4-sulfonic acid 3-[4-amino-3-(naphthalene-1-sulfonylmethyl)-phenoxy]-propyl ester Ethanol (30 mL) and 10% palladium on carbon (0.439 g) were added to a hot solution of toluene-4-sulfonic acid 2-[3-(naphthalene-1-sulfonylmethyl)-4-nitro-phenoxy]-propyl ester (0.785 g, 1.41 mmol) in hot, anhydrous THF (40 mL). The reaction mixture was hydrogenated on the Parr apparatus for 2 hours (starting pressure of 43 psi). The reaction mixture was then filtered over Celite and concentrated. It was dried at 75° C. in vacuo for 20 minutes to yield toluene-4-sulfonic acid 3-[4-amino-3-(naphthalene-1-sulfonylmethyl)-phenoxy]-propyl ester as a brown-green semi-solid (0.627 g, 84.4%). Mass Spectrum (+EI, [M+H]$^+$) m/z 526.

$^1$HNMR (500 MHz, DMSO-$d_6$): δ8.61 (d, 1H, J=8.42 Hz), 8.25 (d, 1H, J=8.17 Hz), 8.02-8.07 (m, 2H), 7.59-7.72 (m, 5H), 7.39 (d, 2H, J=7.93 Hz), 6.56 (d, 1H, J=8.17 Hz), 6.44-6.47 (m, 1H), 6.01 (d, 1H, J=2.81 Hz), 4.62 (s, 2H), 3.98-4.01 (m, 2H), 3.36-3.39 (m, 2H), 2.35 (s, 3H), 1.71-1.79 ppm (m, 2H).

Step 6

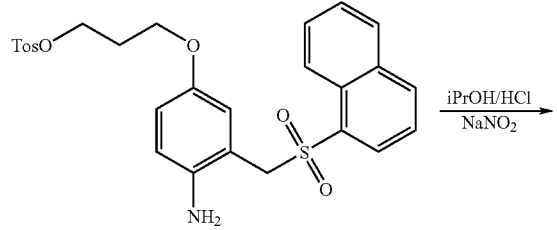

Toluene-4-sulfonic acid 3-[3-(naphthalene-1-sulfonyl)-1H-indazol-5-yloxy]-propyl ester Isopropanol (205 mL) and 1.0N hydrochloric acid (200 mL) were added to toluene-4-sulfonic acid 3-[4-amino-3-(naphthalene-1-sulfonylmethyl)-phenoxy]-propyl ester (8.1 g, 15 mmol). The reaction mixture was heated because of limited solubility. Sodium nitrite (1.6 g, 2.3 mmol) in water (22 mL) was then added. More isopropanol (100 mL) was added to reaction mixture for increased solubility. After stirring at ambient temperature for 1 hour, sodium carbonate was added to basic pH. This reaction mixture was then stirred at ambient temperature for 30 minutes. After concentrating, the residue was partitioned in ethyl acetate and water. The organic phase was then washed with brine, dried with anhydrous magnesium sulfate, filtered and concentrated. The residue was purified by flash chromatography using 50% ethyl acetate in hexane. A light amber semi-solid (3.3 g, 41%), toluene-4-sulfonic acid 3-[3-(naphthalene-1-sulfonyl)-1H-indazol-5-yloxy]-propyl ester, was obtained. Mass Spectrum (−EI, [M−H]$^-$) m/z 535. $^1$HNMR (500 MHz, DMSO-$d_6$): δ14.08(s, 1H), 8.78 (d, 1H, J=8.78 Hz), 8.55 (dd, 1H, J=7.44 Hz and 1.22 Hz), 8.28 (d, 1H, J=8.17 Hz), 8.02-8.04 (m, 1H), 7.73-7.77 (m, 1H), 7.55-7.65 (m, 4H), 7.48 (d, 1H, J=9.15 Hz), 7.03-7.06 (m, 3H), 6.88-6.91 (m, 1H), 4.17 (t, 2H, J=5.98 Hz), 3.85-3.88 (m, 2H), 2.00-2.03 (m, 2H), 1.97 ppm (s, 3H). Elemental Analysis for $C_{27}H_{24}N_2O_6S_2 \cdot 0.10$ mol $H_2O$: Calcd: C, 60.23; H, 4.53; N, 5.20; Found: C, 59.92; H, 4.30; N, 5.17.

Step 7

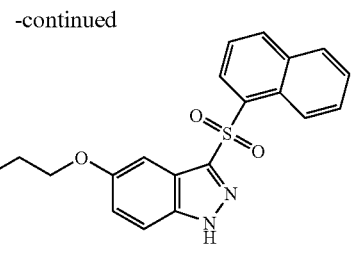

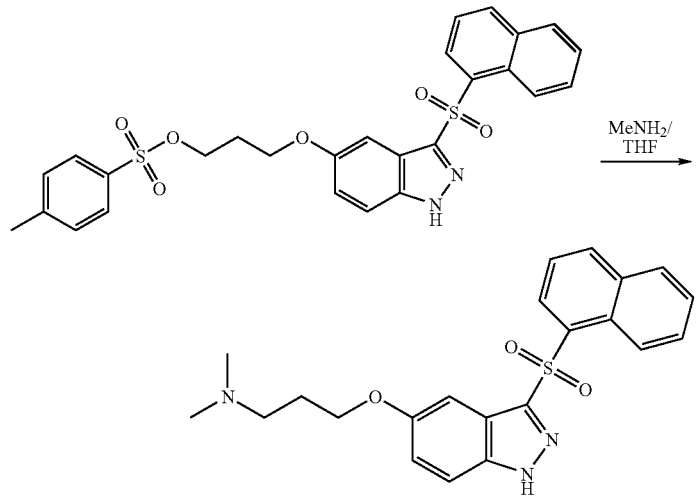

Dimethyl{3-[3-(naphthalene-1-sulfonyl)-1H-indazol-5-yloxy]-propyl}-amine

A solution of toluene-4-sulfonic acid 3-[3-(naphthalene-1-sulfonyl)-1H-indazol -5-yloxy]-propyl ester (1.02 g, 1.89 mmol) in 2.0 M dimethylamine in THF (20 mL, 40 mmol) was stirred for 16 hours at 70° C. in a sealed tube. After cooling to ambient temperature, the reaction mixture was concentrated and partitioned in chloroform and aqueous sodium bicarbonate. The organic phase was washed with brine, dried with anhydrous magnesium sulfate, filtered and concentrated. The residue was purified by flash chromatography using 0.5% ammonium hydroxide/5.0% methanol in chloroform. Dimethyl-{3-[3-(naphthalene-1-sulfonyl)-1H-indazol-5-yloxy]-propyl}-amine was obtained as a light yellow solid (0.453 g, 58.5%). Methanol and ethereal hydrochloride were then added to this compound. The resulting solution was concentrated and dried for 14 hours at 84° C. in vacuo. Dimethyl-{3-[3-(naphthalene -1-sulfonyl)-1H-indazol-5-yloxy]-propyl}-amine hydrochloride as a very light yellow solid (0.455 g) was obtained: MP: 264-5° C.; Mass Spectrum (–EI, [M–H]⁻) m/z 408.

$^1$HNMR (500 MHz, DMSO-$d_6$): δ14.17(s, 1H), 10.19 (s, 1H), 8.75 (d, 1H, J=8.67 Hz), 8.53 (dd, 1H, J=7.44 Hz and 1.22 Hz), 8.27 (d, 1H, J=8.30 Hz), 8.02-8.04 (m, 1H), 7.71-7.75 (m, 1H), 7.54-7.65 (m, 3H), 7.29 (d, 1H, J=2.08 Hz), 7.07-7.10 (m, 1H), 4.07-4.10 (m, 2H), 3.19-3.23 (m, 2H), 2.76 (s, 6H), 2.11-2.18 ppm (m, 2H). Elemental Analysis for $C_{22}H_{23}N_3O_3S \cdot 1.00$ mol HCl: Calcd: C, 59.25; H, 5.42; N, 9.42; Found: C, 58.97; H, 5.58; N, 9.23.

EXAMPLE 15

Methyl-{3-[3-(naphthalene-1-sulfonyl)-1H-indazol-5-yloxy]-propyl}-amine

A solution of toluene-4-sulfonic acid 3-[3-(naphthalene-1-sulfonyl)-1H-indazol-5-yloxy]-propyl ester (0.422 g, 0.786 mmol) in 2.0 M methylamine in THF (8.0 mL, 16 mmol). was stirred for 15 hours at 70° C. in a sealed tube. After cooling to ambient temperature, the reaction mixture was concentrated and partitioned in ethyl acetate and aqueous sodium bicarbonate. The organic phase was washed with brine. The aqueous phases were extracted with chloroform, and both organic phases were combined and dried with anhydrous magnesium sulfate, filtered and concentrated. The residue was purified by flash chromatography using 0.75% ammonium hydroxide/7.5% methanol in chloroform. Methyl-{3-[3-(naphthalene-1-sulfonyl)-1H-indazol-5-yloxy]-propyl}-amine was obtained as a light yellow foam (0.209 g, 67.2%). Methanol and ethereal hydrochloride were added to the compound. The resulting solution was concentrated and dried for 14 hours at 84° C. in vacuo. The hydrochloride was obtained as a light yellow foam (0.217 g). Mass Spectrum (–EI, [M–H]⁻) m/z 394.
$^1$HNMR (500 MHz, DMSO-$d_6$): δ14.16 (s, 1H), 8.74-8.76 (m, 1H), 8.67 (s, br, 2H), 8.52 (dd, 1H, J=7.44 Hz and 1.22 Hz), 8.27 (d, 1H, J=8.30 Hz), 8.02-8.05 (m, 1H), 7.70-7.75 (m, 1H), 7.54-7.65 (m, 3H), 7.29 (d, 1H, J=2.19 Hz), 7.08-7.11 (m, 1H), 4.09 (t, 2H, J=5.98 Hz), 3.05 (s, br, 2H), 2.55 (s, 3H), 2.05-2.11 ppm (m, 2H). Elemental Analysis for $C_{21}H_{21}N_3O_3S \cdot 1.00$ mol HCl $\cdot 0.45$ mol $H_2O$: Calcd: C, 57.32; H, 5.25; N, 9.55; Found: C, 57.64; H, 5.33; N, 9.39.

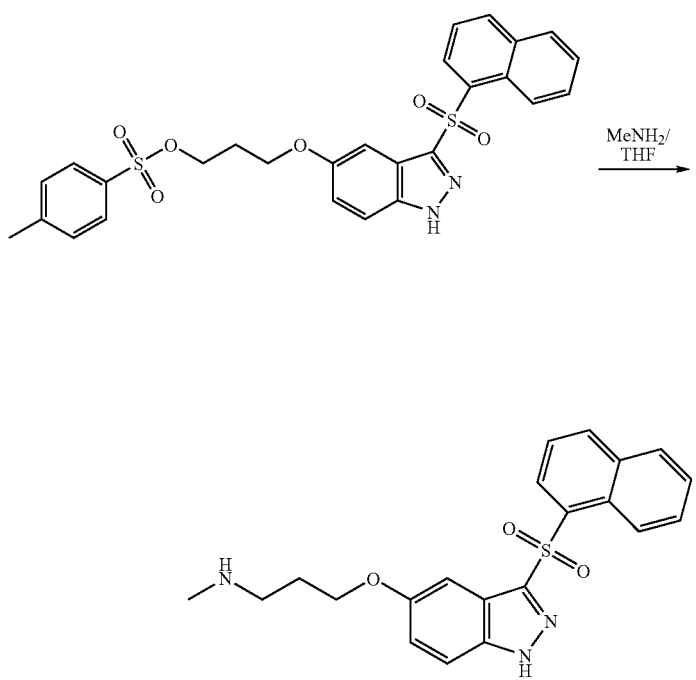

EXAMPLE 16

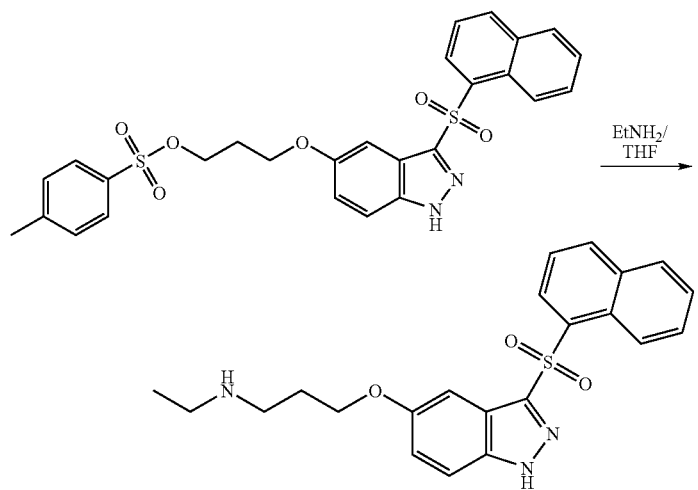

Ethyl-{3-[3-(naphthalene-1-sulfonyl)-1H-indazol-5-yloxy]-propyl}-amine

A solution of toluene-4-sulfonic acid 3-[3-(naphthalene-1-sulfonyl)-1H-indazol -5-yloxy]-propyl ester (0.080 mg, 0.15 mmol) in 10 mL of 2.0 M ethylamine/THF (20 mmoles) was stirred at 90° C. for about 2 hours in a sealed tube. After cooling to ambient temperature the reaction mixture was solvent evaporated. It was dissolved in ethyl acetate and washed twice with aqueous sodium bicarbonate. The organic phase was dried over anhydrous magnesium sulfate, filtered and concentrated. The residue was purified by flash chromatography using 0.75% ammonium hydroxide/7.5% methanol in chloroform. Drying at 66° C. in vacuo for 20 minutes yielded ethyl-{3-[3-(naphthalene-1-sulfonyl)-1H-indazol-5-yloxy]-propyl}-amine as a light yellow foam (43.0 mg, 70.0%). This was dissolved in methanol and ethereal hydrochloride was added. Concentrating and drying in vacuo at 83° C. for 16 hours gave the hydrochloride as a pale yellow semi-solid (41.7 mg, 62.3%). Mass Spectrum (+EI, [M+H]$^+$) m/z 410; $^1$HNMR (500 MHz, DMSO-d$_6$): δ14.14-14.18 (br, 1H), 8.74-8.76 (m, 1H), 8.56-8.72 (br, 2H), 8.52 (dd, 1 h, J=7.44 Hz and 1.22 Hz), 8.27 (d, 1H, J=8.29 Hz), 8.03-8.05 (m, 1H), 7.71-7.75 (m, 1H), 7.54-7.65 (m, 3H), 7.29 (d, 1H, J=2.08 Hz), 7.07-7.10 (m, 1H), 4.09-4.12 (m, 2H), 3.03-3.07 (m, 2H), 2.90-2.97 (m, 2H), 2.05-2.12 (m, 2H), 1.15-1.19 ppm (m, 3H). Elemental Analysis for C$_{22}$H$_{23}$N$_3$O$_3$S.1.00 mol HCl.1.20 mol H$_2$O: Calcd: C, 56.51; H, 5.69; N, 8.99; Found: C, 56.20; H, 5.36; N, 8.81.

EXAMPLE 17

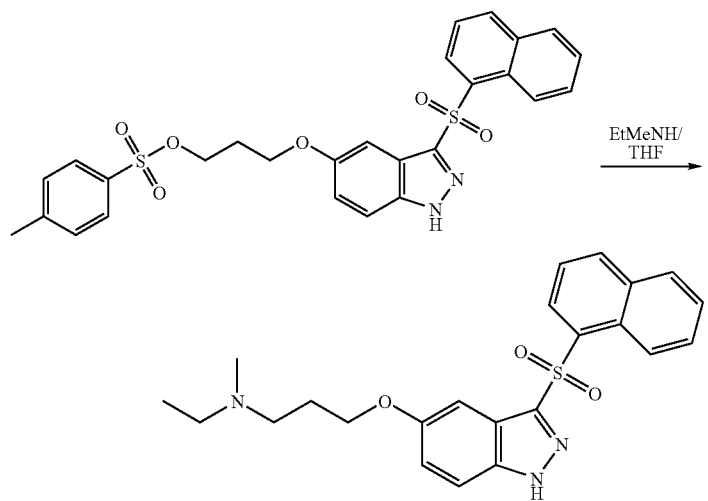

Ethyl-methyl-{3-[3-(naphthalene-1-sulfonyl)-1H-indazol-5-yloxy]-propyl}-amine A solution of toluene-4-sulfonic acid 3-[3-(naphthalene-1-sulfonyl)-1H-indazol-5-yloxy]-propyl ester (0.080 mg, 0.15 mmol) and methyethylamine (0.45-0.75 mmol) was stirred at 90° C. for about 2 hours in a sealed tube. After cooling to ambient temperature the reaction mixture was solvent evaporated. It was dissolved in ethyl acetate and washed twice with aqueous sodium bicarbonate. The organic phase was dried over anhydrous magnesium sulfate, filtered and concentrated. The residue was dissolved in methanol, and ethereal hydrochloride was added. The mixture was then concentrated and dried for 29 hours at 80° C. in vacuo. Ethyl-methyl-{3-[3-(naphthalene-1-sulfonyl)-1H-indazol-5-yloxy]-propyl}-amine hydrochloride was a tan semi-solid (53.2 mg, 77.1%); Mass Spectrum (+EI, [M+H]$^+$) m/z 424. $^1$HNMR (500 MHz, DMSO-d$_6$): δ14.14-14.17 (br, 1H), 9.71-9.77 (br, 1H), 8.74-8.76 (m, 1H), 8.52 (dd, 1H, J=7.44 Hz and 1.22 Hz), 8.27 (d, 1H, J=8.30 Hz), 8.03-8.05 (m, 1H), 7.70-7.74 (m, 1H), 7.56-7.64 (m, 3H), 7.29 (d, 1H, J=2.19 Hz), 7.08-7.10 (m, 1H), 4.08-4.11 (m, 2H), 3.04-3.25 (m, 2H), 2.72 (s, 3H), 1.18-1.21 ppm (m, 3H). Elemental Analysis for C$_{23}$H$_{25}$N$_3$O$_3$S. 1.00 mol HCl.0.90 mol H$_2$O: Calcd: C, 58.01; H, 5.88; N, 8.82; Found: C, 58.37; H, 5.55; N, 8.50.

EXAMPLE 18

Diethyl-{3-[3-(naphthalene-1-sulfonyl)-1H-indazol-5-yloxy]-propyl}-amine

A solution of toluene-4-sulfonic acid 3-[3-(naphthalene-1-sulfonyl)-1H-indazol-5-yloxy]-propyl ester (0.080 mg, 0.15 mmol) and diethylamine (0.45-0.75 mmol) in THF (10 mL) was stirred at 90° C. for about 2 hours in a sealed tube. After cooling to ambient temperature the reaction mixture was solvent evaporated. It was dissolved in ethyl acetate and washed twice with aqueous sodium bicarbonate. The organic phase was dried over anhydrous magnesium sulfate, filtered and concentrated. The residue was dissolved in methanol and chloroform, and ethereal hydrochloride was added. The mixture was concentrated and dried in vacuo at 80° C. for 17 hours. Diethyl-{3-[3-(naphthalene-1-sulfonyl)-1H-indazol-5-yloxy]-propyl}-amine hydrochloride was a tan foam (69.9 mg, 98.3%); Mass Spectrum (+EI, [M+H]$^+$) m/z 438. $^1$HNMR (500 MHz, DMSO-d$_6$): δ14.13-14.11 (br, 1H), 9.59-9.63 (br, 1H), 8.75 (d, 1H, J=8.42 Hz), 8.51 (dd, 1H, J=7.44 Hz and 1.10 Hz), 8.27 (d, 1H, J=8.29 Hz), 8.03-8.05 (m, 1H), 7.70-7.74 (m, 1H), 7.52-7.64 (m, 3H), 7.05-7.11 (m, 2H), 4.10 (t, 2H, J=5.98 Hz), 3.11-3.25 (m, 6H), 2.09-2.24 (m, 2H), 1.18 ppm (t, 6H, J=7.20 Hz).

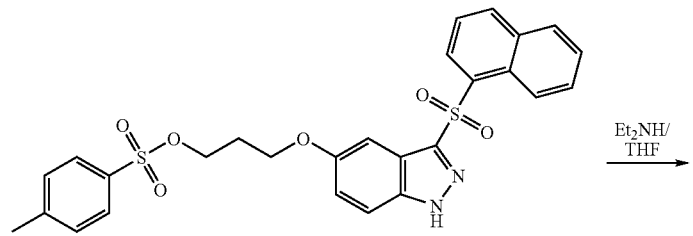

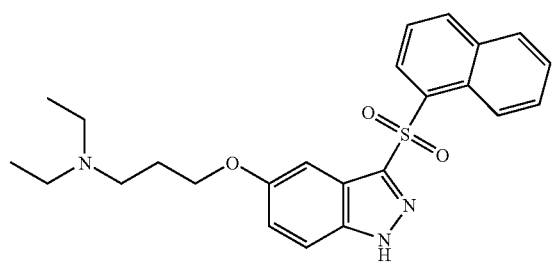

EXAMPLE 19

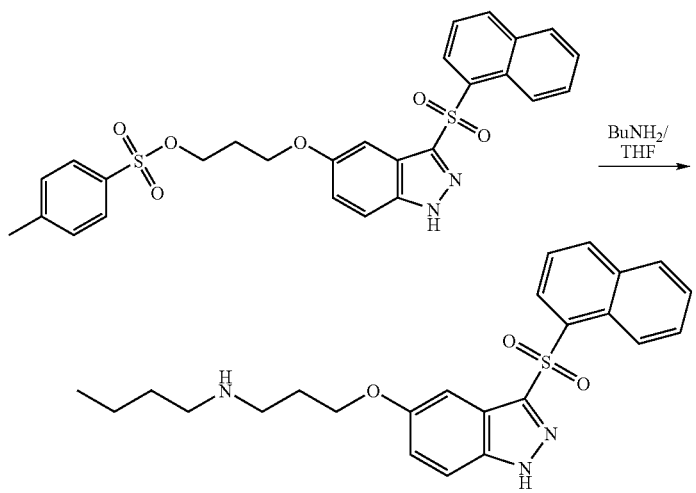

Butyl-{3-[3-(naphthalene-1-sulfonyl)-1H-indazol-5-yloxy]-propyl}-amine

A solution of toluene-4-sulfonic acid 3-[3-(naphthalene-1-sulfonyl)-1H-indazol -5-yloxy]-propyl ester (0.080 mg, 0.15 mmol) and butylamine (0.45-0.75 mmol) in THF (10 mL) was stirred at 90° C. for about 2 hours in a sealed tube. After cooling to ambient temperature the reaction mixture was solvent evaporated. It was dissolved in ethyl acetate and washed twice with aqueous sodium bicarbonate. The organic phase was dried over anhydrous magnesium sulfate, filtered and concentrated. The residue was dissolved in methanol, and ethereal hydrochloride was added. Concentrating and drying in vacuo at 80° C. for 17 hours yielded butyl-{3-[3-(naphthalene-1-sulfonyl)-1H-indazol-5-yloxy]-propyl}-amine hydrochloride as a light orange semi-solid (43.3 mg, 60.9%); Mass Spectrum (+EI, [M+H]$^+$) m/z 438. $^1$HNMR (500 MHz, DMSO-d$_6$): δ13.8-14.2 (br, 1H), 8.75 (d, 1H, J=8.66 Hz), 8.50-8.52 (m, 1H), 8.27 (d, 1H, J=8.30 Hz), 8.03-8.05 (m, 1H), 7.71-7.75 (m, 1H), 7.54-7.64 (m, 3H), 7.29 (d, 1H, J=2.07 Hz), 7.07-7.10 (m, 1H), 4.08-4.11 (m, 2H), 3.04-3.08 (m, 2H), 2.86-2.90 (m, 2H), 2.06-2.13 (m, 2H), 1.52-1.59 (m, 2H), 1.26-1.33 (m, 4H), 0.88-0.84 ppm (m, 3H).

EXAMPLE 20

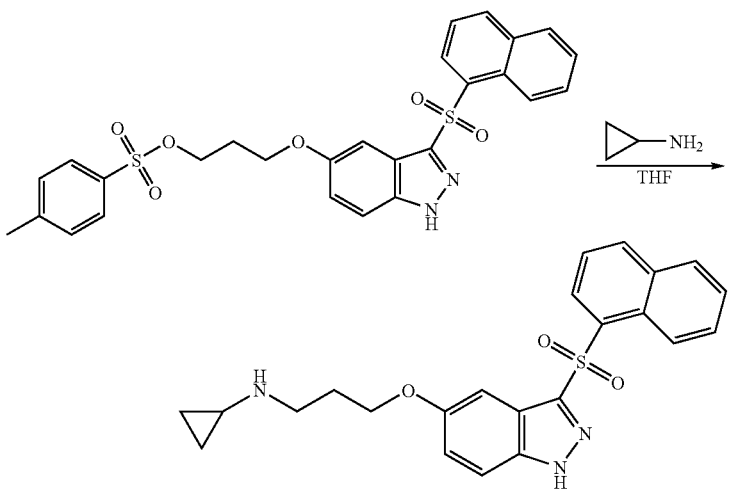

Cyclopropyl-{3-[3-(naphthalene-1-sulfonyl)-1H-indazol-5-yloxy]-propyl}-amine A solution of toluene-4-sulfonic acid 3-[3-(naphthalene-1-sulfonyl)-1H-indazol-5-yloxy]-propyl ester (0.080 mg, 0.15 mmol) and cyclopropylamine (0.45-0.75 mmol) in THF (10 mL) was stirred at 90° C. for about 2 hours in a sealed tube. After cooling to ambient temperature the reaction mixture was solvent evaporated. It was dissolved in ethyl acetate and washed twice with aqueous sodium bicarbonate. The organic phase was dried over anhydrous magnesium sulfate, filtered and concentrated. The residue was purified twice by flash chromatography using 0.75% ammonium hydroxide/7.5% methanol in chloroform and 0.5% ammonium hydroxide/ 5.0% methanol in chloroform to give cyclopropyl-{3-[3-(naphthalene-1-sulfonyl)-1H-indazol-5-yloxy]-propyl}-amine as a clear yellow film (51.0 mg, 80.7%). This compound was dissolved in methanol, and ethereal hydrochloride was added. Concentrating and drying in vacuo for 24 hours at 83° C. gave the hydrochloride as a yellow foam (48.9 mg, 71.2%); Mass Spectrum (+EI, [M+H]$^+$) m/z 422. $^1$HNMR (500 MHz, DMSO-d$_6$): δ14.15 (s, 1H), 9.01 (s, 2H), 8.74-8.76 (m, 1H), 8.51-8.53 (m, 1H), 8.27 (d, 1H, J=8.29 Hz), 8.02-8.05 (m, 1H), 7.71-7.75 (m, 1H), 7.51-7.65 (m, 3H), 7.29 (d, 1H, J=2.19 Hz), 7.08-7.11 (m, 1H), 4.11 (t, 2H, J=6.10 Hz), 3.11-3.20 (br, s, 2H), 2.65-2.75 (m, 1H), 2.08-2.15 (m, 2H), 0.83-0.87 (m, 2H), 0.70-0.77 ppm (m, 2H). Elemental Analysis for C$_{23}$H$_{23}$N$_3$O$_3$S.1.00 mol HCl.0.70 mol H$_2$O: Calcd: C, 58.70; H, 5.44; N, 8.93; Found: C, 58.70; H, 5.09; N, 8.68.

EXAMPLE 21

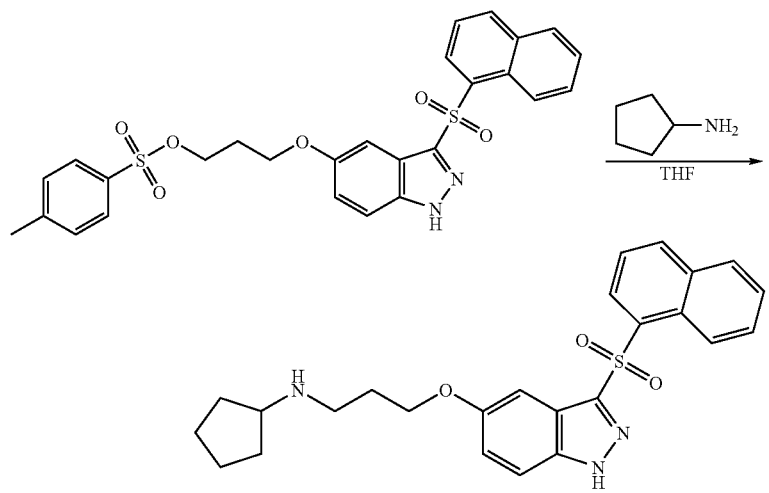

Cyclopentyl-{3-[3-(naphthalene-1-sulfonyl)-1H-indazol-5-yloxy]-propyl}-amine

A solution of toluene-4-sulfonic acid 3-[3-(naphthalene-1-sulfonyl)-1H-indazol-5-yloxy]-propyl ester (0.080 mg, 0.15 mmol) and cyclopentylamine (0.45-0.75 mmol) in THF (10 mL) was stirred at 90° C. for 2 hours in a sealed tube. After cooling to ambient temperature, the reaction mixture was solvent evaporated. It was partitioned in ethyl acetate and washed twice with aqueous sodium bicarbonate. The organic phase was dried over anhydrous magnesium sulfate, filtered and concentrated. The residue was purified by flash chromatography using 0.75% ammonium hydroxide/7.5% methanol in chloroform to give cyclopentyl-{3-[3-(naphthalene-1-sulfonyl)-1H-indazol-5-yloxy]-propyl}-amine as a beige foam (70.6 mg, 100%). This compound was dissolved in methanol, and ethereal hydrochloride was added. Concentrating and drying in vacuo for 12.5 hours at 83° C. gave the hydrochloride as a light brown foam (69.7 mg, 95.6%); Mass Spectrum (+EI, [M+H]$^+$) m/z 450. $^1$HNMR (500 MHz, DMSO-d$_6$): δ14.15-14.21 (br, 1H), 8.70-8.83 (m, 3H), 8.51-8.53 (m, 1H), 8.27 (d, 1H, J=8.30 Hz), 8.03-8.05 (m, 1H), 7.71-7.75 (m, 1H), 7.54-7.65 (m, 3H), 7.30 (d, 1H, J=2.20 Hz), 7.09 (dd, 1H, J=9.15 Hz and 2.31 Hz), 4.11 (t, 2H, J=6.10 Hz), 3.43-3.49 (m, 1H), 3.06 (br, s, 2H), 2.05-2.14 (m, 2H), 1.88-1.96 (m, 2H), 1.43-1.71 ppm (m, 6H). Elemental Analysis for C$_{25}$H$_{27}$N$_3$O$_3$S.1.00 mol HCl.0.75 mol H$_2$O: Calcd: C, 60.11; H, 5.95; N, 8.41; Found: C, 59.71; H, 5.83; N, 8.25.

EXAMPLE 22

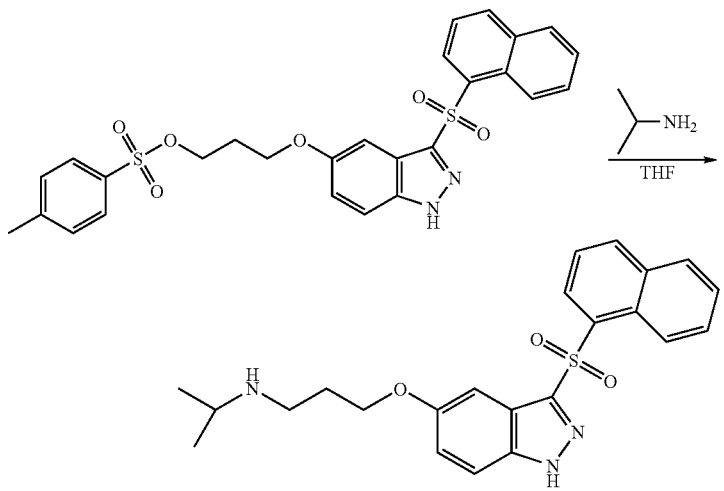

Isopropyl-{3-[3-(naphthalene-1-sulfonyl)-1H-indazol-5-yloxy]-propyl}-amine

A solution of toluene-4-sulfonic acid 3-[3-(naphthalene-1-sulfonyl)-1H-indazol-5-yloxy]-propyl ester (0.080 mg, 0.15 mmol) and isopropylamine (0.45-0.75 mmol) in THF (10 mL) was stirred at 90° C. for about 2 hours in a sealed tube. After cooling to ambient temperature the reaction mixture was solvent evaporated. It was dissolved in ethyl acetate and washed twice with aqueous sodium bicarbonate. The organic phase was dried over anhydrous magnesium sulfate, filtered and concentrated. The residue was purified by flash chromatography using 0.75% ammonium hydroxide/7.5% methanol in chloroform. The compound was dissolved in methanol and ethereal hydrochloride was added. Concentrating and drying for in vacuo 16 hours 83° C. gave isopropyl-{3-[3-(naphthalene-1-sulfonyl)-1H-indazol-5-yloxy]-propyl}-amine hydrochloride as a light yellow foam (48.6 mg, 70.4%); Mass Spectrum (+EI, [M+H]$^+$) m/z 424. $^1$HNMR (500 MHz, DMSO-d$_6$): δ14.15-14.16 (br, 1H), 8.75 (d, 1H, J=8.78 Hz), 8.60-8.70 (br, 2H), 8.52 (dd, 1H, J=7.45 Hz and 1.22 Hz), 8.27 (d, 1H, J=8.29 hz), 8.03-8.05 (m, 1H), 7.71-7.75 (m, 1H), 7.54-7.65 (m, 3H), 7.30 (d, 1H, J=2.20 Hz), 7.08-7.11 (m, 1H), 4.09-4.13 (m, 2H), 3.05 (s, br, 2H), 2.07-2.13 (m, 2H), 1.22 ppm (d, 6H, J=6.46 Hz) Elemental Analysis for C$_{23}$H$_{25}$N$_3$O$_3$S.1.00 mol HCl.0.55 mol H$_2$O: Calcd: C, 58.79; H, 5.81; N, 8.94; Found: C, 58.46; H, 5.61; N, 8.72.

EXAMPLE 23

3-(Naphthalene-1-sulfonyl)-5-(3-pyrrolidin-1-yl-propoxy)-1H-indazole

A solution of toluene-4-sulfonic acid 3-[3-(naphthalene-1-sulfonyl)-1H-indazol-5-yloxy]-propyl ester (0.080 mg, 0.15 mmol) and pyrrolidine (0.45-0.75 mmol) in THF (10 mL) was stirred at 90° C. for about 2 hours in a sealed tube. After cooling to ambient temperature the reaction mixture was solvent evaporated. It was dissolved in ethyl acetate and washed twice with aqueous sodium bicarbonate. The organic phase was dried over anhydrous magnesium sulfate, filtered and concentrated. The residue was dissolved in methanol and chloroform, and ethereal hydrochloride was added. Concentrating and drying in vacuo at 80° C. for 17 hours gave 3-(naphthalene-1-sulfonyl)-5-(3-pyrrolidin-1-yl-propoxy)-1H-indazole hydrochloride as a brown semi-solid (19.7 mg, 27.8%); Mass Spectrum (+EI, [M+H]$^+$) m/z 436. $^1$HNMR (500 MHz, DMSO-d$_6$): δ14.13 (s, 1H), 10.00-10.03 (br, 1H), 8.75 (d, 1H, J=8.66 Hz), 8.51-8.53 (m, 1H), 8.27 (d, 1H, J=8.30 Hz), 8.03-8.05 (m, 1H), 7.71-7.74 (m, 1H), 7.54-7.64 (m, 3H), 7.29 (d, 1H, J=2.20 Hz), 7.07-7.10 (m, 1H), 4.08-4.11 (m, 2H), 3.51-3.58 (m, 2H), 2.95-3.06 (m, 2H), 2.10-2.17 (m, 2H), 1.89-1.99 (m, 2H), 1.77-1.87 ppm (m, 2H).

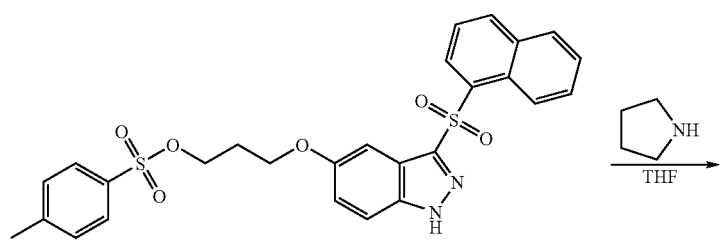

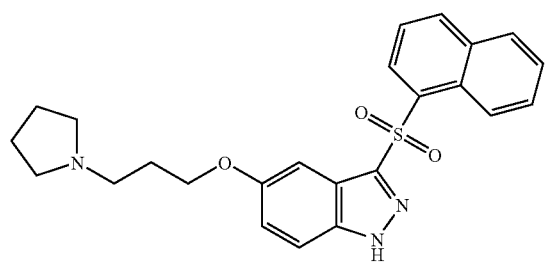

EXAMPLE 24

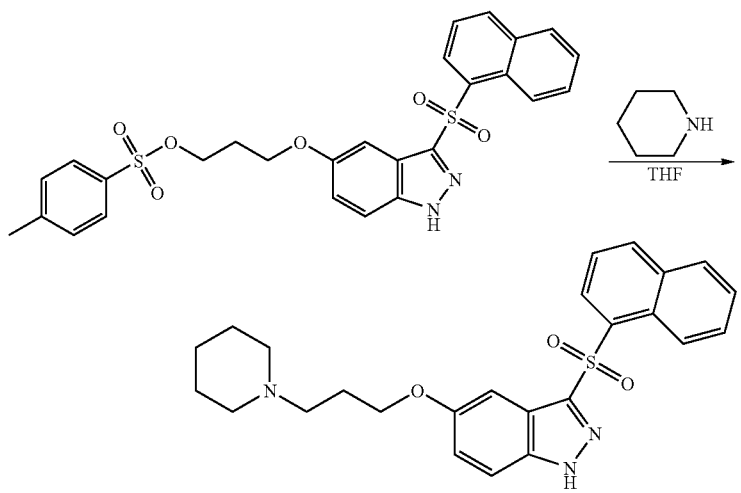

3-(Naphthalene-1-sulfonyl)-5-(3-piperidin-1-yl-propoxy)-1H-indazole

A solution of toluene-4-sulfonic acid 3-[3-(naphthalene-1-sulfonyl)-1H-indazol-5-yloxy]-propyl ester (0.080 mg, 0.15 mmol) and piperidine (0.45-0.75 mmol) in THF (10 mL) was stirred at 90° C. for about 2 hours in a sealed tube. After cooling to ambient temperature the reaction mixture was solvent evaporated. It was dissolved in ethyl acetate and washed twice with aqueous sodium bicarbonate. The organic phase was dried over anhydrous magnesium sulfate, filtered and concentrated. The residue was dissolved in methanol, and ethereal hydrochloride was added. Concentrating and drying at 80° C. for 29 hours in vacuo gave 3-(naphthalene-1-sulfonyl)-5-(3-piperidin-1-yl-propoxy)-1H-indazole hydrochloride as a brown semi-solid (49.0 mg, 67.2%); Mass Spectrum (−EI, [M−H]$^-$) m/z 448. $^1$HNMR (500 MHz, DMSO-d$_6$): δ14.14 (s, 1H), 9.59-9.66 (br, 1H), 8.75 (d, 1H, J=8.54 Hz), 8.51-8.53 (m, 1H), 8.27 (d, 1H, J=8.30 Hz), 8.03-8.05 (m, 1H), 7.71-7.74 (m, 1H), 7.54-7.65 (m, 3H), 7.29 (d, 1H, J=2.20 Hz), 7.08 (dd, 1H, J=9.15 Hz and 2.32 Hz), 4.09 (t, 2H, J=5.98 Hz), 3.42-3.45 (m, 2H), 3.16-3.25 (m, 2H), 2.82-2.96 (m, 2H), 2.13-2.29 (m, 2H), 1.58-1.80 (m, 5H), 1.30-1.40 ppm (m, 1H). Elemental Analysis for C$_{25}$H$_{27}$N$_3$O$_3$S.1.00 mol HCl.1.00 mol H$_2$O: Calcd: C, 59.57; H, 6.00; N, 8.34; Found: C, 59.36; H, 5.82; N, 8.24.

EXAMPLE 25

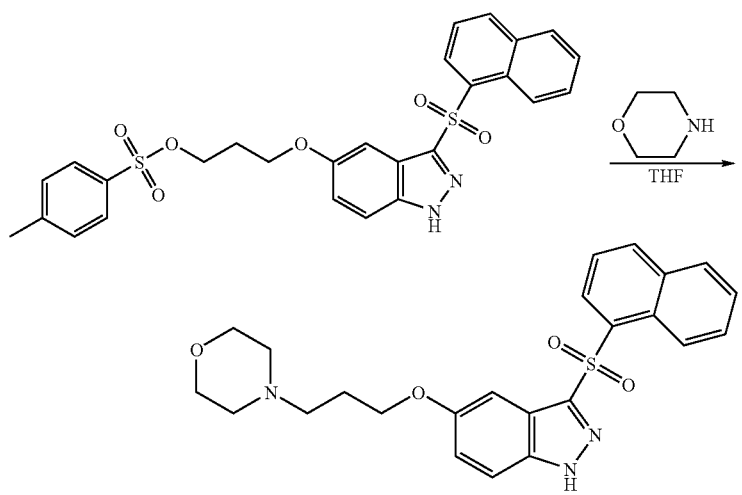

5-(3-Morpholin-4-yl-propoxy)-3-(naphthalene-1-sulfonyl)-1H-indazole

A solution of toluene-4-sulfonic acid 3-[3-(naphthalene-1-sulfonyl)-1H-indazol-5-yloxy]-propyl ester (0.080 mg, 0.15 mmol) and morpholine (0.45-0.75 mmol) in THF (10 mL) was stirred at 90° C. for about 2 hours in a sealed tube. After cooling to ambient temperature the reaction mixture was solvent evaporated. It was dissolved in ethyl acetate and washed twice with aqueous sodium bicarbonate. The organic phase was dried over anhydrous magnesium sulfate, filtered and concentrated. The residue was purified by flash chromatography using 0.5% ammonium hydroxide/5.0% methanol in chloroform. 5-(3-Morpholin-4-yl-propoxy)-3-(naphthalene-1-sulfonyl)-1H-indazole as a light yellow solid (74.4 mg, 100%) was obtained. This product was dissolved in methanol, and ethereal hydrochloride was added. Concentrating and drying in vacuo 83° C. for 24 hours yielded the hydrochloride as a yellow foam (74.5 mg, 100%); Mass Spectrum (+EI, [M+H]$^+$) m/z 452. $^1$HNMR (500 MHz, DMSO-$d_6$): δ14.15 (s, 1H), 10.56-10.62 (br, 1H), 8.75 (d, 1H, J=8.66 Hz), 8.52 (dd, 1H, J=7.44 Hz and 1.22 Hz), 8.27 (d, 1H, J=8.30 Hz), 8.02-8.05 (m, 1H), 7.71-7.75 (m, 1H), 7.54-7.65 (m, 3H), 7.29 (d, 1H, J=2.32 Hz), 7.07-7.10 (m, 1H), 4.10 (t, 2H, J=5.86 Hz), 3.93-3.96 (m, 2H), 3.71-3.77 (m, 2H), 3.43-3.46 (m, 2H), 2.99-3.15 (m, 2H), 2.14-2.22 ppm (m, 2H). Elemental Analysis for $C_{24}H_{25}N_3O_5S \cdot 1.00$ mol HCl·1.30 mol $H_2O$: Calcd: C, 56.36; H, 5.36; N, 8.22; Found: C, 56.05; H, 5.65; N, 8.09.

EXAMPLE 26

3-[3-(Naphthalene-1-sulfonyl)-1H-indazol-5-yloxy]-propylamine

Step 1

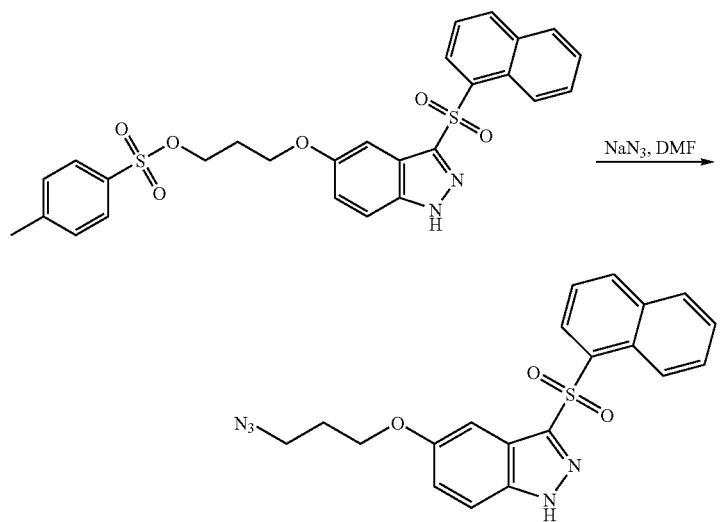

Step 2

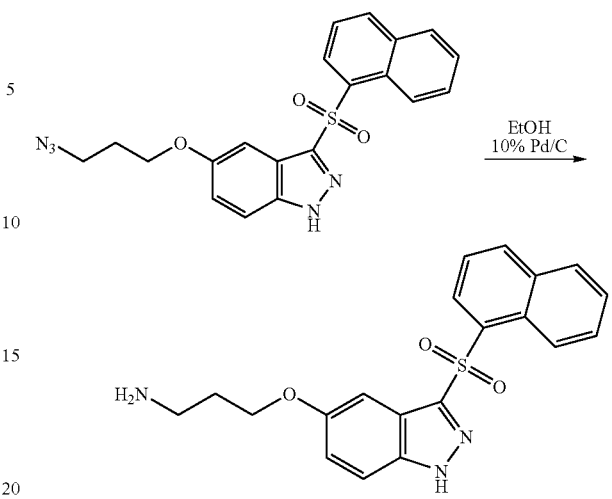

5-(3-Azido-propoxy)-3-(naphthalene-1-sulfonyl)-1H-indazole

3-[3-(Naphthalene-1-sulfonyl)-1H-indazol-5-yloxy]-propylamine

Sodium azide (0.425 g, 6.54 mmol) was added to a solution of toluene-4-sulfonic acid 3-[3-(naphthalene-1-sulfonyl)-1H-indazol-5-yloxy]-propyl ester (1.16 g, 2.16 mmol) in DMF (20 mL). The reaction mixture was stirred at 80° C. for 15 hours in a sealed tube. After cooling to ambient temperature, it was poured into excess water and extracted with ethyl acetate. The organic phase was washed with 10% ammonium chloride/water solution, water and brine. It was dried with anhydrous magnesium sulfate, filtered, concentrated and dried at 73° C. in vacuo for 45 minutes to yield 5-(3-azido-propoxy)-3-(naphthalene-1-sulfonyl)-1H-indazole as an amber gum (0.770 g, 87.7%); Mass Spectrum (−EI, [M−H]$^−$) m/z 406. $^1$HNMR (400 MHz, DMSO-$d_6$): δ14.05 (br, 1H), 8.64-8.68 (m, 1H), 8.53 (dd, 1H, J=7.42 Hz and 1.16 Hz), 8.25-8.28 (m, 1H), 8.01-8.05 (m, 1H), 7.70-7.74 (m, 1H), 7.52-7.64 (m, 3H), 7.26 (d, 1H, J=2.08 Hz), 7.08 (dd, 1H, J=9.16 Hz and 2.32 Hz), 4.06 (t, 2H, J=6.14 Hz), 3.49-3.52 (m, 2H), 1.96-1.99 ppm (m, 2H).

5-(3-Azido-propoxy)-3-(naphthalene-1-sulfonyl)-1H-indazole (0.763 g, 1.87 mmol) was dissolved in hot ethanol (125 mL). 10% Palladium on carbon (0.16 g) was added, and the reaction mixture was shaken and hydrogenated on the Parr apparatus for 2 hours, starting pressure 51 psi. Additional 1% Palladium on carbon (0.32 g) was added, and the reaction mixture was again hydrogenated on the Parr apparatus for 2 hours. It was then filtered over Celite and concentrated. The residue was purified by flash chromatography with 0.75% ammonium hydroxide/7.5% methanol in chloroform. The product was further purified by HPLC using a gradient of chloroform/methanol in heptane/TFA. 3-[3-(Naphthalene-1-sulfonyl)-1H-indazol-5-yloxy]-propylamine as a light yellow foam (0.229 g, 32.1%) resulted. Methanol and ethereal hydrochloride were added. The mixture was concentrated and dried at 83° C. in vacuo for 12 hours to yield the hydrochloride as a light buff foam (0.235 g). Mass Spectrum (−EI, [M−H]$^−$) m/z 380. $^1$HNMR (500 MHz, DMSO-$d_6$): δ14.15 (s, 1H), 8.75 (d, 1H, J=8.67 Hz), 8.50-8.52 (m, 1H), 8.27 (d, 1H, J=8.30 Hz), 8.02-8.05 (m, 1H), 7.86 (s, br, 3H), 7.71-7.75 (m, 1H), 7.54-7.64 (m, 3H), 7.29 (d, 1H, J=2.20 Hz), 7.08-7.11 (m, 1H), 4.09 (t, 2H, J=6.10 Hz), 2.94-2.99 (m, 2H), 2.00-2.07 ppm (m, 2H). Elemental Analysis for $C_{20}H_{19}N_3O_3S \cdot 1.00$ mol HCl $\cdot 0.40$ mol $H_2O$: Calcd: C, 56.51; H, 4.93; N, 9.88; Found: C, 56.21; H, 5.12; N, 9.56.

EXAMPLE 27

Dimethyl-{2-[3-(naphthalene-1-sulfonyl)-1H-indazol-5-yloxy]-ethyl}-amine

Step 1

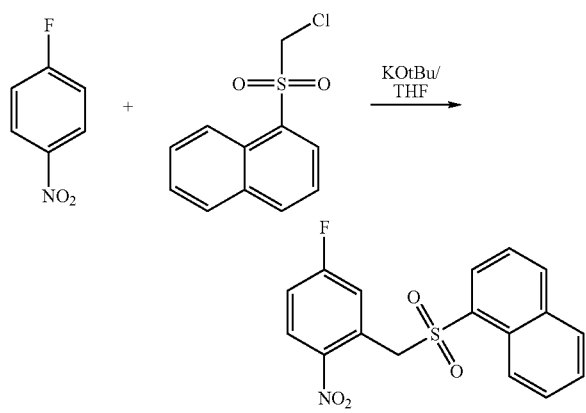

1-(5-Fluoro-2-nitro-phenylmethanesulfonyl)-naphthalene

To a chilled mixture of 1-chloromethanesulfonyl-naphthalene (21.7 g, 90.1 mmol) and 1-fluoro-4-nitrobenzene (9.6 mL, 90 mmol) in dry THF (220 mL) was dropwise added 1.0 M potassium tent-butoxide in THF (193 mL, 193 mmol). The reaction mixture was stirred at ambient temperature under nitrogen for 1 hour, 10 minutes. Glacial acetic acid (17 mL, 300 mmol) was then added. The reaction mixture was concentrated and partitioned in warm ethyl acetate and brine. The organic phase was dried with anhydrous magnesium sulfate, filtered and concentrated. The solid residue was stirred in ether, filtered and dried at 65° C. in vacuo for 16 hours. This yielded a brown/rust-colored solid (22.2 g, 71.4%) as 1-(5-fluoro-2-nitro-phenylmethanesulfonyl)-naphthalene: MP: 155-156° C.; Mass Spectrum (–EI, [M–H]⁻) m/z 344. ¹HNMR (300 MHz, DMSO-$d_6$): δ8.50-8.52 (m, 1H), 8.33 (d, 1H, J=8.30 Hz), 8.06-8.14 (m, 2H), 7.97 (dd, 1H, J=7.32 Hz and 1.22 Hz), 7.62-7.74 (m, 3H), 7.44-7.48 (m, 3H), 7.23-7.26 (m, 1H), 5.23 ppm (s, 2H). Elemental Analysis for $C_{17}H_{12}FNO_4S$: Calcd: C, 59.12; H, 3.50; N, 4.06; Found: C, 58.77; H, 3.30; N, 3.92.

Step 2

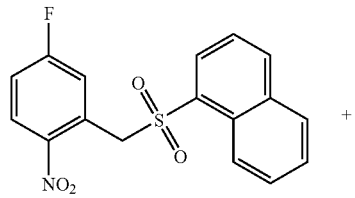

2-[3-(Naphthalene-1-sulfonylmethyl)-4-nitro-phenoxy]-ethanol

A mixture of 1-(5-fluoro-2-nitro-phenylmethanesulfonyl)-naphthalene (14.6 g, 42.3 mmol) and ethylene glycol (35 mL, 630 mmol) in 1.0 N potassium tert-butoxide in THF (90 mL, 90 mmol) was refluxed under nitrogen for one hour. After cooling to ambient temperature, the reaction mixture was concentrated. Excess water was added to the residue, and the mixture was poured into ice/2N hydrochloric acid. It was extracted with ethyl acetate and washed with water and brine. It was then dried with anhydrous magnesium sulfate, filtered, concentrated and dried in vacuo at 80° C. for 25 minutes to yield 2-[3-(naphthalene-1-sulfonylmethyl)-4-nitro-phenoxy]-ethanol as a brown gum (14.3 g, 87.2%). Mass Spectrum (–EI, [M–H]⁻) m/z 386. ¹HNMR (500 MHz, DMSO-$d_6$): δ8.56-8.57 (m, 1H), 8.35 (d, 1H, J=8.24 Hz), 8.14-8.15 (m, 1H), 8.00-8.02 (m, 2H), 7.65-7.75 (m, 3H), 7.11-7.13 (m, 1H), 6.89 (d, 1H, J=2.90 Hz), 5.27 (s, 2H), 4.92 (t, 1H, J=5.49 Hz), 3.93-3.95 (m, 2H), 3.67 ppm (dd, 2H, J=9.91 Hz and 5.34 Hz). Elemental Analysis for $C_{19}H_{17}NO_6S \cdot 0.25$ mol $H_2O$: Calcd: C, 58.23; H, 4.50; N, 3.57; Found: C, 57.83; H, 4.25; N, 3.50.

Step 3

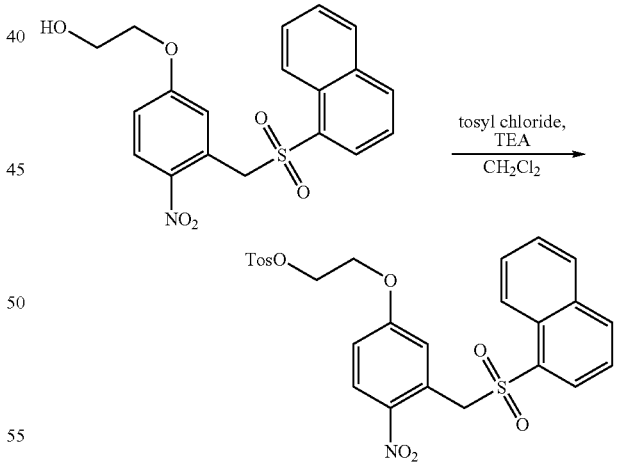

Toluene-4-sulfonic acid 2-[3-(naphthalene-1-sulfonylmethyl)-4-nitro-phenoxy]-ethyl ester A solution of 2-[3-(naphthalene-1-sulfonylmethyl)-4-nitro-phenoxy]-ethanol (14.3 g, 36.9 mmol), p-toluenesulfonylchloride (14.9 g, 78.2 mmol) and triethylamine (23 mL, 170 mmol) in methylene chloride (400 mL) was stirred under nitrogen at ambient temperature for 2 hours, 45 minutes. The reaction mixture was then concentrated and partitioned in methylene chloride and aqueous sodium bicarbonate. The organic phase was washed with brine, dried with anhydrous magnesium sulfate, filtered and concentrated. The residue was purified by flash chromatography with 25-75% ethyl acetate in hexane and 100% ethyl acetate. Drying for 25 minutes in vacuo at 80° C. yielded toluene-4-sulfonic acid 2-[3-(naphthalene-1-sulfonylmethyl)-4-nitro-phenoxy]-ethyl ester as a rust-colored solid (15.7 g, 78.5%). Mass Spectrum (+EI, [M+H]$^+$) m/z 542. $^1$HNMR (500 MHz, DMSO-d$_6$): 88.53 (dd, 1H, J=8.18 Hz and 1.10 Hz), 8.31 (d, 1H, J=8.30 Hz), 8.09-8.11 (m, 1H), 7.94-7.99 (m, 2H), 7.62-7.75 (m, 5H), 7.42 (d, 2H, J=7.93 Hz), 6.98 (dd, 1H, J=9.15 Hz and 2.93 Hz), 6.80 (d, 1H, J=2.81 Hz), 5.20 (s, 2H), 4.28-4.30 (m, 2H), 4.10-4.12 (m, 2H), 2.37 ppm (s, 3H).

Step 4

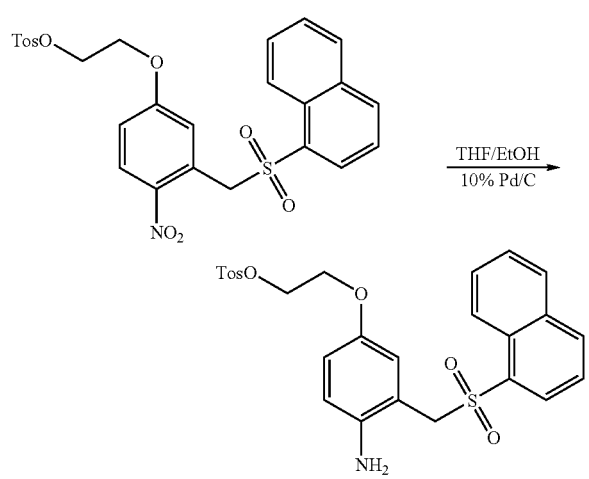

Toluene-4-sulfonic acid 2-[4-amino-3-(naphthalene-1-sulfonylmethyl)-phenoxy]-ethyl ester Ethanol (180 mL) and 10% palladium on carbon (5.2 g) were added to a hot solution of toluene-4-sulfonic acid 2-[3-(naphthalene-1-sulfonylmethyl)-4-nitro-phenoxy]-ethyl ester (11.5 g, 21.2 mmol) in THF (180 mL). This mixture was shaken on the Parr hydrogenation apparatus for 5 hours, with a starting pressure of 47 psi. It was then filtered over Celite, concentrated and dried in vacuo at 80° C. for 30 minutes to give toluene-4-sulfonic acid 2-[4-amino-3-(naphthalene-1-sulfonylmethyl)-phenoxy]-ethyl ester as a dark brown gum (9.5 g, 88.0%). Mass Spectrum (+EI, [M+H]$^+$) m/z 512. $^1$HNMR (500 MHz, DMSO-d$_6$): 88.61 (d, 1H, J=8.41 Hz), 8.25 (d, 1H, J=8.30 Hz), 8.03-8.08 (m, 2H), 7.59-7.75 (m, 5H), 7.43 (d, 2H, J=7.93 Hz), 6.49-6.53 (m, 2H), 6.11 (d, 1H, J=2.68 Hz), 4.65-4.77 (br, 2H), 4.59 (s, 2H), 4.09-4.11 (m, 2H), 3.63-3.65 (m, 2H), 2.38 ppm (s, 3H).

Step 5

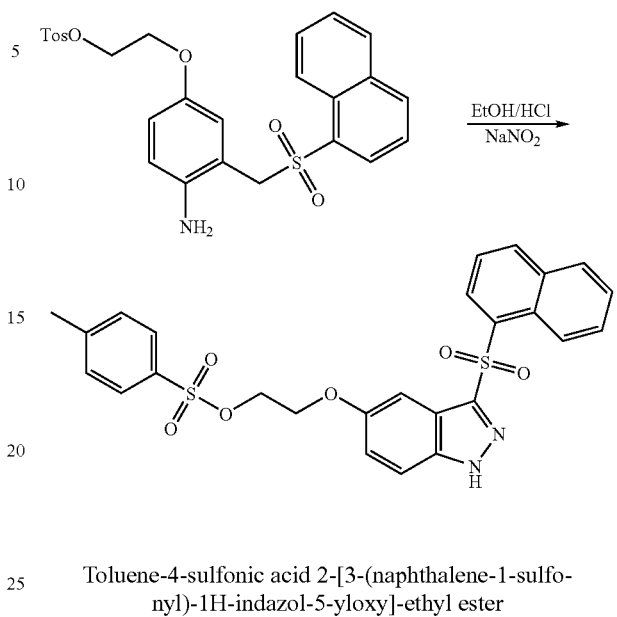

Toluene-4-sulfonic acid 2-[3-(naphthalene-1-sulfonyl)-1H-indazol-5-yloxy]-ethyl ester Ethanol (430 mL) in two portions and 1 N hydrochloric acid (200 mL) were added to toluene-4-sulfonic acid 2-[4-amino-3-(naphthalene-1-sulfonylmethyl)-phenoxy]-ethyl ester (6.5 g, 13 mmol). A solution of sodium nitrite (1.5 g, 22 mmol) in water was then added to the reaction mixture. The reaction was heated to aid in solubility. After stirring at ambient temperature for 2 hours, solid sodium carbonate was added to basic pH. The reaction mixture was stirred at ambient temperature for one hour. It was then solvent evaporated and partitioned in water and ethyl acetate. The organic phase was washed with brine, dried with anhydrous magnesium sulfate, filtered and concentrated. The residue was purified by flash chromatography with 2% methanol in chloroform. Drying at 63° C. in vacuo yielded toluene-4-sulfonic acid 2-[3-(naphthalene-1-sulfonyl)-1H-indazol-5-yloxy]-ethyl ester a buff-colored foam (3.9 g, 59%); Mass Spectrum (+EI, [M+H]$^+$) m/z 523. $^1$HNMR (500 MHz, DMSO-d$_6$): δ14.09 (s, 1H), 8.76 (d, 1H, J=8.78 Hz), 8.52-8.55 (m, 1H), 8.27 (d, 1H, J=8.30 Hz), 8.02-8.04 (m, 1H), 7.64-7.74 (m, 3H), 7.55-7.63 (m, 2H), 7.50 (d, 1H, J=9.15 Hz), 7.27 (d, 2H, J=8.05 Hz), 7.14 (d, 1H, J=2.20 Hz), 6.94 (dd, 1H, J=9.15 Hz and 2.44 Hz), 4.32-4.34 (m, 2H), 4.18-4.20 (m, 2H), 2.25 ppm (s, 3H). Elemental Analysis for C$_{26}$H$_{22}$N$_2$O$_6$S$_2$: Calcd: C, 59.76; H, 4.24; N, 5.36; Found: C, 59.69; H, 4.28; N, 5.14.

Step 6

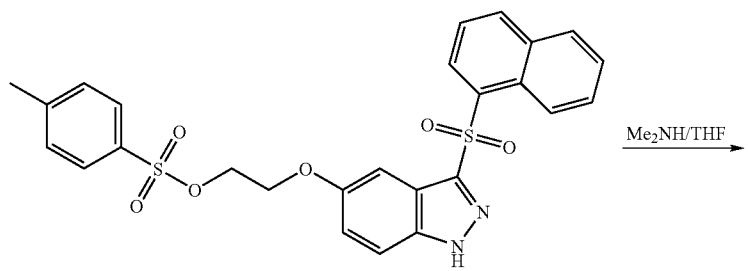

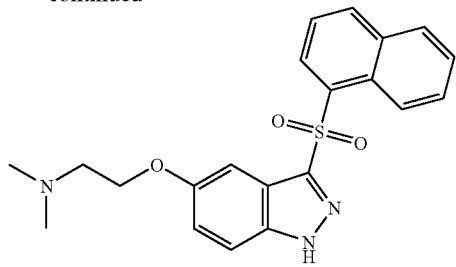

Dimethyl-{2-[3-(naphthalene-1-sulfonyl)-1H-indazol-5-yloxy]-ethyl}-amine

A solution of toluene-4-sulfonic acid 2-[3-(naphthalene-1-sulfonyl)-1H-indazol -5-yloxy]-ethyl ester (0.382 g, 0.731 mmol) in 2.0 M dimethylamine in THF (8 mL, 16 mmol) was stirred for 4 hours at 70° C. in a sealed tube. After cooling to ambient temperature, the reaction mixture was concentrated and partitioned in ethyl acetate and aqueous sodium bicarbonate. The organic phase was washed with water and brine, dried with anhydrous magnesium sulfate, filtered and concentrated. Drying at 80° C. for 20 minutes in vacuo yielded dimethyl-{2-[3-(naphthalene-1-sulfonyl)-1H-indazol -5-yloxy]-ethyl}-amine as a light yellow solid (0.212 g, 73.4%). Methanol, chloroform and etheric hydrochloride were added. The resulting solution was concentrated and dried for 15 hours at 78° C. in vacuo. The hydrochloride as a buff foam (0.217 g) was obtained. Mass Spectrum (+EI, [M+H]⁺) m/z 396. ¹HNMR (500 MHz, DMSO-$d_6$): δ14.20 (s, 1H), 10.05 (s, 1H), 8.74-8.77 (m, 1H), 8.52 (dd, 1H, J=7.44 Hz and 1.22 Hz), 8.27 (d, 1H, J=8.17 Hz), 8.03-8.05 (m, 1H), 7.70-7.74 (m, 1H), 7.56-7.65 (m, 3H), 7.37 (d, 1H, J=2.20 Hz), 7.15-7.18 (m, 1H), 4.37-4.39 (m, 2H), 3.51 (t, 2H, J=4.76 Hz), 2.83 ppm (s, 6H). Elemental Analysis for $C_{21}H_{21}N_3O_3S \cdot 1.00$ mol $HCl \cdot 0.70$ mol $H_2O$: Calcd: C, 56.74; H, 5.31; N, 9.45; Found: C, 56.72; H, 5.33; N, 9.06.

Isopropyl-{2-[3-(naphthalene-1-sulfonyl)-1H-indazol-5-yloxy]-ethyl}-amine

A solution of step 6 (1.01 g, 1.93 mmol) and isopropylamine (2.0 mL, 23 mmol) in THF (25 mL) was stirred for 16 hours at 70° C. in a sealed tube. More isopropylamine (2.0 mL, 23 mmol) was added, and the reaction mixture was stirred at 80° C. for 20 hours in a sealed tube. After cooling to ambient temperature, the reaction mixture was concentrated and partitioned in ethyl acetate and aqueous sodium bicarbonate. The organic phase was washed with brine, dried with anhydrous magnesium sulfate, filtered and concentrated. The residue was purified by flash chromatography using 0.75% ammonium hydroxide/7.5% methanol in chloroform. After concentrating and drying in vacuo at 72° C. for 25 minutes, isopropyl-{2-[3-(naphthalene-1-sulfonyl)-1H-indazol-5-yloxy]-ethyl}-amine was obtained as a light orange solid (0.313 g, 39.6%). Methanol, chloroform and ethereal hydrochloride were added to this compound. The resulting solution was concentrated and dried for 16 hours at 84° C. in vacuo. The hydrochloride was a light brown foam (0.332 g). Mass Spectrum (+EI, [M+H]⁺) m/z 410. ¹HNMR (500 MHz, DMSO-$d_6$): δ14.22 (s, 1H), 8.86 (s, 2H), 8.74-8.77 (m, 1H), 8.53 (dd, 1H, J=7.44 Hz and 1.22 Hz), 8.27 (d, 1H, J=8.30 Hz), 8.03-8.05 (m, 1H), 7.71-7.75 (m, 1H), 7.56-7.65 (m, 3H), 7.34 (d, 1H, J=2.32 Hz), 7.16 (dd, 1H, J=9.15 Hz and 2.44 Hz), 4.29-4.32 (m, 2H), 1.25 ppm (d, 6H, J=6.59 Hz).

EXAMPLE 28

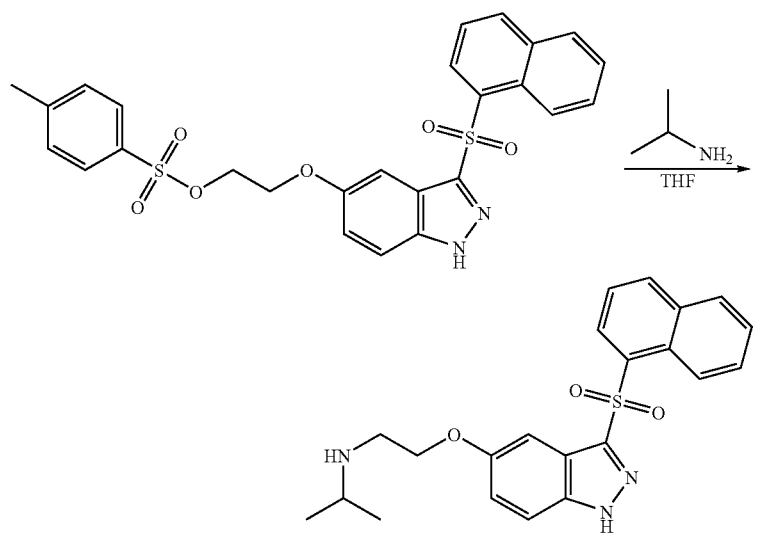

Elemental Analysis for $C_{22}H_{23}N_3O_3S \cdot 1.00$ mol $HCl \cdot 0.35$ mol $H_2O$: Calcd: C, 58.43; H, 5.50; N, 9.29; Found: C, 58.03; H, 5.25; N, 8.94.

EXAMPLE 29

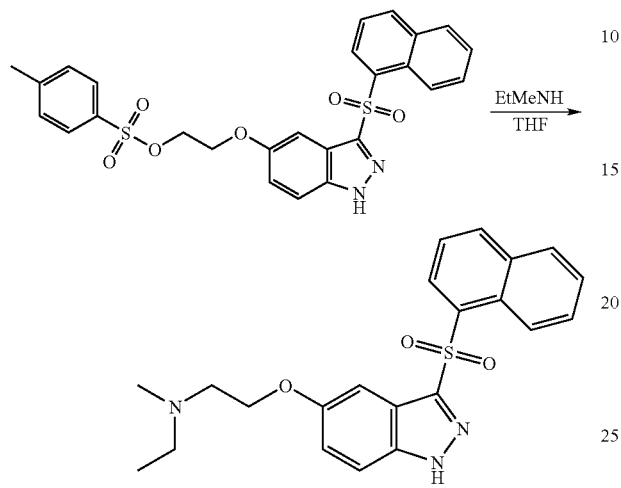

Ethyl-methyl-{2-[3-(naphthalene-1-sulfonyl)-1H-indazol-5-yloxy]-ethyl}-amine

A solution of toluene-4-sulfonic acid 2-[3-(naphthalene-1-sulfonyl)-1H-indazol-5-yloxy]-ethyl ester (1.18 g, 2.26 mmol) and ethylmethylamine (2.0 mL, 23 mmol) in THF (20 mL) was stirred for 16 hours at 70° C. in a sealed tube. More ethylmethylamine (2.0 mL, 23 mmol) was added, and the reaction mixture was heated to 80° C. for 20 hours in a sealed tube. After cooling to ambient temperature, the reaction mixture was concentrated and partitioned in ethyl acetate and aqueous sodium bicarbonate. The organic phase was washed with brine, dried with anhydrous magnesium sulfate, filtered and concentrated. The residue was purified by flash chromatography using 0.75% ammonium hydroxide/7.5% methanol in chloroform. Drying in vacuo at 69° C. for 20 minutes yielded ethyl-methyl-{2-[3-(naphthalene-1-sulfonyl)-1H-indazol-5-yloxy]-ethyl}-amine as a buff foam (0.409 g, 44.2%). Methanol, chloroform and ethereal hydrochloride were added. The resulting solution was concentrated and dried for 16 hours at 84° C. in vacuo. The hydrochloride was obtained as a buff semi-solid (0.424 g). Mass Spectrum (+EI, [M+H]$^+$) m/z 410. $^1$HNMR (500 MHz, DMSO-d$_6$): δ14.21 (s, 1H), 10.00-10.01 (s, 1H), 8.74-8.77 (m, 1H), 8.52 (dd, 1H, J=7.44 Hz and 1.22 Hz), 8.27 (d, 1H, J=8.29 Hz), 8.03-8.05 (m, 1H), 7.73 (dd, 1H, J=8.06 Hz and 7.57 Hz), 7.56-7.65 (m, 3H), 7.37 (d, 1H, J=2.20 Hz), 7.15-7.18 (m, 1H), 4.40 (t, 2H, J=5.00 Hz), 3.53-3.59 (m, 1H), 3.39-3.49 (m, 1H), 3.21-3.25 (m, 1H), 3.10-3.20 (m, 1H), 2.81 (d, 3H, J=4.88 Hz), 1.21-1.25 ppm (m, 3H). Elemental Analysis for $C_{22}H_{23}N_3O_3S \cdot 1.00$ mol $HCl \cdot 0.30$ mol $H_2O$:

Calcd: C, 58.54; H, 5.49; N, 9.31;

Found: C, 58.30; H, 5.52; N, 8.91.

EXAMPLE 30

2-[3-(Naphthalene-1-sulfonyl)-1H-indazol-5-yloxy]-ethylamine

Step 1

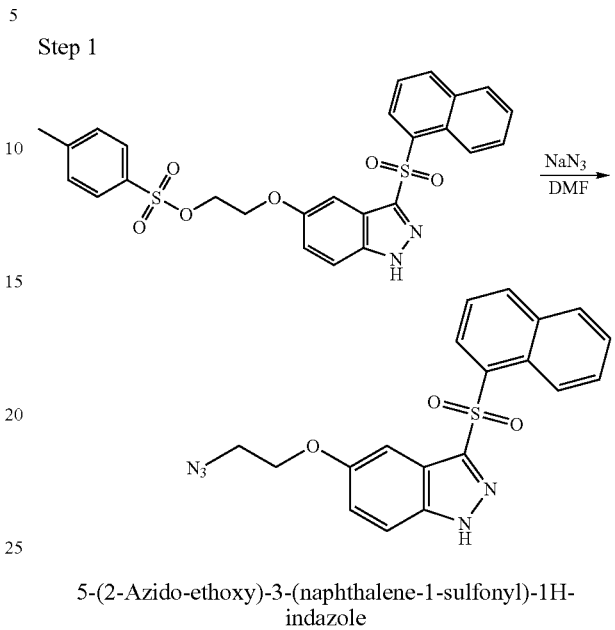

5-(2-Azido-ethoxy)-3-(naphthalene-1-sulfonyl)-1H-indazole

Sodium azide (0.79 g, 12 mmol) was added to a solution of toluene-4-sulfonic acid 2-[3-(naphthalene-1-sulfonyl)-1H-indazol-5-yloxy]-ethyl ester (2.06 g, 3.94 mmol) in DMF (20 mL). The reaction mixture was stirred at 80° C. for 12 hours in a sealed tube. After cooling to ambient temperature, it was poured into excess water and extracted with ethyl acetate. The organic phase was washed with 10% ammonium chloride/water solution, water and brine. It was dried with anhydrous magnesium sulfate, filtered, concentrated and dried at 72° C. in vacuo for 40 minutes to yield 5-(2-azido-ethoxy)-3-(naphthalene-1-sulfonyl)-1H-indazole as a amber gum/foam (1.34 g, 86.5%). Mass spectrum (−EI, [M−H]$^−$) m/z 392. $^1$HNMR (400 MHz, DMSO-d$_6$): δ8.78 (d, 1H, J=8.70 Hz), 8.56 (dd, 1H, J=7.43 Hz and 1.16 Hz), 8.29 (d, 1H, J=8.35 Hz), 8.06 (d, 1H, J=7.66 Hz), 7.72-7.76 (m, 1H), 7.57-7.67 (m, 3H), 7.31 (d, 1H, J=2.32 Hz), 7.12 (dd, 1H, J=9.16 Hz and 2.32 Hz), 4.22-4.24 (m, 2H), 3.67-3.69 ppm (m, 2H).

Step 2

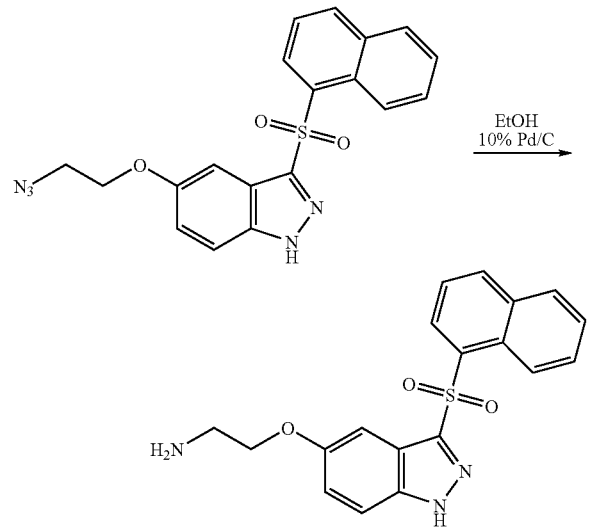

2-[3-(Naphthalene-1-sulfonyl)-1H-indazol-5-yloxy]-ethylamine

To 5-(2-azido-ethoxy)-3-(naphthalene-1-sulfonyl)-1H-indazole (1.34 g, 3.41 mmol) in hot ethanol (210 mL) was added 10% palladium on carbon (0.8 g). The reaction mixture was hydrogenated on the Parr apparatus for 1.25 hours, starting pressure 49 psi. It was then filtered over Celite and concentrated. The residue was purified by flash chromatography with 0.5% ammonium hydroxide/5.0% methanol in chloroform. Drying in vacuo at 63° C. for 20 minutes gave 2-[3-(naphthalene-1-sulfonyl)-1H-indazol-5-yloxy]-ethylamine as a light yellow foam resulted (0.775 g, 57.0%). Methanol and ethereal hydrochloride were added. Drying in vacuo for 16 hours 68° C. yielded the hydrochloride as a yellow foam (0.825 g). Mass spectrum (−EI, [M−H]⁻) m/z 366. ¹HNMR (500 MHz, DMSO-$d_6$): δ14.22 (s, 1H), 8.75 (d, 1H, J=8.66 Hz), 8.51-8.53 (m, 1H), 8.27 (d, 1H, J=8.29 Hz), 8.10 (s, br, 3H), 8.03-8.05 (m, 1H), 7.71-7.75 (m, 1H), 7.56-7.65 (m, 3H), 7.33 (d, 1H, J=2.19 Hz), 7.13-7.16 (m, 1H), 4.21 (t, 2H, J=5.00 Hz), 3.23 ppm (s, 2H). Elemental Analysis for $C_{19}H_{17}N_3O_3S.1.00$ mol HCl.0.55 mol $H_2O$: Calcd: C, 55.15; H, 4.65; N, 10.15; Found: C, 55.54; H, 4.90; N, 10.12.

EXAMPLE 31

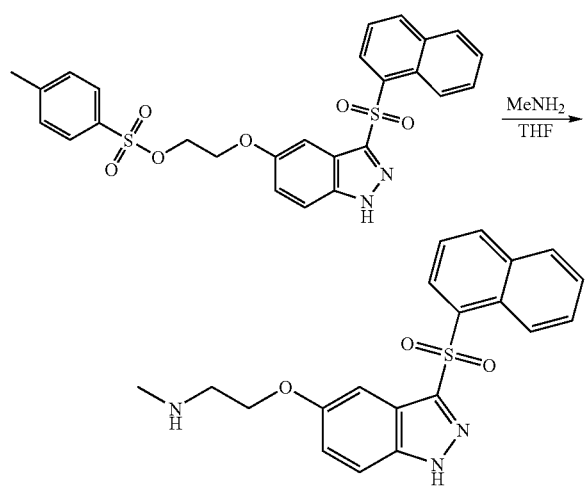

Methyl-{2-[3-(naphthalene-1-sulfonyl)-1H-indazol-5-yloxy]-ethyl}-amine

A solution of toluene-4-sulfonic acid 2-[3-(naphthalene-1-sulfonyl)-1H-indazol-5-yloxy]-ethyl ester (200 mg, 0.383 mmol) in 2.0 M methylamine in THF (10 mL, 20 mmol) was stirred at 70° C. for 2-3 hours in a sealed tube. After cooling to ambient temperature, the reaction mixture was solvent evaporated and partitioned in ethyl acetate and aqueous sodium bicarbonate. The organic phase was dried with anhydrous magnesium sulfate, filtered and concentrated. It was dissolved in methanol, and ethereal hydrochloride was added. The mixture was concentrated and dried for about 16 hours at 70° C. in vacuo to give methyl-{2-[3-(naphthalene-1-sulfonyl)-1H-indazol-5-yloxy]-ethyl}-amine hydrochloride as a pale yellow foam (100 mg, 62.5%); Mass Spectrum (−EI, [M−H]⁻) m/z 380. ¹HNMR (400 MHz, DMSO-$d_6$): δ14.21 (br, s, 1H), 8.85-8.91 (s, 2H), 8.74-8.75 (m, 1H), 8.51-8.53 (m, 1H), 8.26-8.28 (m, 1H), 8.03-8.05 (m, 1H), 7.71-7.74 (m, 1H), 7.56-7.64 (m, 3H), 7.34 (d, 1H, J=2.20 Hz), 7.14-7.17 (m, 1H), 4.27-4.30 (m, 2H), 3.32-3.34 (m, 2H), 2.61 ppm (s, 3H). Elemental Analysis for $C_{20}H_{19}N_3O_3S.1.00$ mol HCl.1.40 $H_2O$: Calcd: C, 54.21; H, 5.19; N, 9.48; Found: C, 54.31; H, 4.80; N, 9.10.

EXAMPLE 32

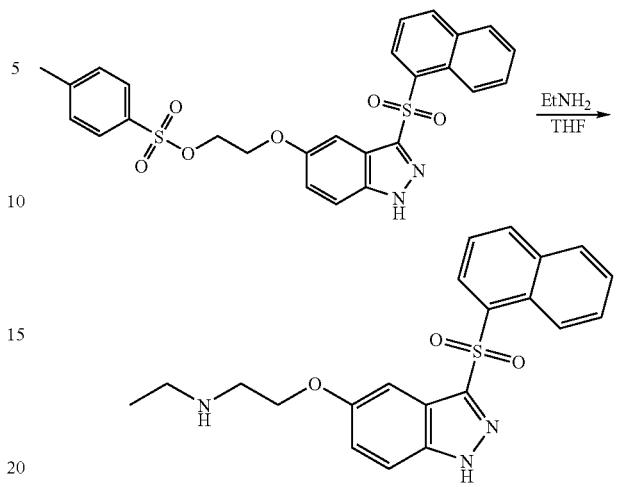

Ethyl-{2-[3-(naphthalene-1-sulfonyl)-1H-indazol-5-yloxy]-ethyl}-amine

A solution of toluene-4-sulfonic acid 2-[3-(naphthalene-1-sulfonyl)-1H-indazol-5-yloxy]-ethyl ester (200 mg, 0.383 mmol) in 2.0 M ethylamine (10 mL, 20 mmol) was stirred at 70° C. for 2-3 hours in a sealed tube. After cooling to ambient temperature, the reaction mixture was solvent evaporated and partitioned in ethyl acetate and aqueous sodium bicarbonate. The organic phase was dried with anhydrous magnesium sulfate, filtered and concentrated. It was dissolved in methanol, and ethereal hydrochloride was added. The mixture was concentrated and dried for 16 hours in vacuo at 70° C. to give ethyl-{2-[3-(naphthalene-1-sulfonyl)-1H-indazol-5-yloxy]-ethyl}-amine hydrochloride as a pale yellow foam (30 mg, 18.2%). Mass Spectrum (−EI, [M−H]⁻) m/z 394. ¹HNMR (500 MHz, DMSO-$d_6$): δ14.18 (s, 1H), 8.75 (d, 3H, J=8.54 Hz), 8.51-8.53 (m, 1H), 8.27 (d, 1H, J=8.17 Hz), 8.03-8.05 (m, 1H), 7.70-7.74 (m, 1H), 7.56-7.65 (m, 3H), 7.34 (d, 1H, J=2.20 Hz), 7.16 (dd, 1H, J=9.15 Hz and 2.32 Hz), 4.26-4.29 (m, 2H), 3.31-3.34 (m, 2H), 3.01-3.05 (s, br, 2H), 1.18-1.21 ppm (m, 3H).

EXAMPLE 33

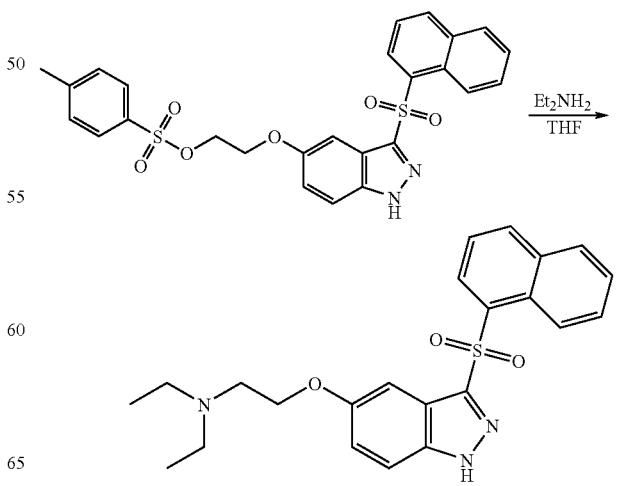

Diethyl-{2-[3-(naphthalene-1-sulfonyl)-1H-indazol-5-yloxy]-ethyl}-amine

A solution of toluene-4-sulfonic acid 2-[3-(naphthalene-1-sulfonyl)-1H-indazol-5-yloxy]-ethyl ester (200 mg, 0.383 mmol) and diethylamine (1.1-1.5 mmol) in THF (10 mL) was stirred at 70° C. for 2-3 hours in a sealed tube. After cooling to ambient temperature, the reaction mixture was solvent evaporated and partitioned in ethyl acetate and aqueous sodium bicarbonate. The organic phase was dried with anhydrous magnesium sulfate, filtered and concentrated. It was dissolved in methylene chloride and methanol, and ethereal hydrochloride was added. The mixture was concentrated and dried in vacuo at 67° C. for 16 hours to give diethyl-{2-[3-(naphthalene-1-sulfonyl)-1H-indazol-5-yloxy]-ethyl}-amine hydrochloride as an off-white foam (148 mg, 84.1%); Mass Spectrum (−EI, [M−H]⁻) m/z 422. ¹HNMR (400 MHz, DMSO-d$_6$): δ14.20 (s, 1H), 9.91 (s, 1H), 8.75 (d, 1H, J=8.54 Hz), 8.51-8.53 (m, 1H), 8.27 (d, 1H, J=8.29 Hz), 8.03-8.05 (m, 1H), 7.71-7.75 (m, 1H), 7.55-7.65 (m, 3H), 7.36 (d, 1H, J=2.20 Hz), 7.15 (dd, 1H, J=9.15 Hz and 2.32 Hz), 4.39 (t, 2H, J=4.39 Hz), 3.51 (d, br, 2H, J=3.91 Hz), 3.12-3.24 (m, 4H), 1.23 ppm (t, 6H, J=7.20 Hz). Elemental Analysis for $C_{23}H_{25}N_3O_3S \cdot 1.00$ mol HCl$\cdot 0.80$ mol $H_2O$: Calcd: C, 58.23; H, 5.86; N, 8.86; Found: C, 57.92; H, 5.52; N, 8.59.

EXAMPLE 34

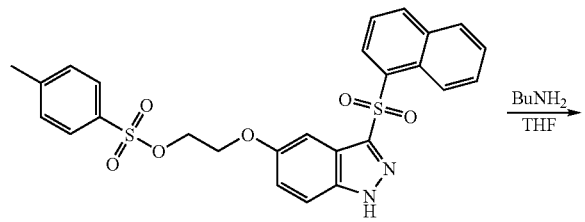

Butyl-{2-[3-(naphthalene-1-sulfonyl)-1H-indazol-5-yloxy]-ethyl}-amine

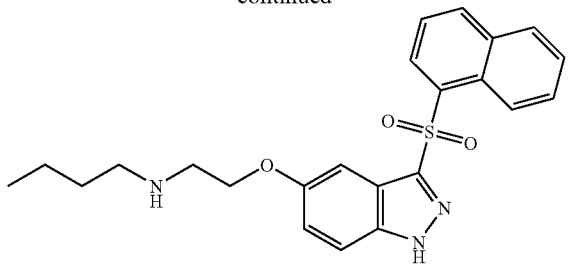

A solution of toluene-4-sulfonic acid 2-[3-(naphthalene-1-sulfonyl)-1H-indazol-5-yloxy]-ethyl ester (200 mg, 0.383 mmol) and butylamine (1.1-1.5 mmol) in THF (10 mL) was stirred at 70° C. for 2-3 hours in a sealed tube. After cooling to ambient temperature, the reaction mixture was solvent evaporated and partitioned in ethyl acetate and aqueous sodium bicarbonate. The organic phase was dried with anhydrous magnesium sulfate, filtered and concentrated. It was dissolved in methylene chloride and methanol, and ethereal hydrochloride was added. The mixture was concentrated and dried for 16 hours in vacuo at 67° C. to give butyl-{2-[3-(naphthalene-1-sulfonyl)-1H-indazol-5-yloxy]-ethyl}-amine hydrochloride as a light orange foam (166 mg, 94.3%); Mass Spectrum (−EI, [M−H]⁻) m/z 422. ¹HNMR (500 MHz, DMSO-d$_6$): δ8.74-8.76 (m, 1H), 8.51-8.53 (m, 1H), 8.27 (d, 1H, J=8.29 Hz), 8.03-8.05 (m, 1H), 7.71-7.74 (m, 1H), 7.56-7.65 (m, 3H), 7.34 (d, 1H, J=2.20 Hz), 7.16 (dd, 1H, J=9.15 Hz and 2.22 Hz), 4.28-4.30 (m, 2H), 3.32-3.35 (m, 2H), 2.93-2.97 (m, 2H), 1.55-1.63 (m, 2H), 1.27-1.36 (m, 2H), 0.85-0.89 ppm (m, 3H).

EXAMPLE 35

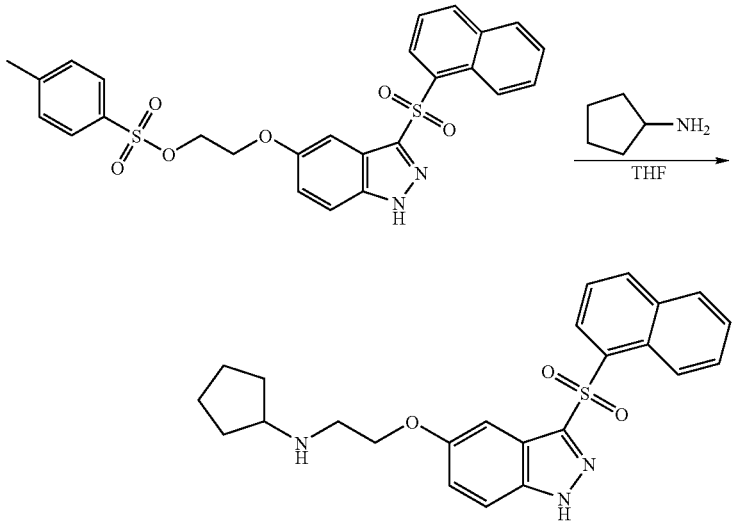

Cyclopentyl-{2-[3-(naphthalene-1-sulfonyl)-1H-indazol-5-yloxy]-ethyl}-amine

A solution of toluene-4-sulfonic acid 2-[3-(naphthalene-1-sulfonyl)-1H-indazol-5-yloxy]-ethyl ester (200 mg, 0.383 mmol) and cyclopentylamine (1.1-1.5 mmol) in THF (10 mL) was stirred at 70° C. for 2-3 hours in a sealed tube. After cooling to ambient temperature, the reaction mixture was solvent evaporated and partitioned in ethyl acetate and aqueous sodium bicarbonate. The organic phase was dried with anhydrous magnesium sulfate, filtered and concentrated. It was dissolved in methylene chloride and methanol, and ethereal hydrochloride was added. The mixture was concentrated and dried in vacuo at 67° C. for 17 hours to give cyclopentyl-{2-[3-(naphthalene-1-sulfonyl)-1H-indazol-5-yloxy]-ethyl}-amine hydrochloride as a brown foam (148 mg, 81.8%); Mass Spectrum (−EI, [M−H]⁻) m/z 436. ¹HNMR (500 MHz, DMSO-$d_6$): δ14.20 (s, 1H), 8.89-8.93 (s, br, 2H), 8.74-8.76 (m, 1H), 8.51-8.53 (m, 1H), 8.28 (d, 1H, J=8.29 Hz), 8.03-8.05 (m, 1H), 7.71-7.75 (m, 1H), 7.56-7.65 (m, 3H), 7.34 (d, 1H, J=2.32 Hz), 7.15-7.18 (m, 1H), 4.28-4.30 (m, 2H), 3.51-3.57 (m, 1H), 3.32-3.36 (m, 2H), 1.93-2.00 (m, 2H), 1.44-1.73 ppm (m, 6H). Elemental Analysis for $C_{24}H_{25}N_3O_3S.1.00$ HCl.0.70 mol HCl: Calcd: C, 59.48; H, 5.70; N, 8.67; Found: C, 59.67; H, 5.86; N, 8.32.

Cyclopropyl-{2-[3-(naphthalene-1-sulfonyl)-1H-indazol-5-yloxy]-ethyl}-amine

A solution of toluene-4-sulfonic acid 2-[3-(naphthalene-1-sulfonyl)-1H-indazol-5-yloxy]-ethyl ester (200 mg, 0.383 mmol) and cyclopropylamine (1.1-1.5 mmol) in THF (10 mL) was stirred at 70° C. for 2-3 hours in a sealed tube. After cooling to ambient temperature, the reaction mixture was solvent evaporated and partitioned in ethyl acetate and aqueous sodium bicarbonate. The organic phase was dried with anhydrous magnesium sulfate, filtered and concentrated. It was dissolved in methanol and ethereal hydrochloride was added. The mixture was concentrated and dried in vacuo at 70° C. for 16 hours to give cyclopropyl-{2-[3-(naphthalene-1-sulfonyl)-1H-indazol-5-yloxy]-ethyl}-amine hydrochloride as a yellow foam (58 mg, 34%); Mass spectrum (−EI, [M−H]⁻) m/z 406. ¹HNMR (400 MHz, DMSO-$d_6$): δ14.20 (s, 1H), 9.19 (s, br, 2H), 8.74-8.76 (m, 1H), 8.52 (dd, 1H, J=7.45 Hz and 1.22 Hz), 8.27 (d, 1H, J=8.30 Hz), 8.02-8.05 (m, 1H), 7.71-7.75 (m, 1H), 7.56-7.65 (m, 3H), 7.34 (d, 1H, J=2.19 Hz), 7.16 (dd, 1H, J=9.15 Hz and 2.32 Hz), 4.30-4.33 (m, 2H), 3.43 (br, s, 2H), 2.76-2.77 (m, 1H), 0.84-0.88 (m, 2H), 0.71-0.76 ppm (m, 2H). Elemental Analysis for $C_{22}H_{21}N_3O_4S.1.00$ HCl.0.60 mol HCl: Calcd: C, 58.11; H, 5.14; N, 9.24; Found: C, 57.83; H, 4.81; N, 8.91.

EXAMPLE 36

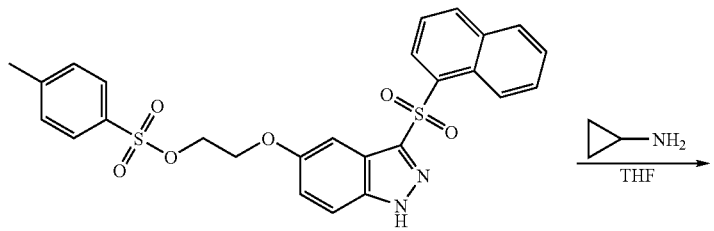

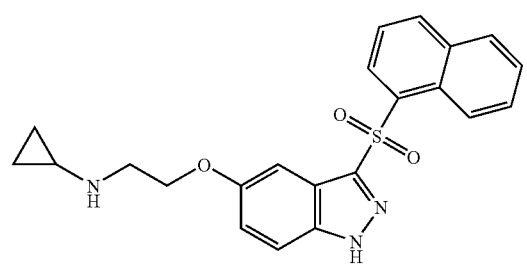

EXAMPLE 37

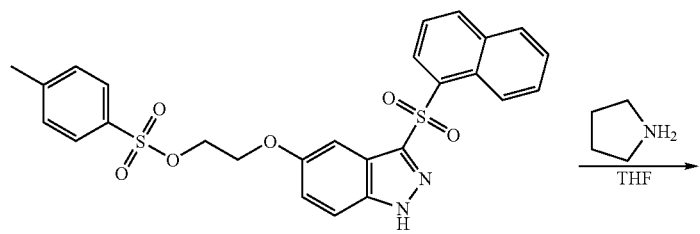

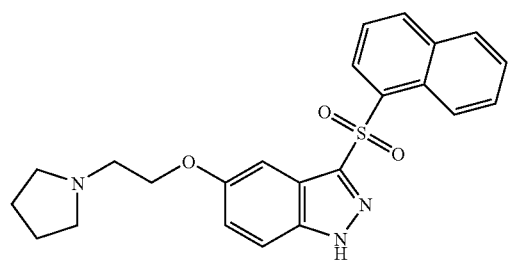

3-(Naphthalene-1-sulfonyl)-5-(2-pyrrolidin-1-yl-ethoxy)-1H-indazole

A solution of toluene-4-sulfonic acid 2-[3-(naphthalene-1-sulfonyl)-1H-indazol -5-yloxy]-ethyl ester (200 mg, 0.383 mmol) and pyrrolidine (1.1-1.5 mmol) in THF (10 mL) was stirred at 70° C. for 2-3 hours in a sealed tube. After cooling to ambient temperature, the reaction mixture was solvent evaporated and partitioned in ethyl acetate and aqueous sodium bicarbonate. The organic phase was dried with anhydrous magnesium sulfate, filtered and concentrated. It was dissolved in methanol and ethereal hydrochloride was added. The mixture was concentrated and dried in vacuo at 67° C. for 20 hours to give 3-(naphthalene-1-sulfonyl)-5-(2-pyrrolidin-1-yl-ethoxy)-1H-indazole hydrochloride as a light brown foam (97.8 mg, 55.9%); Mass Spectrum (−EI, [M−H]$^-$) m/z 420. $^1$HNMR (500 MHz, DMSO-d$_6$): δ14.19 (s, 1H), 10.26-10.29 (br, 1H), 8.74-8.77 (m, 1H), 8.53 (dd, 1H, J=7.44 Hz and 1.22 Hz), 8.27 (d, 1H, J=8.29 Hz), 8.03-8.05 (m, 1H), 7.71-7.74 (m, 1H), 7.55-7.65 (m, 3H), 7.36 (d, 1H, J=2.19 Hz), 7.16-7.19 (m, 1H), 4.36-4.38 (m, 2H), 3.58 (s, br, 4H), 3.06-3.19 (s, br, 2H), 1.81-2.05 ppm (br, m, 4H).

EXAMPLE 38

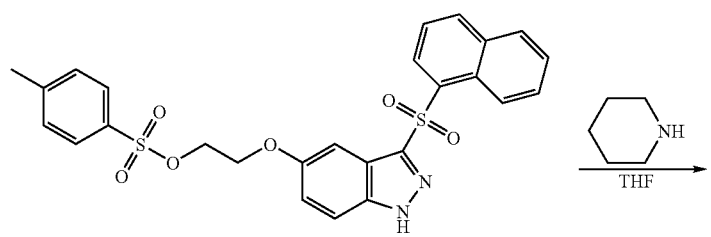

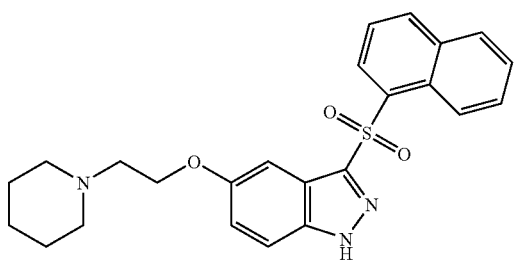

3-(Naphthalene-1-sulfonyl)-5-(2-piperidin-1-yl-ethoxy)-1H-indazole

A solution of the toluene-4-sulfonic acid 2-[3-(naphthalene-1-sulfonyl)-1H-indazol-5-yloxy]-ethyl ester (200 mg, 0.383 mmol) and piperidine (1.1-1.5 mmol) in THF (10 mL) was stirred in a sealed tube for about 16 hours at 70° C. After cooling to ambient temperature, the reaction mixture was solvent evaporated and partitioned in ethyl acetate and aqueous sodium bicarbonate. The organic phase was dried with anhydrous magnesium sulfate, filtered and concentrated. It was dissolved in methanol and chloroform, concentrated and dried in vacuo at 70° C. for 16 hours to give 3-(Naphthalene-1-sulfonyl)-5-(2-piperidin-1-yl-ethoxy)-1H-indazole hydrochloride as a pale yellow foam (106 mg, 58.6%). Mass Spectrum (−EI, [M−H]⁻) m/z 434.

$^1$HNMR (500 MHz, DMSO-$d_6$): δ14.18 (s, 1H), 9.77-9.84 (br, 1H), 8.75 (d, 1H, J=8.78 Hz), 8.51-8.53 (m, 1H), 8.27 (d, 1H, J=8.30 Hz), 8.03-8.05 (m, 1H), 7.70-7.74 (m, 1H), 7.56-7.65 (m, 3H), 7.35 (d, 1H, J=2.20 Hz), 7.15 (dd, 1H, J=9.15 Hz and 2.32 Hz), 4.40-4.41 (m, 2H), 3.44-3.50 (m, 3H), 2.90-3.06 (m, 2H), 1.61-1.76 (m, 5H), 1.31-1.41 ppm (m, 2H). Elemental Analysis for $C_{24}H_{25}N_3O_4S$.1.00 HCl.0.70 mol HCl: Calcd: C, 59.48; H, 5.70; N, 8.67; Found: C, 59.22; H, 5.63; N, 8.30.

EXAMPLE 39

5-(2-Morpholin-4-yl-ethoxy)-3-(naphthalene-1-sulfonyl)-1H-indazole

A solution of toluene-4-sulfonic acid 2-[3-(naphthalene-1-sulfonyl)-1H-indazol-5-yloxy]-ethyl ester (200 mg, 0.383 mmol) and morpholine (1.1-1.5 mmol) in THF (10 mL) was stirred at 70° C. for 2-3 hours in a sealed tube. After cooling to ambient temperature, the reaction mixture was solvent evaporated and triturated with ether and ethyl acetate. The resulting solid was then dissolved in ethyl acetate and washed with aqueous sodium bicarbonate. The organic phase was dried with anhydrous magnesium sulfate, filtered, concentrated. The residue was dissolved in methylene chloride and methanol, and ethereal hydrochloride was added. The mixture was concentrated and dried in vacuo at 67° C. for 17 hours to give 5-(2-morpholin-4-yl-ethoxy)-3-(naphthalene-1-sulfonyl)-1H-indazole hydrochloride as a light brown semi-solid (0.176 g, 96.7%); Mass Spectrum (+EI, [M+H]⁺) m/z 438.

$^1$HNMR (500 MHz, DMSO-$d_6$): δ14.19 (s, 1H), 10.61-10.66 (br, 1H), 8.74-8.76 (m, 1H), 8.52 (dd, 1H, J=7.44 Hz and 1.22 Hz), 8.27 (d, 1H, J=8.29 Hz), 8.03-8.05 (m, 1H), 7.71-7.75 (m, 1H), 7.56-7.65 (m, 3H), 7.36 (d, 1H, J=1.40 Hz), 7.15-7.17 (dd, 1H, J=9.15 Hz and 2.32 Hz), 4.44 (s, br, 2H), 3.93-3.96 (m, 2H), 3.72-3.78 (m, 2H), 3.42-3.69 (m, 4H), 3.12-3.23 ppm (m, 2H). Elemental Analysis for $C_{23}H_{23}N_3O_4S$.1.00 HCl.0.50 mol HCl: Calcd: C, 57.20; H, 5.22; N, 8.70; Found: C, 57.28; H, 5.24; N, 8.45.

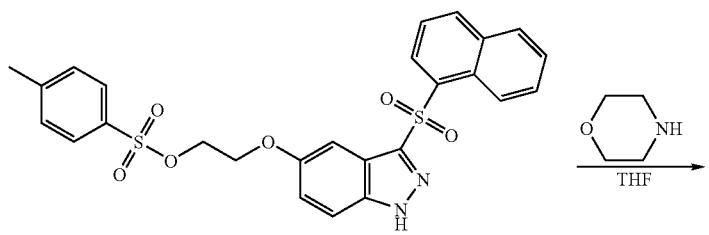

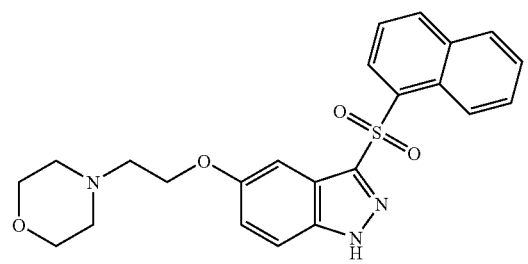

EXAMPLE 40

Methyl-{2-[1-methyl-3-(naphthalene-1-sulfonyl)-1H-indazol-5-yloxy]-ethyl}-amine

Step 1

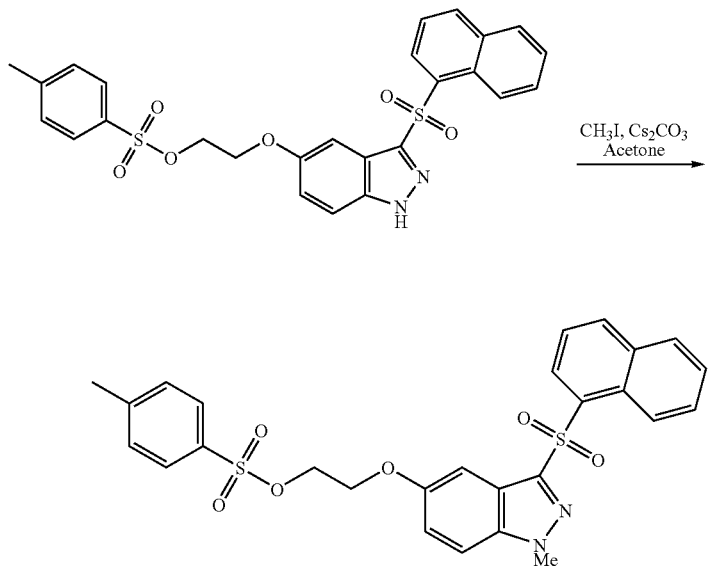

Toluene-4-sulfonic acid 2-[1-methyl-3-(naphthalene-1-sulfonyl)-1H-indazol-5-yloxy]-ethyl ester Methyliodide (0.06 mL, 0.96 mmol) was added to a chilled mixture of toluene -4-sulfonic acid 2-[3-(naphthalene-1-sulfonyl)-1H-indazol-5-yloxy]-ethyl ester (0.401 g, 0.767 mmol) and cesium carbonate (0.29 g, 0.89 mmol) in acetone (10 mL). The reaction mixture was stirred at ambient temperature under nitrogen for 3 hours. It was then partitioned in ethyl acetate and water. The organic phase was washed with brine, dried with anhydrous magnesium sulfate, filtered and concentrated. The residue was purified by flash chromatography with 25-40% ethyl acetate in hexane, 100% chloroform and 1% methanol in chloroform. Drying at 65° C. in vacuo for yielded toluene-4-sulfonic acid 2-[1-methyl-3-(naphthalene-1-sulfonyl)-1H-indazol-5-yloxy]-ethyl ester as a buff foam (0.224 g, 54.4%). $^1$HNMR (400 MHz, DMSO-$d_6$): δ 8.27 (d, 1H, J=8.54 Hz), 8.55 (dd, 1H, J=7.42 Hz and 1.16 Hz), 8.30 (d, 1H, J=8.35 Hz), 8.05-8.07 (m, 1H), 7.72-7.76 (m, 3H), 7.60-7.70 (m, 3H), 7.31 (d, 2H, J=8.01 Hz), 7.18 (d, 1H, J=2.20 Hz), 7.00-7.03 (m, 1H), 4.35-4.37 (m, 2H), 4.22-4.24 (m, 2H), 4.07 (s, 3H), 2.28 ppm (s, 3H).

Step 2

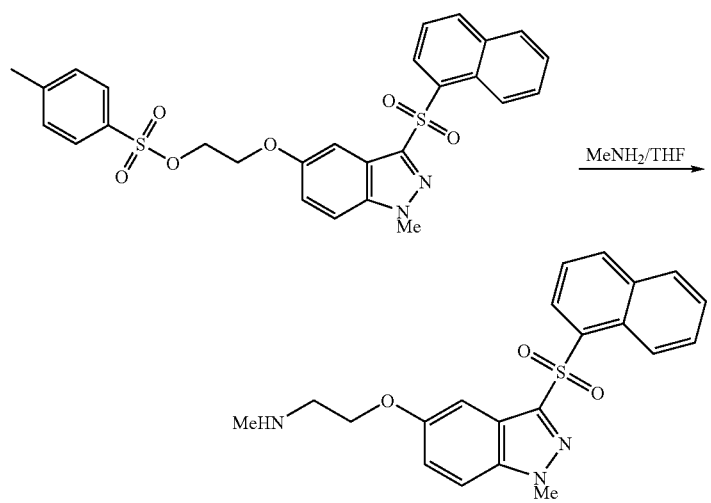

81

Methyl-{2-[1-methyl-3-(naphthalene-1-sulfonyl)-1H-indazol-5-yloxy]-ethyl}-amine A solution of toluene-4-sulfonic acid 2-[1-methyl-3-(naphthalene-1-sulfonyl)-1H-indazol-5-yloxy]-ethyl ester (0.351 g, 0.654 mmol) in 2.0 M methylamine in THF (10 mL, 20 mmol) was heated and stirred in a sealed tube at 78° C. for 1 hour, 40 minutes. Additional methylamine in THF (2.0 mL, 4.0 mmol) of was added, and the reaction mixture was stirred at 80° C. for 16.5 hours in a sealed tube. After cooling to ambient temperature, the reaction mixture was solvent evaporated. It was partitioned with ethyl acetate and aqueous sodium bicarbonate. It was washed with brine, dried with anhydrous magnesium sulfate, filtered, concentrated and dried at 80° C. in vacuo for 20 minutes, resulting in methyl-{2-[1-methyl-3-(naphthalene-1-sulfonyl)-1H-indazol-5-yloxy]-ethyl}-amine as a yellow gum (0.198 g, 76.4%). This was dissolved in chloroform, and ethereal hydrochloride was added. The solid was filtered and dried at 83° C. in vacuo for 25 hours. A buff solid (0.156 g) was obtained: MP: 272-4° C.(dec).; Mass Spectrum (+EI, [M+H]$^+$) m/z 396. $^1$HNMR (500 MHz, DMSO-$d_6$): δ8.89 (s, br, 2H), 8.73-8.75 (m, 1H), 8.50-8.52 (M, 1H), 8.26-8.28 (m, 1H), 8.03-8.05 (m, 1H), 7.71-7.74 (m, 2H), 7.56-7.66 (m, 2H), 7.37 (d, 1H, J=2.07 Hz), 7.19-7.22 (m, 1H), 4.29-4.31 (m, 2H), 4.05 (s, 3H), 3.34 (t, 2H, J=4.39 Hz), 2.62 ppm (s, 3H). Elemental Analysis for $C_{21}H_{21}N_3O_3S \cdot 1.00$ mol HCl $\cdot 0.60$ mol $H_2O$: Calcd: C, 56.97; H, 5.28; N, 9.49; Found: C, 56.91; H, 5.27; N, 9.14.

EXAMPLE 41

82

Dimethyl-{2-[1-methyl-3-(naphthalene-1-sulfonyl)-1H-indazol-5-yloxy]-ethyl}-amine A solution of toluene-4-sulfonic acid 2-[1-methyl-3-(naphthalene-1-sulfonyl)-1H-indazol-5-yloxy]-ethyl ester (0.39 g, 0.73 mmol) in 2.0 M dimethylamine in THF (10 mL, 20 mmol) was stirred for 16.5 hours at 80° C. in a sealed tube. After cooling to ambient temperature, the reaction mixture was solvent evaporated. The residue was partitioned in ethyl acetate and aqueous sodium bicarbonate. The organic phase was washed with brine, dried with anhydrous magnesium sulfate, filtered, concentrated and dried at 80° C. in vacuo for 35 minutes to give dimethyl-{2-[1-methyl-3-(naphthalene-1-sulfonyl)-1H-indazol-5-yloxy]-ethyl}-amine a light brown-orange semi-solid (0.257 g, 86.2%). This was dissolved in chloroform, and ethereal hydrochloride was added. The mixture was concentrated and dried for 25 hours at 83° C. in vacuo to give the hydrochloride as a buff-colored foam (0.254 g). Mass Spectrum (+EI, [M+H]$^+$) m/z 410. $^1$HNMR (500 MHz, DMSO-$d_6$): δ10.25 (s, 1H), 8.74-8.76 (m, 1H), 8.51 (dd, 1H, J=7.44 Hz and 1.22 Hz), 8.26-8.28 (m, 1H), 8.03-8.05 (m, 1H), 7.71-7.74 (m, 2H), 7.56-7.66 (m, 2H), 7.39 (d, 1H, J=2.08 Hz), 7.22 (dd, 1H, J=9.28 Hz and 2.32 Hz), 4.39-4.42 (m, 2H), 4.05 (s, 3H), 3.50-3.52 (m, 2H), 2.83 ppm (s, 6H).

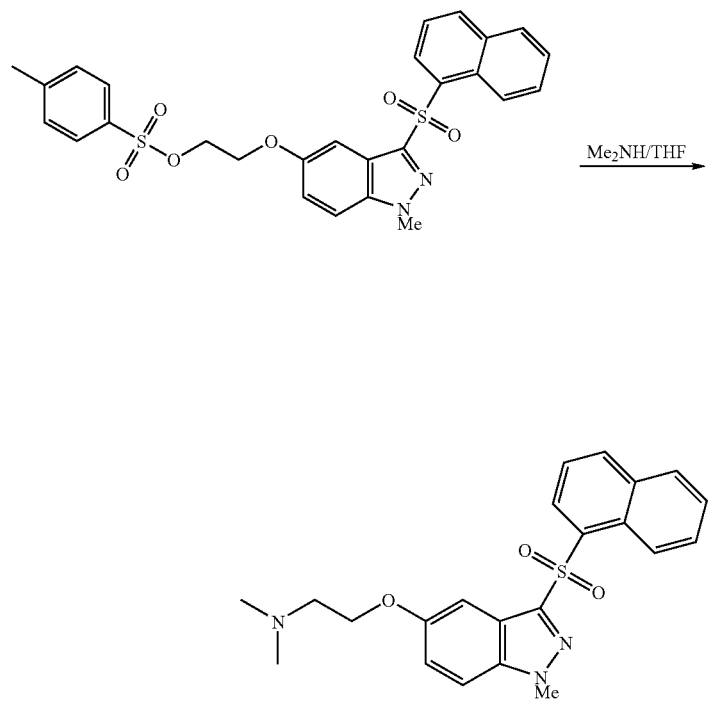

EXAMPLE 42

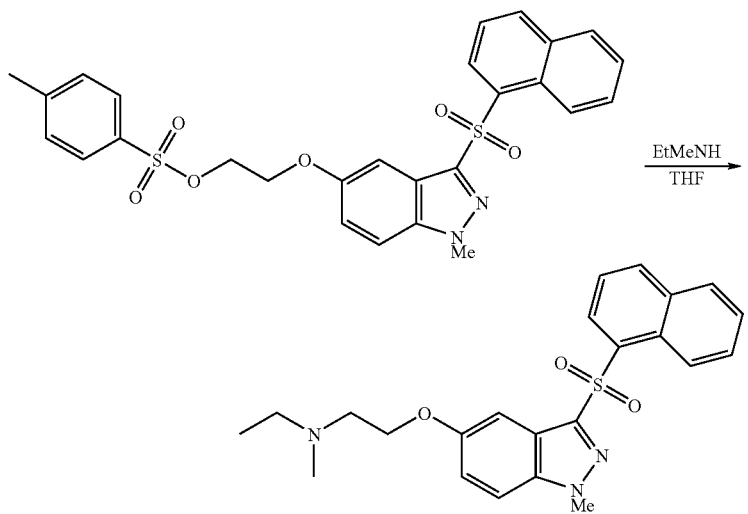

Ethyl-methyl-{2-[1-methyl-3-(naphthalene-1-sulfonyl)-1H-indazol-5-yloxy]-ethyl}-amine A solution of toluene-4-sulfonic acid 2-[1-methyl-3-(naphthalene-1-sulfonyl)-1H-indazol-5-yloxy]-ethyl ester (0.398 g, 0.742 mmol) and ethylmethylamine (2.0 mL, 23 mmol) in THF (10 mL) was stirred at 80° C. in a sealed tube for 16.5 hours. After cooling to ambient temperature, the reaction mixture was solvent evaporated. The residue was partitioned in ethyl acetate and aqueous sodium bicarbonate. The organic phase was washed with brine, dried with anhydrous magnesium sulfate, filtered, concentrated and dried at 80° C. in vacuo for 20 minutes to give ethyl-methyl-{2-[1-methyl-3-(naphthalene-1-sulfonyl)-1H-indazol-5-yloxy]-ethyl}-amine as a light brown gum (0.227 g, 72.3%). This was dissolved in chloroform, and etheric hydrochloride was added. The mixture was concentrated and dried for 25 hours at 83° C. in vacuo to give the hydrochloride as a buff-colored foam (0.254 g); Mass Spectrum (+EI, [M+H]$^+$) m/z 424. $^1$HNMR (500 MHz, DMSO-$d_6$): δ10.26-10.27 (s, br, 1H), 8.75 (d, 1H, J=8.66 Hz), 8.50-8.53 (m, 1H), 8.27 (d, 1H, J=8.17 Hz), 8.04 (d, 1H, J=7.56 Hz), 7.71-7.75 (m, 2H), 7.56-7.66 (m, 2H), 7.38 (d, 1H, J=2.19 H) 7.22 (dd, 1H, J=9.15 Hz and 2.32 Hz), 4.43 (t, 2H, J=4.88 Hz), 4.05 (s, 3H), 3.40-3.60 (m, 3H), 3.10-3.20 (br, 1H), 2.80 (s, 3H), 1.22-1.26 ppm (m, 3H).

EXAMPLE 43

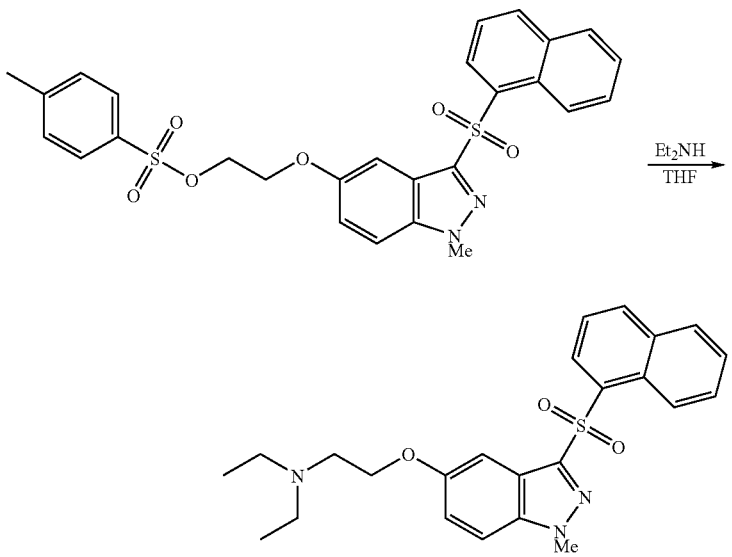

Diethyl-{2-[1-methyl-3-(naphthalene-1-sulfonyl)-1H-indazol-5-yloxy]-ethyl}-amine A solution of toluene-4-sulfonic acid 2-[1-methyl-3-(naphthalene-1-sulfonyl)-1H-indazol-5-yloxy]-ethyl ester (0.385 g, 0.717 mmol) and diethylamine (2.0 mL, 19 mmol) in THF (10 mL) was stirred at 80° C. in a sealed tube for 16.5 hours. After cooling to ambient temperature, the reaction mixture was solvent evaporated. The residue was partitioned in chloroform and aqueous sodium bicarbonate. The organic phase was washed with brine, dried with anhydrous magnesium sulfate, filtered, concentrated and dried at 80° C. in vacuo for 20 minutes to give diethyl-{2-[1-methyl-3-(naphthalene-1-sulfonyl)-1H-indazol-5-yloxy]-ethyl}-amine a clear amber gum (0.269 g, 85.7%). This was dissolved in chloroform, and ethereal hydrochloride was added. The mixture was concentrated and dried for 25 hours at 83° C. in vacuo to give the hydrochloride as a brown foam (0.253 g); Mass Spectrum (+EI, [M+H]$^+$) m/z 438. $^1$HNMR (500 MHz, DMSO-d$_6$): δ10.11-10.12 (br, 1H), 8.74 (d, 1H, J=8.66 Hz), 8.50-8.52 (m, 1H), 8.27 (d, 1H, J=8.29 Hz), 8.03-8.05 (m, 1H), 7.71-7.75 (m, 2H), 7.56-7.66 (m, 2H), 7.37 (d, 1H, J=2.20 Hz), 7.21 (dd, 1H, J=9.27 Hz and 2.32 Hz), 4.41-4.43 (m, 2H), 4.05 (s, 3H), 3.49-3.52 (m, 2H), 3.15-3.25 (m, 4H), 1.22-1.25 ppm (m, 6H).

EXAMPLE 44

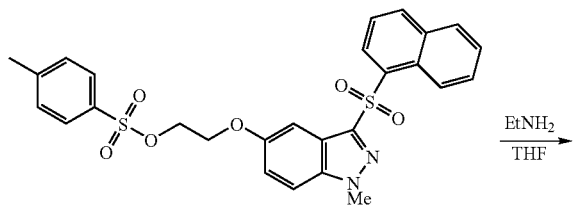

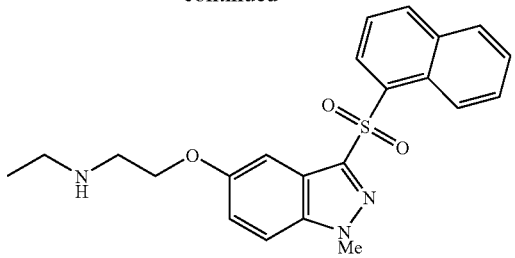

Ethyl-{2-[1-methyl-3-(naphthalene-1-sulfonyl)-1H-indazol-5-yloxy]-ethyl}-amine A solution of toluene-4-sulfonic acid 2-[1-methyl-3-(naphthalene-1-sulfonyl)-1H-indazol-5-yloxy]-ethyl ester (0.413 g, 0.770 mmol) and 2.0 M ethylamine in THF (10 mL, 20 mmol) in THF (10 mL) was stirred at 80° C. in a sealed tube for 16.5 hours. After cooling to ambient temperature, the reaction mixture was solvent evaporated. The residue was partitioned in ethyl acetate and aqueous sodium bicarbonate. The organic phase was washed with brine, dried with anhydrous magnesium sulfate, filtered, concentrated and dried at 80° C. in vacuo for 20 minutes to give ethyl-{2-[1-methyl-3-(naphthalene-1-sulfonyl)-1H-indazol-5-yloxy]-ethyl}-amine as a dark yellow solid (0.292 g, 92.7%). This was dissolved in chloroform and methanol, and ethereal hydrochloride was added. The mixture was concentrated and dried for 25 hours at 83° C. in vacuo to give the hydrochloride as a beige solid (0.227 g) MP 276-7° C.dec.; Mass Spectrum (+EI, [M+H]$^+$) m/z 410. $^1$HNMR (500 MHz, DMSO-d$_6$): δ8.95 (s, br, 2H), 8.75 (d, 1H, J=8.79 Hz), 8.52 (dd, 1H, J=7.45 Hz and 1.22 Hz), 8.27 (d, 1H, J=8.30 Hz), 8.04 (d, 1H, J=7.57 Hz), 7.71-7.75 (m, 2H), 7.56-7.66 (m, 2H), 7.36 (d, 1H, J=2.07 Hz), 7.22 (dd, 1H, J=9.15 Hz and 2.31 Hz), 4.30-4.33 (m, 2H), 4.05 (s, 3H), 3.33-3.34 (m, 2H), 2.99-3.05 (m, 2H), 1.19-1.23 ppm (m, 3H). Elemental Analysis for C$_{22}$H$_{23}$N$_3$O$_3$S.1.00 mol HCl.0.40 mol H$_2$O: Calcd: C, 58.31; H, 5.52; N, 9.27; Found: C, 58.62; H, 5.54; N, 9.11.

EXAMPLE 45

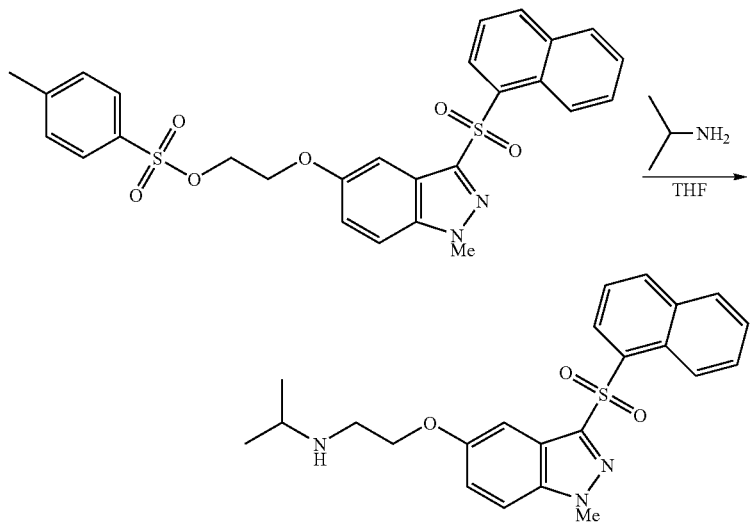

Isopropyl-{2-[1-methyl-3-(naphthalene-1-sulfonyl)-1H-indazol-5-yloxy]-ethyl}-amine A solution of toluene-4-sulfonic acid 2-[1-methyl-3-(naphthalene-1-sulfonyl)-1H-indazol-5-yloxy]-ethyl ester (0.433 g, 0.807 mmol) and isopropylamine (1.0 mL, 12 mmol) in THF (10 mL) was stirred at 80° C. in a sealed tube for 15 hours. Additional isopropylamine (1.0 mL, 12 mmol) was added, and the reaction mixture was stirred at 80° C. for 21 hours. It was allowed to cool to room temperature, and partitioned in ethyl acetate and aqueous sodium bicarbonate. The organic phase was washed with water and brine. It was dried with anhydrous magnesium sulfate, filtered and concentrated. The residue was purified by flash chromatography using 0.25% ammonium hydroxide/2.5% methanol in chloroform. Drying at 63° C. in vacuo for 30 minutes yielded isopropyl-{2-[1-methyl-3-(naphthalene-1-sulfonyl)-1H-indazol-5-yloxy]-ethyl}-amine as a yellow semi-solid 0.198 g, 57.9%). This was dissolved in chloroform, and ethereal hydrochloride was added. The precipitate was filtered and dried at 85° C. in vacuo for 13 hours to give the hydrochloride as an off-white solid (0.180 g): MP: 274-6° C. (dec).; Mass Spectrum (+EI, [M+H]$^+$) m/z 424.

$^1$HNMR (500 MHz, DMSO-$d_6$): δ8.83 (s, br, 2H), 8.74 (d, 1H, J=8.79 Hz), 8.51 (dd, 1H, J=7.44 Hz and 1.22 Hz), 8.27 (d, 1H, J=8.30 Hz), 8.03-8.05 (m, 1H), 7.71-7.75 (m, 2H), 7.56-7.66 (m, 2H), 7.36 (d, 1H, J=2.20 Hz), 7.20-7.23 (m, 1H), 4.30-4.33 (m, 2H), 4.06 (s, 3H), 3.30-3.38 (m, 3H), 1.25 ppm (d, 6H, J=6.46 Hz). Elemental Analysis for C23H25N3O3S.1.00 mol HCl.0.10 mol H2O: Calcd: C, 59.82; H, 5.72; N, 9.10; Found: C, 59.53; H, 5.66; N, 9.06.

EXAMPLE 46

1-Methyl-3-(naphthalene-1-sulfonyl)-5-(2-pyrrolidin-1-yl-ethoxy)-1H-indazole A solution of toluene-4-sulfonic acid 2-[1-methyl-3-(naphthalene-1-sulfonyl)-1H-indazol-5-yloxy]-ethyl ester (0.421 g, 0.785 mmol) and pyrrolidine (1.0 mL, 12 mmol) in THF (10 mL) was stirred at 80° C. in a sealed tube for 15 hours. After cooling to ambient temperature, the reaction mixture was solvent evaporated and partitioned in ethyl acetate and aqueous sodium bicarbonate. The organic phase was washed with brine, dried with anhydrous magnesium sulfate, filtered and concentrated. The residue was purified by flash chromatography with 0.25% ammonium hydroxide/2.5% methanol in chloroform. Drying at 68° C. in vacuo for 1 hour resulted in 1-methyl-3-(naphthalene-1-sulfonyl)-5-(2-pyrrolidin-1-yl-ethoxy)-1H-indazole as a light brown semi-solid (0.159 g, 46.5%). This was dissolved in chloroform, and ethereal hydrochloride was added. The precipitate was filtered, dissolved in methanol and concentrated. Drying at 85° C. in vacuo for 13 hours yielded the hydrochloride as a light orange semi-solid (0.156 g); Mass Spectrum (+EI, [M+H]$^+$) m/z 436. $^1$HNMR (500 MHz, DMSO-$d_6$): 810.60-10.61 (s, br, 1H), 8.75 (d, 1H, J=8.66 Hz), 8.51-8.53 (m, 1H), 8.27 (d, 1H, J=8.29 Hz), 8.04 (d, 1H, J=7.93 Hz), 7.71-7.74 (m, 2H), 7.56-7.67 (m, 2H), 7.37 (d, 1H, J=2.20 Hz), 7.22-7.25 (m, 1H), 4.39-4.41 (m, 2H), 4.05 (s, 3H), 3.57-3.60 (m, 4H), 3.06-3.14 (m, 2H), 1.95-2.01 (m, 2H), 1.86-1.92 ppm (m, 2H). Elemental Analysis for C$_{24}$H$_{25}$N$_3$O$_3$S.1.00 mol HCl.1.00 mol H$_2$O: Calcd: C, 58.82; H, 5.76; N, 8.58; Found: C, 58.77; H, 6.00; N, 8.47.

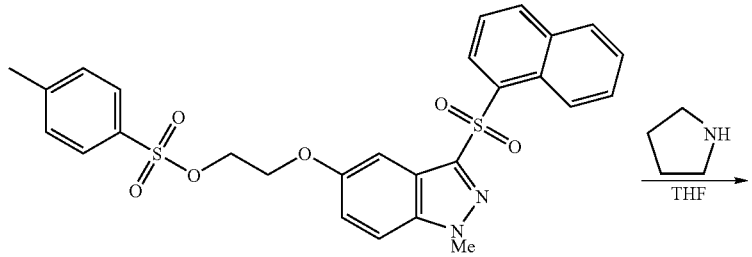

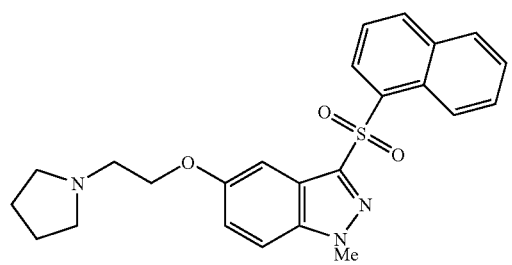

EXAMPLE 47

{2-[1-Benzyl-3-(naphthalene-1-sulfonyl)-1H-indazol-5-yloxy]-ethyl}-ethyl-methyl-amine Step 1

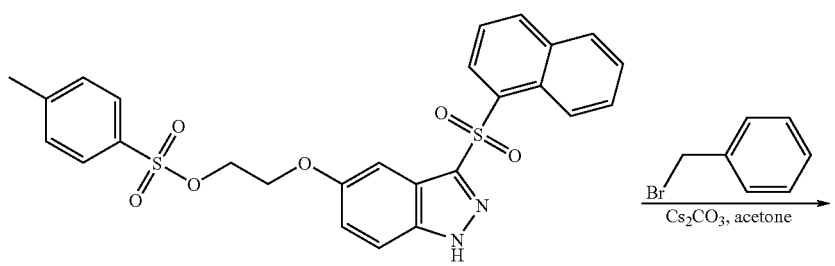

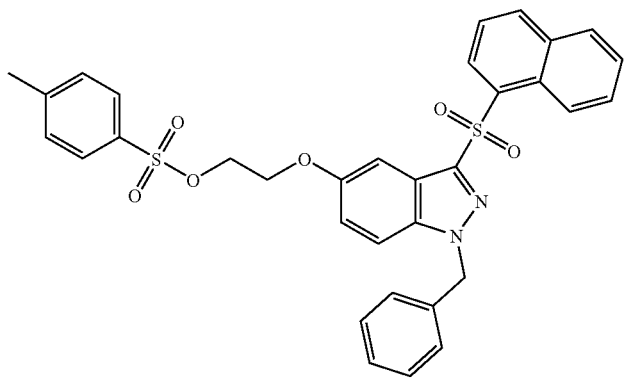

Toluene-4-sulfonic acid 2-[1-benzyl-3-(naphthalene-1-sulfonyl)-1H-indazol-5-yloxy]-ethyl ester Benzyl bromide (0.46 mL, 3.9 mmol) was added to a stirring suspension of toluene-4-sulfonic acid 2-[3-(naphthalene-1-sulfonyl)-1H-indazol-5-yloxy]-ethyl ester (1.85 g, 3.54 mmol) and cesium carbonate (1.28 g, 3.93 mmol) in acetone (60 mL). The reaction mixture was stirred under nitrogen at ambient temperature for 1.5 hours. It was then poured into excess water and extracted with chloroform. The organic phase was washed with brine, dried with anhydrous magnesium sulfate, filtered and concentrated. The residue was purified by flash chromatography with 40-50% ethyl acetate in hexane. Drying at 80° C. in vacuo for 30 minutes yielded toluene-4-sulfonic acid 2-[1-benzyl-3-(naphthalene-1-sulfonyl)-1H-indazol-5-yloxy]-ethyl ester as a light buff foam (1.39 g, 64.1%); Mass Spectrum (+EI, [M+H]$^+$) m/z 613. $^1$HNMR (500 MHz, DMSO-d$_6$): δ8.74-8.77 (m, 1H), 8.55-8.57 (m, 1H), 8.25-8.27 (m, 1H), 8.01-8.05 (m, 1H), 7.64-7.76 (m, 4H), 7.58-7.64 (m, 2H), 7.25 (d, 2H, J=7.93 Hz), 7.10-7.19 (m, 5H), 7.07 (d, 1H, J=2.19 Hz), 6.94-6.97 (m, 1H), 5.69 (s, 2H), 4.30-4.32 (m, 2H), 4.14-4.16 (m, 2H), 2.18 ppm (s, 3H). Elemental Analysis for $C_{33}H_{28}N_2O_6S_2$.0.60 mol $H_2O$: Calcd: C, 63.57; H, 4.72; N, 4.49; Found: C, 63.17; H, 4.63; N, 4.30.

Step 2

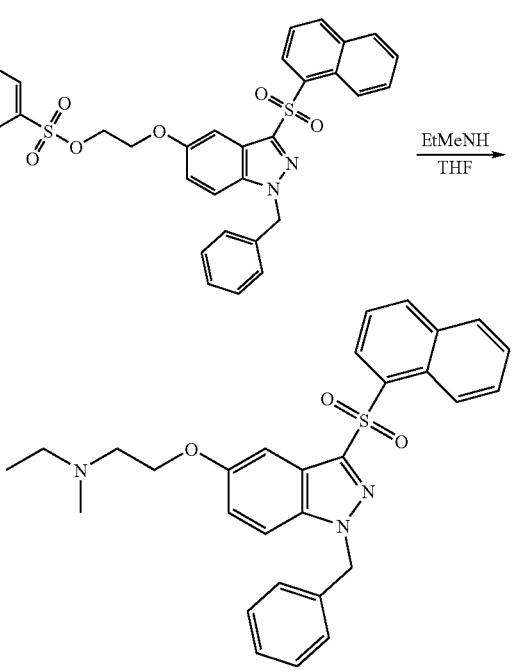

{2-[1-Benzyl-3-(naphthalene-1-sulfonyl)-1H-indazol-5-yloxy]-ethyl}-ethyl-methyl-amine A solution of toluene-4-sulfonic acid 2-[1-benzyl-3-(naphthalene-1-sulfonyl)-1H-indazol-5-yloxy]-ethyl ester (0.363 g, 0.592 mmol) and ethylmethylamine (2.0 mL, 23 mmol) in THF (8 mL) was stirred at 70° C. for 2.5 hours in a sealed tube. After cooling to ambient temperature, the residue was partitioned in ethyl acetate and aqueous sodium bicarbonate. The organic phase was washed with brine, dried with anhydrous magnesium sulfate, filtered and concentrated. Drying at 80° C. in vacuo for 30 minutes gave {2-[1-benzyl-3-(naphthalene-1-sulfonyl)-1H-indazol-5-yloxy]-ethyl}-ethyl-methyl-amine as a yellow foam/gum (0.241 g, 81.4%). This was dissolved in chloroform, and ethereal hydrochloride was added. The mixture was concentrated and dried in vacuo for 13 hours to yield the hydrochloride as a buff foam (0.242 g). Mass Spectrum (+EI, [M+H]$^+$) m/z 500. $^1$HNMR (500 MHz, DMSO-d$_6$): δ10.04-10.10 (s, br, 1H), 8.74-8.77 (m, 1H), 8.54-8.56 (m, 1H), 8.27 (d, 1H, J=8.29 Hz), 8.02-8.05 (m, 1H), 7.79 (d, 1H, J=9.28 Hz), 7.70-7.74 (m, 1H), 7.55-7.67 (m, 2H), 7.28 (d, 1H, J=2.19 Hz), 7.04-7.20 (m, 6H), 5.70 (s, 2H), 4.35 (s, 2H), 3.33-3.41 (br, 2H), 3.01-3.19 (br, 2H), 2.73 (s, 3H), 1.17-1.21 ppm (m, 3H). Elemental Analysis for C$_{29}$H$_{29}$N$_3$O$_3$S.1.00 mol HCl.1.10 mol H$_2$O: Calcd: C, 62.66; H, 5.84; N, 7.56; Found: C, 62.73; H, 6.19; N, 7.17.

EXAMPLE 48

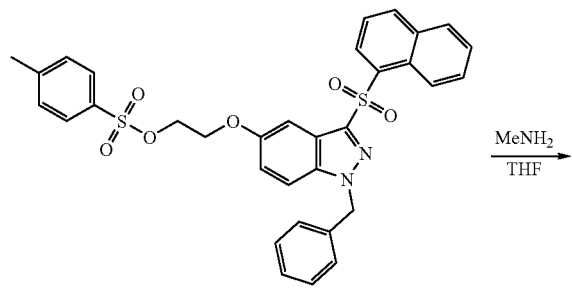

MeNH$_2$
THF

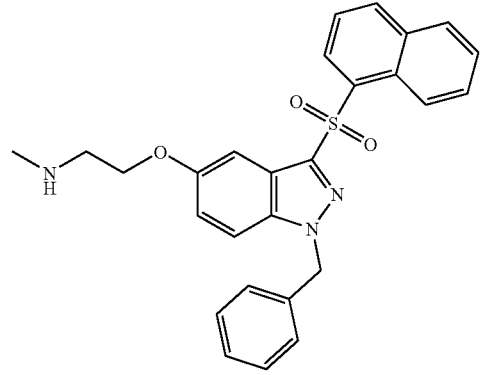

{2-[1-Benzyl-3-(naphthalene-1-sulfonyl)-1H-indazol-5-yloxy]-ethyl}-methyl-amine A solution of toluene-4-sulfonic acid 2-[1-benzyl-3-(naphthalene-1-sulfonyl)-1H-indazol-5-yloxy]-ethyl ester (0.476 g, 0.777 mmol) in 2.0 M methylamine in THF (8.0 mL, 16 mmol) was stirred at 70° C. in a sealed tube for 3 hours. After cooling to ambient temperature and concentrating, the residue was partitioned in ethyl acetate and aqueous sodium bicarbonate. The organic phase was washed with water and brine. It was dried with anhydrous magnesium sulfate, filtered and concentrated. Drying at 80° C. in vacuo for 20 minutes gave {2-[1-benzyl-3-(naphthalene-1-sulfonyl)-1H-indazol-5-yloxy]-ethyl}-methyl-amine as a clear, dark yellow gum (0.324 g, 88.5%). This was dissolved in chloroform, and ethereal hydrochloride was added. The mixture was concentrated and dried at 81° C. in vacuo for 13 hours. The hydrochloride as a light orange foam (0.330 g) resulted; Mass Spectrum (+EI, [M+H]$^+$) m/z 472. $^1$HNMR (500 MHz, DMSO-d$_6$): δ8.86 (s, 2H), 8.74-8.77 (m, 1H), 8.54-8.56 (m, 1H), 8.27 (d, 1H, J=8.30 Hz), 8.02-8.05 (m, 1H), 7.79 (d, 1H, J=9.15 Hz), 7.70-7.74 (m, 1H), 7.58-7.65 (m, 2H), 7.27 (d, 1H, J=3.30 Hz), 7.09-7.18 (m, 6H), 5.70 (s, 2H), 4.24-4.27 (m, 2H), 2.59 ppm (s, 3H). Elemental Analysis for C27H25N3O3S2.1.00 HCl.0.55 mol H2O: Calcd: C, 62.61; H, 5.27; N, 8.11; Found: C, 62.23; H, 5.45; N, 7.72.

EXAMPLE 49

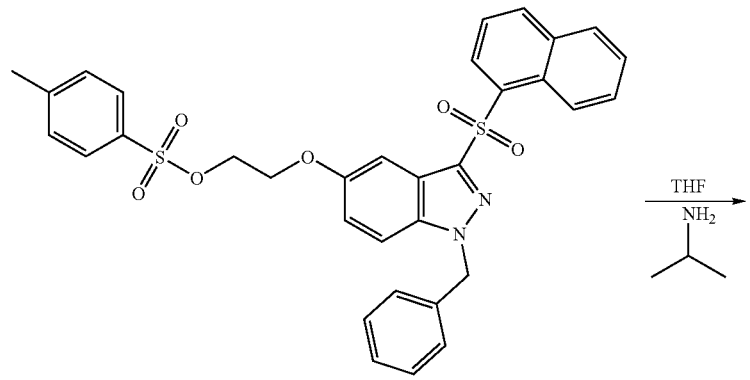

THF
NH$_2$

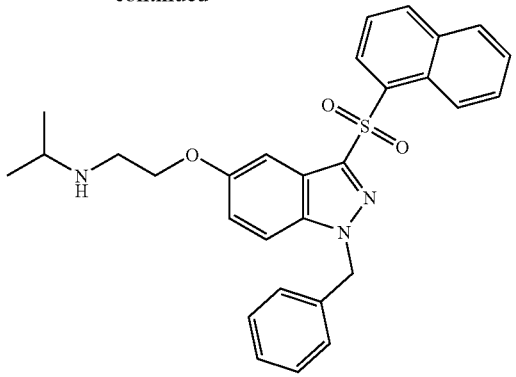

{2-[1-Benzyl-3-(naphthalene-1-sulfonyl)-1H-indazol-5-yloxy]-ethyl}-isopropyl-amine A solution of toluene-4-sulfonic acid 2-[1-benzyl-3-(naphthalene-1-sulfonyl)-1H-indazol-5-yloxy]-ethyl ester (0.444 g, 0.725 mmol) and isopropylamine (2.0 mL, 23 mmol) in THF (8 mL) was stirred at 70° C. in a sealed tube for 3 hours. More isopropylamine (2.0 mL, 23 mmol) was then added, and the reaction mixture was stirred at 80° C. in a sealed tube for 16.5 hours. After cooling somewhat, the reaction mixture was solvent evaporated and partitioned in ethyl acetate and aqueous sodium bicarbonate. The organic phase was then washed with water and brine. It was dried with anhydrous magnesium sulfate, filtered and concentrated. Drying at 80° C. in vacuo for 20 minutes gave {2-[1-benzyl-3-(naphthalene-1-sulfonyl)-1H-indazol-5-yloxy]-ethyl}-isopropyl-amine as a yellow semi-solid (0.290 g, 80.1% mmol). This was dissolved in chloroform, and ethereal hydrochloride was added. The mixture was concentrated and dried for 13 hours in vacuo at 81° C. The result was the hydrochloride as a buff foam (0.273 g); Mass Spectrum (+EI, [M+H]$^+$) m/z 500.

$^1$HNMR (500 MHz, DMSO-d$_6$): δ8.80 (s, 2H), 8.74-8.78 (m, 1H), 8.55 (dd, 1H, J=7.44 Hz and 1.22 Hz), 8.27 (d, 1H, J=8.29 Hz), 8.01-8.05 (m, 1H), 7.79 (d, 1H, J=9.15 Hz), 7.70-7.74 (m, 1H), 7.58-7.65 (m, 2H), 7.27 (d, 1H, J=2.20 Hz), 7.09-7.19 (m, 6H), 5.70 (s, 2H), 4.26-4.28 (m, 2H), 3.31 (s, 3H), 1.23 ppm (d, 6H, J=6.47 Hz). Elemental Analysis for C$_{29}$H$_{29}$N$_3$O$_3$S.1.00 HCl.0.7 mol H$_2$O: Calcd: C, 63.48; H, 5.77; N, 7.66;

Found: C, 63.10; H, 5.67; N, 7.37.

EXAMPLE 50

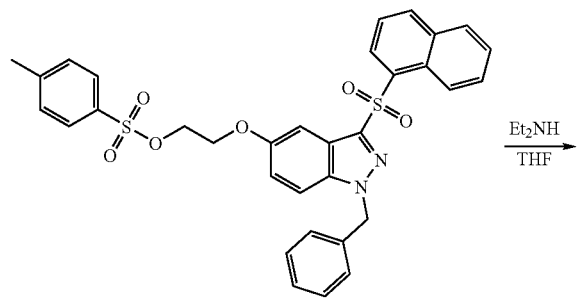

{2-[1-Benzyl-3-(naphthalene-1-sulfonyl)-1H-indazol-5-yloxy]-ethyl}-diethyl-amine A solution of toluene-4-sulfonic acid 2-[1-benzyl-3-(naphthalene-1-sulfonyl)-1H-indazol-5-yloxy]-ethyl ester (0.449 g, 0.733 mmol) and diethylamine (2.0 mL, 19 mmol) in THF (7.5 mL) was stirred at 70° C. in a sealed tube for 3 hours. More diethylamine (2.0 mL, 19 mmol) was then added, and the reaction mixture was stirred at 80° C. in a sealed tube for 16.5 hours. After cooling somewhat, the reaction mixture was solvent evaporated and partitioned in ethyl acetate and aqueous sodium bicarbonate. The organic phase was then washed with water and brine. It was dried with anhydrous magnesium sulfate, filtered and concentrated. Drying at 82° C. in vacuo for 35 minutes gave {2-[1-benzyl-3-(naphthalene-1-sulfonyl)-1H-indazol-5-yloxy]-ethyl}-diethyl-amine as a light brown-yellow semi-solid (0.365 g, 97.1% mmol). This was dissolved in chloroform, and ethereal hydrochloride was added. The mixture was concentrated and dried for 13 hours in vacuo at 81° C. The result was the hydrochloride as a light orange semi-solid (0.332 g); Mass Spectrum (+EI, [M+H]$^+$) m/z 514. $^1$HNMR (500 MHz, DMSO-d$_6$): δ10.15-10.18 (s, 1H), 8.74-8.76 (m, 1H), 8.56 (dd, 1H, J=7.44 Hz and 1.22 Hz), 8.26 (d, 1H, J=8.29 Hz), 8.02-8.05 (m, 1H), 7.78 (d, 1H, J=9.15 Hz), 7.70-7.74 (m, 1H), 7.58-7.65 (m, 2H), 7.26 (s, 1H), 7.08-7.19 (m, 6H), 5.70 (s, 2H), 4.25 (s, br, 2H), 3.39-3.55 (br, s, 2H), 3.15 (br, s, 3H), 1.13-1.19 ppm (s, br, 6H). Elemental Analysis for C$_{30}$H$_{31}$N$_3$O$_3$S.1.00 HCl.0.75 mol H$_2$O: Calcd: C, 63.93; H, 5.99; N, 7.46; Found: C, 63.59; H, 5.94; N, 7.23.

EXAMPLE 51

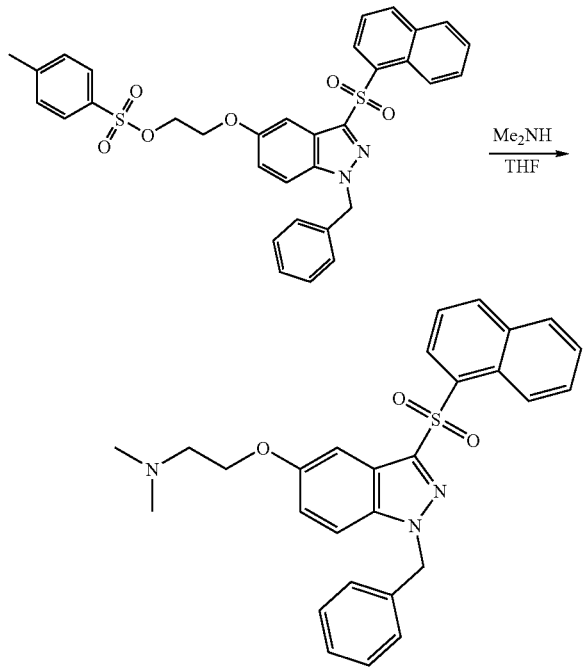

{2-[1-Benzyl-3-(naphthalene-1-sulfonyl)-1H-indazol-5-yloxy]-ethyl}-dimethyl-amine A solution of toluene-4-sulfonic acid 2-[1-benzyl-3-(naphthalene-1-sulfonyl)-1H-indazol-5-yloxy]-ethyl ester (0.432 g, 0.705 mmol) in 2.0 M dimethylamine in THF (8.0 mL, 16 mmol) was stirred at 70° C. in a sealed tube for 3 hours. After cooling somewhat, the reaction mixture was solvent evaporated and partitioned in ethyl acetate and aqueous sodium bicarbonate. The organic phase was then washed with water and brine. It was dried with anhydrous magnesium sulfate, filtered and concentrated. Drying at 80° C. in vacuo for 20 minutes gave {2-[1-benzyl-3-(naphthalene-1-sulfonyl)-1H-indazol-5-yloxy]-ethyl}-dimethyl-amine as a yellow solid (0.288 g, 84.2% mmol). This was dissolved in chloroform, and ethereal hydrochloride was added. The mixture was concentrated and dried for 13 hours in vacuo at 81° C. The result was the hydrochloride as a buff foam (0.294 g); Mass Spectrum (+EI, [M+H]$^+$) m/z 486. $^1$HNMR (500 MHz, DMSO-d$_6$): δ10.11 (s, 1H), 8.74-8.77 (m, 1H), 8.54-8.56 (m, 1H), 8.27 (d, 1H, J=8.30 Hz), 8.03-8.05 (m, 1H), 7.79 (d, 1H, J=9.15 Hz), 7.70-7.74 (m, 1H), 7.58-7.65 (m, 2H), 7.30 (d, 1H, J=2.20 Hz), 7.08-7.19 (m, 6H), 5.70 (s, 2H), 4.34-4.37 (m, 2H), 3.48 (t, 2H, J=4.76 Hz), 2.80 ppm (s, 6H). Elemental Analysis for C$_{28}$H$_{27}$N$_3$O$_3$S.1.00 HCl.1.55 mol H$_2$O: Calcd: C, 61.15; H, 5.70; N, 7.64; Found: C, 61.33; H, 5.59; N, 7.24.

EXAMPLE 52

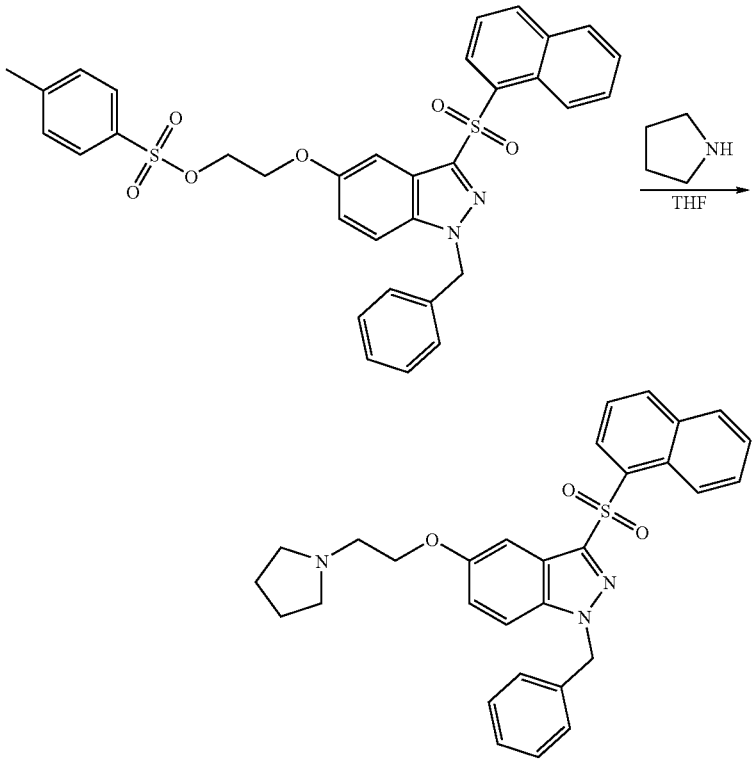

1-Benzyl-3-(naphthalene-1-sulfonyl)-5-(2-pyrrolidin-1-yl-ethoxy)-1H-indazole

A solution of toluene-4-sulfonic acid 2-[1-benzyl-3-(naphthalene-1-sulfonyl)-1H-indazol-5-yloxy]-ethyl ester (0.379 g, 0.619 mmol) and pyrrolidine (1.0 mL, 12 mmol) in THF (80 mL) was stirred at 70° C. in a sealed tube for 3 hours. The reaction mixture was solvent evaporated and partitioned in ethyl acetate and aqueous sodium bicarbonate. The organic phase was then washed with water and brine. It was dried with anhydrous magnesium sulfate, filtered and concentrated. Drying at 80° C. in vacuo for 25 minutes gave 1-benzyl-3-(naphthalene-1-sulfonyl)-5-(2-pyrrolidin-1-yl-ethoxy)-1H-indazole as a yellow-orange solid (0.259 g, 82.0% mmol). This was dissolved in chloroform, and ethereal hydrochloride was added. The mixture was concentrated and dried for 13 hours in vacuo at 81° C. The result was the hydrochloride as a buff foam (0.267 g); Mass Spectrum (+EI, [M+H]$^+$) m/z 512.

$^1$HNMR (500 MHz, DMSO-d$_6$): δ10.42 (s, 1H), 8.74-8.77 (m, 1H), 8.56 (dd, 1H, J=7.44 Hz and 1.22 Hz), 8.27 (d, 1H, J=8.30 Hz), 8.02-8.05 (m, 1H), 7.79 (d, 1H, J=9.27 Hz), 7.70-7.74 (m, 1H), 7.55-7.65 (m, 2H), 7.28 (d, 1H, J=2.07 Hz), 7.08-7.20 (m, 6H), 5.70 (s, 2H), 4.33-4.36 (m, 2H), 3.54 (br, s, 4H), 3.07 (s, br, 2H), 1.79-2.01 ppm (m, 4H). Elemental Analysis for C$_{30}$H$_{29}$N$_3$O$_3$S.1.00 HCl.1.25 mol H$_2$O: Calcd: C, 63.15; H, 5.74; N, 7.36; Found: C, 62.82; H, 5.74; N, 6.99.

EXAMPLE 53

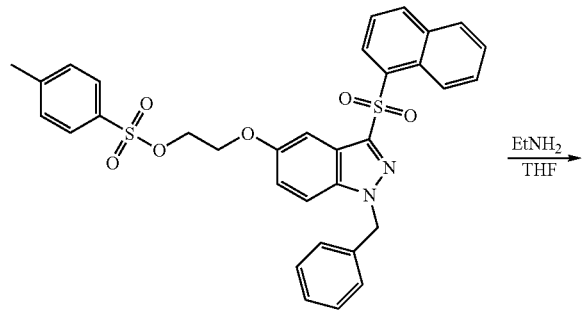

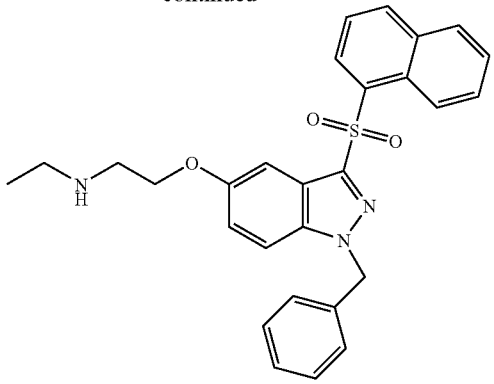

{2-[1-Benzyl-3-(naphthalene-1-sulfonyl)-1H-indazol-5-yloxy]-ethyl}-ethyl-amine

A solution of toluene-4-sulfonic acid 2-[1-benzyl-3-(naphthalene-1-sulfonyl)-1H-indazol-5-yloxy]-ethyl ester (0.430 g, 0.702 mmol) and 2.0 M ethylamine in THF (4.8 mL, 9.6 mmol) was stirred at 70° C. in a sealed tube for 3 hours. After cooling to ambient temperature, the reaction mixture was solvent evaporated and partitioned in ethyl acetate and aqueous sodium bicarbonate. The organic phase was washed with water and brine. It was dried with anhydrous magnesium sulfate, filtered and concentrated. The residue was purified by flash chromatography with 5.0-7.5% methanol in chloroform and by HPLC with 5-50% (chloroform/methanol (8:2)/TEA) in heptane/TEA. The result was {2-[1-benzyl-3-(naphthalene-1-sulfonyl)-1H-indazol-5-yloxy]-ethyl}-ethyl-amine as a yellow semi-solid (0.0528 g, 15.5%). This was dissolved in chloroform, and ethereal hydrochloride was added. The mixture was concentrated and dried for 14 hours at 82° C. in vacuo to give the hydrochloride as a light orange semi-solid (0.0546 g); Mass Spectrum (+EI, [M+H]$^+$) m/z 486. $^1$HNMR (500 MHz, DMSO-d$_6$): δ8.74-8.77 (m, 1H), 8.65-8.72 (br, s, 2H), 8.55 (dd, 1H, J=7.32 Hz and 1.22 Hz), 8.26-8.28 (m, 1H), 8.03-8.05 (m, 1H), 7.79 (d, 1H, J=9.15 Hz), 7.70-7.74 (m, 1H), 7.58-7.65 (m, 2H), 7.27 (d, 1H, J=2.07 Hz), 7.09-7.18 (m, 6H), 5.70 (s, 2H), 4.23-4.26 (m, 2H), 3.29-3.32 (m, 2H), 2.97-3.02 (m, 2H), 1.16-1.19 ppm (m, 3H). Elemental Analysis for C$_{28}$H$_{27}$N$_3$O$_3$S.1.00 HCl.0.80 mol H$_2$O: Calcd: C, 62.69; H, 5.56; N, 7.83; Found: C, 62.38; H, 5.38; N, 7.58.

EXAMPLE 54

{2-[1-(3-Chloro-benzyl)-3-(naphthalene-1-sulfonyl)-1H-indazol-5-yloxy]-ethyl}-dimethyl-amine Step 1

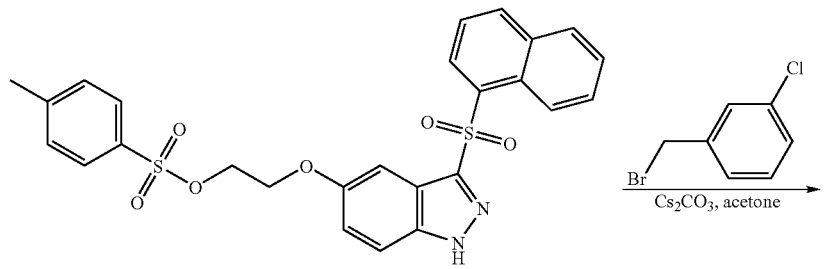

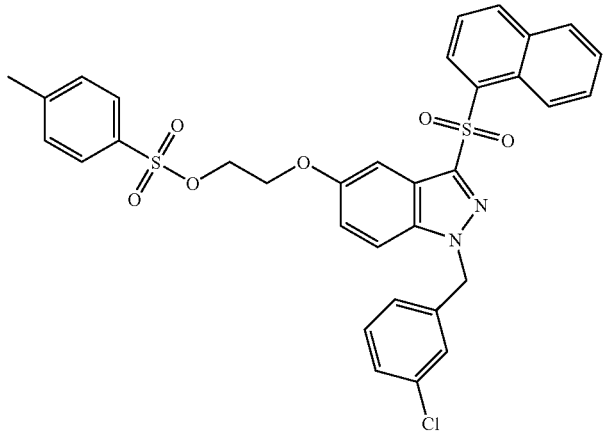

Toluene-4-sulfonic acid 2-[1-(3-chloro-benzyl)-3-(naphthalene-1-sulfonyl)-1H-indazol-5-yloxy]-ethyl ester 3-Chlorobenzylbromide (0.90 mL, 6.8 mmol) was added to a stirring suspension of toluene-4-sulfonic acid 2-[3-(naphthalene-1-sulfonyl)-1H-indazol-5-yloxy]-ethyl ester (3.24 g, 6.20 mmol) and cesium carbonate (2.21 g, 6.78 mmol) in acetone (80 mL). The mixture was stirred at ambient temperature under nitrogen for 2 hours. It was then poured into excess water and extracted with chloroform. The organic phase was washed with brine, dried with anhydrous magnesium sulfate, filtered and concentrated. The residue was purified by flash chromatography using 30-35% ethyl acetate in hexane. Drying at 65° C. in vacuo for 30 minutes gave toluene-4-sulfonic acid 2-[1-(3-chloro-benzyl)-3-(naphthalene-1-sulfonyl)-1H-indazol-5-yloxy]-ethyl ester as a dark yellow foam (2.55 g, 63.6%); Mass Spectrum (+EI, [M+H]$^+$) m/z 647. $^1$HNMR (500 MHz, DMSO-d$_6$): δ8.73-8.75 (m, 1H), 8.55-8.57 (m, 1H), 8.27 (d, 1H, J=8.30 Hz), 8.01-8.04 (m, 1H), 7.67-7.75 (m, 4H), 7.56-7.63 (m, 2H), 7.17-7.27 (m, 5H), 7.05-7.07 (m, 2H), 6.98 (dd, 1H, J=9.28 Hz and 2.32 Hz), 5.71 (s, 2H), 4.31-4.33 (m, 2H), 4.15-4.17 (m, 2H), 2.17 ppm (s, 3H). Elemental Analysis for $C_{33}H_{27}ClN_2O_6S_2$: Calcd: C, 61.25; H, 4.21; N, 4.33; Found: C, 60.93; H, 4.22; N, 4.21.

Step 2

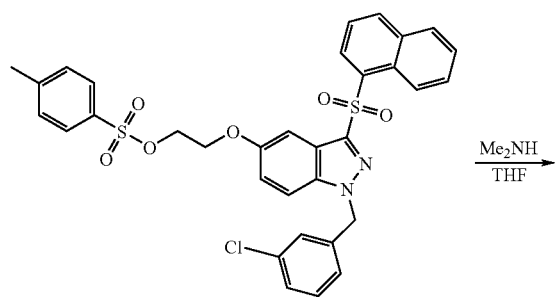

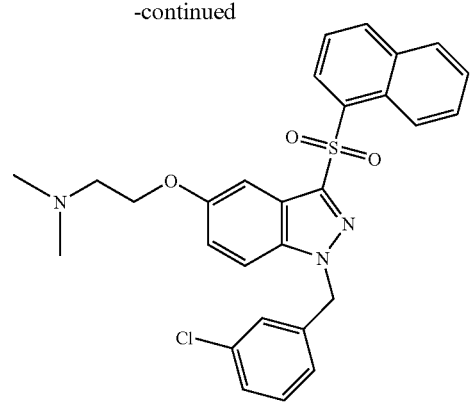

{2-[1-(3-Chloro-benzyl)-3-(naphthalene-1-sulfonyl)-1H-indazol-5-yloxy]-ethyl}-dimethyl-amine A solution of toluene-4-sulfonic acid 2-[1-(3-chloro-benzyl)-3-(naphthalene-1-sulfonyl)-1H-indazol-5-yloxy]-ethyl ester (0.344 g, 0.532 mmol) in 2.0 M dimethylamine in THF (8.0 mL, 16.0 mmol) was stirred at 70° C. in a sealed tube for 2 hours. After cooling to ambient temperature, the reaction mixture was solvent evaporated. It was partitioned with ethyl acetate and aqueous sodium bicarbonate. The organic phase was washed with brine, dried with anhydrous magnesium sulfate, filtered and concentrated. Drying at 80° C. in vacuo for 20 minutes gave {2-[1-(3-chloro-benzyl)-3-(naphthalene-1-sulfonyl)-1H-indazol-5-yloxy]-ethyl}-dimethyl-amine as a dark yellow gum (0.261 g, 94.6%). This was dissolved in chloroform, and ethereal hydrochloride was added. The mixture was concentrated and dried in vacuo at 82° C. for 14 hours. The result was the hydrochloride as a light orange foam (0.252 g); Mass Spectrum (+EI, [M+H]$^+$) m/z 520. $^1$HNMR (500 MHz, DMSO-d$_6$): δ9.92-9.94 (br, s, 1H), 8.73-8.75 (m, 1H), 8.56 (dd, 1H, J=7.32 Hz and 1.10 Hz), 8.27 (d, 1H, J=8.29 Hz), 8.02-8.05 (m, 1H), 7.82 (d, 1H, J=9.15 Hz), 7.70-7.74 (m, 1H), 7.58-7.64 (m, 2H), 7.31 (d, 1H, J=2.32 Hz), 7.15-7.27 (m, 3H), 7.04 (d, 1H, J=7.68 Hz), 5.73 (s, 2H), 4.34-4.37 (m, 2H), 3.47-3.49 (m, 2H), 2.81 ppm (s, 6H).

EXAMPLE 55

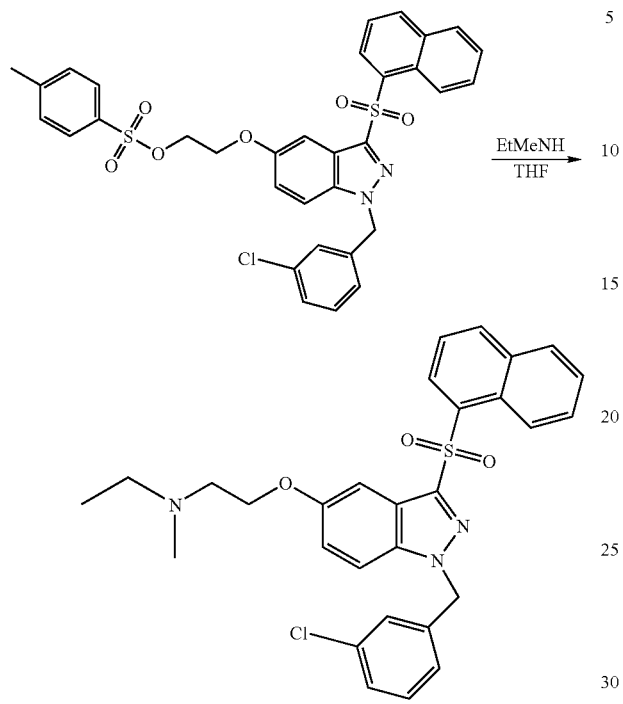

{2-[1-(3-Chloro-benzyl)-3-(naphthalene-1-sulfonyl)-1H-indazol-5-yloxy]-ethyl}-ethyl-methyl-amine A solution of toluene-4-sulfonic acid 2-[1-(3-chloro-benzyl)-3-(naphthalene-1-sulfonyl)-1H-indazol-5-yloxy]-ethyl ester (0.350 g, 0.541 mmol) and ethylmethylamine (1.0 mL, 12 mmol) in THF (8 mL) was stirred for 2 hours in a sealed tube at 70° C. Additional ethylmethylamine (1.0 mL, 12 mmol) was added, and the reaction mixture was stirred at 80° C. in sealed tube for 2 hours. After cooling to ambient temperature, the reaction mixture was solvent evaporated and partitioned in ethyl acetate and aqueous sodium bicarbonate. The organic phase was then washed with brine, dried with anhydrous magnesium sulfate, filtered and concentrated. It was dried at 80° C. for 20 minutes in vacuo to yield {2-[1-(3-chloro-benzyl)-3-(naphthalene-1-sulfonyl)-1H-indazol-5-yloxy]-ethyl}-ethyl-methyl-amine as a yellow semi-solid (0.268 g, 92.7%). This was dissolved in chloroform, and ethereal hydrochloride was added. The mixture was then concentrated and dried in vacuo at 82° C. for 14 hours. The result was the hydrochloride as a light orange foam (0.266 g); Mass Spectrum (+EI, [M+H]$^+$) m/z 534. $^1$HNMR (500 MHz, DMSO-$d_6$): δ9.90-9.93 (s, br, 1H), 8.73-8.75 (m, 1H), 8.54-8.57 (m, 1H), 8.27 (d, 1H, J=8.29 Hz), 8.02-8.05 (m, 1H), 7.82 (d, 1H, J=9.27 Hz), 7.70-7.74 (m, 1H), 7.56-7.63 (m, 2H), 7.30 (d, 1H, J=2.20 Hz), 7.15-7.26 (m, 4H), 7.04 (d, 1H, J=7.57 Hz), 5.73 (s, 2H), 4.36-4.38 (m, 2H), 3.40-3.55 (m, 3H), 3.09-3.14 (br, 1H), 2.78 (s, 3H), 1.19-1.23 ppm (m, 3H). Elemental Analysis for $C_{29}H_{28}ClN_3O_3S \cdot 1.00$ HCl$\cdot 0.75$ mol $H_2O$: Calcd: C, 59.64; H, 5.26; N, 7.19; Found: C, 59.24; H, 5.17; N, 6.89.

EXAMPLE 56

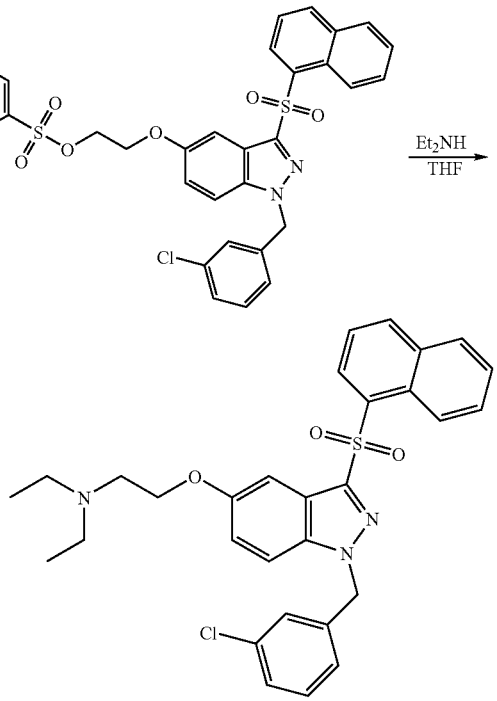

{2-[1-(3-Chloro-benzyl)-3-(naphthalene-1-sulfonyl)-1H-indazol-5-yloxy]-ethyl}-diethyl-amine A solution of toluene-4-sulfonic acid 2-[1-(3-chloro-benzyl)-3-(naphthalene-1-sulfonyl)-1H-indazol-5-yloxy]-ethyl ester (0.338 g, 0.522 mmol) and diethylamine (1.0 mL, 9.7 mmol) in THF (8 mL) was stirred at 70° C. in a sealed tube for 2 hours. Additional diethylamine (1.0 mL, 9.7 mmol) added, and the reaction mixture was stirred at 80° C. in a sealed tube for 2 hours. A third portion of diethylamine (1.0 mL, 9.7 mmol) was added to the reaction mixture, and it was stirred at 80° C. in a sealed tube for 30 hours. The reaction mixture was then solvent evaporated and partitioned in ethyl acetate and brine. It was dried with anhydrous magnesium sulfate, filtered and concentrated. Drying at 80° C. in vacuo for 20 minutes yielded {2-[1-(3-chloro-benzyl)-3-(naphthalene-1-sulfonyl)-1H-indazol-5-yloxy]-ethyl}-diethyl-amine as a light brown semi-solid (0.278 g, 97.2%). It was dissolved in chloroform, and ethereal hydrochloride was added. The mixture was concentrated and dried in vacuo at 82° C. for 14 hours. The result was the hydrochloride as a brown foam (0.275 g); Mass Spectrum (+EI, [M+H]$^+$) m/z 548. $^1$HNMR (500 MHz, DMSO-$d_6$): δ9.86-9.88 (s, 1H), 8.72-8.75 (m, 1H), 8.56 (dd, 1H, J=7.44 Hz and 1.22 Hz), 8.27 (d, 1H, J=8.30 Hz), 8.02-8.05 (m, 1H), 7.82 (d, 1H, J=9.15 Hz), 7.70-7.74 (m. 1H), 7.57-7.63 (m, 2H), 7.29 (d, 1H, J=2.20 Hz), 7.24-7.26 (m, 1H), 7.15-7.21 (m, 3H), 7.03 (d, 1H, J=7.68 Hz), 5.73 (s, 2H), 4.35-4.38 (m, 2H), 3.49 (d, br, 2H, J=4.52 Hz), 3.14-3.25 (m, 4H), 1.19-1.23 ppm (m, 6H). Elemental Analysis for $C_{30}H_{30}ClN_3O_3S \cdot 1.00$ HCl$\cdot 0.55$ mol $H_2O$: Calcd: C, 60.61; H, 5.44; N, 7.07; Found: C, 60.21; H, 5.44; N, 6.73.

EXAMPLE 57

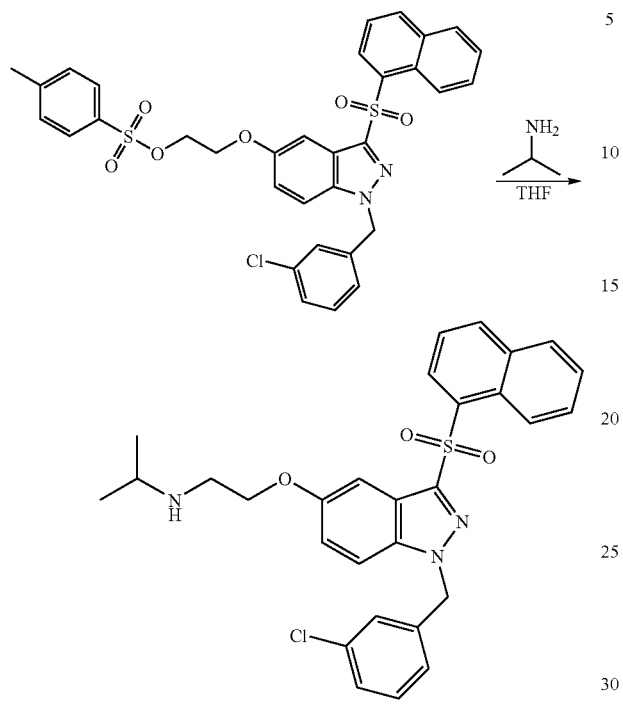

{2-[1-(3-Chloro-benzyl)-3-(naphthalene-1-sulfonyl)-1H-indazol-5-yloxy]-ethyl}-isopropyl-amine A solution of toluene-4-sulfonic acid 2-[1-(3-chloro-benzyl)-3-(naphthalene-1-sulfonyl)-1H-indazol-5-yloxy]-ethyl ester (0.339 g, 0.524 mmol) and isopropylamine (1.0 mL, 12 mmol) in THF (8 mL) was stirred at 70° C. in a sealed tube for 2 hours. Isopropylamine (1.0 mL, 12 mmol) was added, and the reaction mixture was stirred at 80° C. in a sealed tube for 2 hours. Isopropylamine (1.0 mL, 12 mmol) was added to the reaction mixture, and it was stirred at 80° C. in a sealed tube for 30 hours. After cooling to ambient temperature, the reaction mixture was solvent evaporated and partitioned in ethyl acetate and aqueous sodium bicarbonate. It was washed with brine, dried with anhydrous magnesium sulfate, filtered, concentrated and dried in vacuo for 20 minutes at 80° C. to give {2-[1-(3-chloro-benzyl)-3-(naphthalene-1-sulfonyl)-1H-indazol-5-yloxy]-ethyl}-isopropyl-amine as a yellow solid (0.280 g, 100%). It was dissolved in chloroform, and ethereal hydrochloride was added. The resulting solid was filtered and dried at 82° C. in vacuo for 14 hours. The result was the hydrochloride as a pale yellow solid (0.236 g): MP: 206-8° C.; Mass Spectrum (+EI, [M+H]$^+$) m/z 534. $^1$HNMR (500 MHz, DMSO-d$_6$): δ8.65-8.76 (m, 3H), 8.54-8.56 (m, 1H), 8.27 (d, 1H, J=8.17 Hz), 8.02-8.05 (m, 1H), 7.82 (d, 1H, J=9.27 Hz), 7.72 (dd, 1H, J=8.07 Hz and 7.57 Hz), 7.57-7.63 (m, 2H), 7.24-7.28 (m, 2H), 7.16-7.21 (m, 3H), 7.05 (d, 1H, J=7.81 Hz), 5.73 (s, 2H), 4.27 (t, 2H, J=5.00 Hz), 3.31-3.37 (m, 3H), 1.23 ppm (d, 6H, J=6.69 Hz). Elemental Analysis for C$_{29}$H$_{28}$ClN$_3$O$_3$S.1.00 HCl: Calcd: C, 61.05; H, 5.12; N, 7.36; Found: C, 60.68; H, 5.26; N, 7.14.

EXAMPLE 58

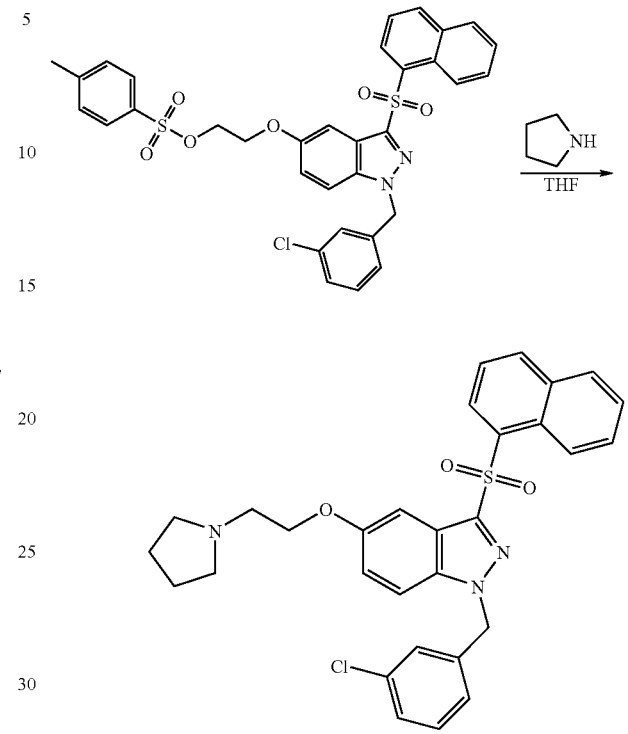

1-(3-Chloro-benzyl)-3-(naphthalene-1-sulfonyl)-5-(2-pyrrolidin-1-yl-ethoxy)-1H-indazole A solution of toluene-4-sulfonic acid 2-[1-(3-chloro-benzyl)-3-(naphthalene-1-sulfonyl)-1H-indazol-5-yloxy]-ethyl ester (0.359 g, 0.555 mmol) and pyrrolidine (1.0 mL, 12 mmol) in THF (8 mL) was stirred at 70° C. in a sealed tube for 2 hours. After cooling to ambient temperature, the reaction mixture was solvent evaporated. It was then partitioned in ethyl acetate and aqueous sodium bicarbonate. The organic phase was washed with brine, dried with anhydrous magnesium sulfate, filtered, concentrated and dried in vacuo at 80° C. for 20 minutes to give 1-(3-chloro-benzyl)-3-(naphthalene-1-sulfonyl)-5-(2-pyrrolidin-1-yl-ethoxy)-1H-indazole as a yellow semi-solid (0.266 g, 87.8%). This was dissolved in chloroform, and ethereal hydrochloride was added. The mixture was concentrated and dried at 82° C. in vacuo for 14 hours to yield the hydrochloride as a light orange foam (0.205 g); Mass Spectrum (+EI, [M+H]$^+$) m/z 546. $^1$HNMR (500 MHz, DMSO-d$_6$): δ10.18-10.19 (s, 1H), 8.73-8.75 (m, 1H), 8.55-8.57 (m, 1H), 8.27 (d, 1H, J=8.30 Hz), 8.02-8.04 (m, 1H), 7.82 (d, 1H, J=9.15 Hz), 7.70-7.74 (m, 1H), 7.57-7.64 (m, 2H), 7.15-7.29 (m, 5H), 7.04 (d, 1H, J=7.69 Hz), 5.73 (s, 2H), 4.33-4.35 (m, 2H), 3.55 (br, s, 4H), 3.07-3.15 (s, br, 2H), 1.81-2.02 ppm (br, m, 4H). Elemental Analysis for C$_{30}$H$_{28}$ClN$_3$O$_3$S.1.00 HCl.0.70 mole H$_2$O: Calcd: C, 60.54; H, 5.15; N, 7.06; Found: C, 60.16; H, 5.11; N, 6.74.

EXAMPLE 59

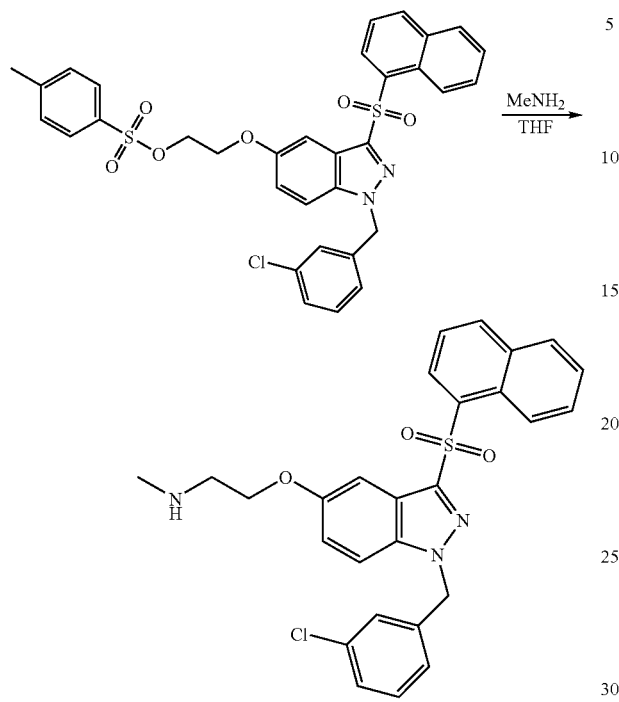

{2-[1-(3-Chloro-benzyl)-3-(naphthalene-1-sulfonyl)-1H-indazol-5-yloxy]-ethyl}-methyl-amine A solution of toluene-4-sulfonic acid 2-[1-(3-chloro-benzyl)-3-(naphthalene-1-sulfonyl)-1H-indazol-5-yloxy]-ethyl ester (0.367 g, 0.567 mmol) in 2.0 M methylamine in THF (8.0 mL, 16 mmol) was stirred at 70° C. in a sealed tube for 2 hours. After cooling to ambient temperature, the reaction mixture was solvent evaporated. The residue was partitioned in ethyl acetate and aqueous sodium bicarbonate. The organic phase was then washed with brine, dried with anhydrous magnesium sulfate, filtered and concentrated. The residue was purified by HPLC with 25-60% (chloroform/methanol 8:2/TEA) in heptane/TEA. Concentration and drying at 60° C. in vacuo yielded {2-[1-(3-chloro-benzyl)-3-(naphthalene-1-sulfonyl)-1H-indazol-5-yloxy]-ethyl}-methyl-amine as a light yellow foam (0.190 g, 66.2%). This was dissolved in chloroform, and ethereal hydrochloride was added. The mixture was then concentrated and dried in vacuo for 29 hours at 80° C. The hydrochloride as an off-white foam resulted (0.206 g); Mass Spectrum (+EI, [M+H]$^+$) m/z 506. $^1$HNMR (500 MHz, DMSO-d$_6$): δ8.71-8.76 (m, 3H), 8.54-8.56 (m, 1H), 8.27 (d, 1H, J=8.30 Hz), 8.02-8.05 (m, 1H), 7.82 (d, 1H, J=9.27 Hz), 7.70-7.74 (m, 1H), 7.57-7.63 (m, 2H), 7.24-7.28 (m, 2H), 7.16-7.20 (m, 3H), 7.05 (d, 1H, J=7.69 Hz), 5.73 (s, 2H), 4.24-4.26 (m, 2H), 3.30-3.32 (m, 2H), 2.60 ppm (s, 4H). Elemental Analysis for $C_{27}H_{24}ClN_3O_3S.1.00$ HCl.1.50 mole H$_2$O: Calcd: C, 56.94; H, 4.96; N, 7.38; Found: C, 56.64; H, 4.88; N, 7.06.

EXAMPLE 60

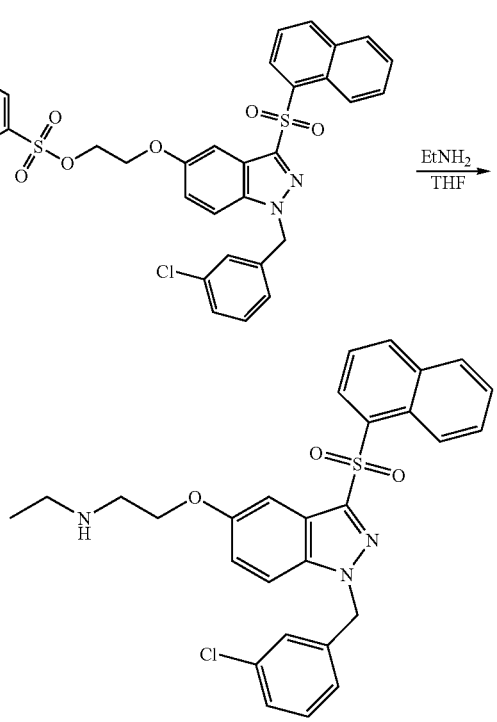

{2-[1-(3-Chloro-benzyl)-3-(naphthalene-1-sulfonyl)-1H-indazol-5-yloxy]-ethyl}-ethyl-amine A solution of toluene-4-sulfonic acid 2-[1-(3-chloro-benzyl)-3-(naphthalene-1-sulfonyl)-1H-indazol-5-yloxy]-ethyl ester (0.415 g, 0.641 mmol) in 2.0 M ethylamine in THF (8.0 mL, 16.0 mmol) was stirred at 70° C. for 3 hours and then at 80° C. for 19 hours. The reaction mixture was allowed to cool to ambient temperature and solvent evaporated. It was partitioned in ethyl acetate and aqueous sodium bicarbonate. The organic phase was washed with brine, dried with magnesium sulfate, filtered and concentrated. Drying in vacuo at 80° C. for 20 minutes resulted in {2-[1-(3-chloro-benzyl)-3-(naphthalene-1-sulfonyl)-1H-indazol-5-yloxy]-ethyl}-ethyl-amine as an orange semi-solid (0.270 g, 81.1%). This was dissolved in chloroform, and ethereal hydrochloride was added. The mixture was concentrated and dried in vacuo at 83° C. for 16 hours. The hydrochloride as a pale orange foam resulted (0.276 g); Mass Spectrum (+EI, [M+H]$^+$) m/z 520. $^1$HNMR (500 MHz, DMSO-d$_6$): δ8.71-8.77 (m, 3H), 8.55 (dd, 1H, J=7.44 Hz and 1.22 Hz), 8.27 (d, 1H, J=8.29 Hz), 8.02-8.05 (m, 1H), 7.82 (d, 1H, J=9.15 Hz), 7.70-7.74 (m, 1H), 7.57-7.64 (m, 2H), 7.24-7.28 (m, 2H), 7.16-7.21 (m, 3H), 7.05 (d, 1H, J=7.56 Hz), 5.73 (s, 2H), 4.24-4.27 (m, 2H), 3.30-3.32 (m, 2H), 2.97-3.03 (m, 2H), 1.16-1.20 ppm (m, 3H). Elemental Analysis for $C_{28}H_{26}ClN_3O_3S.1.00$ HCl.0.60 mole H$_2$O: Calcd: C, 59.28; H, 5.01; N, 7.41; Found: C, 58.95; H, 5.06; N, 7.14.

EXAMPLE 61

3-(1-naphthylsulfonyl)-5-(4-piperidin-1-ylbutoxy)-1H-indazole

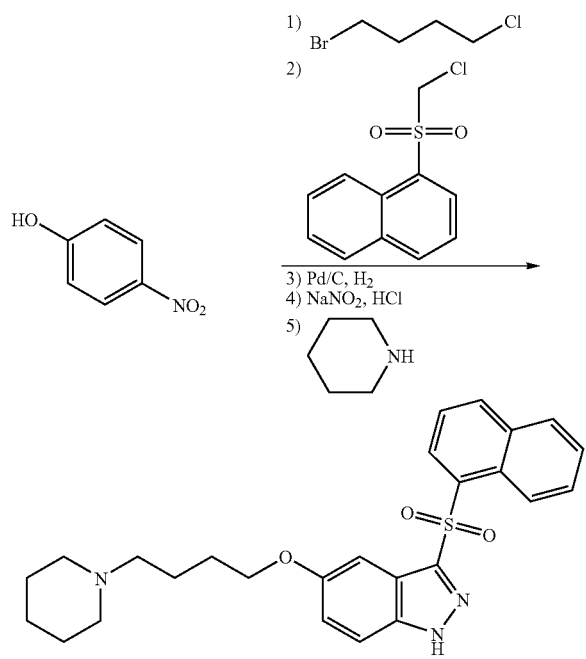

Step 1

1-(4-Chloro-butoxy)-4-nitro-benzene

A mixture of para-nitrophenol (0.83 g, 6 mmoles), 1-bromo-4-chloro-butane (1.23 g, 7.2 mmoles), and $K_2CO_3$ (1.24 g, 9 mmoles) was stirred together in DMF at 80° C. for 1 hour. Reaction mixture was diluted with $H_2O$, extracted with EtOAc, washed with water (2×), brine (1×), dried over $Na_2SO_4$, and concentrated under vacuum. The crude product was purified by HPLC using as eluent 30% EtOAc/hexane to afford the title compound as an off-white solid (1.28 g, 5.6 mmoles).

Step 2

1-[5-(4-Chloro-butoxy)-2-nitro-phenylmethanesulfonyl]-naphthalene

A mixture of 1-(4-chloro-butoxy)-4-nitrobenzene (1.28 g, 5.6 mmoles) and 1-chloromethane-sulfonyl-naphthalene (1.6 g, 6.72 mmoles) was stirred in THF (50 ml) at −78° C., in a round bottom flask under nitrogen. A solution of 1M potassium t-butoxide was added dropwise (16.8 ml, 16.8 mmoles) over a half an hour period. Temperature was allowed to rise to −40° C., and the reaction mixture was stirred at this temperature for 5 hours. The reaction mixture was poured into cold 2N HCl, extracted with EtOAc, dried over $Na_2SO_4$, and concentrated under vacuum. Compound was recrystallized from $CH_2Cl_2$/hexane to afford the title compound as an off-white solid (1.94 g, 4.5 mmoles).

Step 3

4-(4-Chloro-butoxy)-2-(naphthalene-1-sulfonylmethyl)-phenyl amine

A mixture of 1-[5-(4-chloro-butoxy)-2-nitro-phenylmethanesulfonyl]-naphthalene (1.94 g, 4.5 mmoles) and 10% Pd/C in THF (20 mL), methanol (20 mL), and formic acid (5 mL) was hydrogenated in a Parr hydrogenation bottle (250 mL) at 40 lb/in² for 20 hours. The mixture was filtered through Celite, and the filtrate was diluted with EtOAc, washed with water, dried over $Na_2SO_4$, and concentrated under vacuum. The crude product was purified by flash chromatography using as eluent 5% EtOAc/$CH_2Cl_2$ to afford the title compound as an off-white solid (1.54 g, 3.8 mmoles).

Step 4

5-(4-Chloro-butoxy)-3-(naphthalene-1-sulfonyl)-1-H-indazole

A mixture of 4-(4-chloro-butoxy)-2-(naphthalene-1-sulfonylmethyl)-phenyl amine (1.54 g, 3.8 mmoles) in THF (7 mL), and 4M HCl (15 mL) was stirred in a round bottom flask, under nitrogen, at 3° C. A solution of sodium nitrite (0.34 g, 4.0 mmoles) in $H_2O$ (1 mL) was added dropwise. The reaction mixture was poured into a cold solution of saturated sodium bicarbonate (100 mL) and extracted with EtOAc. Compound was dried over $Na_2SO_4$, and concentrated under vacuum to afford the title compound as an off white solid (1.55 g, 3.75 mmoles).

Step 5

A mixture of 5-(4-chloro-butoxy)-3-(naphthalene-1-sulfonyl)-1-H-indazole (0.065 g, 0.12 mmoles) and piperidine (0.48 mmoles) in DMF (1 mL) was stirred under nitrogen at 100° C. overnight. Mixture was cooled to room temperature, diluted with water, extracted with EtOAc, washed with water (2×), brine (1×), dried over $Na_2SO_4$, and concentrated under vacuum. Compound was purified by flash chromatography using as eluent 5% $CH_3OH$/EtOAc. The purified compound was dissolved in methanol, 1M HCl in ether (0.1 mL, 0.1 mmoles) was added, and the compound was dried to afford the title compound 3-(1-naphthylsulfonyl)-5-(4-piperidin-1-ylbutoxy)-1H-indazole as the HCl salt, MS: (ES⁺) 463 [M+H]⁺

EXAMPLES 62-67

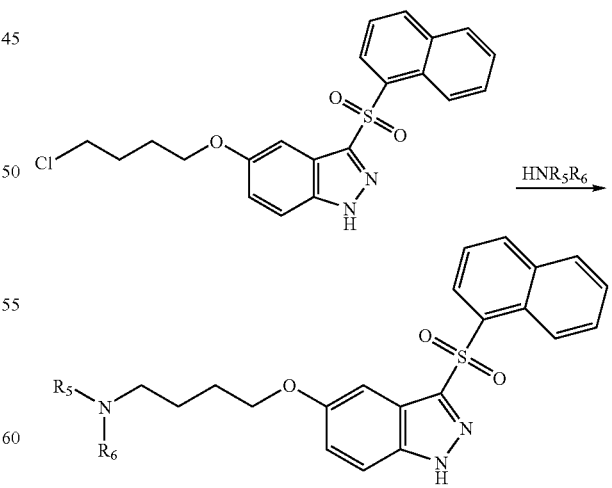

Using essentially the same procedure described in Example 61, Step 5 and employing an appropriate amine, the compounds shown on Table I were obtained and identified by HPLC and mass spectral analyses.

TABLE I

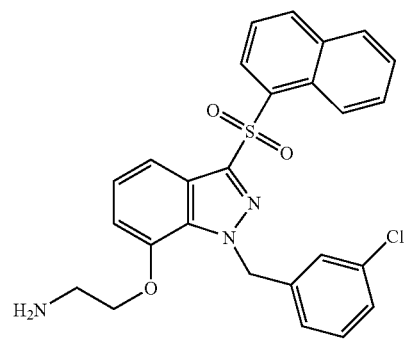

| Ex. No. | R5 | R6 | [M + H]+ |
|---|---|---|---|
| 62 | CH₃ | H | 465 |
| 63 | C₂H₅ | H | 424 |
| 64 | CH₃ | CH₃ | 424 |
| 65 | CH₃ | n-propyl | 452 |
| 66 | C₂H₅ | C₂H₅ | 452 |
| 67 | —CH₂CH₂CH₂CH₂— | | 450 |

EXAMPLE 68

(4-{[3-(1-naphthylsulfonyl)-1H-indazol-5-yl]oxy}butyl)amine

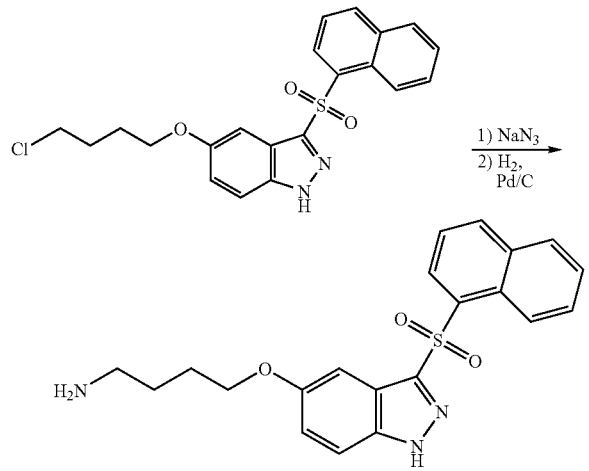

Step 1

A mixture of 5-(4-chloro-butoxy)-3-(naphthalene-1-sulfonyl)-1-H-indazole (0.065 g, 0.12 mmoles) and sodium azide (0.24 mmoles) in DMSO (1 mL) was stirred under nitrogen at 90° C. for 5 hours. Mixture was cooled to room temperature, diluted with water, extracted with EtOAc, washed with water (2×), brine (1×), dried over Na₂SO₄, and concentrated under vacuum. Compound was purified by flash chromatography using as eluent 5% CH₃OH/EtOAc.

Step 2.

The azide prepared in step 1 was subjected to hydrogenation over 10% Pd/C in THF (2 mL), and methanol (8 mL) in a Parr hydrogenation bottle (250 mL) at 52 lb/in² for 2 hours. The mixture was filtered through Celite, and the filtrate was concentrated under vacuum. The crude product was recrystallized from CH₂Cl₂/hexane, 1M HCl in ether (0.9 ml, 0.9 mmoles) was added, then evaporated to afford the title compound—(4-{[3-(1-naphthylsulfonyl)-1H-indazol-5-yl]oxy}butyl)amine as an off-white HCl salt (0.04 g, 0.1 mmoles), MS: (ES⁻) 394[M−H]⁻

EXAMPLE 69

(2-{[1-(3-Chlorobenzyl)-3-(1-naphthylsulfonyl)-1-H-indazol-7-yl]oxy}ethyl) amine Step 1

1-(2-Chloro-ethoxy)-2-nitro-benzene

A mixture of ortho-nitrophenol (5.0 g, 35.8 mmoles) and 2-chloroethanol (9.5 ml, 143 mmoles) in THF (50 mL), in a round bottom flask, under nitrogen, was stirred at room temperature. Triphenylphosphine (14 g, 53.7 mmoles) was added, followed by diethylazodicarboxylate dropwise (8.5 mL, 53.7 mmoles). The reaction mixture was stirred overnight at room temperature. The reaction mixture was diluted with water, extracted with EtOAc, washed with water (1×), brine (1×), dried (Na₂SO₄), and concentrated under vacuum. The crude product was purified by flash chromatography using as eluent 40% EtOAc/hexane to give the title compound as an off-white solid (5.6 g, 28 mmoles).

Step 2

1-Chloromethane-sulfonyl-naphthalene

A mixture of naphthalene-1-sulfonyl chloride (10.0 g, 44 mmoles), sodium sulfite (11.12 g, 88 mmoles), and sodium bicarbonate (7.4 g, 88 mmoles) in water (50 mL) was heated to 100° C. for one hour. The crude sodium sulfinate solution was allowed to cool for 30 minutes, and then treated with bromochloromethane (43 mL, 661 mmoles) and tetra-N-butylammonium bromide (1.4 g, 4.4 mmoles). The resultant mixture was heated to 75° C. overnight. All solvents were removed under vacuum. Compound was recrystallized from CH₂Cl₂/hexane to give the title compound as an off white solid (10.62 g, 44 mmoles).

Step 3

1-[3-(2-Chloro-ethoxy)-2-nitro-phenyl-methane-sulfonyl]-naphthalene

A mixture of 1-(2-chloro-ethoxy)-2-nitrobenzene (1.2 g, 6 mmoles) and 1-chloromethane-sulfonyl-naphthalene (2.16 g, 9 mmoles) was stirred in THF (50 ml) at −78° C., in a round bottom flask under nitrogen. A solution of 1M potassium t-butoxide was added drop wise (18 mL, 18 mmoles) over a half an hour period. Temperature was allowed to rise to −40° C., and the reaction mixture was stirred at this temperature for 5 hours. The reaction mixture was poured into cold 2N HCl, extracted with EtOAc, dried over $Na_2SO_4$, and concentrated under vacuum. Compound was recrystallized from $CH_2Cl_2$/hexane to afford the title compound as an off-white solid (1.4 g, 3 mmoles).

Step 4

2-(2-Chloro-ethoxy)-6-(naphthalene-1-sulfonylmethyl)-phenyl amine

A mixture of 1-[3-(2-chloro-ethoxy)-2-nitro-phenyl-methanesulfonyl]-naphthalene (1.24 g, 3.5 mmoles) and 10% Pd/C in THF (20 mL), methanol (5 mL), and formic acid (5 mL) was hydrogenated in a Parr hydrogenation bottle (250 mL) at 40 lb/in$^2$ for 20 hours. The mixture was filtered through Celite, and the filtrate was diluted with EtOAc, washed with water, dried over $Na_2SO_4$, and concentrated under vacuum. The crude product was purified by flash chromatography using as eluent 5% EtOAc/$CH_2Cl_2$ to afford the title compound as an off-white solid (1.0 g, 3.1 mmoles).

Step 5

7-(2-Chloro-ethoxy)-3-(naphthalene-1-sulfonyl)-1-H-indazole

A mixture of 2-(2-chloro-ethoxy)-6-(naphthalene-1-sulfonylmethyl)-phenyl amine (0.97 g, 3 mmoles) in THF (7 mL), and 4M HCl (15 mL) was stirred in a round bottom flask, under nitrogen, at 3° C. A solution of sodium nitrite (0.21 g, 3.15 mmoles) in $H_2O$ (1 mL) was added dropwise. The reaction mixture was poured into a cold solution of saturated sodium bicarbonate (100 mL) and extracted with EtOAc. Compound was dried over $Na_2SO_4$, and concentrated under vacuum to afford the title compound as an off white solid (0.9 g, 2.7 mmoles).

Step 6

1-(3-Chloro-benzyl)-7-(2-chloro-ethoxy)-3-(naphthalene-1-sulfonyl)-1-H-indazole

A mixture of 7-(2-chloro-ethoxy)-3-(naphthalene-1-sulfonyl)-1-H-indazole (0.7 g, 1.8 mmoles), 3-chloro-benzyl bromide (0.28 mL, 2.17 mmoles), and cesium carbonate (0.7 g, 2.17 mmoles) in DMF (5 mL) was stirred together in a round bottom flask at room temperature for 30 minutes. Reaction mixture was diluted with $H_2O$, extracted with EtOAc, washed with water (2×), brine (1×), dried over $Na_2SO_4$, and concentrated under vacuum. The crude product was purified by HPLC using as eluent 30% EtOAc/hexane to afford the title compound as an off-white solid (0.55 g, 1.1 mmoles).

Step 7

7-(2-Azido-ethoxy)-3-(naphthalene-1-sulfonyl)-1-H-indazole

A mixture of 1-(3-chloro-benzyl)-7-(2-chloro-ethoxy)-3-(naphthalene-1-sulfonyl)-1-H-indazole (0.25 g, 0.49 mmoles) and sodium azide (0.04 g, 0.58 mmoles) in DMSO (3 mL) was stirred together in a round bottom flask under nitrogen at 90° C. for 3 hours. Reaction mixture was cooled to room temperature, diluted with water, extracted with EtOAC, washed with water (2×), brine (1×), dried over $Na_2SO_4$, and concentrated under vacuum to afford the title compound as an off white solid (0.23 g, 0.44 mmoles).

Step 8

(2-{[1-(3-Chlorobenzyl)-3-(1-naphthylsulfonyl)-1-H-indazol-7-yl]oxy}ethyl)amine

A mixture of 7-(2-azido-ethoxy)-3-(naphthalene-1-sulfonyl)-1-H-indazole (0.23 g, 0.44 mmoles) and 10% Pd/C in THF (2 mL), and methanol (5 mL) was hydrogenated in a Parr hydrogenation bottle (250 mL) at 52 lb/in$^2$ for 2 hours. The mixture was filtered through Celite, and the filtrate was concentrated under vacuum. The crude product was purified by flash chromatography using as eluent 5% $CH_3OH/CH_2Cl_2$ to afford an off-white solid (0.2 g, 0.4 mmoles), MS: (ES$^+$) 493 [M+H]$^+$

EXAMPLE 70

(2-{[1-(3-Chlorobenzyl)-3-(1-naphthylsulfonyl)-1-H-indazol-7-yl]oxy}ethyl) methylamine

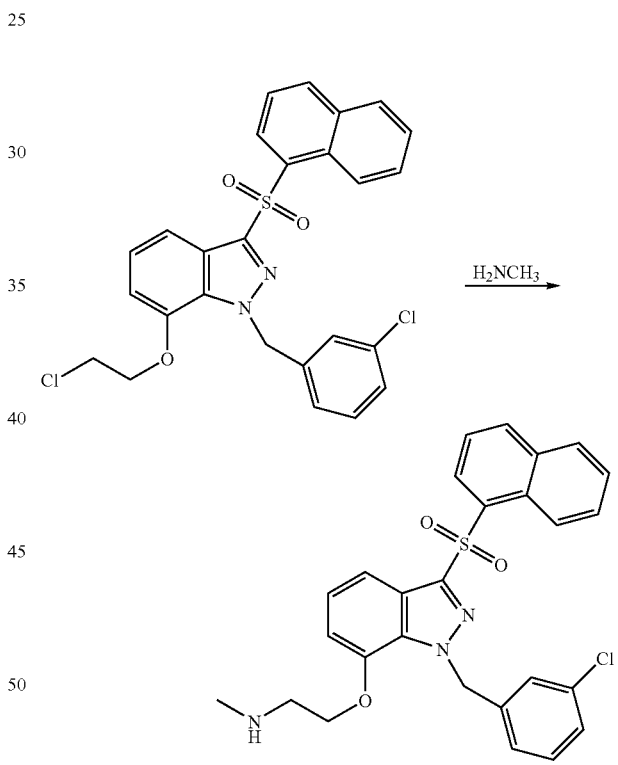

A mixture of 1-(3-chloro-benzyl)-7-(2-chloro-ethoxy)-3-(naphthalene-1-sulfonyl)-1-H-indazole (0.065 g, 0.12 mmoles) and methylamine (0.48 mmoles) in DMF (1 mL) was stirred under nitrogen at 100° C. overnight. Mixture was cooled to room temperature, diluted with water, extracted with EtOAc, washed with water (2×), brine (1×), dried over $Na_2SO_4$, and concentrated under vacuum. Compound was purified by flash chromatography using as eluent 5% $CH_3OH$/EtOAc. The purified compound was dissolved in methanol, 1M HCl in ether (0.1 mL, 0.1 mmoles) was added, and compound was dried to afford the title compound as the HCl salt, MS: (ES$^+$) 507 [M+H]$^+$.

EXAMPLES 71-75

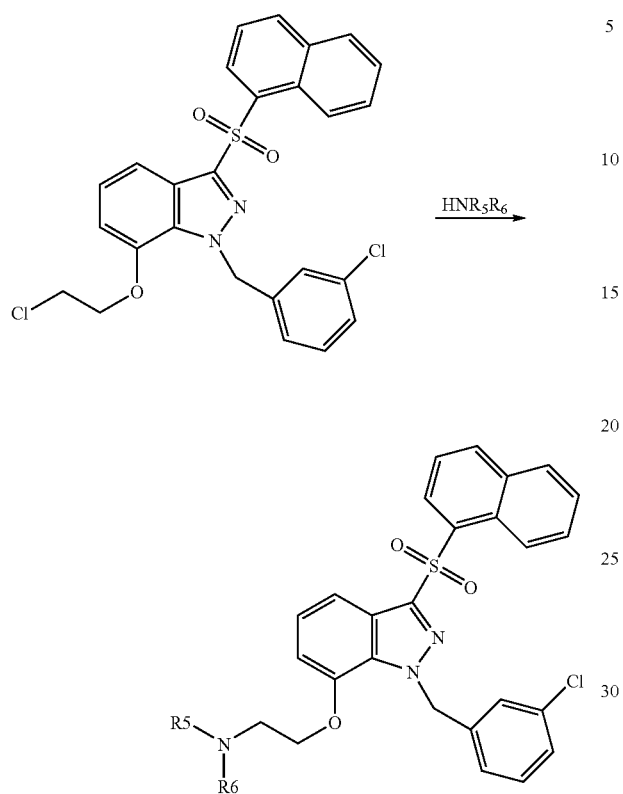

Using essentially the same procedure described in Example 70 and employing an appropriate amine, the compounds shown in Table II were obtained and identified by HPLC and mass spectral analyses.

TABLE II

| Ex. No. | R5 | R6 | [M + H]⁺ |
|---|---|---|---|
| 71 | $C_2H_5$ | H | 522 |
| 72 | $C_2H_5$ | $C_2H_5$ | 549 |
| 73 | n-butyl | H | 549 |
| 74 | —$CH_2CH_2CH_2CH_2CH_2$— | | 561 |
| 75 | —$CH_2CH_2CH_2CH_2$— | | 547 |

EXAMPLE 76

(2-{[3-(1-naphthylsulfonyl)-1-H-indazol-7-yl]oxy}ethyl)amine

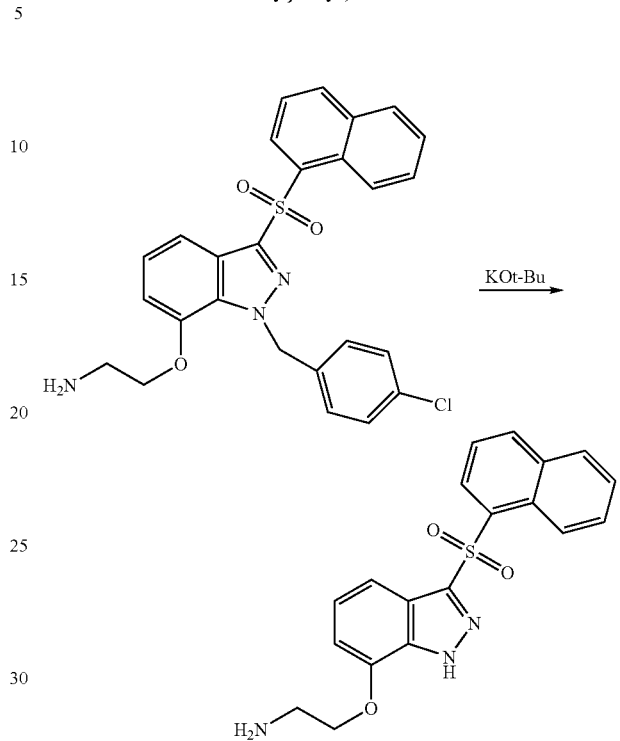

A mixture of 0.075 g of 1-(3-chlorobenzyl)-3-(1-naphthylsulfonyl)-7-(2-amine-1-ylethoxy)-1-H-indazole, DMSO (1 mL) and t-BuOH (0.2 mL) was stirred at room temperature in a round bottom flask under oxygen atmosphere. A solution of potassium t-butoxide (0.98 mL, 0.98 mmoles) was added dropwise and the reaction mixture stirred for 1 hr. Reaction mixture was quenched with saturated ammonium chloride, extracted with EtOAc, dried over $Na_2SO_4$, and concentrated under vacuum. Crude compound was purified by flash chromatography using 10% $CH_3OH/CH_2Cl_2$. The purified compounds were dissolved in methanol, 1M HCl in ether (0.1 mL, 0.1 mmoles) was added, and compound was dried to afford the title compound as the HCl salt, MS: (ES⁺) 368 [M+H]⁺.

EXAMPLES 77-81

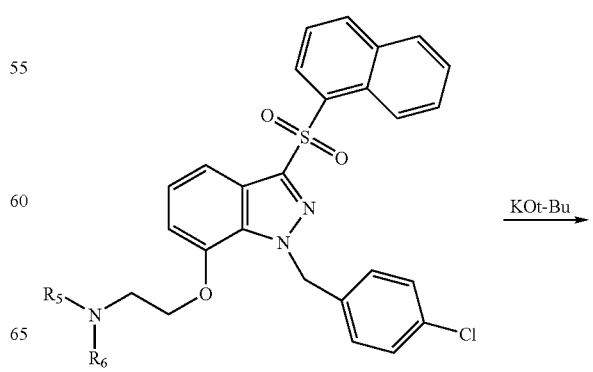

-continued

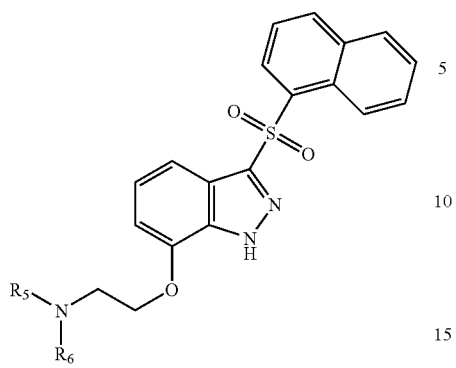

Using essentially the same procedure described in Example 76 and employing the appropriate indazol-7-yloxy-ethanamine substrate, the compounds shown in Table III were obtained and identified by HPLC and mass spectral analyses.

TABLE III

| Ex. No. | R5 | R6 | [M + H]⁺ |
|---|---|---|---|
| 77 | CH₃ | H | 382 |
| 78 | CH₃ | CH₃ | 396 |
| 79 | C₂H₅ | H | 396 |
| 80 | —CH₂CH₂CH₂CH₂CH₂— | | 436 |
| 81 | —CH₂CH₂CH₂CH₂— | | 422 |

EXAMPLES 82-93

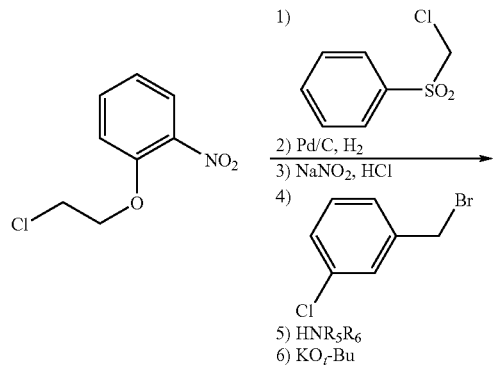

-continued

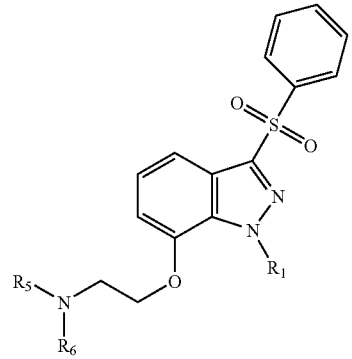

Step 1

1-Benzene-sulfonyl-methyl-3-(2-chloro-ethoxy)-2-nitro-benzene

A mixture of 1-(2-chloro-ethoxy)-2-nitrobenzene (1.2 g, 6 mmoles) and chloromethyl phenyl sulfone (2.16 g, 9 mmoles) was stirred in THF (50 mL) at −78° C., in a round bottom flask under nitrogen. A solution of 1M potassium t-butoxide was added dropwise (18 mL, 18 mmoles) over a half an hour period. Temperature was allowed to rise to −40° C., and the reaction mixture was stirred at this temperature for 5 hours. The reaction mixture was poured into cold 2N HCl, extracted with EtOAc, dried over Na₂SO₄, and concentrated under vacuum. Compound was recrystallized from CH₂Cl₂/hexane to afford the title compound as an off-white solid (1.5 g, 4.2 mmoles).

Steps 2-6

Using essentially the same procedures described in Example 69 steps 34, and Examples 70 and 76, the compounds shown in Table IV were obtained and identified by HPLC and mass spectral analyses.

TABLE IV

| Ex. No. | R1 | R5 | R6 | [M + H]⁺ |
|---|---|---|---|---|
| 82 | 3-Cl-benzyl | CH₃ | H | 457 |
| 83 | 3-Cl-benzyl | C₂H₅ | H | 471 |
| 84 | 3-Cl-benzyl | C₂H₅ | C₂H₅ | 499 |
| 85 | 3-Cl-benzyl | n-butyl | H | 499 |
| 86 | 3-Cl-benzyl | —CH₂CH₂CH₂CH₂— | | 497 |
| 87 | 3-Cl-benzyl | —CH₂CH₂CH₂CH₂CH₂— | | 511 |
| 88 | H | CH₃ | H | 332 |
| 89 | H | C₂H₅ | H | 346 |

TABLE IV-continued

| Ex. No. | R1 | R5 | R6 | [M + H]+ |
|---|---|---|---|---|
| 90 | H | $C_2H_5$ | $C_2H_5$ | 374 |
| 91 | H | n-butyl | H | 374 |
| 92 | H | —$CH_2CH_2CH_2CH_2$— | | 372 |
| 93 | H | —$CH_2CH_2CH_2CH_2CH_2$— | | 386 |

EXAMPLES 94-105

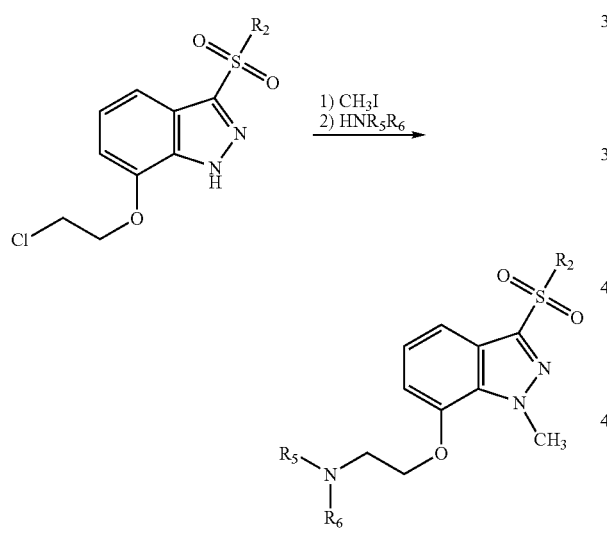

Step 1

7-(2-Chloro-ethoxy)-1-methyl-3-(naphthalene-1-sulfonyl)-1H-indazole

A mixture of 7-(2-chloro-ethoxy)-3-(naphthalene-1-sulfonyl)-1-H-indazole (0.7 g, 1.8 mmoles), methyl iodide (0.28 mL, 2.17 mmoles), and potassium carbonate (0.29 g, 2.17 mmoles) in DMF (10 mL) was stirred together in a round bottom flask at room temperature for 2 hours. Reaction mixture was diluted with $H_2O$, extracted with EtOAc, washed with water (2x), brine (1x), dried over $Na_2SO_4$, and concentrated under vacuum. The crude product was purified by HPLC using as eluent 30% EtOAc/hexane to afford the title compound as an off-white solid, 0.55 g, 1.375 mmoles.

Step 2

Using essentially the same procedure described in Example 70 and employing the appropriate 3-arylsulfonyl-1-methylindazole substrate and desired amine and conversion into HCl salts, the compounds shown in Table V are obtained and identified by HPLC and mass spectral analyses.

TABLE V

| Ex. No. | R2 | R5 | R6 | [M + H]+ |
|---|---|---|---|---|
| 94 | 1-naphthyl | H | H | 419 |
| 95 | 1-naphthyl | $C_2H_5$ | H | 410 |
| 96 | 1-naphthyl | $CH_3$ | $CH_3$ | 410 |
| 97 | 1-naphthyl | $C_2H_5$ | $C_2H_5$ | 438 |
| 98 | 1-naphthyl | n-butyl | H | 438 |
| 99 | 1-naphthyl | —$CH_2CH_2CH_2CH_2CH_2$— | | 450 |
| 100 | 1-naphthyl | —$CH_2CH_2CH_2CH_2$— | | 436 |
| 101 | phenyl | $CH_3$ | H | 346 |
| 102 | phenyl | $C_2H_5$ | H | 360 |
| 103 | phenyl | $C_2H_5$ | $C_2H_5$ | 388 |
| 104 | phenyl | —$CH_2CH_2CH_2CH_2$— | | 386 |
| 105 | phenyl | —$CH_2CH_2CH_2CH_2CH_2$— | | 400 |

EXAMPLE 106

(2-{[1-(3-Chlorobenzyl)-5-fluoro-3-(1-naphthylsulfonyl)-1H-indazol-7-yl]oxy}ethyl)amine

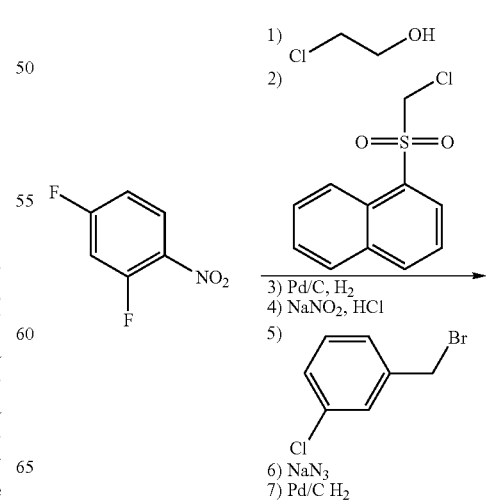

-continued

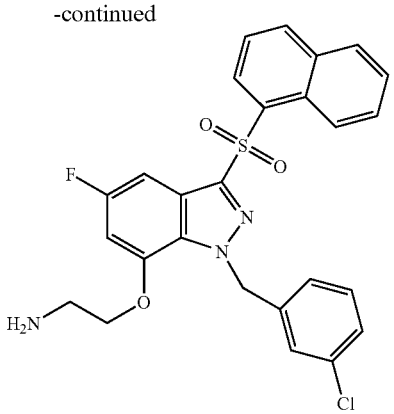

Step 1

2-(2-Chloro-ethoxy)-4-fluoro-1-nitro-benzene

In a round bottom flask under nitrogen, 2-chloro-ethanol (8.3 mL, 120 mmoles) in THF (40 mL) was cooled to 0° C. LDA (60 mL, 120 mmoles) was added dropwise, while maintaining the temperature constant at 0° C. The mixture was stirred at this temperature for 15 minutes, followed by the addition of 2,4-difluoronitrobenzene (11 mL, 100 mmoles). The mixture was stirred at room temperature overnight. Reaction mixture was diluted with water, extracted with EtOAc, washed with brine (1×), dried over $Na_2SO_4$, and concentrated under vacuum, to afford the title compound as an off-white solid (20.0 g, 91 mmoles).

Step 2

1-[3-(2-Chloro-ethoxy)-5-fluoro-2-nitro-phenylmethanesulfonyl]-naphthalene

A mixture of 2-(2-chloro-ethoxy)-4-fluoro-1-nitrobenzene (1.3 g, 6 mmoles) and 1-chloromethane-sulfonyl-naphthalene (2.16 g, 9 mmoles) was stirred in THF (50 mL) at −78° C., in a round bottom flask under nitrogen. A solution of 1M potassium t-butoxide was added drop wise (18 mL, 18 mmoles) over a half an hour period. Temperature was allowed to rise to −40° C., and the reaction mixture was stirred at this temperature for 5 hours. The reaction mixture was poured into cold 2N HCl, extracted with EtOAc, dried over $Na_2SO_4$, and concentrated under vacuum. Compound was recrystallized from $CH_2Cl_2$/hexane to afford the title compound as an off-white solid (2.25 g, 5.3 mmoles).

Step 3

2-(2-Chloro-ethoxy)-4-fluoro-6-(naphthalene-1-sulfonyl-methyl)-phenylamine

A mixture of 1-[3-(2-Chloro-ethoxy)-5-fluoro-2-nitro-phenylmethanesulfonyl]-naphthalene (1.0 g, 2.36 mmoles) in ethanol (25 mL) was stirred under nitrogen in a round bottom flask at 60° C. 10% Pd/C was added, and the temperature was increased to 80° C. Hydrazine hydrate (2.0 mL) was added dropwise and the mixture was stirred at reflux for 3 hours. Reaction mixture was filtered off through Celite, and the solution was washed with $H_2O$ (3×), dried over $Na_2SO_4$, and concentrated under vacuum to afford the title compound as an off white solid (0.91 g, 2.31 mmoles).

Step 4

7-(2-Chloro-ethoxy)-5-fluoro-3-(naphthalene-1-sulfonyl)-1H-indazole

A mixture of 2-(2-chloro-ethoxy)-4-fluoro-6-(naphthalene-1-sulfonyl-methyl)-phenylamine (0.91 g, 2.31 mmoles) in THF (7 mL), and 4M HCl (15 mL) was stirred in a round bottom flask, under nitrogen, at 3° C. A solution of sodium nitrite (0.16 g, 2.4 mmoles) in $H_2O$ (1 mL) was added dropwise. The reaction mixture was poured into a cold solution of saturated sodium bicarbonate (100 mL) and extracted with EtOAc. Compound was dried over $Na_2SO_4$, and concentrated under vacuum to afford the title compound as an off white solid (0.9 g, 2.2 mmoles).

Step 5

1-(3-Chloro-benzyl)-7-(2-chloro-ethoxy)-5-fluoro-3-(naphthalene-1-sulfonyl)-1H-indazole A mixture of 7-(2-chloro-ethoxy)-5-fluoro-3-(naphthalene-1-sulfonyl)-1H-indazole (0.9 g, 2.2 mmoles), 3-chlorobenzyl bromide (0.35 mL, 2.7 mmoles), and cesium carbonate (0.87 g, 2.7 mmoles) in DMF (5 mL) was stirred together in a round bottom flask at room temperature for 30 minutes. Reaction mixture was diluted with $H_2O$, extracted with EtOAc, washed with water (2×), brine (1×), dried over $Na_2SO_4$, and concentrated under vacuum. The crude product was purified by HPLC using as eluent 30% EtOAc/hexane to afford the title compound as an off-white solid (0.85 g, 2 mmoles).

Step 6

7-(2-Azido-ethoxy)-1-(3-chloro-benzyl)-5-fluoro-3-(naphthalene-1-sulfonyl)-1H-indazole A mixture of 1-(3-chloro-benzyl)-7-(2-chloro-ethoxy)-5-fluoro-3-(naphthalene -1-sulfonyl)-1H-indazole (0.1 g, 0.19 mmoles) and sodium azide (0.014 g, 0.22 mmoles) in DMSO (3 mL) was stirred together in a round bottom flask under nitrogen at 90° C. for 3 hours. Reaction mixture was cooled to room temperature, diluted with water, extracted with EtOAC, washed with water (2×), brine (1×), dried over $Na_2SO_4$, and concentrated under vacuum to afford the title compound as an off white solid (0.09 g, 0.17 mmoles).

Step 7

(2-{[1-(3-Chlorobenzyl)-5-fluoro-3-(1-naphthylsulfonyl)-1H-indazol-7-yl]oxy}ethyl)amine A mixture of 7-(2-azido-ethoxy)-1-(3-chloro-benzyl)-5-fluoro-3-(naphthalene-1-sulfonyl)-1H-indazole (0.09 g, 0.17 mmoles) and 10% Pd/C in THF (5 mL), and methanol (15 mL) was hydrogenated in a Parr hydrogenation bottle (250 mL) at 52 Ib/in² for 2 hours. The mixture was filtered through Celite, and the filtrate was concentrated under vacuum. The crude product was purified by flash chromatography using as eluent 5% $CH_3OH/CH_2Cl_2$ to afford the title compound as an off-white solid (0.08 g, 0.14 mmoles), MS: (ES+) 511 [M+H]⁺.

EXAMPLE 107

(2-{[1-(3-chlorobenzyl)-5-fluoro-3-(1-naphthylsulfo-nyl)-1H-indazol-7-yl]oxy}ethyl)methylamine Hydrochloride

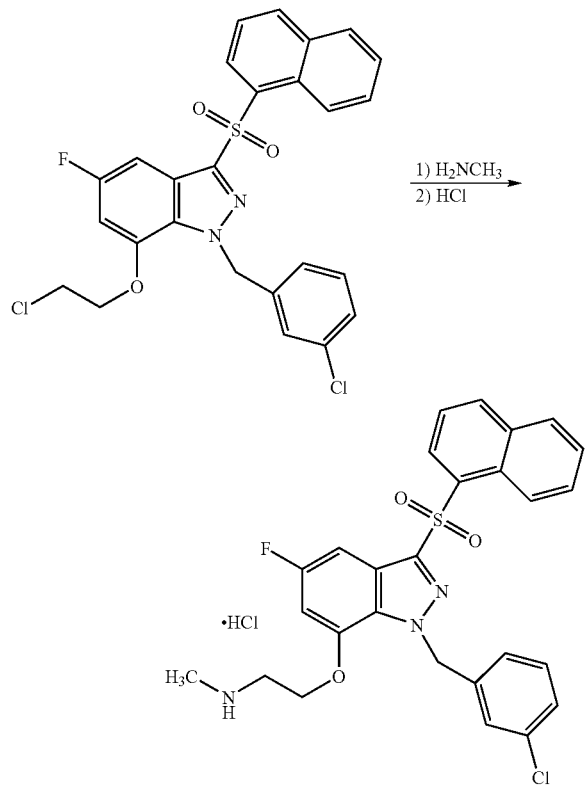

A mixture of 1-(3-chloro-benzyl)-7-(2-chloro-ethoxy)-5-fluoro-3-(naphthalene-1-sulfonyl)-1H-indazole (0.075 g, 0.14 mmoles) and methylamine (0.56 mmoles) in DMSO (1 mL) was stirred under nitrogen at 100° C. for 4 hours. Mixture was cooled to room temperature, diluted with water, extracted with EtOAc, washed with water (2×), brine (1×), dried over $Na_2SO_4$, and concentrated under vacuum. Compound was purified by flash chromatography using as eluent 5% $CH_3OH$/EtOAc. The purified compound was dissolved in methanol, 1M HCl in ether (0.1 mL, 0.1 mmoles) was added, and compound was dried to afford the title compound as the HCl salt.

MS: $(ES^+)$ 525 $[M+H]^+$

EXAMPLES 108-118

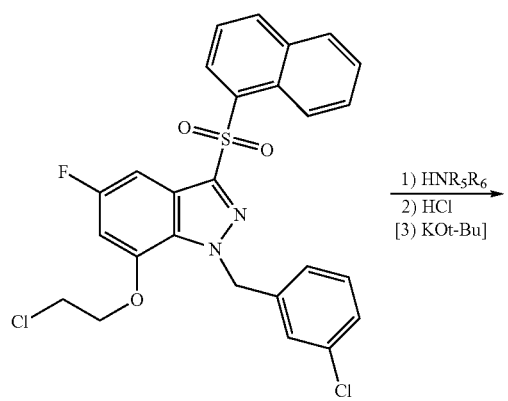

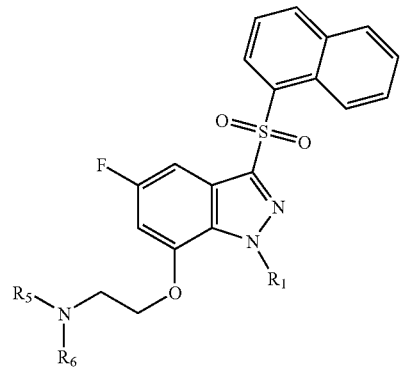

Using essentially the same procedures described in Examples 107 and 76 and employing the desired amine, the compounds shown in Table VI were obtained and identified by HPLC and mass spectral analyses.

TABLE VI

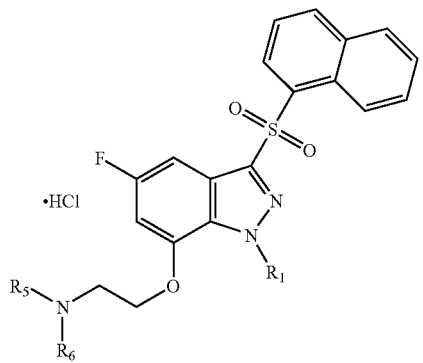

| Ex. No. | R1 | R5 | R6 | [M + H]+ |
|---|---|---|---|---|
| 108 | 3-Cl-benzyl | $C_2H_5$ | H | 539 |
| 109 | 3-Cl-benzyl | $CH_3$ | $CH_3$ | 539 |
| 110 | 3-Cl-benzyl | $C_2H_5$ | $C_2H_5$ | 567 |
| 111 | 3-Cl-benzyl | —$CH_2CH_2CH_2CH_2CH_2$— | | 579 |
| 112 | 3-Cl-benzyl | —$CH_2CH_2CH_2CH_2$— | | 565 |
| 113 | H | $CH_3$ | H | 400 |
| 114 | H | $C_2H_5$ | H | 414 |
| 115 | H | $CH_3$ | $CH_3$ | 414 |
| 116 | H | $C_2H_5$ | $C_2H_5$ | 442 |
| 117 | H | —$CH_2CH_2CH_2CH_2CH_2$— | | 454 |
| 118 | H | —$CH_2CH_2CH_2CH_2$— | | 440 |

EXAMPLES 119-127

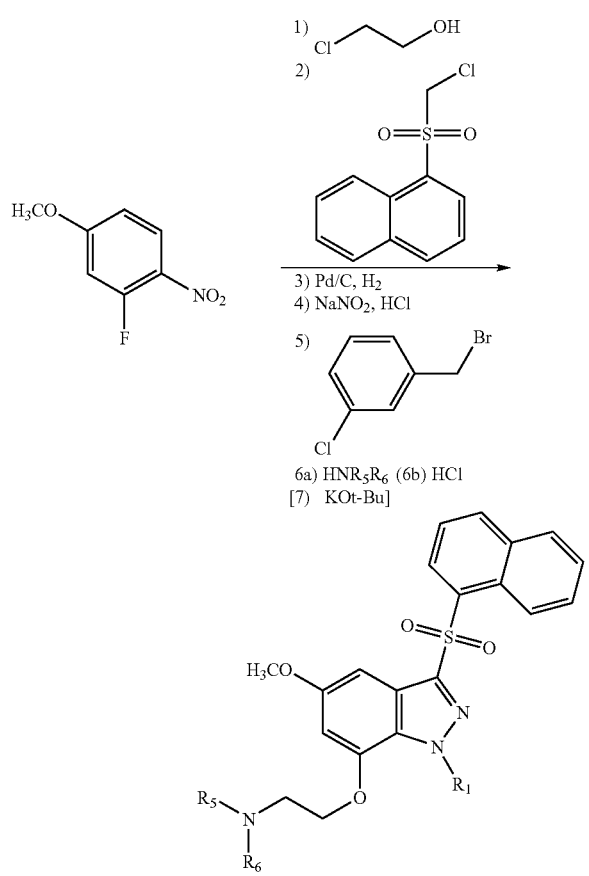

Step 1) 2-(2-Chloroethoxy)-4-methoxy-1-nitrobenzene

To a mixture of 2-chloroethanol (0.7 mL, 10.5 mmoles) in THF (20 mL), cooled to 0° C. was added 2M LDA (5.25 mL, 10.5 mmoles) dropwise. When the addition of LDA was complete, the mixture was stirred for an additional 15 minutes, and then 2-fluoro-4-methoxy-1-nitrobenzene (1.5 g, 8.8 mmoles) was added. The mixture was allowed to warm to room temperature, and stirred at this temperature overnight. Reaction mixture was diluted with water, extracted with EtOAc, washed with brine (1×), dried over $Na_2SO_4$, and concentrated under vacuum. The crude compound was recrystallized from $CH_2Cl_2$/hexane to give the title compound (1.5 g, 6.5 mmoles).

Step 2) 1-[3-(2-Chloro-ethoxy)-5-methoxy-2-nitro-phenylmethanesulfonyl]-naphthalene A mixture of 2-(2-chloro-ethoxy)-4-methoxy-1-nitrobenzene (1.4 g, 6 mmoles) and 1-chloromethane-sulfonyl-naphthalene (1.4 g, 6 mmoles) was stirred in THF (50 mL) at −78° C., in a round bottom flask under nitrogen. A solution of 1M potassium t-butoxide was added dropwise (18 mL, 18 mmoles) over a half an hour period. Temperature was allowed to rise to −40° C., and the reaction mixture was stirred at this temperature for 4 hours. The reaction mixture was poured into cold 2N HCl, extracted with EtOAc, dried over $Na_2SO_4$, and concentrated under vacuum. Compound was recrystallized from $CH_2Cl_2$/hexane to afford the title compound as an off-white solid (2 g, 4.6 mmoles).

Step 3) 2-(2-Chloro-ethoxy)-4-methoxy-6-(naphthalene-1-sulfonylmethyl)-phenylamine A mixture of 1-[3-(2-chloro-ethoxy)-5-methoxy-2-nitrophenylmethanesulfonyl]-naphthalene (1.0 g, 2.5 mmoles) in ethanol (25 mL) was stirred under nitrogen in a round bottom flask at 60° C. 10% Pd/C was added, and the temperature was increased to 80° C. Hydrazine hydrate (2.0 mL) was added dropwise and the mixture was stirred at reflux for 3 hours. Reaction mixture was filtered off through Celite, and the solution was washed with $H_2O$ (3×), dried over $Na_2SO_4$, and concentrated under vacuum to afford the title compound as an off white solid (1.0 g, 2.46 mmoles).

Step 4) 7-(2-Chloro-ethoxy)-5-methoxy-3-(naphthalene-1-sulfonyl)-1H-indazole

A mixture of 2-(2-chloro-ethoxy)-4-methoxy-6-(naphthalene-1-sulfonylmethyl)-phenylamine (1.0 g, 2.46 mmoles) in THF (7 mL), and 4M HCl (15 mL) was stirred in a round bottom flask, under nitrogen, at 3° C. A solution of sodium nitrite (0.17 g, 2.6 mmoles) in $H_2O$ (1 mL) was added dropwise. The reaction mixture was poured into a cold solution of saturated sodium bicarbonate (100 mL) and extracted with EtOAc. Compound was dried over $Na_2SO_4$, and concentrated under vacuum to afford the title compound as an off white solid (1.0 g, 2.39 mmoles).

Step 5) 1-(3-Chloro-benzyl)-7-(2-chloro-ethoxy-5-methoxy-3-(naphthalene-1-sulfonyl)-1H-indazole A mixture of 7-(2-chloro-ethoxy)-5-methoxy-3-(naphthalene-1-sulfonyl)-1H-indazole (1.0 g, 2.39 mmoles), 3-chlorobenzyl bromide (0.35 mL, 2.7 mmoles), and cesium carbonate (0.87 g, 2.7 mmoles) in DMF (5 mL) was stirred together in a round bottom flask at room temperature for 10 minutes. Reaction mixture was diluted with $H_2O$, extracted with EtOAc, washed with water (2×), brine (1×), dried over $Na_2SO_4$, and concentrated under vacuum. The crude product was purified by HPLC using as eluent 30% EtOAc/hexane to afford the title compound as an off-white solid 1.1 g, 2 mmoles).

Steps 6 and 7) Amination and Debenzylation

Using essentially the same procedures described in Examples 107 and 76 and employing the 7-(2-chloroethoxy)-5-methoxy-3-naphthylsulfonylindazole substrate and the desired amine, the compounds shown on Table VII were obtained and identified by HPLC and mass spectral analyses.

TABLE VII

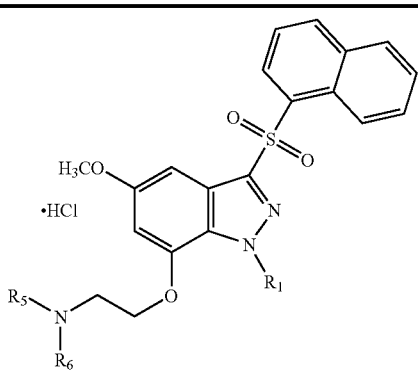

| Ex. No. | R1 | R5 | R6 | [M + H]+ |
|---|---|---|---|---|
| 119 | 3-Cl-benzyl | $CH_3$ | H | 537 |
| 120 | 3-Cl-benzyl | $C_2H_5$ | H | 551 |

TABLE VII-continued

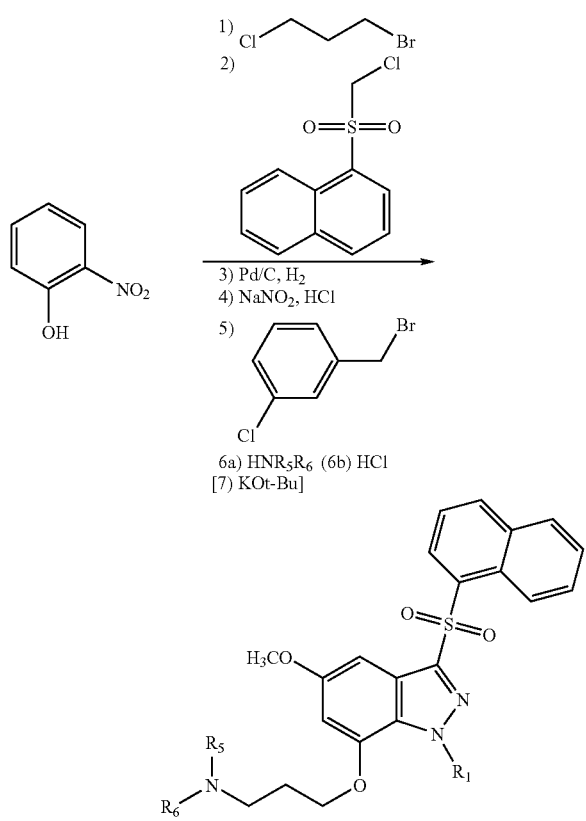

| Ex. No. | R1 | R5 | R6 | [M + H]+ |
|---|---|---|---|---|
| 121 | 3-Cl-benzyl | CH₃ | CH₃ | 551 |
| 122 | 3-Cl-benzyl | —CH₂CH₂CH₂CH₂CH₂— | | 591 |
| 123 | 3-Cl-benzyl | —CH₂CH₂CH₂CH₂— | | 577 |
| 124 | H | CH₃ | H | 412 |
| 125 | H | CH₃ | CH₃ | 426 |
| 126 | H | —CH₂CH₂CH₂CH₂CH₂— | | 466 |
| 127 | H | —CH₂CH₂CH₂CH₂— | | 452 |

EXAMPLES 128-138

Step 1) 1-(3-Chloro-propoxy)-2-nitro-benzene

A mixture of ortho-nitrophenol (0.83 g, 6 mmoles), 1-bromo-3-chloropropane (1.1 g, 7.2 mmoles), and K₂CO₃ (1.24 g, 9 mmoles) was stirred together in DMF at 80° C. for 1 hour. Reaction mixture was diluted with H₂O, extracted with EtOAc, washed with water (2×), brine (1×), dried over Na₂SO₄, and concentrated under vacuum. The crude product was purified by HPLC using as eluent 30% EtOAc/hexane to afford the title compound as an off-white solid (1.2 g, 5.6 mmoles).

Step 2) 1-[3-(3-Chloro-propoxy)-2-nitro-phenyl-methanesulfonyl]-naphthalene

A mixture of 1-(3-chloro-propoxy)-2-nitrobenzene (1.2 g, 6 mmoles) and 1-chloromethane-sulfonyl-naphthalene (2.16 g, 9 mmoles) was stirred in THF (50 mL) at −78° C., in a round bottom flask under nitrogen. A solution of 1M potassium t-butoxide was added dropwise (18 mL, 18 mmoles) over a half hour period. Temperature was allowed to rise to 40° C., and the reaction mixture was stirred at this temperature for 5 hours. The reaction mixture was poured into cold 2N HCl, extracted with EtOAc, dried over Na₂SO₄, and concentrated under vacuum. Compound was recrystallized from CH₂Cl₂/hexane to afford the title compound as an off-white solid (1.9 g, 4.5 mmoles).

Step 3) 2-(3-Chloro-propoxy)-6-(naphthalene-1-sulfonylmethyl)-phenylamine

A mixture of 1-[3-(3-chloro-propoxy)-2-nitro-phenylmethanesulfonyl]-naphthalene (1.9 g, 4.5 mmoles) and 10% Pd/C in THF (20 mL), methanol (20 mL), and formic acid (5 mL) was hydrogenated in a Parr hydrogenation bottle (250 mL) at 40 lb/in² for 20 hours. The mixture was filtered through Celite, and the filtrate was diluted with EtOAc, washed with water, dried over Na₂SO₄, and concentrated under vacuum. The crude product was purified by flash chromatography using as eluent 5% EtOAc/CH₂Cl₂ to afford the title compound as an off-white solid (1.66 g, 4.25 mmoles).

Step 4) 7-(3-Chloro-propoxy)-3-(naphthalene-1-sulfonyl)-1-H-indazole

A mixture of 2-(3-chloro-propoxy)-6-(naphthalene-1-sulfonylmethyl)-phenyl amine (1.66 g, 4.25 mmoles) in THF (7 mL), and 4M HCl (15 mL) was stirred in a round bottom flask, under nitrogen, at 3° C. A solution of sodium nitrite (0.3 g, 4.4 mmoles) in H₂O (1 mL) was added dropwise. The reaction mixture was poured into a cold solution of saturated sodium bicarbonate (100 mL) and extracted with EtOAc. Compound was dried over Na₂SO₄, and concentrated under vacuum to afford the title compound as an off white solid (1.6 g, 4 mmoles).

Step 5) 1-(3-Chloro-benzyl)-7-(3-chloro-propoxy)-3-(naphthalene-1-sulfonyl)-1-H-indazole A mixture of 7-(3-chloro-propoxy)-3-(naphthalene-1-sulfonyl)-1-H-indazole (0.7 g, 1.75 mmoles), 3-chloro-benzyl-bromide (0.28 mL, 2.17 mmoles), and cesium carbonate (0.7 g, 2.17 mmoles) in DMF (5 mL) was stirred together in a round bottom flask at room temperature for 10 minutes. Reaction mixture was diluted with H₂O, extracted with EtOAc, washed with water (2×), brine (1×), dried over Na₂SO₄, and concentrated under vacuum. The crude product was purified by HPLC using as eluent 30% EtOAc/hexane to afford the title compound as an off-white solid (0.87 g, 1.66 mmoles).

Steps 6 and 7) Amination and Debenzylation

Using essentially the same procedures described in Examples 107 and 76 and employing the 7-(3-chloropropoxy)-3-naphthylsulfonylindazole substrate and the desired amine, the compounds shown in Table VIII were obtained and identified by HPLC and mass spectral analyses. (Amination was run in parallel manner on a heated carousel in 3-dram vials.)

TABLE VIII

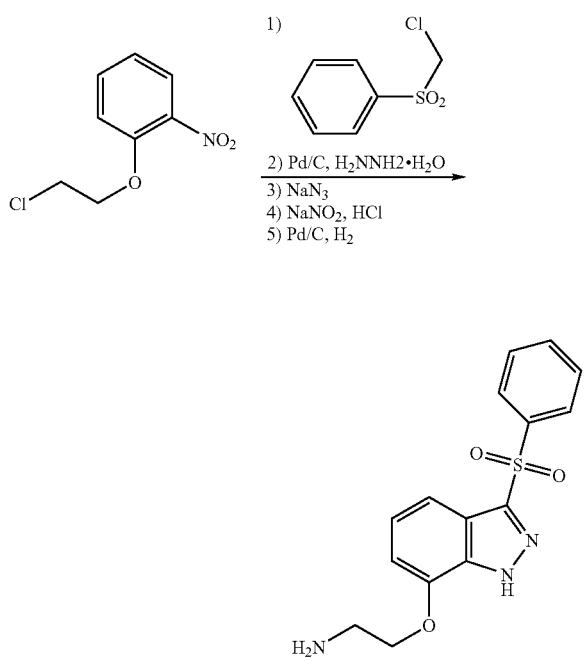

| Ex. No. | R1 | R5 | R6 | [M + H]+ |
|---|---|---|---|---|
| 128 | 3-Cl-benzyl | $CH_3$ | H | 521 |
| 129 | 3-Cl-benzyl | $C_2H_5$ | H | 535 |
| 130 | 3-Cl-benzyl | $CH_3$ | $CH_3$ | 535 |
| 131 | 3-Cl-benzyl | $C_2H_5$ | $C_2H_5$ | 563 |
| 132 | 3-Cl-benzyl | —$CH_2CH_2CH_2CH_2CH_2$— | | 575 |
| 133 | 3-Cl-benzyl | —$CH_2CH_2CH_2CH_2$— | | 561 |
| 134 | H | $CH_3$ | H | 396 |
| 135 | H | $C_2H_5$ | H | 410 |
| 136 | H | $CH_3$ | $CH_3$ | 410 |
| 137 | H | $C_2H_5$ | $C_2H_5$ | 438 |
| 138 | H | —$CH_2CH_2CH_2CH_2CH_2$— | | 450 |

EXAMPLE 139

2-{[3-Phenylsulfonyl)-1H-indazol-7-yl]oxy}ethanamine

Step 1) 1-Benzenesulfonylmethyl-3-(2-chloroethoxy)-2-nitrobenzene

A mixture of 1-(2-chloro-ethoxy)-2-nitrobenzene (0.5 g, 2.5 mmoles) and 1-chloromethane-sulfonyl-benzene (0.56 g, 2.97 mmoles) was stirred in THF (10 mL) at −78° C., in a round bottom flask under nitrogen. A solution of 1M potassium t-butoxide was added dropwise (7.45 mL, 7.44 mmoles) over a half an hour period. Temperature was allowed to rise to −40° C., and the reaction mixture was stirred at this temperature for 5 hours. The reaction mixture was poured into cold 2N HCl, extracted with EtOAc, dried over $Na_2SO_4$, and concentrated under vacuum. Compound was recrystallized from $CH_2Cl_2$/hexane to afford the title compound as an off-white solid (0.57 g, 1.6 mmoles).

Step 2) 2-Benzenesulfonylmethyl-6-(2-chloro-ethoxy)-phenylamine

A mixture of 1-benzenesulfonylmethyl-3-(2-chloro-ethoxy)-2-nitrobenzene (0.57 g, 1.6 mmoles) in ethanol (10 mL) was stirred under nitrogen in a round bottom flask at 60° C. 10% Pd/C was added, and the temperature was increased to 80° C. Hydrazine hydrate (1.5 mL) was added dropwise and the mixture was stirred at reflux for 3 hours. Reaction mixture was filtered off through Celite, and the solution was washed with $H_2O$ (3×), dried over $Na_2SO_4$, and concentrated under vacuum to afford the title compound as an off white solid (0.5 g, 1.53 mmoles).

Step 3) 2-(2-Azido-ethoxy)-6-benzene-sulfonylmethyl-phenylamine

A mixture of 2-benzenesulfonylmethyl-6-(2-chloro-ethoxy)-phenylamine (0.5 g, 1.53 mmoles) and sodium azide (0.15 g, 2.29 mmoles) in DMSO (10 mL) was stirred together in a round bottom flask under nitrogen at 90° C. for 3 hours. Reaction mixture was cooled to room temperature, diluted with water, extracted with EtOAC, washed with water (2×), brine (1×), dried over $Na_2SO_4$, and concentrated under vacuum. Crude compound was purified by normal phase HPLC using as eluent 40% EtOAc/hexane to afford the title compound as an off white solid (0.39 g, 1.17 mmoles).

Step 4) 7-(2-Azido-ethoxy)-3-benzenesulfonyl-1H-indazole

A mixture of 2-(2-azido-ethoxy-6-benzene-sulfonylmethyl-phenylamine (0.39 g, 1.17 mmoles) in THF (2 mL), and 4M HCl (10 mL) was stirred in a round bottom flask, under nitrogen, at 3° C. A solution of sodium nitrite (0.08 g, 1.23 mmoles) in $H_2O$ (1 mL) was added dropwise. The reaction mixture was poured into a cold solution of saturated sodium bicarbonate (100 mL) and extracted with EtOAc. Compound was dried over $Na_2SO_4$, and concentrated under vacuum to afford the title compound as an off white solid (0.3 g, 0.87 mmoles).

Step 5) 2-{[3-Phenylsulfonyl)-1H-indazol-7-yl]oxy}ethanamine

A mixture of 7-(2-azido-ethoxy)-3-benzenesulfonyl-1H-indazole (0.3 g, 0.87 mmoles) and 10% Pd/C in THF (2 mL), and methanol (8 mL) was hydrogenated in a Parr hydrogenation bottle (250 mL) at 52 lb/in² for 2 hours. The mixture was filtered through Celite, and the filtrate was concentrated under vacuum. The crude product was recrystallized from $CH_2Cl_2$/hexane, 1M HCl in ether (0.9 mL, 0.9 mmoles) was added, then dried, to afford the title compound as an off-white HCl salt (0.2 g, 0.6 mmoles), MS: (ES+) 317 [M+H]+

EXAMPLE 140

2-{[5-Fluoro-3-phenylsulfonyl)-1H-indazol-7-yl]oxy}ethanamine

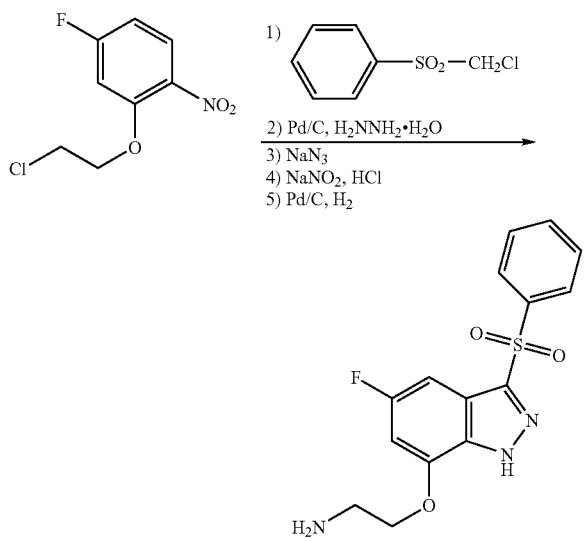

Step 1) 1-Benzenesulfonylmethyl-3-(2-chloro-ethoxy)-5-fluoro-2-nitro-benzene A mixture of 2-(2-chloroethoxy)-4-fluoro-1-nitrobenzene (1.3 g, 6 mmoles) and 1-chloromethane-sulfonyl-benzene (1.7 g, 9 mmoles) was stirred in THF (50 mL) at −78° C., in a round bottom flask under nitrogen. A solution of 1M potassium t-butoxide was added dropwise (18 mL, 18 mmoles) over a half hour period. Temperature was allowed to rise to 40° C., and the reaction mixture was stirred at this temperature for 5 hours. The reaction mixture was poured into cold 2N HCl, extracted with EtOAc, dried over $Na_2SO_4$, and concentrated under vacuum. Compound was recrystallized from $CH_2Cl_2$/hexane to afford the title compound as an off-white solid (1.98 g, 5.3 mmoles).

Step 2) 2-Benzenesulfonylmethyl-6-(2-chloro-ethoxy)-4-fluorophenylamine

A mixture of 1-benzenesulfonylmethyl-3-(2-chloro-ethoxy)-5-fluoro-2-nitrobenzene (1.98 g, 5.3 mmoles) in ethanol (25 mL) was stirred under nitrogen in a round bottom flask at 60° C. 10% Pd/C was added, and the temperature was increased to 80° C. Hydrazine hydrate (2.0 mL) was added dropwise and the mixture was stirred at reflux for 3 hours. Reaction mixture was filtered off through Celite, and the solution was washed with $H_2O$ (3×), dried over $Na_2SO_4$, and concentrated under vacuum to afford the title compound as an off white solid (1.67 g, 4.87 mmoles).

Step 3) 2-(2-Azido-ethoxy)-6-benzenesulfonylmethyl-4-fluoro-phenylamine

A mixture of 2-benzenesulfonylmethyl-6-(2-chloro-ethoxy)-4-fluorophenylamine (1.67 g, 4.87 mmoles) and sodium azide (0.38 g, 5.84 mmoles) in DMSO (20 mL) was stirred together in a round bottom flask under nitrogen at 90° C. for 3 hours. Reaction mixture was cooled to room temperature, diluted with water, extracted with EtOAC, washed with water (2×), brine (1×), dried over $Na_2SO_4$, and concentrated under vacuum to afford the title compound as an off white solid (1.44 g, 4.14 mmoles).

Step 4) 7-(2-Azido-ethoxy)-3-benzenesulfonyl-5-fluoro-1H-indazole

A mixture of 2-(2-azido-ethoxy-6-benzene-sulfonylmethyl-4-fluoro-phenylamine (1.44 g, 4.14 mmoles) in THF (5 mL), and 4M HCl (20 mL) was stirred in a round bottom flask, under nitrogen, at 3° C. A solution of sodium nitrite (0.28 g, 4.34 mmoles) in $H_2O$ (2 mL) was added dropwise. The reaction mixture was poured into a cold solution of saturated sodium bicarbonate (100 mL) and extracted with EtOAc. Compound was dried over $Na_2SO_4$, and concentrated under vacuum to afford the title compound as an off white solid (1.34 g, 3.72 mmoles).

Step 5) 2-{[5-Fluoro-3-phenylsulfonyl)-1H-indazol-7-yl]oxy}ethanamine

A mixture of 7-(2-azido-ethoxy)-3-benzenesulfonyl-5-fluoro-1H-indazole (0.3 g, 0.83 mmoles) and 10% Pd/C in THF (2 mL), and methanol (8 mL) was hydrogenated in a Parr hydrogenation bottle (250 mL) at 52 $lb/in^2$ for 2 hours. The mixture was filtered through Celite, and the filtrate was concentrated under vacuum. The crude product was recrystallized from $CH_2Cl_2$/hexane, 1M HCl in ether (0.8 mL, 0.8 mmoles) was added, then dried, to afford the title compound as an off-white HCl salt (0.2 g, 0.59 mmoles), MS: $(ES^+)$ 336 $[M+H]^+$

EXAMPLE 141

2-{[3-1-Naphthylsulfonyl)-1H-indazol-4-yl]oxy}ethanamine

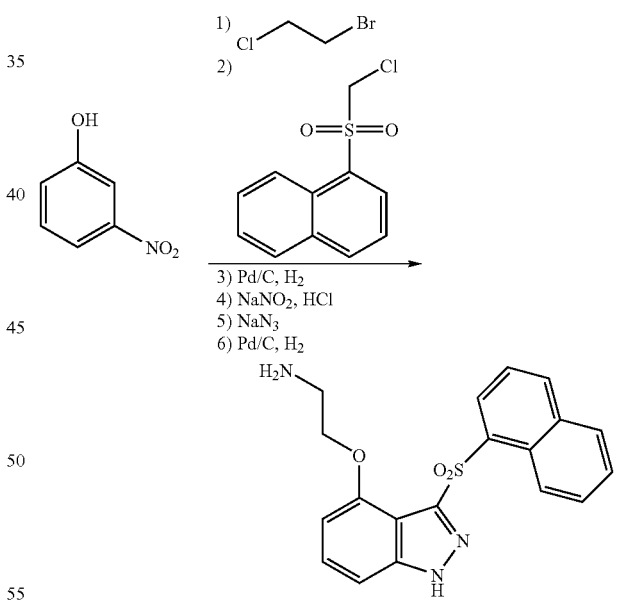

Step 1) 1-(2-Chloroethoxy)-3-nitrobenzene

A mixture of 3-nitrophenol (0.83 g, 6 mmoles), bromochloroethane (1.03 g, 7.2 mmoles), and $K_2CO_3$ (1.24 g, 9 mmoles) was stirred together in DMF at room temperature for 1 hour. Reaction mixture was diluted with $H_2O$, extracted with EtOAc, washed with water (2×), brine (1×), dried over $Na_2SO_4$, and concentrated under vacuum. The crude product was purified by HPLC using as eluent 30% EtOAc/hexane to afford the title compound as an off-white solid (1.12 g, 5.6 mmoles).

Step 2) 1-[2-(2-Chloroethoxy)-6-nitrophenylmethanesulfonyl]naphthalene

A mixture of 1-(2-chloro-ethoxy)-3-nitrobenzene (1.12 g, 5.6 mmoles) and 1-chloromethane-sulfonyl-naphthalene (1.6 g, 6.72 mmoles) was stirred in THF (50 mL) at −78° C., in a round bottom flask under nitrogen. A solution of 1M potassium t-butoxide was added dropwise (16.8 mL, 16.8 mmoles) over a half an hour period. Temperature was allowed to rise to −40° C., and the reaction mixture was stirred at this temperature for 5 hours. The reaction mixture was poured into cold 2N HCl, extracted with EtOAc, dried over $Na_2SO_4$, and concentrated under vacuum. Compound was purified by normal phase HPLC using as eluent 40% EtOAc/hexane to afford the title compound as an off-white solid (0.9 g, 2.24 mmoles), and 1-[4-(2-chloro-ethoxy)-2-nitro-phenylmethanesulfonyl]-naphthalene (0.79 g, 2.1 mmoles).

Step 3) 3-(2-Chloro-ethoxy)-2-(naphthalene-1-sulfonylmethyl)-phenyl amine

A mixture of 1-[2-(2-Chloro-ethoxy)-6-nitro-phenylmethanesulfonyl]-naphthalene (0.9 g, 2.24 mmoles) and 10% Pd/C in THF (10 mL), methanol (10 mL), and formic acid (2 mL) was hydrogenated in a Parr hydrogenation bottle (250 mL) at 40 lb/in² for 20 hours. The mixture was filtered through Celite, and the filtrate was diluted with EtOAc, washed with water, dried over $Na_2SO_4$, and concentrated under vacuum to afford the title compound as an off-white solid (0.78 g, 2.1 mmoles).

Step 4) 4-(2-Chloro-ethoxy)-3-(naphthalene-1-sulfonyl)-1-H-indazole

A mixture of 3-(2-chloro-ethoxy)-2-(naphthalene-1-sulfonylmethyl)-phenyl amine (0.78 g, 2.1 mmoles) in THF (5 mL), and 4M HCl (10 mL) was stirred in a round bottom flask, under nitrogen, at 3° C. A solution of sodium nitrite (0.15 g, 2.2 mmoles) in $H_2O$ (1 mL) was added dropwise. The reaction mixture was poured into a cold solution of saturated sodium bicarbonate (100 mL) and extracted with EtOAc. Compound was dried over $Na_2SO_4$, and concentrated under vacuum to afford the title compound as an off white solid (0.74 g, 1.93 mmoles).

Step 5) 4-(2-Azido-ethoxy)-3-(naphthalene-1-sulfonyl)-1H-indazole

A mixture of 4-(2-chloro-ethoxy)-3-(naphthalene-1-sulfonyl)-1-H-indazole (0.2 g, 0.5 mmoles) and sodium azide (0.04 g, 0.62 mmoles) in DMSO (2 mL) was stirred together in a round bottom flask under nitrogen at 90° C. for 3 hours. Reaction mixture was cooled to room temperature, diluted with water, extracted with EtOAC, washed with water (2×), brine (1×), dried over $Na_2SO_4$, and concentrated under vacuum. Crude compound was purified by normal phase HPLC using as eluent 40% EtOAc/hexane to afford the title compound as an off white solid (0.17 g, 0.45 mmoles).

Step 6) 2-{[3-1-Naphthylsulfonyl)-1H-indazol-4-yl]oxy}ethanamine

A mixture of 4-(2-azido-ethoxy)-3-(naphthalene-1-sulfonyl)-1H-indazole (0.17 g, 0.45 mmoles) and 10% Pd/C in THF (2 mL), and methanol (8 mL) was hydrogenated in a Parr hydrogenation bottle (250 mL) at 52 lb/in² for 2 hours. The mixture was filtered through Celite, and the filtrate was concentrated under vacuum. The crude product was recrystallized from $CH_2Cl_2$/hexane, 1M HCl in ether (0.4 mL, 0.4 mmoles) was added, then dried to afford the title compound as an off-white HCl salt (0.15 g, 0.4 mmoles), MS: (ES⁺) 369 [M+H]⁺

EXAMPLE 142

N-Methyl-2-{[3-naphthylsulfonyl)-1H-indazol-4-yl]oxy}ethanamine Hydrochloride

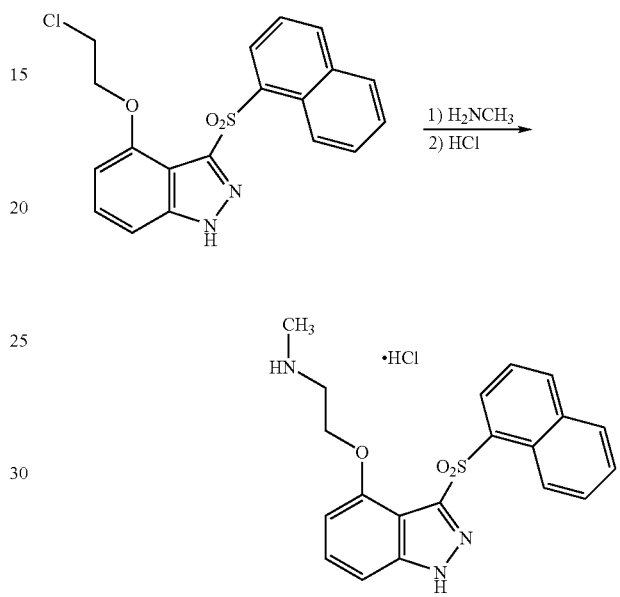

A mixture of 4-(2-chloro-ethoxy)-3-(naphthalene-1-sulfonyl)-1-H-indazole (0.075 g, 0.19 mmoles) and methylamine (0.28 mL, 0.56 mmoles) in DMSO (1 mL) was stirred under nitrogen at 100° C. for 4 hours. Mixture was cooled to room temperature, diluted with water, extracted with EtOAc, washed with water (2×), brine (1×), dried over $Na_2SO_4$, and concentrated under vacuum. Compound was purified by flash chromatography using as eluent 5% $CH_3OH$/EtOAc. The purified compound was dissolved in methanol, 1M HCl in ether (0.2 mL, 0.2 mmoles) was added, then dried to afford the title compound as the HCl salt (0.07 g, 0.19 mmoles), MS: (ES⁺) 417 [M+H]⁺

EXAMPLES 143-145

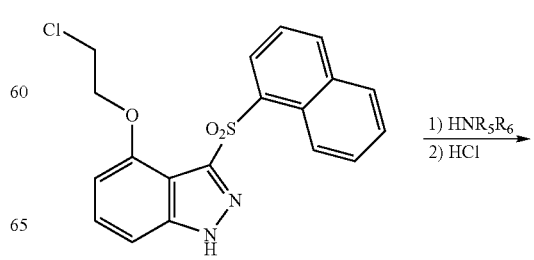

-continued

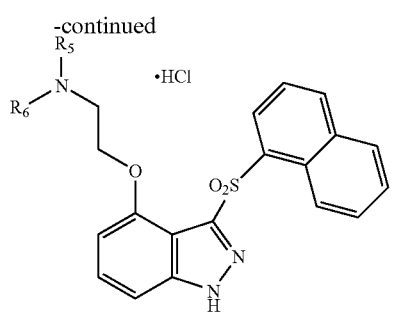

Using essentially the same procedure described in Example 142 and employing the desired amine, the compounds shown in Table IX were obtained and identified by HPLC and mass spectral analyses.

TABLE IX

| Ex. No. | R5 | R6 | [M + H]+ |
|---|---|---|---|
| 143 | CH₃ | CH₃ | 397 |
| 144 | —CH₂CH₂CH₂CH₂CH₂— | | 437 |
| 145 | —CH₂CH₂CH₂CH₂— | | 423 |

EXAMPLE 146

2-{[3-(1-Naphtylsulfonyl)-1H-indazol-6-yl]oxy}ethanamine

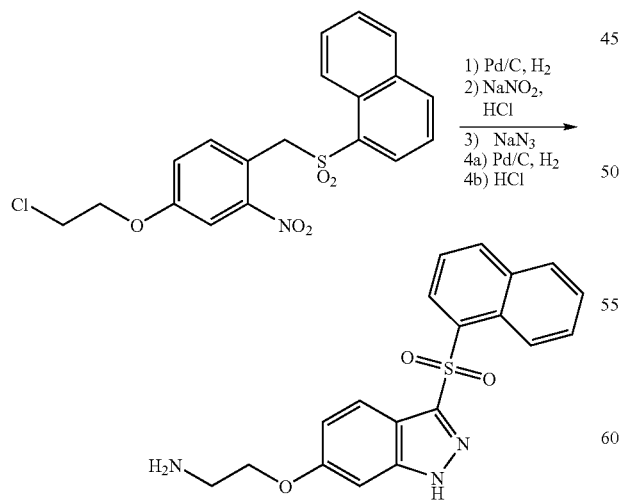

Step 1) 5-(2-Chloro-ethoxy-2-(naphthalene-1-sulfonylmethyl)-phenylamine

A mixture of 1-[4-(2-chloro-ethoxy)-2-nitro-phenylmethanesulfonyl]-naphthalene (0.79 g, 2.1 mmoles) and 10% Pd/C in THF (10 mL), methanol (10 mL), and formic acid (2 mL) was hydrogenated in a Parr hydrogenation bottle (250 mL) at 40 lb/in² for 20 hours. The mixture was filtered through Celite, and the filtrate was diluted with EtOAc, washed with water, dried over Na₂SO₄, and concentrated under vacuum to afford the title compound as an off-white solid (0.74 g, 1.99 mmoles).

Step 2) 6-(2-Chloro-ethoxy)-3-(naphthalene-1-sulfonyl)-1H-indazole

A mixture of 5-(2-chloro-ethoxy)-2-(naphthalene-1-sulfonylmethyl)-phenyl amine (0.74 g, 1.99 mmoles) in THF (5 mL), and 4M HCl (10 mL) was stirred in a round bottom flask, under nitrogen, at 3° C. A solution of sodium nitrite (0.14 g, 2.08 mmoles) in H₂O (1 mL) was added dropwise. The reaction mixture was poured into a cold solution of saturated sodium bicarbonate (100 mL) and extracted with EtOAc. Compound was dried over Na₂SO₄, and concentrated under vacuum to afford the title compound as an off white solid (0.74 g, 1.93 mmoles).

Step 3) 6-(2-Azido-ethoxy)-3-(naphthalene-1-sulfonyl)-1H-indazole

A mixture of 6-(2-chloro-ethoxy)-3-(naphthalene-1-sulfonyl)-1-H-indazole (0.19 g, 0.5 mmoles) and sodium azide (0.04 g, 0.62 mmoles) in DMSO (2 mL) was stirred together in a round bottom flask under nitrogen at 90° C. for 3 hours. Reaction mixture was cooled to room temperature, diluted with water, extracted with EtOAC, washed with water (2×), brine (1×), dried over Na₂SO₄, and concentrated under vacuum. Crude compound was purified by normal phase HPLC using as eluent 40% EtOAc/hexane to afford the title compound as an off white solid (0.17 g, 0.45 mmoles).

Step 4) 2-{[3-(1-Naphtylsulfonyl)-1H-indazol-6-yl]oxy}ethanamine

A mixture of 6-(2-azido-ethoxy)-3-(naphthalene-1-sulfonyl)-1H-indazole (0.17 g, 0.45 mmoles) and 10% Pd/C in THF (2 mL), and methanol (8 mL) was hydrogenated in a Parr hydrogenation bottle (250 mL) at 52 lb/in² for 2 hours. The mixture was filtered through Celite, and the filtrate was concentrated under vacuum. The crude product was recrystallized from CH₂Cl₂/hexane, 1M HCl in ether (0.4 mL, 0.4 mmoles) was added, then dried, to afford the title compound as an off-white HCl salt (0.15 g, 0.4 mmoles), MS: (ES⁺) 368 [M+H]⁺

EXAMPLE 147

N-Methyl-2-{[3-(1-naphthylsulfonyl)-1H-indazol-6-yl]oxy}ethanamine Hydrochloride

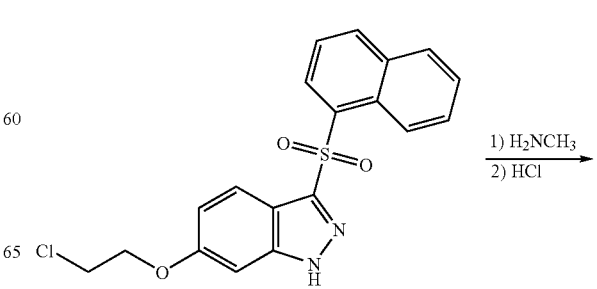

-continued

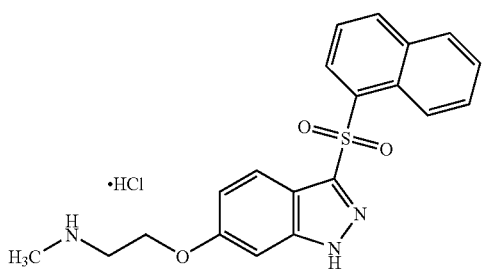

A mixture of 6-(2-chloro-ethoxy)-3-(naphthalene-1-sulfonyl)-1-H-indazole (0.075 g, 0.19 mmoles) and methylamine (0.28 mL, 0.56 mmoles) in DMSO (1 mL) was stirred under nitrogen at 100° C. for 4 hours. Mixture was cooled to room temperature, diluted with water, extracted with EtOAc, washed with water (2×), brine (1×), dried over $Na_2SO_4$, and concentrated under vacuum. Compound was purified by flash chromatography using as eluent 5% $CH_3OH$/EtOAc. The purified compound was dissolved in methanol, 1M HCl in ether (0.2 mL, 0.2 mmoles) was added, then dried, to afford the title compound as the HCl salt (0.07 g, 0.19 mmoles), MS: ($ES^+$) 381 $[M+H]^+$

EXAMPLES 148-150

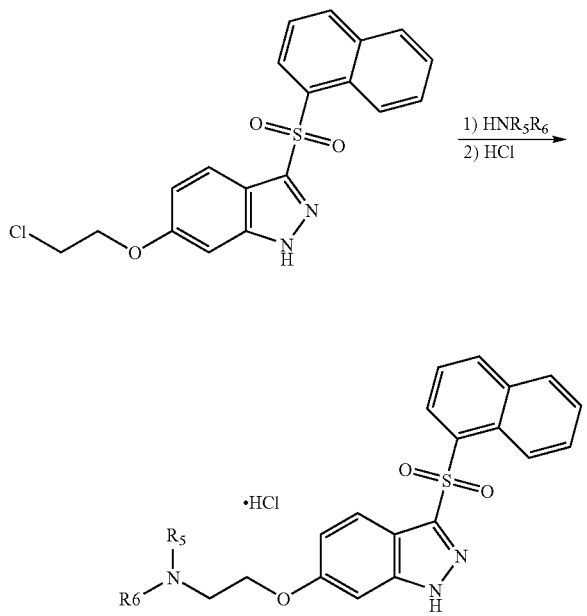

Using essentially the same procedure described in Example 147 and employing the desired amine, the compounds shown in Table X were obtained and identified by HPLC and mass spectral analyses.

TABLE X

| Ex. No. | R5 | R6 | $[M + H]^+$ |
|---|---|---|---|
| 148 | $CH_3$ | $CH_3$ | 396 |
| 149 | —$CH_2CH_2CH_2CH_2CH_2$— | | 436 |
| 150 | —$CH_2CH_2CH_2CH_2$— | | 422 |

EXAMPLE 151

N-[2-(Dimethylamino)ethyl]-3-(1-naphthylsulfonyl)-1H-indazole-5-carboxamide

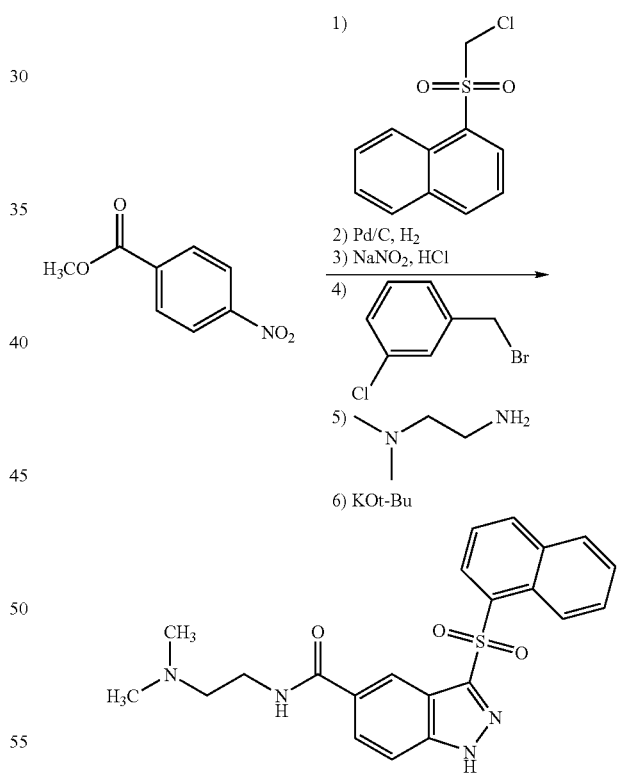

Step 1) 3-(Naphthalene 1-sulfonylmethyl)-4-nitro-benzoic acid methyl ester

A mixture of 4-nitro-benzoic acid methyl ester (0.8 g, 4.4 mmoles) and 1-chloromethane-sulfonyl-naphthalene (1.3 g, 5.3 mmoles) was stirred in THF (50 mL) at −78° C., in a round bottom flask under nitrogen. A solution of 1M potassium t-butoxide was added dropwise (13 mL, 13 mmoles) over a half an hour period. Temperature was allowed to rise to −40° C., and the reaction mixture was stirred at this temperature for 5 hours. The reaction mixture was poured into cold 2N HCl, extracted with EtOAc, dried over Na₂SO₄, and concentrated under vacuum. Compound was purified by normal phase HPLC using as eluent 40% EtOAc/hexane to afford the title compound as an off-white solid (1.5 g, 3.9 mmoles).

Step 2) 4-Amino-3-(naphthalene-1-sulfonylmethyl)benzoic acid methyl ester

A mixture of 3-(naphthalene 1-sulfonylmethyl)-4-nitrobenzoic acid methyl ester (1.5 g, 3.9 mmoles) and 10% Pd/C in THF (10 mL), and methanol (20 mL) was hydrogenated in a Parr hydrogenation bottle (250 mL) at 52 lb/in² overnight. The mixture was filtered through Celite, and the filtrate was concentrated under vacuum to afford the title compound as an off-white solid (0.9 g, 2.5 mmoles).

Step 3) 3-(Naphthalene-1-sulfonyl)-1H-indazole-5-carboxylic acid methyl ester

A mixture of 4-amino-3-(naphthalene-1-sulfonylmethyl) benzoic acid methyl ester (0.9 g, 2.5 mmoles) in THF (5 mL), and 4M HCl (10 mL) was stirred in a round bottom flask, under nitrogen, at 3° C. A solution of sodium nitrite (0.18 g, 2.62 mmoles) in H₂O (1 mL) was added dropwise. The reaction mixture was poured into a cold solution of saturated sodium bicarbonate (100 mL) and extracted with EtOAc. Compound was dried over Na₂SO₄, and concentrated under vacuum to afford the title compound as an off white solid (0.82 g, 2.25 mmoles).

Step 4) 1-(3-Chlorobenzyl)-2-(naphthalene-1-sulfonyl)-1H-indazole-5-carboxylic acid methyl ester A mixture of 3-(naphthalene-1-sulfonyl)-1H-indazole-5-carboxylic acid methyl ester (0.82 g, 2.25 mmoles), 3-chlorobenzyl bromide (0.34 mL, 2.7 mmoles), and cesium carbonate (0.87 g, 2.7 mmoles) in DMF (5 mL) was stirred together in a round bottom flask at room temperature for 30 minutes. Reaction mixture was diluted with H₂O, extracted with EtOAc, washed with water (2×), brine (1×), dried over Na₂SO₄, and concentrated under vacuum. The crude product was purified by HPLC using as eluent 30% EtOAc/hexane to afford the title compound as an off-white solid (1.01 g, 2.07 mmoles).

Step 5) 1-(3-Chloro-benzyl)-3-(naphthalene-1-sulfonyl)-1H-indazole-5-carboxylic acid (2-dimethyl-amino-ethyl)-amide To a solution of dimethyl ethylene diamine (0.02 mL, 0.2 mmoles) in THF (2 mL), cooled to 0° C. was added LDA dropwise (0.15 mL, 0.3 mmoles). To this mixture was then added a solution of 1-(3-chloro-benzyl)-2-(naphthalene-1-sulfonyl)-1H-indazole-5-carboxylic acid methyl ester (0.05 g, 0.1 mmoles) in THF (1 mL). Mixture was allowed to warm slowly to room temperature. Reaction mixture was diluted with water, extracted with EtOAc (1×), CH₂Cl₂ (1×); the organics were washed with brine (1×), and concentrated under vacuo to afford the title compound (0.3 g, 0.04 mmoles).

Step 6) N-[2-(Dimethylamino)ethyl]-3-(1-naphthylsulfonyl)-1H-indazole-5-carboxamide A mixture of 1-(3-chloro-benzyl)-3-(naphthalene-1-sulfonyl)-1H-indazole-5-carboxylic acid (2-dimethyl-amino-ethyl)-amide (0.3 g, 0.04 mmoles), DMSO (1 mL) and t-BuOH (0.2 mL) was stirred at room temperature in a round bottom flask under oxygen atmosphere. A solution of potassium t-butoxide (0.05 mL, 0.05 mmoles) was added dropwise and the reaction mixture stirred for 30 min. Reaction mixture was quenched with saturated ammonium chloride, extracted with EtOAc, dried over Na₂SO₄, and concentrated under vacuum. Crude compound was purified by reverse phase chromatography to afford the title compound, MS: (ES⁺) 423 [M+H]⁺

EXAMPLE 152

3-(1-Naphtylsulfonyl)-N-(2-piperidin-1-ylethyl)-1H-indazole-5-carboxamide

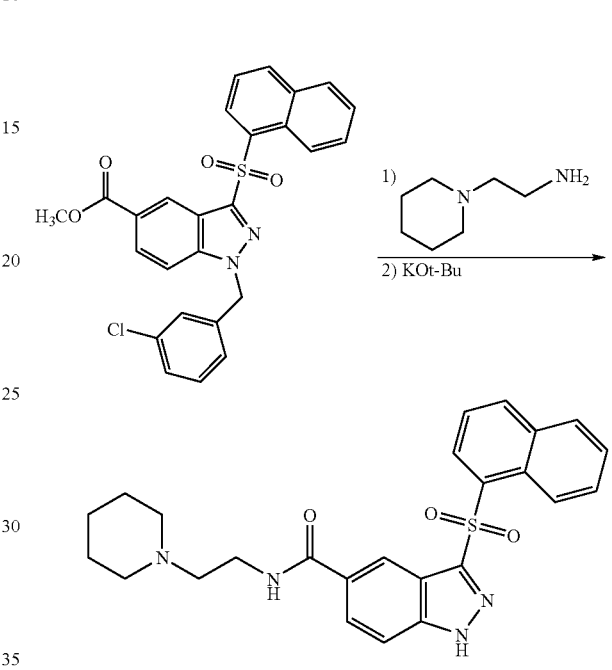

Using essentially the same procedure described in Example 151 and employing 1-(2-aminoethyl)piperidine in step 5, the title compound is obtained and identified by HPLC and mass spectral analyses, MS: (ES⁺) 463 [M+H]⁺.

EXAMPLE 153

N,N, N'-Trimethyl-N'-{[3-(1-naphthylsulfonyl)-1H-indazol-5-yl]methyl}ethane-1,2-diamine

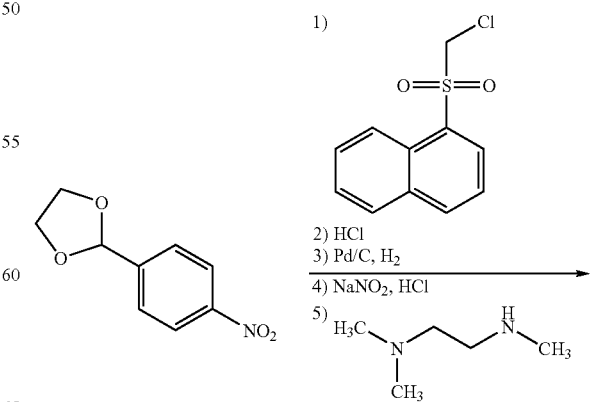

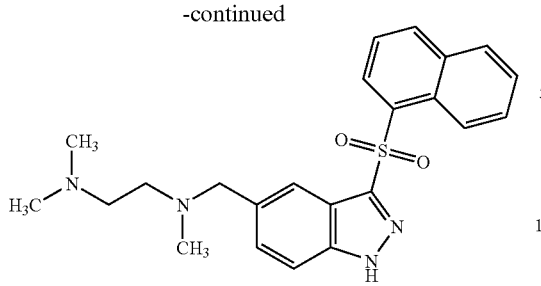

Step 1) 2-[3-(Naphthalene-1-sulfonylmethyl)-4-nitrophenyl]-[1,3]dioxolane

A mixture of 2-(4-Nitro-phenyl)-[1,3]dioxolane (1.85 g, 9.5 mmoles) and 1-chloromethane-sulfonyl-naphthalene (2.74 g, 11.4 mmoles) was stirred in THF (50 mL) at −78° C., in a round bottom flask under nitrogen. A solution of 1M potassium t-butoxide was added dropwise (19 mL, 19 mmoles) over a half an hour period. Temperature was allowed to rise to −40° C., and the reaction mixture was stirred at this temperature for 5 hours. The reaction mixture was poured into cold 2N HCl, extracted with EtOAc, dried over $Na_2SO_4$, and concentrated under vacuum. Compound was purified by normal phase HPLC using as eluent 40% EtOAc/hexane to afford the title compound as an off-white solid (3.03 g, 7.6 mmoles).

Step 2) 3-(Naphthalene-1-sulfonylmethyl)-4-nitrobenzaldehyde

A mixture of 2-[3-(naphthalene-1-sulfonylmethyl)-4-nitro-phenyl]-[1,3]dioxolane (3.03 g, 7.6 mmoles), and 2N HCl (4 mL, 8 mmoles) in THF (30 mL) was stirred at 40° C. for 4 hours. The reaction mixture was cooled to room temperature, diluted with waster, extracted with EtOAc, dried over $Na_2SO_4$, and concentrated under vacuum to yield the title compound (2.56 g, 7.22 mmoles).

Step 3) 4-Amino-3-(naphthalene-1-sulfonylmethyl)benzaldehyde

A mixture of 3-(naphthalene-1-sulfonylmethyl)-4-nitro-benzaldehyde (2.5 g, 7.22 mmoles) and 10% Pd/C in THF (10 mL), and methanol (20 mL) was hydrogenated in a Parr hydrogenation bottle (250 mL) at 52 lb/in$^2$ overnight. The mixture was filtered through Celite, and the filtrate was concentrated under vacuum to afford the title compound as an off-white solid (2.4 g, 6.85 mmoles).

Step 4) 3-(Naphthalene-1-sulfonyl)-1H-indazole-5-carbaldehyde

A mixture of 4-amino-3-(naphthalene-1-sulfonylmethyl)-benzaldehyde (2.4 g, 6.85 mmoles) in THF (10 mL) and 4M HCl (20 mL) was stirred in a round bottom flask at 3° C. A solution of sodium nitrite (0.49 g, 7.19 mmoles in $H_2O$ (2 mL) was added. The reaction mixture was poured into a cold solution of saturated sodium bicarbonate (100 mL) and extracted with EtOAc. Compound was dried over $Na_2SO_4$, and concentrated under vacuum to afford the title compound as an off white solid (1.84 g, 5.5 mmoles).

Step 5) N,N, N'-Trimethyl-N'-{[3-(1-naphthylsulfonyl)-1H-indazol-5-yl]methyl}ethane-1,2-diamine 3-(Naphthalene-1-sulfonyl)-1H-indazole-5-carbaldehyde (0.17 g, 0.5 mmol), trimethyl ethylene diamine (0.6 mmol) and sodium triacetoxyborohydride (0.7 mmol) in dichloroethane (5 mL) was stirred at room temperature for 24 hrs. After completion, the solvent was removed in vacuo, crude material dispersed in water and the pH brought to 3.4. Solid material was filtered off and washed with cold water to afford after drying the target material as a free base. The latter was converted into hydrochloride salt by dissolution in methanol, followed by treatment with the excess of 2N HCl and the evacuation of the volatiles in vacuo to afford the title compound hydrochloride salt, mp>200° C.; MS (APPI) 423 [M+H]

EXAMPLE 154

(3S)—N-{([3-(1-Naphthylsulfonyl)-1H-indazol-5-yl]methyl}pyrrolidin-3-amine Hydrochloride

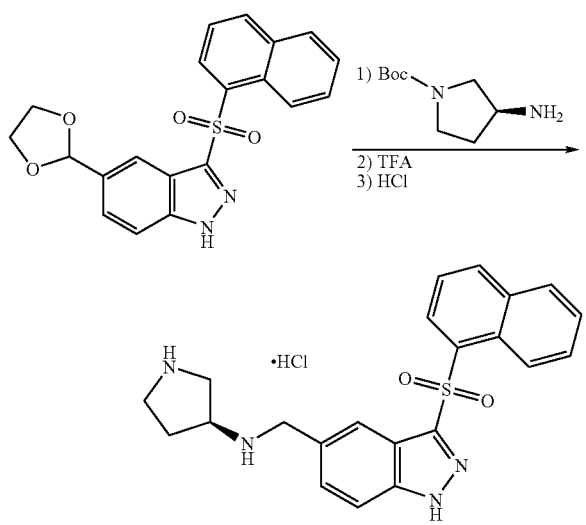

Using essentially the same procedure described in Example 153, step 5, and employing Boc-protected S(−)-pyrrolidin-3-ylamine, followed by the removal of the Boc-group by TFA in methylene chloride and treatment of the free base with 2N HCl, the title product was obtained, mp>200° C.; MS (ES) (M+H)$^+$407.1; MS (ES) (M+H+Na)$^+$429.1

EXAMPLE 155

N{[3-(1-Naphthylsulfonyl)-1H-indazol-5yl]methyl}ethane-1.2-diamine

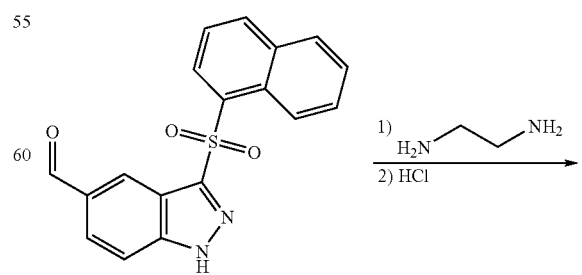

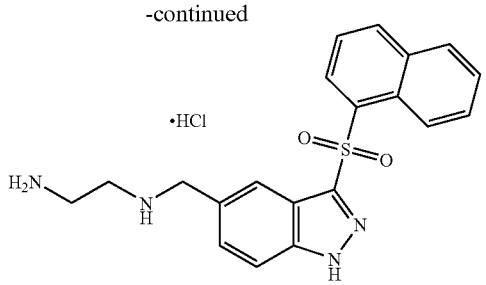

3-(Naphthalene-1-sulfonyl)-1H-indazole-5-carbaldehyde (0.3 mmol) was stirred for 24 hrs with the excess of ethylene diamine (1 mmol) in methanol. Sodium borohydride (0.6 mmol) was added and stirring continued for another 24 hrs. After completion, the volatiles were removed in vacuo, crude material diluted with cold water, acidified to pH 3.4, filtered off, washed on a filter with cold water and dried to afford the target material as a free base. The latter was converted into hydrochloride salt by dissolution in methanol, followed by treatment with the excess of 2N HCl and the evacuation of the volatiles in vacuo to afford the title compound, mp>200° C.; MS (ES$^+$) 381[M+H]$^+$

EXAMPLE 156

N,N-Dimethyl-2-{[3-(1-naphthylsulfonyl)-1H-indazol-5-yl]methoxy}ethanamine

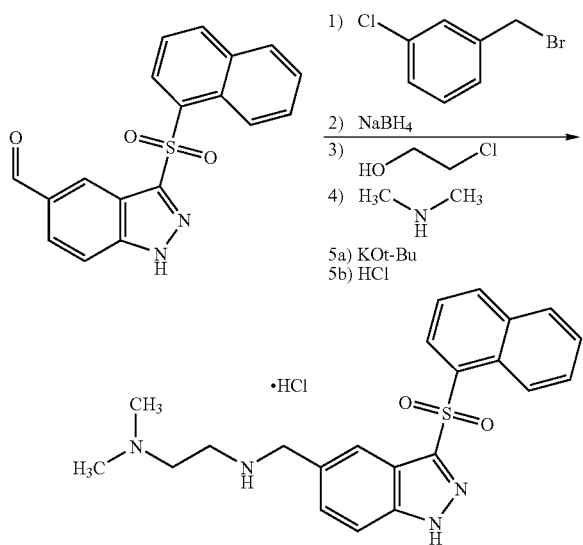

Step 1) 1-(3-Chloro-benzyl)-3-naphthalene-1-sulfonyl)-1H-indazole-5-carbaldehyde A mixture of 3-(1-naphthylsulfonyl)-1H-indazole-5-carbaldehyde (0.17 g, 0.5 mmoles), 3-chlorobenzyl bromide (0.07 mL, 0.6 mmoles), and cesium carbonate (0.19 g, 0.6 mmoles) in DMF (5 mL) was stirred together in a round bottom flask at room temperature for 30 minutes. Reaction mixture was diluted with H$_2$O, extracted with EtOAc, washed with water (2×), brine (1×), dried over Na$_2$SO$_4$, and concentrated under vacuum. The crude product was purified by normal phase HPLC using as eluent 30% EtOAc/hexane to afford the title compound as an off-white solid (0.18 g, 0.4 mmoles).

Step 2) [1-(3-Chlorobenzyl)-3-(1-naphthylsulfonyl)-1H-indazol-5-yl]-methanol 1-(3-Chloro-benzyl)-3-(naphthalene-1-sulfonyl)-1H-indazole-5-carbaldehyde (0.18 g, 0.4 mmol) was dissolved in THF and treated under nitrogen with the excess of sodium borohydride (0.2 mmol). After 1 hr the reaction mixture was diluted with water and the product extracted with methylene chloride to afford after evaporation of the solvent the title compound as a colorless solid (0.18 g, 0.4 mmoles).

Step 3) 1-(3-Chlorobenzyl)-5-(2-chloroethoxymethy)-3-(1-naphthylsulfony)-1H-indazole

[1-(3-Chlorobenzyl)-3-(1-naphthylsulfonyl)-1H-indazol-5-yl]-methanol (0.18 g, 0.4 mmol) and diisopropyl ethyl amine (1 mmol) in methylene chloride were treated at −20° C. with trifluoromethanesulfonic anhydride (0.14 g, 0.5 mmol). After stirring for 30 min an excess of 2-chloroethanol (2 mmol) was added and the mixture stirred for additional 2 hrs at −20° C. and at room temperature for 12 hrs. The reaction mixture was diluted with water, extracted with ethyl acetate and after evaporation of solvent, chromatographed on silica gel using 40% ethyl acetate/hexane as an eluent to afford the target material (0.08 g, 0.16 mmoles).

Step 4) {2-[1-(3-Chlorobenzyl)-3-(naphthalene-1-sulfonyl)-1H-indazol-5-ylmethoxy]ethyl}dimethylamine A mixture of 1-(3-chlorobenzyl)-5-(2-chloroethoxymethy)-3-(1-naphthylsulfony)-1H-indazole (0.08 g, 0.16 mmoles) and dimethylamine (0.28 ml, 0.56 mmoles) in DMSO (1 mL) was stirred under nitrogen at 100° C. for 4 hours. Mixture was cooled to room temperature, diluted with water, extracted with EtOAc, washed with water (2×), brine (1×), dried over Na$_2$SO$_4$, and concentrated under vacuum. Compound was purified by flash chromatography using as eluent 5% CH$_3$OH/EtOAc to afford the title compound (0.08 g, 0.15 mmoles).

Step 5) N,N-Dimethyl-2-{[3-(1-naphthylsulfonyl)-1H-indazol-5-yl]methoxy}ethanamine A mixture of {2-[1-(3-chloro-benzyl)-3-(naphthalene-1-sulfonyl)-1H-indazol-5-ylmethxy]-ethyl}-dimethyl-amine (0.08 g, 015 mmoles) in DMSO (1 mL) and t-BuOH (0.2 mL) was stirred at room temperature in a round bottom flask under oxygen atmosphere. A solution of potassium t-butoxide (0.05 mL, 0.05 mmoles) was added dropwise and the reaction mixture stirred for 30 min. Reaction mixture was quenched with saturated ammonium chloride, extracted with EtOAc, dried over Na$_2$SO$_4$, and concentrated under vacuum. Crude compound was converted into the HCl salt as previously described to afford the title compound, mp>200° C.; MS (ES$^+$) 410[M+H]$^+$.

EXAMPLE 157

N1-[3-(Naphthalene-1-sulfonyl)-1H-indazol-5-yl]-ethane-1,2-diamine dihydrochloride Step 1

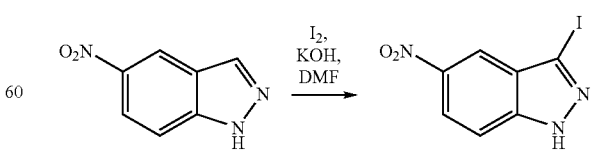

3-Iodo-5-nitro-1H-indazole Iodine (26.46 g, 104.27 mmol) and potassium hydroxide pellets (11.70 g, 208.54 mmol) were successively added into a DMF (104 mL) solution of 5-nitroindazole (8.50 g, 52.13 mmol) at room temperature and stirred for 4 days. The reaction mixture was then poured into NaHSO₃ solution (11.06 g in 200 mL water). The brown color faded away, and the formed yellow precipitate was filtered and washed with water and dried in vacuo to provide the title compound as a yellow solid (14.74 g, 98% yield). MS (ES⁺) m/e 290 (MH⁺)

Step 2

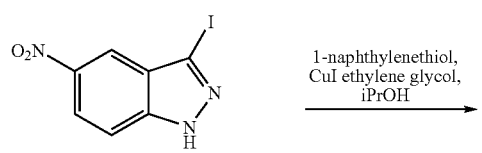

3-(Naphthalen-1-ylsulfanyl)-5-nitro-1H-indazole A mixture of 3-iodo-5-nitro-1H-indazole (10.00 g, 34.60 mmol), 1-naphtylenethiol (5.54 g, 34.60 mmol), CuI (0.659 g, 3.46 mmol), ethylene glycol (4.30 g, 69.20 mmol) in isopropanol (49.40 mL) was heated at 90° C. under nitrogen overnight, cooled, diluted with 30% MeOH in CH₂Cl₂, and passed through a pad of silica gel. The solution was concentrated in vacuo and purified by chromatography with 1% MeOH in CH₂Cl₂ to provide the title compound (5.5 g, 49%). MS (ES⁺) m/e 322 (MH⁺).

Step 3

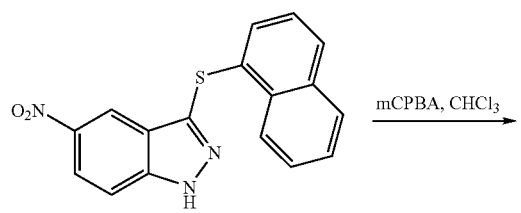

3-(Naphthalene-1-sulfonyl)-1H-indazol-5-ylamine A mixture of 3-(naphthalen-1-ylsulfanyl)-5-nitro-1H-indazole (5.50 g, 17.11 mmol) and 3-chloroperoxybenzoic acid (17.91 g, 103.80 mmol) in CHCl₃ (115 mL) was stirred at room temperature for 4 hr, diluted with EtOAc, washed with Na₂SO₃ solution, water, brine, dried over Na₂SO₄, and concentrated in vacuo to effort the crude intermediate which was carried out directly for the next step reaction without further purification. The mixture of the crude sulfone intermediate, tin mossy (15.79 g, 133.01 mmol) in MeOH and conc. hydrochloric acid was heated at 60° C., diluted with CH₂Cl₂, and neutralized to basic with NaOH or Na₂CO₃ solution. The aqueous layer was extracted with CH₂Cl₂. Combined organic layers were dried over Na₂SO₄ and concentrated in vacuo followed by chromatography purification to provide the title compound (2.50 g, 45% overall yield). MS (ES⁺) m/e 324 (MH⁺)

Step 4

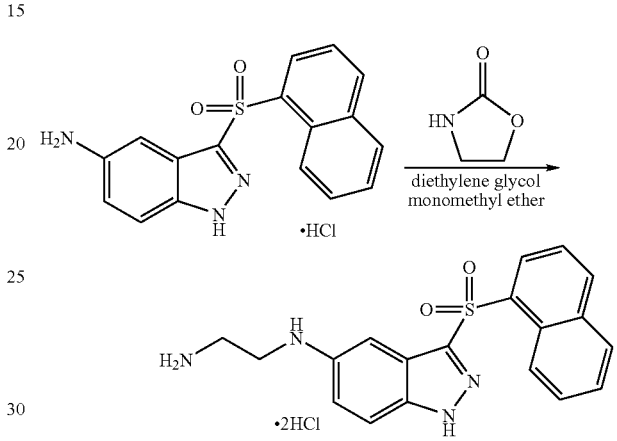

N1-[3-(Naphthalene-1-sulfonyl)-1H-indazol-5-yl]-ethane-1,2-diamine dihydrochloride A mixture of 3-(naphthalene-1-sulfonyl)-1H-indazol-5-ylamine hydrochloride (334 mg, 0.93 mmol), 2-oxazolidone (81 mg, 0.93 mmol), and diethylene glycol monomethyl ether (0.16 mL) was heated at 170° C. overnight, diluted with MeOH, and purified by reverse phase HPLC followed by conversion to HCl salt by treatment with HCl solution to provide the title compound as a white solid (86 mg, 21% yield). MS (ES⁺) m/e 367 (MH⁺)

EXAMPLE 158

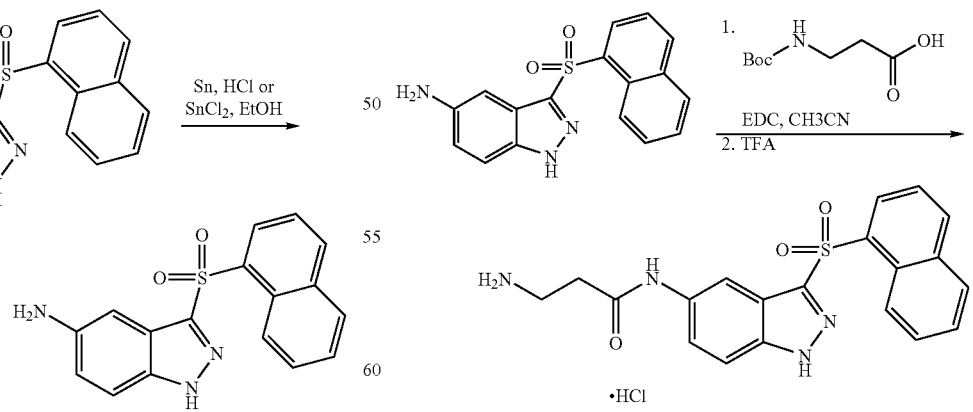

3-Amino-N-[3-(naphthalene-1-sulfonyl)-1H-indazol-5-yl]-propionamide hydrochloride A mixture of 3-(naphthalene-1-sulfonyl)-1H-indazol-5-ylamine (500 mg, 1.55 mmol), N-t-Boc-β-alanine (381 mg, 2.01 mmol), 1-[3-(dimethylamino)

propyl)]-3-ethylcarbodimide hydrochloride (386 mg, 2.01 mmol) in CH₃CN was stirred at room temperature overnight and concentrated to dryness. The resulting residue was subjected to TFA, concentrated, and purified by reverse phase HPLC followed by treatment with HCl solution to provide the title compound as a white solid (180 mg, 24% yield). MS (ES⁺) m/e 395 (MH⁺)

EXAMPLE 159

Step 1

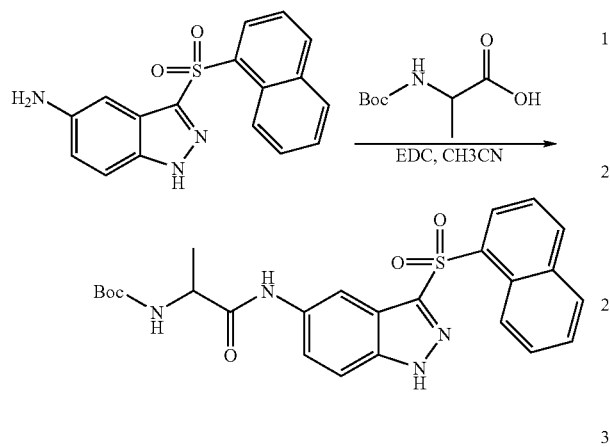

{1-[3-(Naphthalene-1-sulfonyl)-1H-indazol-5-ylcarbamoyl]-ethyl}-carbamic acid tert-butyl ester A mixture of 3-(naphthalene-1-sulfonyl)-1H-indazol-5-ylamine (500 mg, 1.55 mmol), N-t-Boc-alanine (381 mg, 2.01 mmol), 1-[3-(dimethylamino)propyl]-3-ethylcarbodimide hydrochloride (386 mg, 2.01 mmol) in CH₃CN was stirred at room temperature overnight, concentrated, and purified by chromatography with 3% MeOH in CH₂Cl₂ to provide the title compound (110 mg, 48%), characterized by NMR and mass spectral analyses.

Step 2

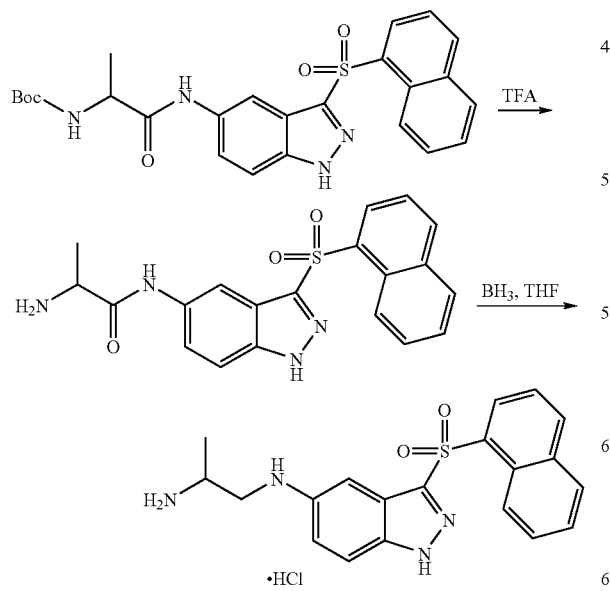

N1-[3-(Naphthalene-1-sulfonyl)-1H-indazol-5-yl]-propane-1,2-diamine hydrochloride {1-[3-(Naphthalene-1-sulfonyl)-1H-indazol-5-ylcarbamoyl]-ethyl}carbamic acid tert-butyl ester (120 mg, 0.37 mmol) was subjected to TFA at room temperature for 2 hr and concentrated to dryness. The resulting residue was heated with BH₃ in THF (1 M, 4.5 mL) at reflux overnight. To the mixture was slowly added HCl (6 M, 1 mL). The resulting solution was heated at 80° C. for 20 min, concentrated, and purified by reverse phase HPLC followed by treatment with HCl solution to provide the title compound (35 mg, 38%). MS (ES⁺) m/e 381 (MH⁺)

EXAMPLE 160

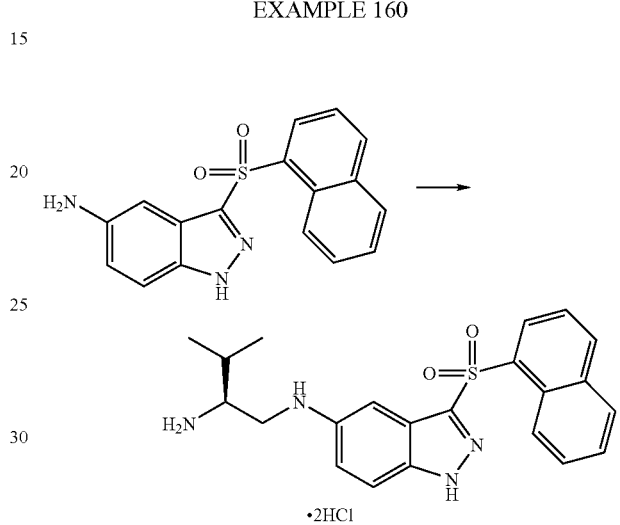

(S)-3-Methyl-N1-[3-(naphthalene-1-sulfonyl)-1H-indazol-5-yl]-butane-1,2-diamine dihydrochloride Using essentially the same procedure described in Example 159 and employing (S)-t-Boc-Valine as the starting material, the title compound was obtained, MS (ES⁺) m/e 409 (MH⁺)

EXAMPLE 161

N1-[3-(Naphthalene-1-sulfonyl)-1H-indazol-7-yl]-ethane-1,2-diamine dihydrochloride

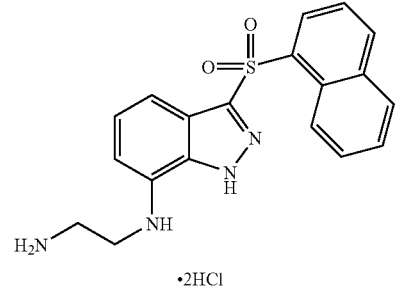

Using essentially the same procedure described in Example 157 (step 4) and employing product from Example 162 (step 1) as the starting material, the title compound was obtained, MS (ES+) m/e 367 (MH⁺)

EXAMPLE 162

3-Dimethylamino-N-[3-(naphthalene-1-sulfonyl)-1H-indazol-7-yl]-propionamide hydrochloride Step 1

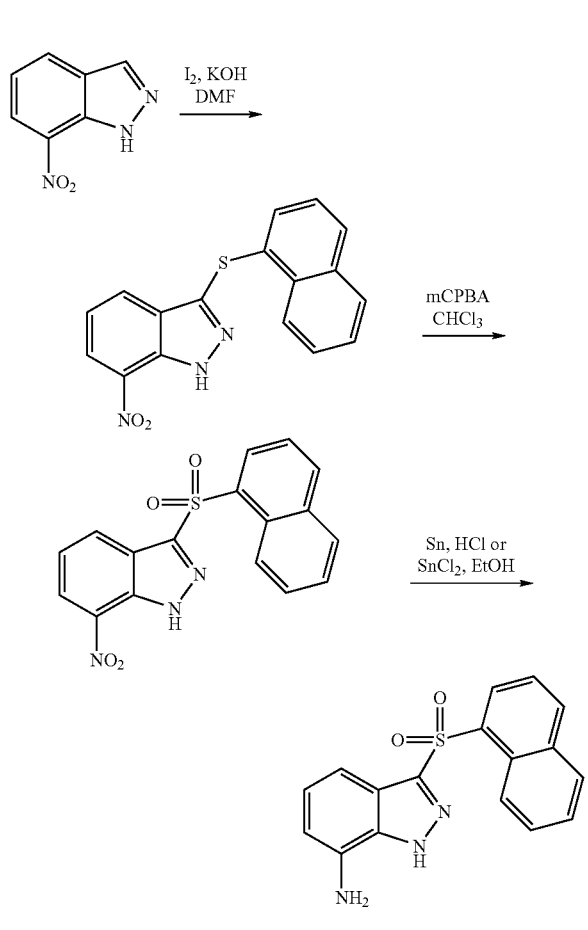

3-(Naphthalene-1-sulfonyl)-1H-indazol-7-ylamine The title compound was prepared according to the procedure described in Example 157 (steps 1-3) and employing 7-nitroindazole as the starting material.

Step 2

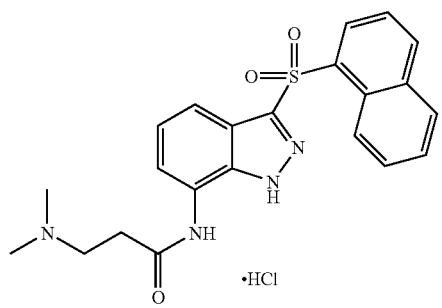

3-Dimethylamino-N-[3-(naphthalene-1-sulfonyl)-1H-indazol-7-yl]-propionamide dihydrochloride The title compound was prepared in a similar manner as described in Example 158 and employing the appropriate starting material. MS (ES⁺) $^{m/e}$ 423 (MH⁺)

EXAMPLE 163

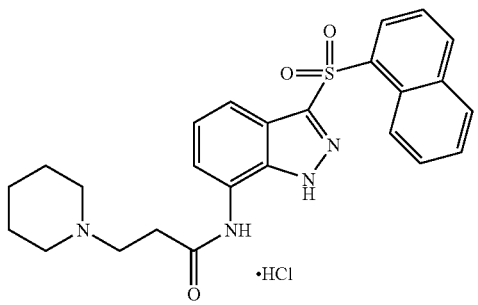

N-[3-(Naphthalene-1-sulfonyl)-1H-indazol-7-yl]-3-piperidin-1-yl-propionamide hydrochloride The title compound was prepared in a similar manner as described in Example 158 and employing the appropriate starting material. MS (ES⁺) m/e 463 (MH⁺)

EXAMPLE 164

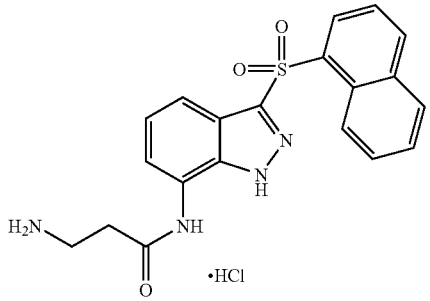

3-Amino-N-[3-(naphthalene-1-sulfonyl)-1H-indazol-7-yl]-propionamide hydrochloride The title compound was prepared in a similar manner as described in Example 158 and employing the appropriate starting material. MS (ES⁺) m/e 395 (MH⁺)

EXAMPLE 165

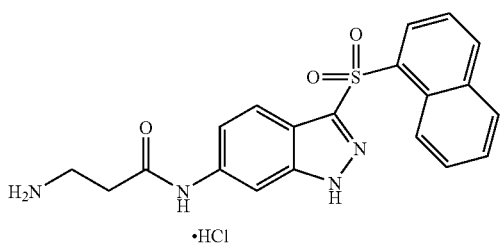

3-Amino-N-[3-(naphthalene-1-sulfonyl)-1H-indazol-6-yl]-propionamide hydrochloride Using essentially the same procedure described in Example 158 and employing 6-amino-3-(1-naphthylsulfonyl)-1H-indazole as the starting material, the title compound was obtained, MS (ES$^+$) m/e 395 (MH$^+$)

EXAMPLE 166

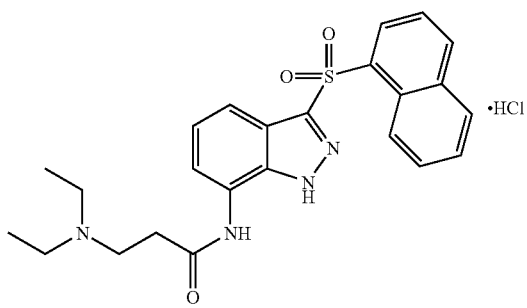

3-Diethylamino-N-[3-(naphthalene-1-sulfonyl)-1H-indazol-7-yl]-propionamide hydrochloride Using essentially the same procedure described in Example 158 and employing 7-amino-3-(1-naphthylsulfonyl)-1H-indazole and the desired amino acid as the starting materials, the title compound was obtained. MS (ES$^+$) m/e 451 (MH$^+$)

EXAMPLE 167

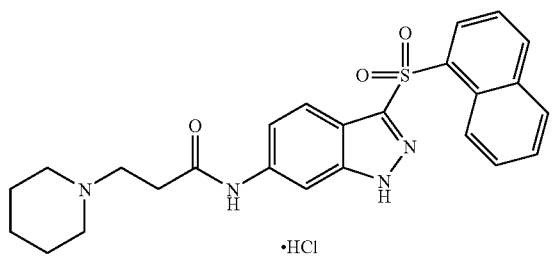

N-[3-(Naphthalene-1-sulfonyl)-1H-indazol-6-yl]-3-piperidin-1-yl-propionamide hydrochloride Using essentially the same procedure described in Example 158 and employing 6-amino-3-(1-naphthylsulfonyl)-1H-indazole and the desired amino acid as the starting materials, the title compound was obtained, MS (ES$^+$) m/e 463 (MH$^+$).

EXAMPLE 168

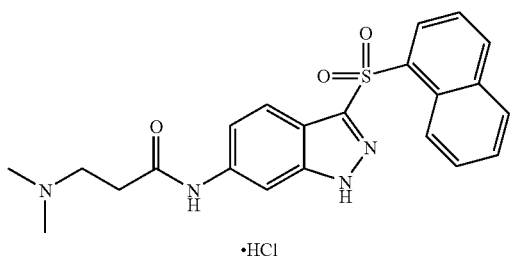

3-Dimethylamino-N-[3-(naphthalene-1-sulfonyl)-1H-indazol-6-yl]-propionamide hydrochloride Using essentially the same procedure described in Example 158 and employing 6-amino-3-(1-naphthylsulfonyl)-1H-indazole and the desired amino acid as starting materials, the title compound was obtained, MS (ES$^+$) m/e 423 (MH$^+$).

EXAMPLE 169

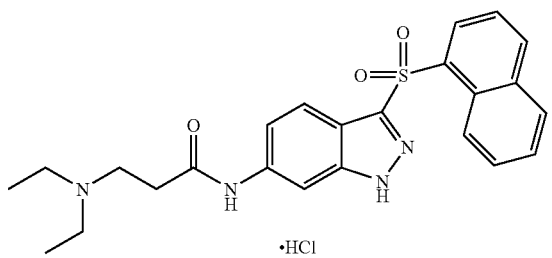

3-Diethylamino-N-[3-(naphthalene-1-sulfonyl)-1H-indazol-6-yl]-propionamide hydrochloride Using essentially the same procedure described in Example 158 and employing 6-amino-3-(1-naphthylsulfonyl)-1H-indazole and the desired amino acid as starting materials, the title compound was obtained, MS (ES$^+$) m/e 451 (MH$^+$).

EXAMPLE 170

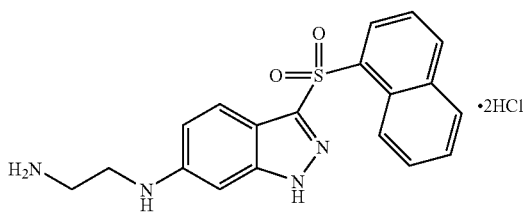

N1-[3-(Naphthalene-1-sulfonyl)-1H-indazol-6-yl]-ethane-1,2-diamine dihydrochloride Using essentially the same procedure described in Example 158 and employing 6-amino-3-(1-naphthylsulfonyl)-1H-indazole as starting material, the title compound was obtained, MS (ES$^+$) m/e 367 (MH$^+$).

EXAMPLE 171

N,N-Dimethyl-N-{2-[3-(phenylsulfonyl)-1H-indazol-7-yl]ethyl}amine hydrochloride

Step 1

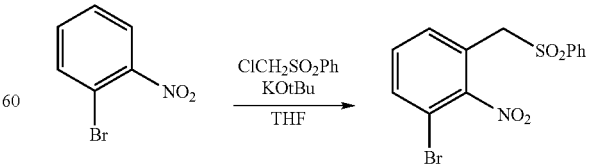

3-Bromo-2-nitrobenzyl phenyl sulfone To a stirred solution of 1-bromo-2-nitrobenzene (10.1 g, 50 mmol) and chloromethylphenylsulfone (9.5 g, 50 mmol) in dry THF (100 mL) at -65° C. under nitrogen is added 1.0M KOtBu in THF (110 mL, 110 mmol). The deep purple reaction is allowed to warm to 0° C. over 1.5 hours and then treated with glacial acetic acid (8 mL). The reaction is diluted with water (200 mL) and saturated aqueous NaHCO$_3$ (200 mL), and then extracted with CH$_2$Cl$_2$ (2×400 mL). The extracts are dried (MgSO$_4$) and concentrated in vacuo to a light orange solid. Trituration with ethyl acetate and hexanes affords the title compound as a pale yellow solid (13 g, 73%). Mp: 138-141° C. MS (ES-): 354 (M-H)

Step 2

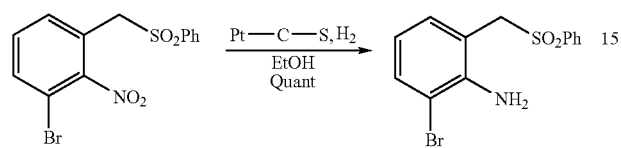

6-Bromo-2-[(phenylsulfonyl)methyl]aniline Catalytic hydrogenation of 6-bromo-2-nitrobenzyl phenyl sulfone (0.36 g, 1 mmol) in the presence of platinum on carbon, disulfided and hydrogen (45 psi) in ethyl alcohol (40 mL) for 1 hour gives a reaction mixture. The reaction mixture is filtered through celite and concentrated in vacuo to give the title compound as a light brown solid (0.32 g, 99%). Mp: 174-177° C. MS (ES+): 326 (M+H)

Step 3

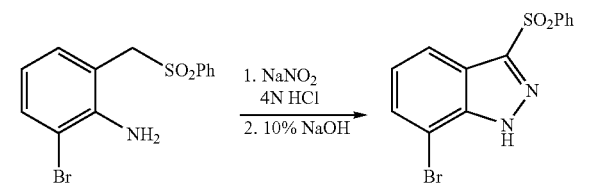

7-Bromo-3-(phenylsulfonyl)-1H-indazole A solution of NaNO$_2$ (0.91 g, 13.35 mmol) in H$_2$O (10 mL) was added to a solution of 6-bromo-2-[(phenylsulfonyl)methyl]aniline (2.9 g, 8.9 mmol) in 70 mL of 4 NHCl at approximately 5° C. The reaction mixture was stirred for 30 min. at 0° C., and neutralized with 10% NaOH. The resulting solid was collected by filtration, washed with water and purified by flash chromatography (25% ethyl acetate/petroleum ether) to afford the title compound as a pink solid (2.27 g, 91%) Mp: 173-175° C., MS (ES-) 335 (M-H)

Step 4

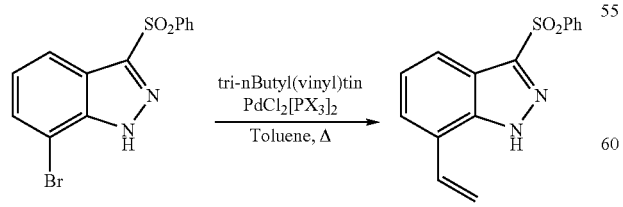

3-(Phenylsulfonyl)-7-vinyl-1H-indazole A mixture of 7-Bromo-3-(phenylsulfonyl)-1H-indazole (2.72 g, 8.07 mmol) and dichlorobis(tri-o-tolylphosphine)-palladium(II) (0.94 g, 1.2 mmol) were dissolved in toluene (220 mL) and stirred for 10 minutes at room temperature under a nitrogen atmosphere. Tributyl(vinyl)tin (3.3 mg, 10.55 mmol) was added and the mixture was refluxed for 15 min or until turned black. The mixture was cooled to room temperature, diluted with ethyl acetate (150 mL), 1 M KF (25 mL) and stirred for 12 hours. The resulting tin salt precipitate was removed by suction filtration and the organic layer was washed with water (100 mL), then brine and dried over MgSO$_4$, filtered and concentrated in vacuo. Purification by flash chromatography (40% ethyl acetate/petroleum ether) gave the title compound as a light yellow solid (2.02 g, 88%). Mp: 129-130° C. MS (ES+): 285 (M+H)

Step 5

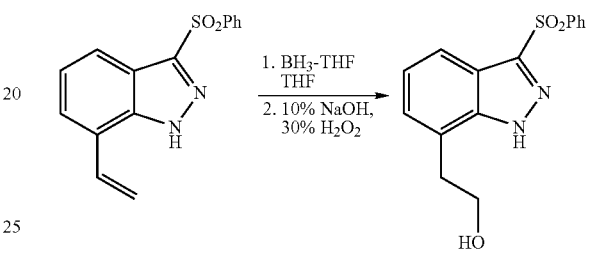

2-[3-(Phenylsulfonyl)-1H-indazol-7-yl]ethanol To a solution of 3-(phenylsulfonyl)-7-vinyl-1H-indazole (2.0 g, 7.04 mmol) in THF (40 mL) at 0° C. was added dropwise BH$_3$-THF (15 mL of 1 M THF solution, 15 mmol). The solution was stirred for 3 hours at 0° C., and H$_2$O (20 mL) was added slowly. To this mixture was added 10% NaOH (17 mL), 30% H$_2$O$_2$ (15 mL) and the mixture was stirred vigorously at room temperature overnight. The mixture was partitioned between ethyl acetate and H$_2$O, and the aqueous layer was extracted with ethyl acetate (2×50 mL). The combined organic layers were washed with brine, dried (MgSO$_4$), filtered and concentrated under reduced pressure. Silica gel chromatography (50% ethyl acetate/dichloromethane) gave the title compound as a white solid (1.42 g, 66%). Mp: 137-138° C. MS (ES+): 303 (M+H)

Step 6

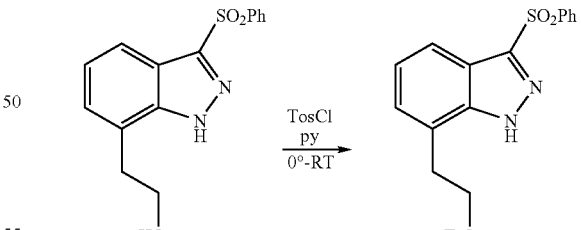

2-[3-(Phenylsulfonyl)-1H-indazol-7-yl]ethyl 4-methylbenzenesulfonate To a solution of 2-[3-(phenylsulfonyl)-1H-indazol-7-yl]ethanol (0.64 g, 2.12 mmol) in anhydrous dichloromethane (30 mL) at 0° C. was added pyridine (0.43 mL) and toluenesulfonyl chloride (0.475 g, 2.5 mmol). The solution was stirred for 12 hours at room temperature. The mixture was concentrated in vacuo and taken up in ethyl acetate (30 mL). The organic layer was washed with 2 M HCl, (2×25 mL), brine, dried (MgSO$_4$), filtered and concentrated under reduced pressure. Silica gel chromatography (50% ethyl acetate/petroleum ether) gave the title compound as a white foam (0.9 g, 93%). Mp: 61-64° C. MS (ES−): 455 (M−H) Step 7

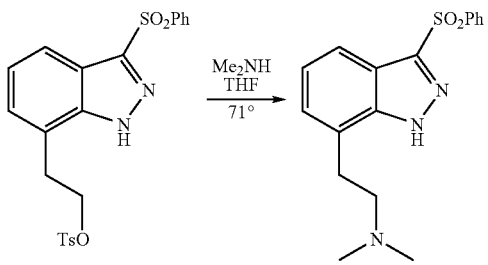

N,N-Dimethyl-N-{2-[3-(phenylsulfonyl)-1H-indazol-7-yl]ethyl}amine hydrochloride A solution of 2-[3-(phenylsulfonyl)-1H-indazol-7-yl]ethyl 4-methylbenzenesulfonate (0.137 g, 0.3 mmol) in anhydrous THF (2 mL) was added an excess of dimethylamine (0.5 mL of 2 M THF solution, 1 mmol) and heated to 71° C. for 24 hours. The mixture was partitioned between ethyl acetate and $H_2O$, and the aqueous layer was extracted with ethyl acetate (10 mL). The combined organic layers were washed with 2 M NaOH, (2×15 mL), brine, dried ($MgSO_4$), filtered and concentrated under reduced pressure. The product was passed through a plug of silica gel eluting with (20% EtOH/2N ammonia/dichloromethane) to give the title compound as a white solid (0.049 g, 77%). This solid was dissolved in diethyl ether and treated with 1 N HCl in diethyl ether (0.12 mL, 0.12 mmol) to afford a white precipitate isolated by vacuum filtration. Mp: 76-80° C. MS (ES−): 328 (M−H)

EXAMPLE 172

N-{2-[3-(phenylsulfonyl)-1H-indazol-7-yl]ethyl}cyclopropanamine hydrochloride

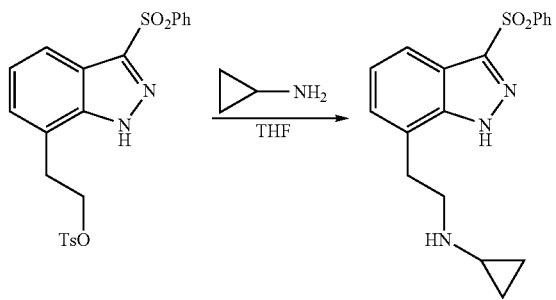

Using essentially the same procedure described in Example 171, step 7, and employing cyclopropyl amine, the title compound was obtained as a white solid, mp 115-117° C., MS: (M+H) 342.

EXAMPLE 173

N-Methyl-N-{2-[3-(phenylsulfonyl)-1H-indazol-7-yl]ethyl}amine trifluoroacetate

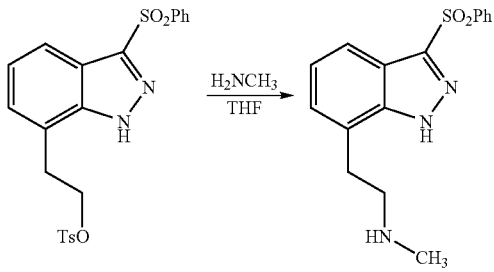

Using essentially the same procedure described in Example 171, step 7, and employing methylamine and sub-stituting trifluoroacetic acid for HCl, the title compound was obtained as a clear glass, MS: (M+H) 316.

EXAMPLE 174

{2-[3-(Phenylsulfonyl)-1H-indazol-7-yl]ethyl}amine Hydrochloride

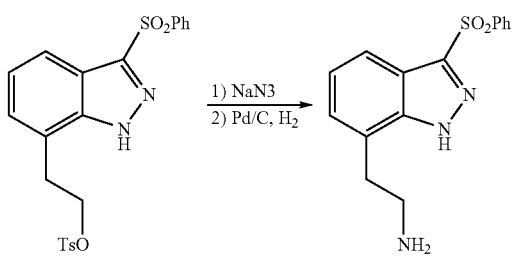

Step 1) 7-(2-Azidoethyl)-3-(phenylsulfonyl)-1H-indazole

A solution of 2-[3-(phenylsulfonyl)-1H-indazol-7-yl]ethyl 4-methylbenzene-sulfonate (0.14 g, 0.3 mmol) in anhydrous DMF (2.5 mL) was added sodium azide (0.06 g, 0.9 mmol) and heated to 100° C. for 6 hours. The mixture was partitioned between ethyl acetate and $H_2O$, and the aqueous layer was extracted with ethyl acetate (10 mL). The combined organic layers were washed with brine (1×15 mL), dried ($MgSO_4$), filtered and concentrated under reduced pressure. Silica gel chromatography (40% Ethyl acetate/petroleum ether) gave the azide as a white solid (0.08 g, 86%). Mp: 105-107° C. MS (ES−): 326 (M−H)

Step 2) {2-[3-(Phenylsulfonyl)-1H-indazol-7-yl]ethyl}amine Hydrochloride 7-(2-Azidoethyl)-3-(phenylsulfonyl)-1H-indazole (0.08 g, 0.20 mmol) was reduced by catalytic hydrogenation in the presence of palladium on carbon and hydrogen (40 psi) in ethanol (30 mL) for 4 hours. The reaction mixture was filtered through Celite and concentrated in vacuo to give a white solid (0.06 g, 99%). This solid was dissolved in diethyl ether and treated with 1 N HCl in diethyl ether (0.21 mL, 0.21 mmol) to afford a tan precipitate isolated by vacuum filtration. Mp: 157-160° C. MS (ES−): 300 (M−H)

EXAMPLE 175

N-Methyl-N-{2-[3-(phenylsulfonyl)-1H-indazol-5-yl]ethyl}amine

Step 1

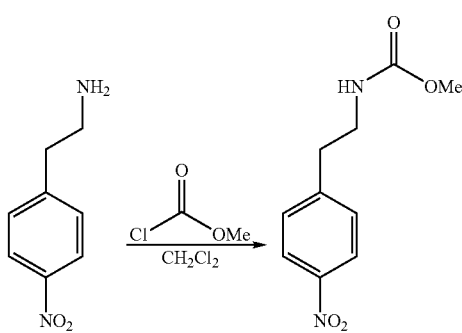

Methyl[2-(4-nitrophenyl)ethyl]carbamate To a stirred solution of [2-(4-nitrophenyl)ethyl]amine (6.06 g, 30 mmol) in CH$_2$Cl$_2$ (75 ml), MeOH (5 mL), and TEA (9.5 mL) at 0° C. was added chloromethylformate (3.39 g, 36 mmol) dropwise. The reaction mixture was stirred at room temperature for 1 hr. concentrated in vacuo, and partitioned between ethyl acetate and water; the aqueous layer was extracted with ethyl acetate. The combined organic layers were washed with water (50 mL) and brine (50 mL). The organic layer was dried (MgSO$_4$), filtered and concentrated under reduced pressure to afford a yellow solid (6.6 g, 98%). Mp: 38° C. MS (ES−): 223 (M−H).

Step 2

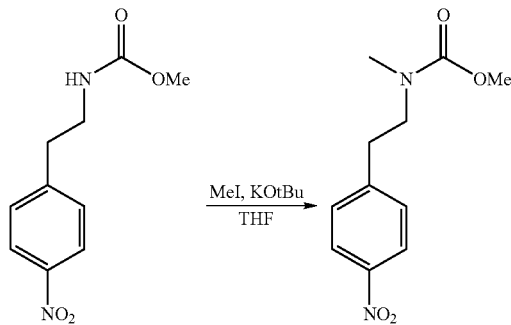

Methyl methyl[2-(4-nitrophenyl)ethyl]carbamate To a stirred solution of methyl[2-(4-nitrophenyl)ethyl]carbamate (224 mg, 1 mmol) in THF (2 mL) was added KO$^t$Bu (201 mg, 1.8 mmol) and MeI (256 mg, 1.8 mmol) sequentially. The reaction mixture was stirred for 12 h at room temperature. The reaction was diluted with water (5 mL), extracted with EtOAc (2×15 mL). The organics were washed with water and brine, dried (MgSO$_4$), filtered and concentrated under reduced pressure. Silica gel chromatography (40% ethyl acetate/petroleum ether) afforded the title compound as a semi solid (160 mg, 67.2%). MS (ES+): 239 (M+H)$^+$.

Step 3

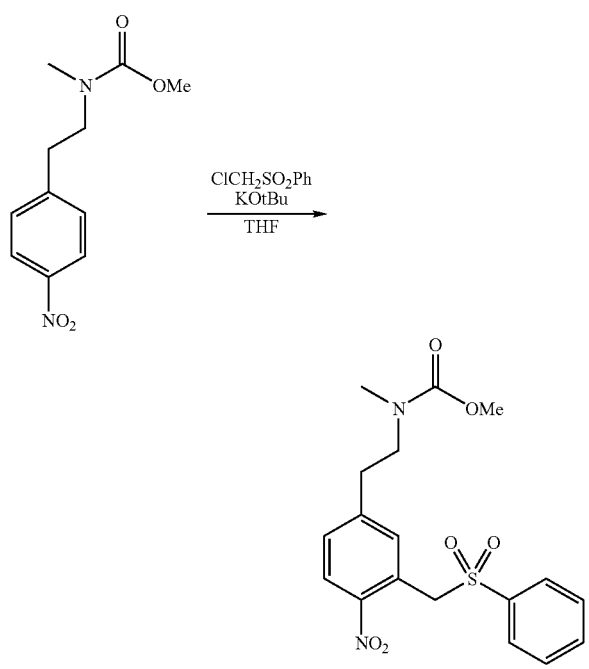

Methyl methyl(2-{4-nitro-3-[(phenylsulfonyl)methyl]phenyl}ethyl)carbamate Using substantially the same manner as described in Example 171, step 1 and employing methyl methyl[2-(4-nitrophenyl)ethyl]carbamate (2.47 g, 10.38 mmol), the title compound was obtained as a white solid, (2.06 g, 51%). Mp: 42° C., MS (ES+): 393 (M+H)$^+$.

Step 4

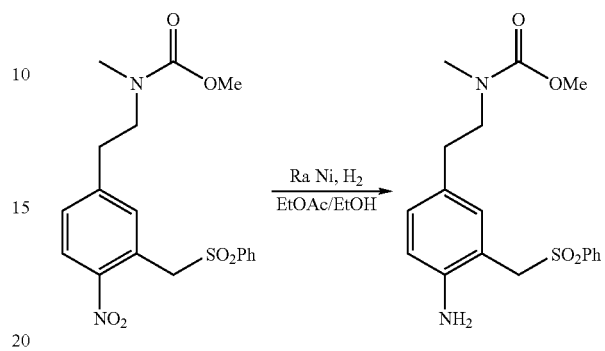

Methyl(2-{4-amino-3-[(phenylsulfonyl)methyl]phenyl}ethyl)methylcarbamate Catalytic hydrogenation of methyl methyl(2-{4-nitro-3-[(phenylsulfonyl)methyl]-phenyl}ethyl)carbamate (1.8 g, 4.6 mmol) in the presence of Raney nickel and hydrogen (45 psi) in ethyl acetate/ethanol (60 mL) for 2 h gives a reaction mixture. The reaction mixture is filtered through celite and concentrated in vacuo to give the title compound as a light brown solid (1.36 g, 82%). Mp: 95-96° C. MS (ES+): 363 (M+H)$^+$.

Step 5

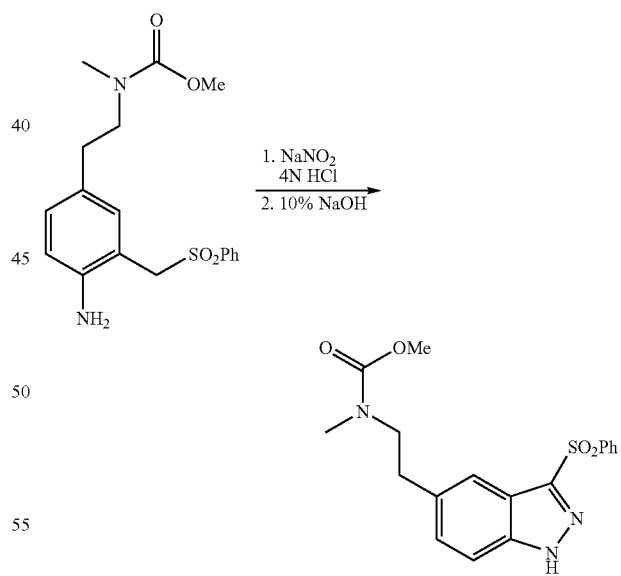

Methyl methyl{2-[3-(phenylsulfonyl)-1H-indazol-5-yl]ethyl}carbamate Using substantially the same procedure described in Example 171, step 3 and employing methyl(2-{4-amino-3-[(phenylsulfonyl)methyl]phenyl}ethyl)methylcarbamate (0.362 g, 1 mmol), the title compound was obtained as a white solid, (0.29 g, 78%). Mp: 145-147° C., MS (ES+): 374 (M+H)$^+$ Step 6

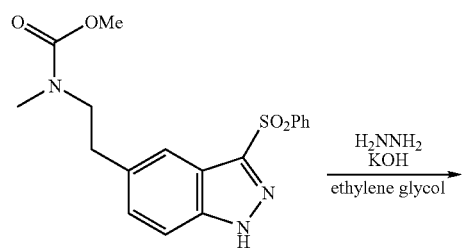

N-Methyl-N-{2-[3-(phenylsulfonyl)-1H-indazol-5-yl]ethyl}amine To a solution of methyl methyl{2-[3-(phenylsulfonyl)-1H-indazol-5-yl]ethyl}carbamate (250 mg, 0.67 mmol) in ethylene glycol (7 mL) was added H$_2$NNH$_2$ (110 mg, 3.35 mmol), KOH (1.38 g 10.05 mmol), and heated to 110° C. overnight. The reaction was cooled to room temperature, water was added and the mixture extracted with CH$_2$Cl$_2$. The organic layers were washed with water, brine, dried (MgSO$_4$) and concentrated under reduced pressure to give a residue which is triturated with CH$_2$Cl$_2$ to afford the title compound as a off white solid 210 mg (99%) Mp: 186-188° C., MS (ES+): 316 (M+H)$^+$

EXAMPLE 176

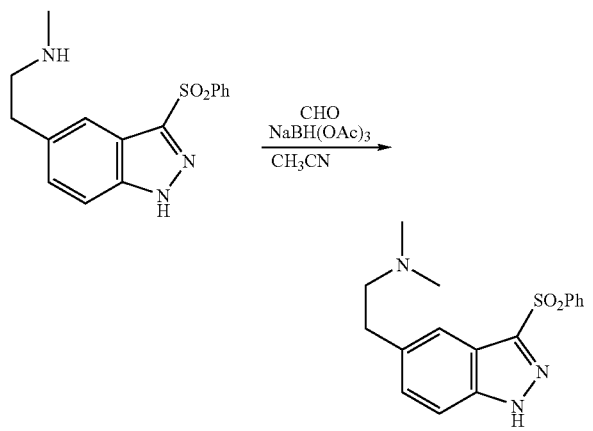

N,N-Dimethyl-N-{2-[3-(phenylsulfonyl)-1H-indazol-5-yl]ethyl}amine hydrochloride To a solution of N-methyl-N-{2-[3-(phenylsulfonyl)-1H-indazol-5-yl]ethyl}amine (38 mg, 0.12 mmol) in acetonitrile (3 mL) was added NaBH(OAc)$_3$ (100 mg, 0.48 mmol), formaldehyde (0.027 mL, 0.36 mmol), and stirred at rt. for 3 hr. The reaction mixture was poured into ice water and MeCN was removed under reduced pressure. The resultant suspension was extracted with CH$_2$Cl$_2$. The organic extracts were washed with water, brine, dried (MgSO$_4$) and concentrated to a residue which was dissolved in MeOH and treated with a slight excess of HCl (1N/Et$_2$O) to afford the desired product as the mono HCl salt (43 mg, 98%) as a white solid. Mp: 108-110° C. MS (ES+): 330 (M+H)$^+$

EXAMPLE 177

N,N-Dimethyl-N-{3-[3-(phenylsulfonyl)-1H-indazol-5-yl]propyl}amine trifluoroacetate Step 1

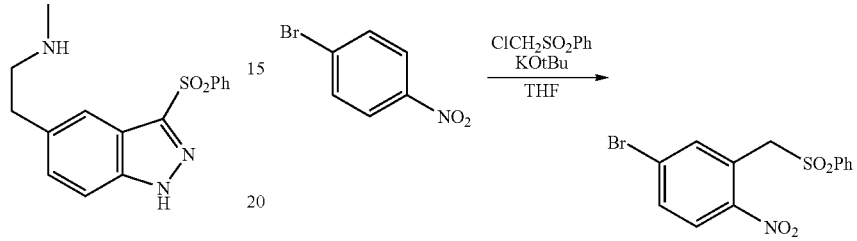

5-Bromo-2-nitrobenzyl phenyl sulfone To a stirred solution of 1-bromo-4-nitrobenzene (5.05 g, 25 mmol) and chloromethylphenylsulfone (4.76 g, 25 mmol) in dry THF (50 mL) at −65° C. under nitrogen is added 1.0M KO$^t$Bu in THF (55 mL, 55 mmol). The deep purple reaction is allowed to warm to 0° C. over 1.5 h and then treated with glacial acetic acid (4 mL). The reaction is diluted with water (100 mL) and saturated aqueous NaHCO$_3$ (100 mL), and then extracted with CH$_2$Cl$_2$ (2×200 mL). The extracts are dried (MgSO$_4$) and concentrated in vacuo to a light orange solid. Trituration with ethyl acetate and hexanes affords the title compound as a pale yellow solid (6.45 g, 72%). Mp: 143-144° C. MS (ES−): 354 (M−H)$^+$ Step 2

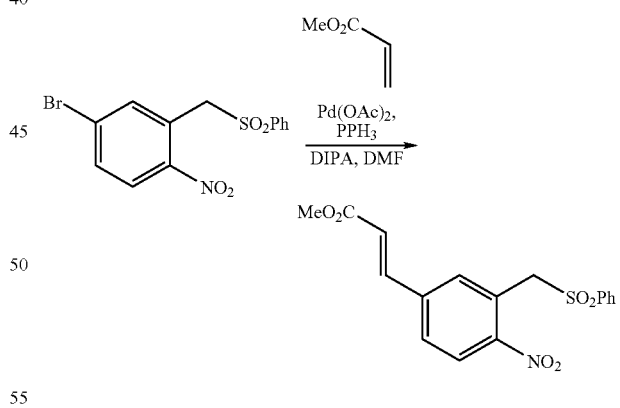

Methyl(2E)-3-{4-nitro-3-[(phenylsulfonyl)methyl]phenyl}acrylate A solution of 5-bromo-2-nitrobenzyl phenyl sulfone (0.356 g, 1 mmol) and methyl acrylate (0.172 g, 2 mmol) in dry DMF (3 mL) was heated at 100° C. under nitrogen in the presence of diisopropyl amine (0.21 mL, 1.75 mmol), Pd(AOc)$_2$ (5 mg, 0.02 mmol), and PPh$_3$ (10 mg, 0.04 mmol) for 3 days. After being cooled to rt., water was added, and the solution was extracted with ethyl acetate (3×15 mL). The organic layers were washed with water then brine and dried (MgSO$_4$). Evaporation of the solvent under reduced pressure gave a residue that was purified by column chromatography (40% ethyl acetate/hexane) to afford the title compound as a yellow solid (0.30 g, 83%). Mp: 165-166° C. MS (ES−): 360 (M−H)+

Step 3

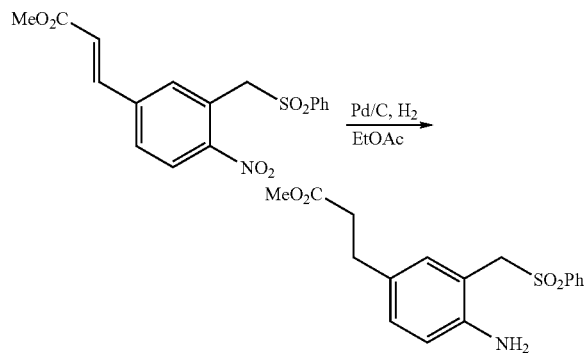

Methyl 3-{4-amino-3-[(phenylsulfonyl)methyl]phenyl}propanoate This compound was prepared by catalytic hydrogenation of methyl(2E)-3-{4-nitro-3-[(phenylsulfonyl)methyl]phenyl}acrylate (3.33 g, 9.22 mmol) in the presence of Palladium on carbon and hydrogen (45 psi) in ethyl acetate (100 ml) for 4 h. The reaction mixture is filtered through celite and concentrated in vacuo to give the title compound as a white solid (3.07 g, 99%). Mp: 59-60° C. MS (ES+): 334 (M+H)+

Step 4

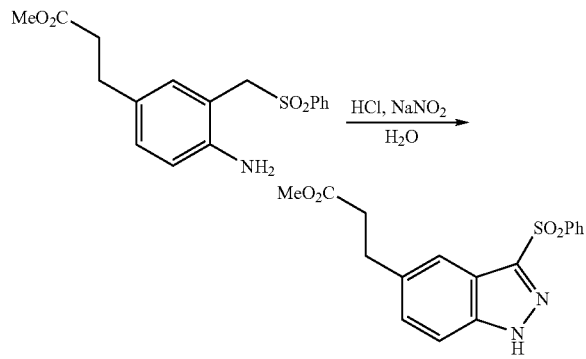

Methyl 3-[3-(phenylsulfonyl)-1H-indazol-5-yl]propanoate Using substantially the same procedure described in Example 171, step 3, and employing methyl 3-{4-amino-3-[(phenylsulfonyl)methyl]phenyl}propanoate (2.8 g, 8.4 mmol), the title compound was obtained as a red solid (2.2 g, 73%). Mp: 115-117° C. MS (ES+): 345 (M+H)+

Step 5

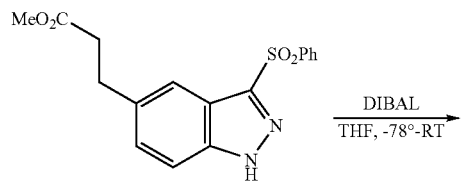

-continued

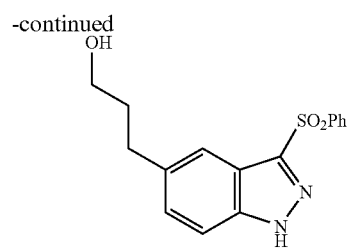

3-[3-(Phenylsulfonyl)-1H-indazol-5-yl]propan-1-ol A solution of methyl 3-[3-(phenylsulfonyl)-1H-indazol-5-yl]propanoate (2.0 g, 5.8 mmol) in anhydrous THF (120 ml) under a $N_2$ atmosphere was cooled to −78° C., treated with DIBAL-H (1.0 M in THF; 23 mL), allowed to warm to room temperature, stirred for 12 h, cooled to 0° C., quenched slowly with a saturated solution of $Na_2SO_4$ (12 mL) and filtered. The filtercake was washed with ethyl acetate. The combined filtrates were dried over $MgSO_4$ and concentrated under reduced pressure. Purification of the resultant residue by flash chromotagraphy (60% ethyl acetate/hexanes) gave the title compound as an off white solid (1.56 g, 83%), mp: 92-96° C. MS (ES+): 317 (M+H)+

Step 6

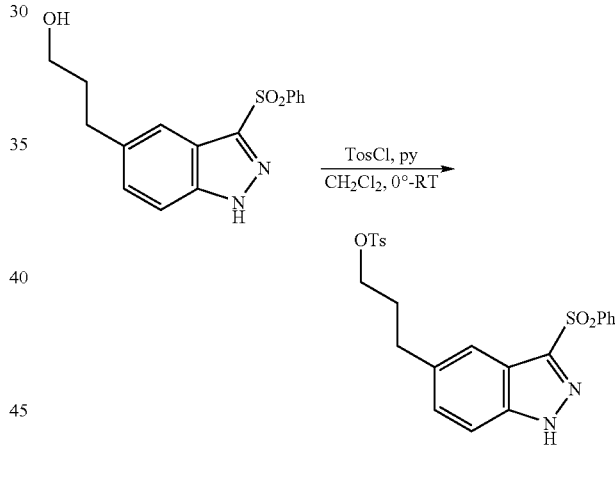

3-[3-(Phenylsulfonyl)-1H-indazol-5-yl]propyl 4-methylbenzenesulfonate Using substantially the same procedure described in Example 171, step 6, and employing 3-[3-(phenylsulfonyl)-1H-indazol-5-yl]propan-1-ol (1.52 g, 4.8 mmol), the title compound was obtained as a white foam (1.28 g, 57%). Mp: 58-60° C. MS (ES+): 471 (M+H)+

Step 7

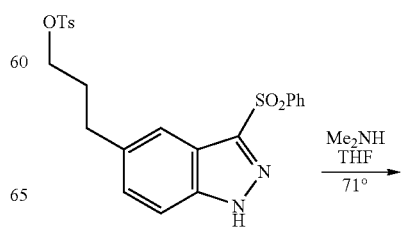

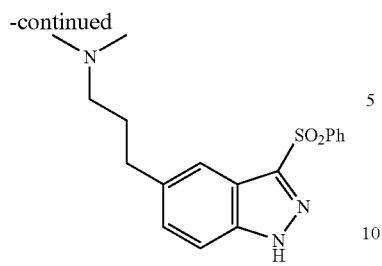

N,N-Dimethyl-N-{3-[3-(phenylsulfonyl)-1H-indazol-5-yl]propyl}amine trifluoroacetate Using substantially the same procedure described in Example 171, step 7, and employing 3-[3-(phenylsulfonyl)-1H-indazol-5-yl]propyl 4-methylbenzenesulfonate (125 mg, 0.26 mmol), the title product was obtained as an off white solid (83 mg, 93%). Mp: 75-80° C. MS (ES+): 344 (M+H)+

EXAMPLE 178

N{3-[3-(Phenylsulfonyl)-1H-indazol-5-yl]propyl}cyclopropanamine trifluoroacetate

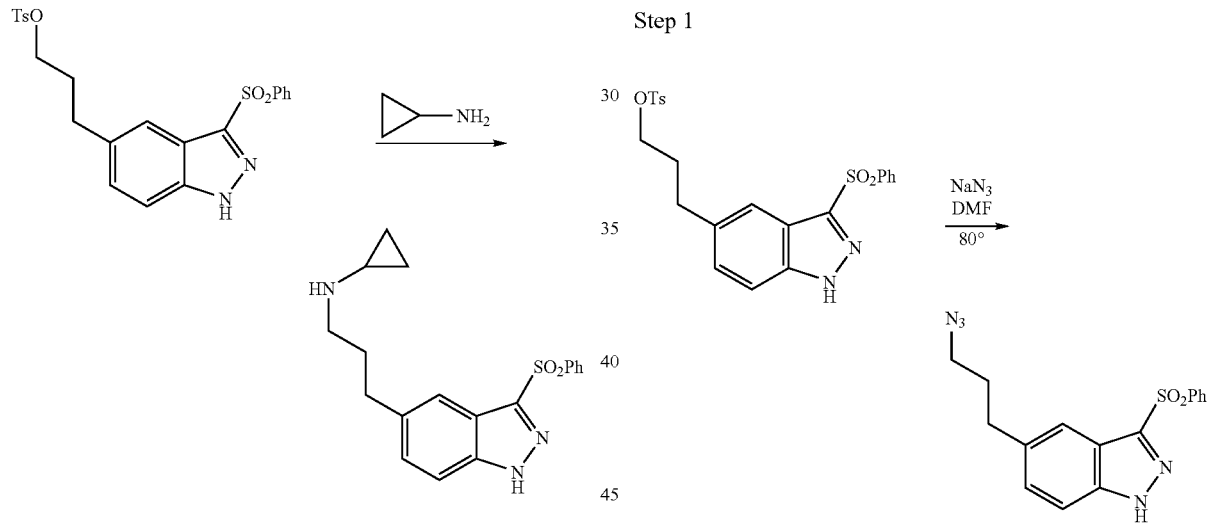

Using essentially the same procedure described in Example 177, step 7 and employing cyclopropyl amine and substituting trifluoroacetic acid for HCl, the title compound was obtained as a white solid, Mp 68-169° C., MS (M+H)+ 356

EXAMPLE 179

N-Isopropyl-N-{3-[3-(phenylsulfonyl)-1H-indazol-5-yl]propyl}amine trifluoroacetate

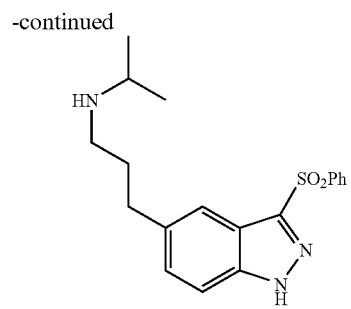

Using essentially the same procedure described in Example 177, step 7 and employing isopropyl amine and substituting trifluoroacetic acid for HCl, the title compound was obtained as a white solid, mp 169-171° C., MS, (M+H)+ 358

EXAMPLE 180

{3-[3-(Phenylsulfonyl)-1H-indazol-5-yl]propyl}amine trifluoroacetate

Step 1

5-(3-Azidopropyl)-3-(phenylsulfonyl)-1H-indazole Using essentially the same procedure described in Example 174, step 1, and employing 3-[3-(phenylsulfonyl)-1H-indazol-5-yl]propyl 4-methylbenzenesulfonate (350 mg, 0.75 mmol), the title compound was obtained as a white solid (220 mg, 86%). Mp: 133-135° C. MS (ES−): 340 (M−H)+

Step 2

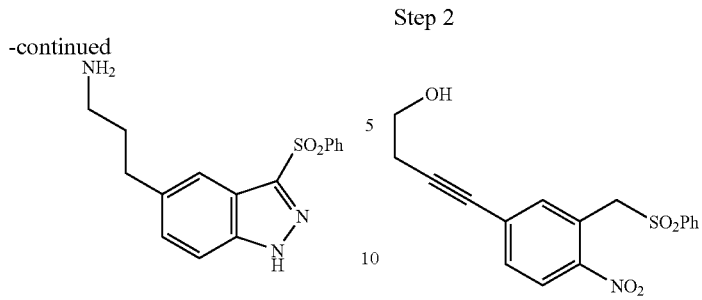

{3-[3-(Phenylsulfonyl)-1H-indazol-5-yl]propyl}amine trifluoroacetate Using essentially the same procedure described in Example 174, Step 2, and employing 5-(3-azidopropyl)-3-(phenylsulfonyl)-1H-indazole (200 mg, 0.59 mmol), the title product was obtained as an off white solid (120 mg, 67%). Mp: 92-94° C. MS (ES+): 316 (M+H)+

EXAMPLE 181

{4-[3-(Phenylsulfonyl)-1H-indazol-5-yl]butyl}amine hydrochloride

Step 1

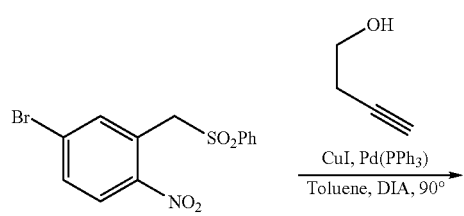

4-{4-Nitro-3-[(phenylsulfonyl)methyl]phenyl}but-3-yn-1-ol A solution of 5-Bromo-2-nitrobenzyl phenyl sulfone (2.5 g, 7.02 mmol), diisopropyl amine (4.92 ml, 35.1 mmol) and homo propargol alcohol (0.59 mL, 7.72 mmol) in degassed toluene (30 mL) was treated simultaneously with CuI (66.8 mg, 0.35 mmol) and tetrakis(triphenylphosphine)-palladium (0) (742 mg, 0.35 mmol), heated to 90° C., stirred for 15 minutes under a nitrogen atmosphere, cooled to room temperature, diluted with ethyl acetate (10 mL), and filtered through celite. The filtrate was washed with water (25 mL), then brine and dried over MgSO4 and concentrated in vacuo. Purification of the resultant residue by flash chromatography (40% ethyl acetate/petroleum ether) gave the title compound as a white solid (2.15 g, 89%). Mp: 129° C. MS (ES−): 344 (M−H)+

Step 2

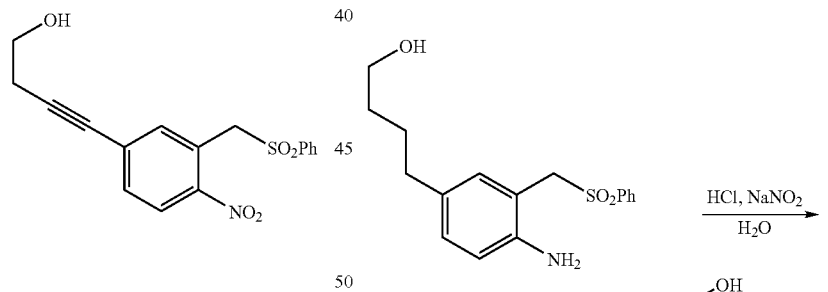

4-{4-Amino-3-[(phenylsulfonyl)methyl]phenyl}butan-1-ol Catalytic hydrogenation of 4-{4-nitro-3-[(phenylsulfonyl)methyl]phenyl}but-3-yn-1-ol (1.0 g, 2.85 mmol) in the presence of Palladium on carbon and hydrogen (45 psi) in ethyl acetate (30 ml) for 24 h gave a reaction mixture. The reaction mixture was filtered through celite and the filtrate was concentrated in vacuo to give the title compound as a yellow solid (0.907 g, 99%). Mp: 70-72.5° C. MS (ES+): 320 (M+H)+

Step 3

4-[3-(Phenylsulfonyl)-1H-indazol-5-yl]butan-1-ol Using essentially the same described in Example 171, Step 3, and employing 4-{4-amino-3-[(phenylsulfonyl)-methyl]phenyl}butan-1-ol (0.725 g, 2.27 mmol), the title product was obtained as a red solid light pink solid (0.605 g, 81%). Mp: 215-216° C. MS (ES+): 331 (M+H)+.

Step 4

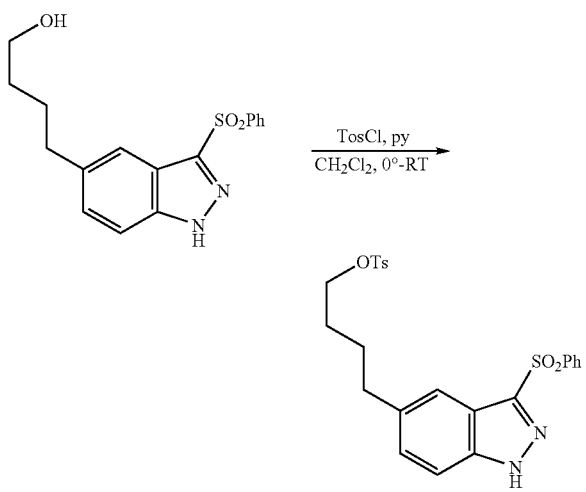

4-[3-(phenylsulfonyl)-1H-indazol-5-yl]butyl 4-methylbenzenesulfonate Using substantially the same procedure described in Example 171, Step 6, and employing 4-[3-(phenylsulfonyl)-1H-indazol-5-yl]butan-1-ol (0.5 g, 1.53 mmol), the title compound was obtained as a light orange solid (0.703 g, 95%). Mp: 157-159° C. MS (ES+): 485 (M+H)$^+$

Step 5

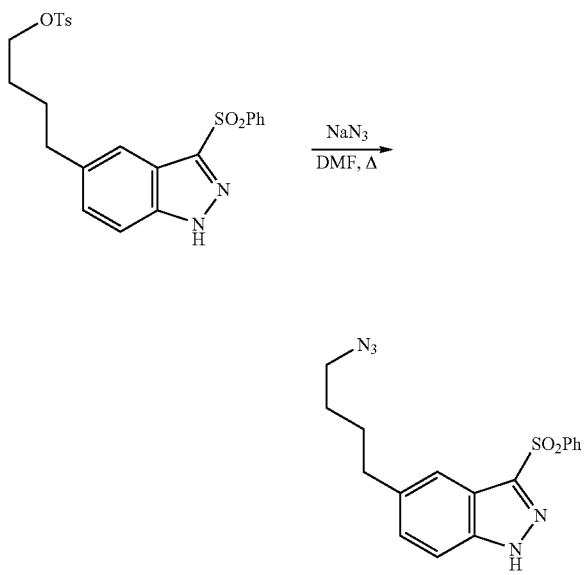

5-(4-Azidobutyl)-3-(phenylsulfonyl)-1H-indazole Using substantially the same procedure described in Example 174, Step 1, and employing 4-[3-(phenylsulfonyl)-1H-indazol-5-yl]butyl 4-methylbenzenesulfonate (133 mg, 0.27 mmol), the title compound was obtained as a clear glass (94 mg, 96%). MS (ES+): 356 (M+H)$^+$

Step 6

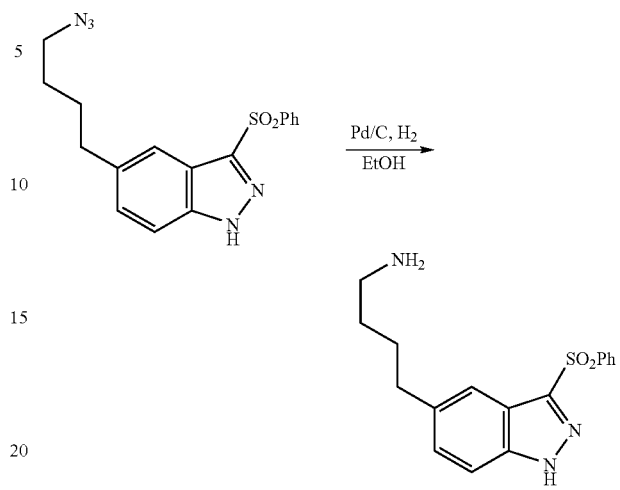

{4-[3-(Phenylsulfonyl)-1H-indazol-5-yl]butyl}amine Using substantially the same procedure described in Example 174, Step 2, and employing 5-(4-azidobutyl)-3-(phenylsulfonyl)-1H-indazole (94 mg, 0.264 mmol), the title compound was obtained as a white solid (65 mg, 86%). Mp: 120-125° C. MS (ES+): 330 (M+H)$^+$

EXAMPLE 182

N,N-Dimethyl-N-{3-[3-(naphthylsulfonyl)-1H-indazol-5-yl]propyl}amine hydrochloride

Step 1

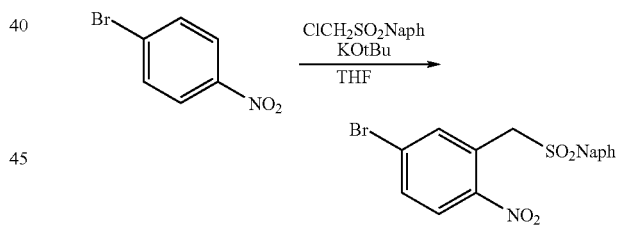

5-Bromo-2-nitrobenzyl naphthyl sulfone Using substantially the same procedure described in Example 177, Step 1, and employing 1-Bromo-4-nitrobenzene (5.05 g, 25 mmol) and chloromethylnaphthylsulfone (7.1 g, 30 mmol), the title product was obtained as a light tan solid (8.6 g, 85%). Mp: 165-168° C. MS (ES−): 404 (M−H)$^+$

Step 2

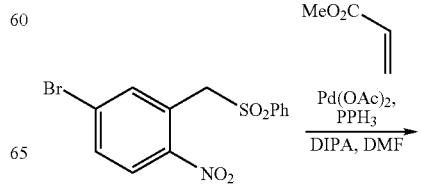

-continued

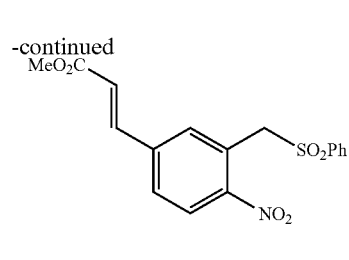

Methyl(2E)-3-{4-nitro-3-[(naphthylsulfonyl)methyl]phenyl} Using substantially the same procedure described in Example 177, Step 2, and employing 5-bromo-2-nitrobenzyl naphthyl sulfone (0.540 g, 1.33 mmol), the title product was obtained as a light tan solid (0.438 g, 80%). Mp: 178° C. MS (ES−): 410 (M−H)+

Step 3

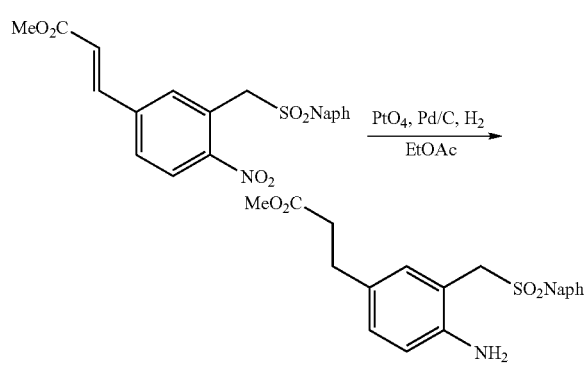

Methyl 3-{4-amino-3-[(naphthylsulfonyl)methyl]phenyl}propanoate Using substantially the same procedure described in Example 177, Step 3, and employing methyl (2E)-3-{4-nitro-3-[(naphthylsulfonyl)methyl]phenyl}acrylate (2.5 g, 6.0 mmol), the title compound was obtained as a brown gum (2.1 g, 90%). MS (ES+): 384 (M+H)+

Step 4

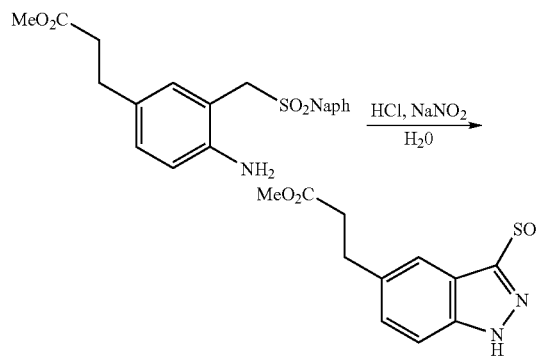

Methyl 3-[3-(Naphthylsulfonyl)-1H-indazol-5-yl]propanoate Using substantially the same procedure described in Example 171, Step 3, and employing methyl 3-{4-amino-3-[(naphthylsulfonyl)methyl]phenyl}propanoate (1.2 g, 3.11 mmol), the title compound was obtained as a light brown solid (1.02 g, 83%). Mp: 60-65° C. MS (ES+): 395 (M+H)+

Step 5

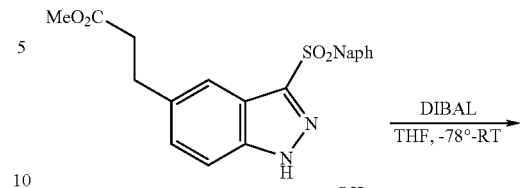

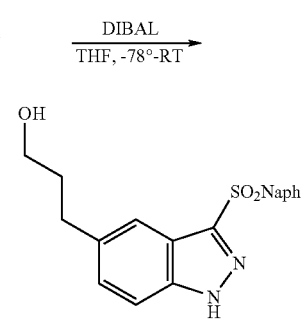

3-[3-(Naphylsulfonyl)-1H-indazol-5-yl]propan-1-ol Using substantially the same procedure described in Example 177, Step 5, and employing methyl 3-[3-(naphthylsulfonyl)-1H-indazol-5-yl]propanoate (1.0 g, 2.5 mmol), the title compound was obtained as a white solid (0.83 g, 89%). Mp: 170° C. MS (ES+): 367 (M+H)+

Step 6

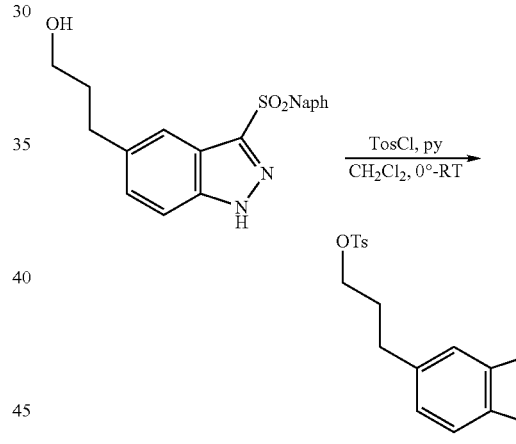

3-[3-(Naphthylsulfonyl)-1H-indazol-5-yl]propyl 4-methylbenzenesulfonate Using substantially the same procedure described in Example 171, Step 6, and employing 3-[3-(naphthylsulfonyl)-1H-indazol-5-yl]propan-1-ol (0.763 g, 2.08 mmol), the title product was obtained as a white foam (0.8 g, 74%). Mp: 66-68° C. MS (ES+): 521 (M+H)+

Step 7

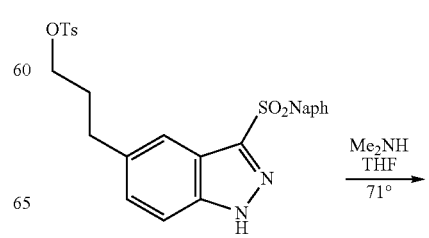

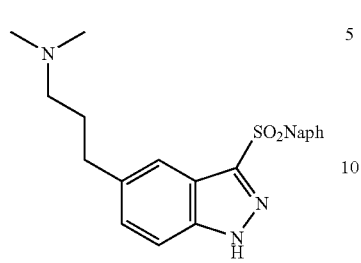

N,N-Dimethyl-N-{3-[3-(naphthylsulfonyl)-1H-indazol-5-yl]propyl}amine hydrochloride Using substantially the same procedure described in Example 171, Step 7, and employing 3-[3-(naphthylsulfonyl)-1H-indazol-5-yl]propyl 4-20 methylbenzenesulfonate (100 mg, 0.19 mmol), the title compound was obtained as an off white solid (73 mg, 99%). Mp: 247-248° C. MS (ES+): 394 (M+H)$^+$

EXAMPLES 183-187

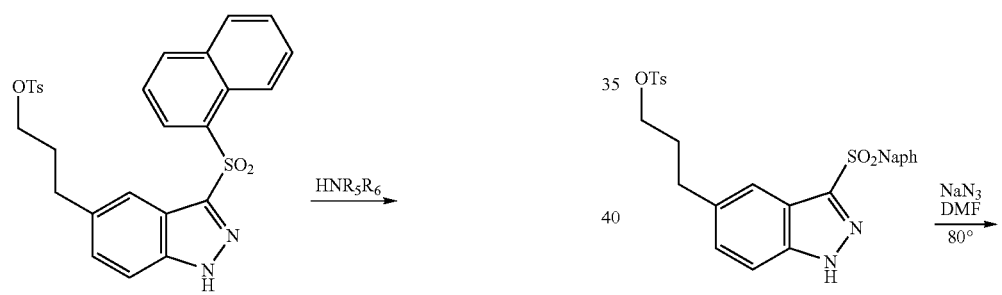

Using essentially the same procedure described in Example 171, Step 7, and employing 3-[3-(naphthylsulfonyl)-1H-indazol-5-yl]propyl 4-methylbenzenesulfonate and the desired amine, the compounds shown in Table X were obtained and identified by HPLC and mass spectral analyses.

TABLE X

| Ex. No. | R5 | R6 | mp ° C. | [M + H]$^+$ |
|---|---|---|---|---|
| 183 | CH$_3$ | H | 155-160 | 380 |
| 184 | C$_2$H$_5$ | H | 228-232 | 393 |
| 185 | isopropyl | H | 160-163 | 408 |
| 186 | C$_2$H$_5$ | CH$_3$ | 205-207 | 408 |
| 187 | —CH$_2$CH$_2$CH$_2$CH$_2$— | | 135-138 | 420 |

EXAMPLE 188

{3-[3-(Naphthylylsulfonyl)-1H-indazol-5-yl]propyl}amine

Step 1

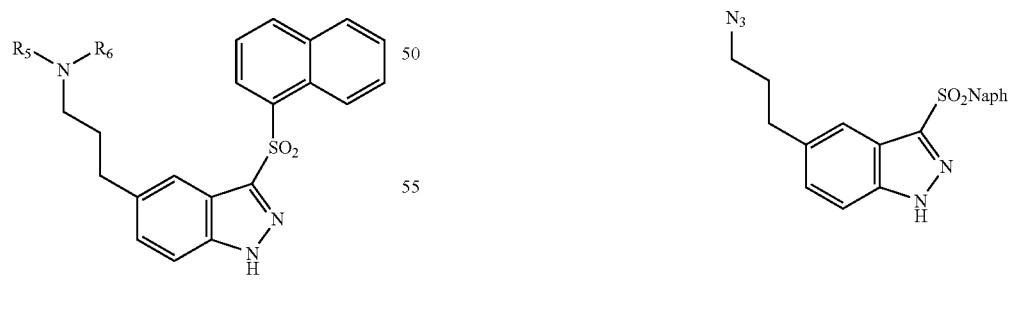

5-(3-Azidopropyl)-3-(naphthylsulfonyl)-1H-indazole Using essentially the same procedure described in Example 174, Step 1, and employing 3-[3-(naphthylsulfonyl)-1H-indazol-5-yl]propyl 4-methylbenzenesulfonate (135 mg, 0.26 mmol), the title compound was obtained as a clear glass (97 mg, 96%). MS (ES−): 390 (M−H)$^+$ Step 2

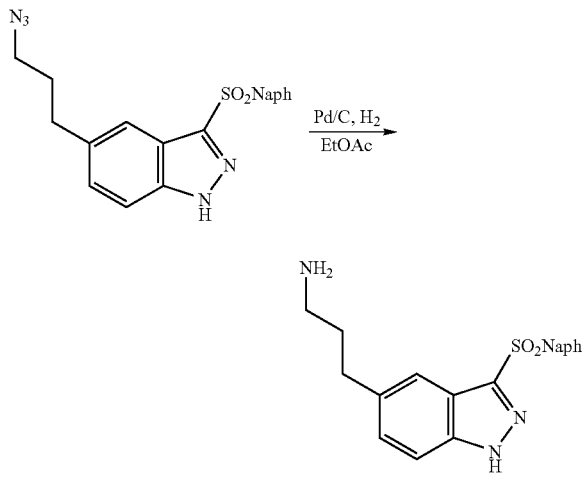

{3-[3-(Naphthylylsulfonyl)-1H-indazol-5-yl]propyl}amine Using essentially the same procedure described in Example 174, Step 2, and employing 5-(3-azidopropyl)-3-(naphthylsulfonyl)-1H-indazole (96 mg, 0.25 mmol), the title compound was obtained as an off white solid (90 mg, 99%). Mp: 92-94° C. MS (ES+): 366 (M+H)$^+$

EXAMPLE 189

{4-[3-(Naphthylsulfonyl)-1H-indazol-5-yl]butyl}amine hydrochloride

Step 1

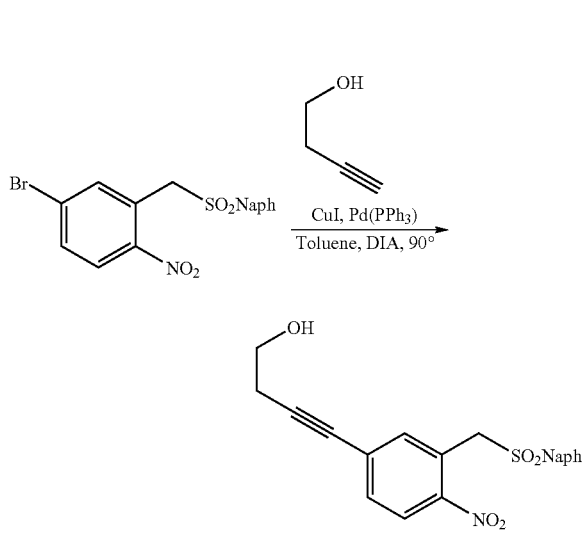

4-{4-Nitro-3-[(naphthylsulfonyl)methyl]phenyl}but-3-yn-1-ol Using substantially the same procedure described in Example 181, Step 1, and employing 5-bromo-2-nitrobenzyl naphthyl sulfone (5000 mg, 12.3 mmol), the title compound was obtained as an off yellow solid (4381 mg, 90%). Mp: 155° C. MS (ES−): 394 (M−H)$^+$ Step 2

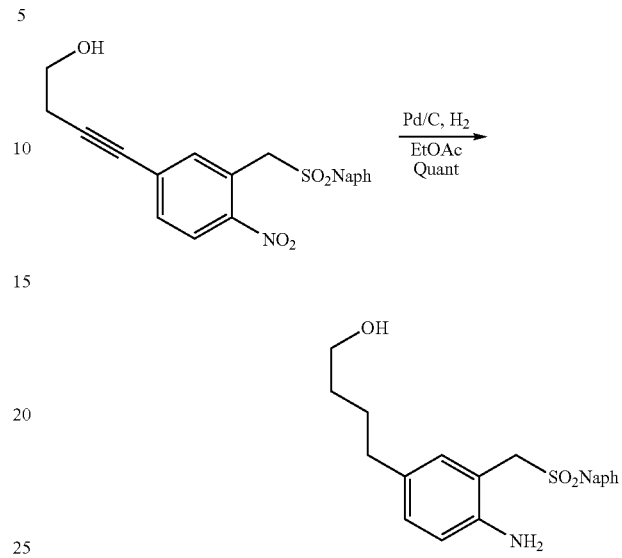

4-{4-Amino-3-[(naphthylsulfonyl)methyl]phenyl}butan-1-ol Using substantially the same procedure described in Example 181, Step 2, and employing 4-{4-nitro-3-[(naphthylsulfonyl)methyl]phenyl}but-3-yn-1-ol (1750 mg, 4.4 mmol), the title compound was obtained as an yellow solid (1616 mg, 99%). Mp: 80-85° C. MS (ES+): 370 (M+H)$^+$ Step 3

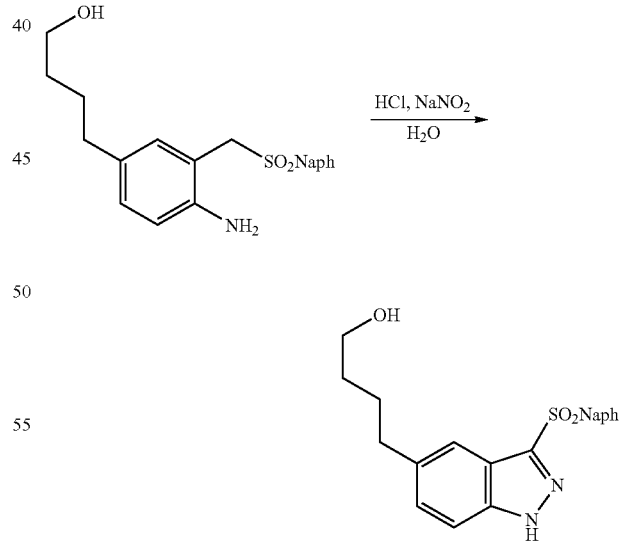

4-[3-(Naphthylsulfonyl)-1H-indazol-5-yl]butan-1-ol Using substantially the same procedure described in Example 171, Step 3, and employing 4-{4-amino-3-[(naphthylsulfonyl)methyl]phenyl}butan-1-ol (1.6 g, 4.3 mmol), the title compound was obtained as a light pink solid (1.64 g, 99%). Mp: 138-139° C. MS (ES−): 379 (M−H)$^+$ Step 4

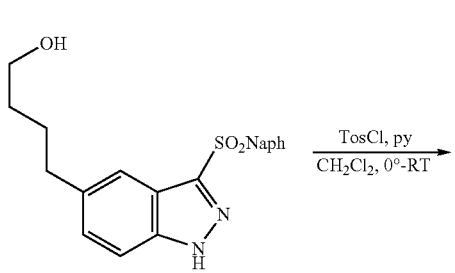

4-[3-(Naphthylsulfonyl)-1H-indazol-5-yl]butyl 4-methylbenzenesulfonate Using substantially the same procedure described in Example 171, Step 6, and employing 4-[3-(naphthylsulfonyl)-1H-indazol-5-yl]butan-1-ol (1.6 g, 4.2 mmol), the title compound was obtained as a white foam (2.02 g, 90%). Mp: 63-66° C. MS (ES+): 535 (M+H)+

Step 5

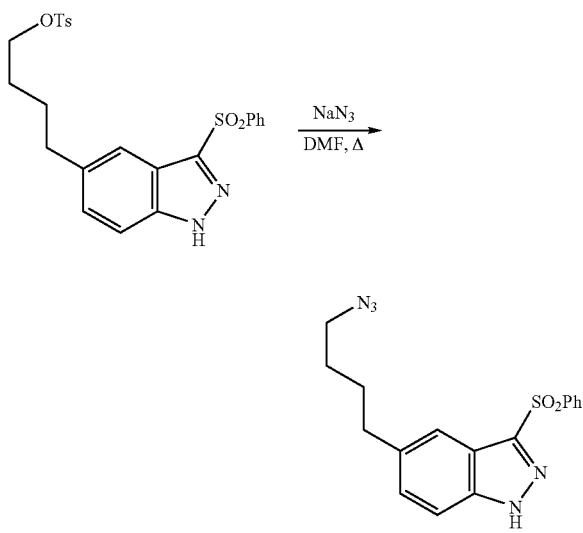

5-(4-Azidobutyl)-3-(naphthylsulfonyl)-1H-indazole Using substantially the same procedure described in Example 174, Step 1, and employing 4-[3-(naphthylsulfonyl)-1H-indazol-5-yl]butyl 4-methylbenzenesulfonate (150 mg, 0.28 mmol), the title compound was obtained as a clear glass (104 mg, 92%). MS (ES+): 406 (M+H)+

Step 6

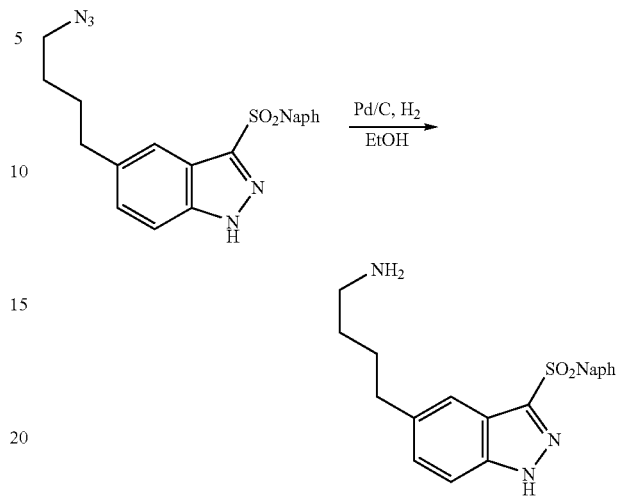

{4-[3-(Naphthylsulfonyl)-1H-indazol-5-yl]butyl}amine hydrochloride Using substantially the same procedure described in Example 17 Step 2, and employing 5-(4-azidobutyl)-3-(naphthylsulfonyl)-1H-indazole (104 mg, 0.25 mmol), the title compound was obtained as a white solid (91 mg, 94%). Mp: 150-152° C. MS (ES+): 380 (M+H)+

EXAMPLES 190-194

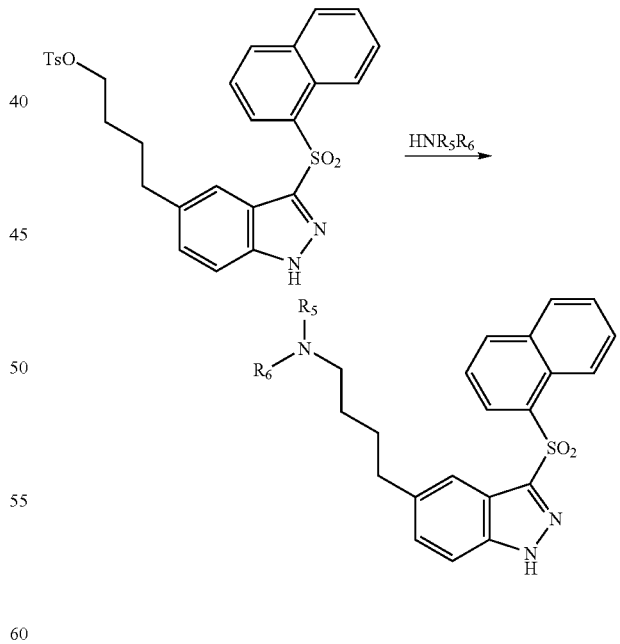

Using essentially the same procedure described in Example 171, Step 7, and employing 3-[3-(naphthylsulfonyl)-1H-indazol-5-yl]butyl 4-methylbenzenesulfonate and the desired amine, the compounds shown in Table XI were obtained and identified by HPLC and mass spectral analyses.

TABLE XI

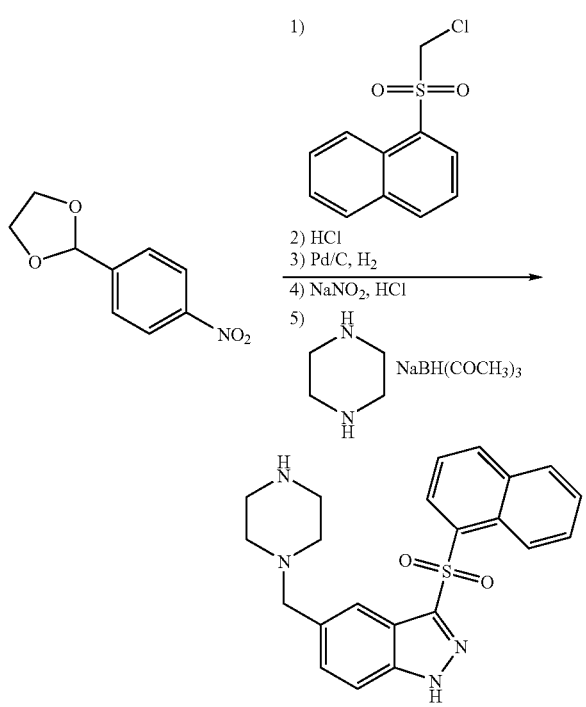

| Ex. No. | R5 | R6 | mp ° C. | [M + H]+ |
|---|---|---|---|---|
| 190 | CH₃ | CH₃ | 232-233 | 408 |
| 191 | C₂H₅ | H | 140-145 | 408 |
| 192 | isopropyl | H | 145-150 | 422 |
| 193 | C₂H₅ | CH₃ | 195-198 | 422 |
| 194 | —CH₂CH₂CH₂CH₂— | | 238-240 | 434 |

EXAMPLE 195

3-(1-Naphthylsulfonyl)-5-(piperazin-1-ylmethyl)-1H-indazole

Step 1:

2-[3-(Naphthalene-1-sulfonylmethyl)-4-nitro-phenyl]-[1,3]dioxolane A mixture of 2-(4-nitro-phenyl)-[1,3]dioxolane (1.85 g, 9.5 mmoles) and 1-chloromethane-sulfonyl-naphthalene (2.74 g, 11.4 mmoles) was stirred in THF (50 ml) at −78° C., in a round bottom flask under nitrogen. A solution of 1M potassium t-butoxide was added dropwise (19 ml, 19 mmoles) over a half an hour period. Temperature was allowed to rise to −40° C., and the reaction mixture was stirred at this temperature for 5 hours. The reaction mixture was poured into cold 2N HCl, extracted with EtOAc, dried over Na₂SO₄, and concentrated under vacuum. Compound was purified by normal phase HPLC on silica column, using as eluent 40% EtOAc/hexane, to afford the title compound as an off-white solid (3.03 g, 7.6 mmoles).

Step 2:

3-(Naphthalene-1-sulfonylmethyl)-4-nitro-benzaldehyde A mixture of 2-[3-(naphthalene-1-sulfonylmethyl)-4-nitrophenyl]-[1,3]dioxolane (3.03 g, 7.6 mmoles), and 2N HCl (4 ml, 8 mmoles) in THF (30 mL) was stirred at 40° C. for 4 hours. The reaction mixture was cooled to room temperature, diluted with water, extracted with CH₂Cl₂, dried over Na₂SO₄, and concentrated under vacuum to yield the title compound (2.56 g, 7.22 mmoles).

Step 3:

4-Amino-3-(naphthalene-1-sulfonylmethyl)-benzaldehyde A mixture of 3-(naphthalene-1-sulfonylmethyl)-4-nitro-benzaldehyde (2.5 g, 7.22 mmoles) and 10% Pd/C in THF (10 mL), and methanol (20 mL) was hydrogenated in a Parr hydrogenation bottle (250 mL) at 52 lb/in² overnight. The mixture was filtered through Celite, and the filtrate was concentrated under vacuum to afford the title compound as an off-white solid (2.4 g, 6.85 mmoles).

Step 4:

3-(Naphthalene-1-sulfonyl)-1H-indazole-5-carbaldehyde A mixture of 4-amino-3-(naphthalene-1-sulfonylmethyl)-benzaldehyde (2.4 g, 6.85 mmoles) in THF (10 mL) and 4M HCl (20 mL) was stirred in a round bottom flask at 3° C. A solution of sodium nitrite (0.49 g, 7.19 mmoles) in H₂O (2 mL) was added. The reaction mixture was poured into a cold solution of saturated sodium bicarbonate (100 mL) and extracted with EtOAc. Compound was dried over Na₂SO₄, and concentrated under vacuum to afford the title compound as an off white solid (1.84 g, 5.5 mmoles).

Step 5:

3-(1-Naphthylsulfonyl)-5-(piperazin-1-ylmethyl)-1H-indazole A mixture of 3-(naphthalene-1-sulfonyl)-1H-indazole-5-carbaldehyde (0.17 g, 0.5 mmol), piperazine (0.2 mL, 2.0 mmol) and sodium triacetoxyborohydride (0.15 g, 0.7 mmol) in dichloroethane (5 mL) was stirred at room temperature for 24 hrs. After completion, the solvent was removed in vacuo, crude material dispersed in water and pH brought to 3.4. Solid material was filtered off and washed with cold water to afford after drying the target material as a free base. The latter was converted into hydrochloride salt by dissolution in methanol, followed by treatment with the excess of 2N HCl and the evacuation of the volatiles in vacuo to afford the title compound as the hydrochloride salt, mp>200° C.; MS (ES) m/z 406.

EXAMPLES 196-201

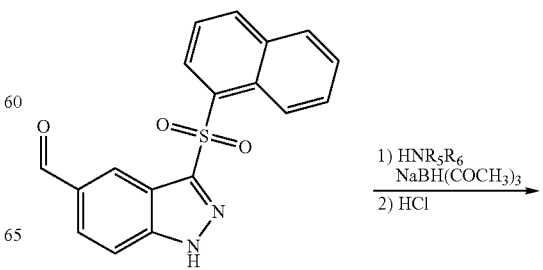

-continued

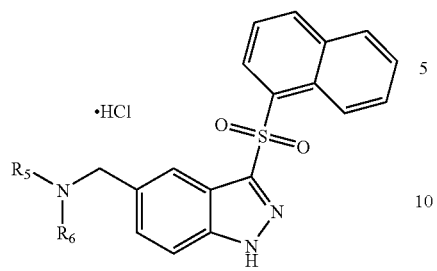

Using essentially the same reductive amination procedure described in Example 195, Step 5, and employing the desired amine and treatment of the free base with HCl; the compounds shown in Table XII were obtained and identified by HPLC and mass spectral analyses.

TABLE XII

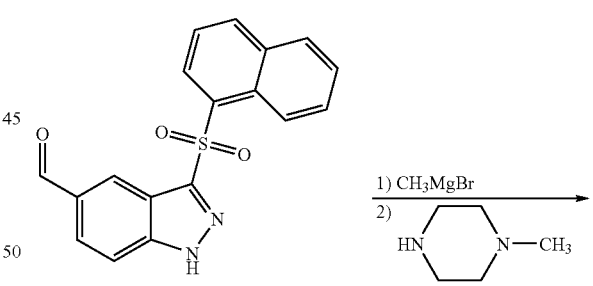

| Ex. No. | NR5R6 | mp ° C. | MS m/z |
|---|---|---|---|
| 196 | 4-methylpiperazin-1-yl | >200 | 419.1 |
| 197 | 3-methylpiperazin-1-yl | >200 | 421.1 |
| 198 | 3,5-dimethylpiperazin-1-yl | >200 | 433.1 |
| 199 | (3S)-3-methylpiperazin-1-yl | 178-181 | 419.2 |
| 200 | (3R)-3-methylpiperazin-1-yl | 179-181 | 419.2 |
| 201 | (3R)-3-aminopyrrolidin-1-yl | >200 | 405.1 |

EXAMPLE 202

3-(1-Naphthylsulfonyl)-5-(piperazin-1 ylcarbonyl)-1H-indazole

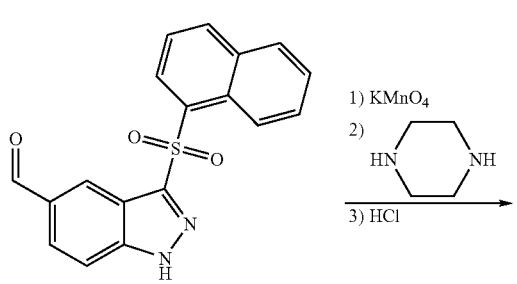

-continued

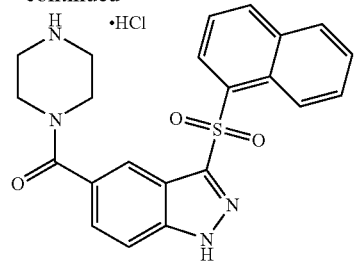

Step 1: 3-(Naphthalene-1-sulfonyl)-1H-indazole-5-carboxylic-acid

A mixture of 3-(naphthalene-1-sulfonyl)-1H-indazole-5-carbaldehyde (0.15 g, 0.44 mmoles) and KMnO$_4$ (0.03 g, 0.29 moles) was stirred in CH$_3$CN/H$_2$O (4:1) for 1 hour. Reaction mixture was acidified with 2N HCl, stirred with saturated sodium bisulfite for 10 minutes, then extracted with EtOAc, dried over Na$_2$SO$_4$ and concentrated in vacuo to afford the title compound (0.13 g, 3.9 mmoles).

Step 2: 3-(1-Naphtylsulfonyl)-5-(piperazin-1 ylcarbonyl)-1H-indazole

A mixture of 3-(naphthalene-1-sulfonyl)-1H-indazole-5-carboxylic-acid (0.13 g, 0.39 mmoles) piperazine (0.036 g, 0.42 mmoles), and 1-[3-(Dimethylamino)propyl-3-ethylcarbodiimide hydrochloride (0.08 g, 0.42 mmoles) was stirred in CH$_2$Cl$_2$ for ½ hour. Reaction mixture was diluted with H$_2$O, extracted with EtOAc, washed with water (2×), brine (1×), dried over Na$_2$SO$_4$, and concentrated under vacuum. The product was converted into the hydrochloride salt by dissolution in methanol, followed by treatment with the excess of 2N HCl and the evacuation of the volatiles in vacuo to afford the title compound hydrochloride salt; Mp: >200° C.; MS (ES) m/z 419.1.

EXAMPLE 203

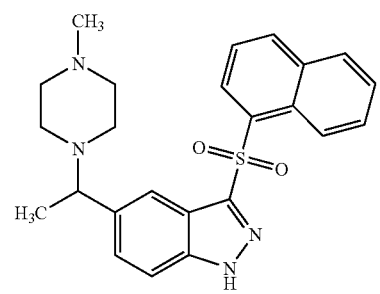

5-[1-(4-Methylpiperazin-1-yl)ethyl]-3-(1-naphthyl-sulfonyl)-1H-indazole

Step 1: 1-[3-(Naphthalene-1-sulfonyl)-1H-indazol-5-yl]-ethanol

A mixture of 3-(naphthalene-1-sulfonyl)-1H-indazole-5-carbaldehyde (0.15 g, 0.44 mmoles) and MeMgBr (0.36 ml of 3M solution in ether, 1.1 mmoles) was stirred in THF at −20° C. to 0° C. for 30 minutes. Reaction mixture was diluted with water, acidified to pH=3 with 2N HCl, then extracted with EtOAc, dried over $Na_2SO_4$ and concentrated in vacuo to afford the title compound (0.13 g, 3.9 mmoles).

Step 2: 5-[1-(4-methylpiperazin-1-yl)ethyl]-3-(1-naphthyl-sulfonyl)-1H-indazole:

A mixture of 1-[3-(naphthalene-1-sulfonyl)-1H-indazol-5-yl]ethanol (0.13 g, 0.38 mmoles), methane sulfonic anhydride (0.16 g, 0.95 mmoles), and triethylamine (0.13 ml, 0.95 mmole) was stirred in $CH_2Cl_2$ from 0° C. to room temperature for 5 hours to afford methanesulfonic acid 1-[3-(naphthalene-1-sulfonyl)-1-H-indazol-5-yl]-ethylester. This reaction mixture was treated with excess N-methyl-piperazine (0.22 g, 2 mmoles). The crude product was purified by flash chromatography using 5% $MeOH/CH_2Cl_2$ to afford the title compound; Mp: 183-185° C., MS (ES) m/z 433.1.

EXAMPLE 204

Evaluation of 5-HT6 Binding Affinity of Test Compounds

The affinity of test compounds for the serotonin 5-$HT_6$ receptor was evaluated in the following manner. Cultured Hela cells expressing human cloned 5-HT6 receptors were harvested and centrifuged at low speed (1,000×g) for 10.0 minutes to remove the culture media. The harvested cells were suspended in half volume of fresh physiological phosphate buffered saline solution and recentrifuged at the same speed. This operation was repeated. The collected cells were then homogenized in ten volumes of 50 mM Tris.HCl (pH 7.4) and 0.5 mM EDTA. The homogenate was centrifuged at 40,000×g for 30.0 min and the precipitate was collected. The obtained pellet was resuspended in 10 volumes of Tris.HCl buffer and recentrifuged at the same speed. The final pellet was suspended in a small volume of Tris.HCl buffer and the tissue protein content was determined in aliquots of 10-25 µl volumes. Bovine Serum Albumin was used as the standard in the protein determination according to the method described in Lowry et al., *J. Biol. Chem.*, 193: 265 (1951). The volume of the suspended cell membranes was adjusted to give a tissue protein concentration of 1.0 mg/ml of suspension. The prepared membrane suspension (10 times concentrated) was aliquoted in 1.0 ml volumes and stored at −70° C. until used in subsequent binding experiments.

Binding experiments were performed in a 96 well microtiter plate format, in a total volume of 200 µl. To each well was added the following mixture: 80.0 µl of incubation buffer made in 50 mM Tris.HCl buffer (pH 7.4) containing 10.0 mM $MgCl_2$ and 0.5 mM EDTA and 20 µl of [$^3$H]-LSD (S.A., 86.0 Ci/mmol, available from Amersham Life Science), 3.0 nM. The dissociation constant, $K_D$ of the [$^3$H]LSD at the human serotonin 5-$HT_6$ receptor was 2.9 nM, as determined by saturation binding with increasing concentrations of [$^3$H]LSD. The reaction was initiated by the final addition of 100.0 µl of tissue suspension. Nonspecific binding was measured in the presence of 10.0 µM methiothepin. The test compounds were added in 20.0 µl volume.

The reaction was allowed to proceed in the dark for 120 minutes at room temperature, at which time, the bound ligand-receptor complex was filtered off on a 96 well unifilter with a Packard Filtermate® 196 Harvester. The bound complex caught on the filter disk was allowed to air dry and the radioactivity is measured in a Packard TopCount® equipped with six photomultiplier detectors, after the addition of 40.0 µl Microscint®-20 scintillant to each shallow well. The unifilter plate was heat-sealed and counted in a PackardTopCount® with a tritium efficiency of 31.0%.

Specific binding to the 5-$HT_6$ receptor was defined as the total radioactivity bound less the amount bound in the presence of 10.0 µM unlabeled methiothepin. Binding in the presence of varying concentrations of test compound was expressed as a percentage of specific binding in the absence of test compound. The results were plotted as log % bound versus log concentration of test compound. Nonlinear regression analysis of data points with a computer assisted program Prism® yielded both the $IC_{50}$ and the $K_i$ values of test compounds with 95% confidence limits. A linear regression line of data points was plotted, from which the $IC_{50}$ value is determined and the $K_i$ value is determined based upon the following equation:

$$K_i = IC_{50}/(1+L/K_D)$$

where L was the concentration of the radioactive ligand used and $K_D$ is the dissociation constant of the ligand for the receptor, both expressed in nM.

Using this assay, the following Ki values were determined. The data are shown in Table XIII, below.

TABLE XIII

| Test Compound (Example No.) | 5-$HT_6$ Binding Ki (nM) |
| --- | --- |
| 1 | B |
| 2 | E |
| 3 | C |
| 4 | A |
| 5 | D |
| 6 | B |
| 7 | C |
| 8 | C |
| 9 | B |
| 10 | E |
| 11 | A |
| 12 | B |
| 13 | D |
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | B |
| 40 | A |
| 41 | A |
| 42 | A |
| 43 | A |
| 44 | A |
| 45 | A |

TABLE XIII-continued

| Test Compound (Example No.) | 5-HT$_6$ Binding Ki (nM) |
|---|---|
| 46 | A |
| 47 | C |
| 48 | C |
| 49 | C |
| 50 | D |
| 51 | B |
| 52 | E |
| 53 | B |
| 54 | B |
| 55 | E |
| 56 | E |
| 57 | D |
| 58 | C |
| 59 | E |
| 60 | B |
| 61 | A |
| 62 | A |
| 63 | A |
| 64 | A |
| 65 | A |
| 66 | A |
| 67 | A |
| 68 | A |
| 69 | C |
| 70 | B |
| 71 | B |
| 72 | D |
| 73 | E |
| 74 | A |
| 75 | B |
| 76 | A |
| 77 | A |
| 78 | A |
| 79 | B |
| 80 | A |
| 81 | A |
| 82 | B |
| 83 | C |
| 84 | E |
| 85 | E |
| 86 | C |
| 87 | E |
| 88 | A |
| 89 | A |
| 90 | A |
| 91 | A |
| 92 | A |
| 93 | A |
| 94 | B |
| 95 | A |
| 96 | E |
| 97 | A |
| 98 | C |
| 99 | A |
| 100 | B |
| 101 | B |
| 102 | C |
| 103 | E |
| 104 | C |
| 105 | E |
| 106 | E |
| 107 | E |
| 108 | E |
| 109 | B |
| 110 | E |
| 111 | E |
| 112 | E |
| 113 | A |
| 114 | A |
| 115 | B |
| 116 | B |
| 117 | A |
| 118 | A |
| 119 | E |
| 120 | E |
| 121 | E |
| 122 | A |
| 123 | E |
| 124 | B |
| 125 | B |
| 126 | A |
| 127 | B |
| 128 | E |
| 129 | E |
| 130 | E |
| 131 | B |
| 132 | C |
| 133 | B |
| 134 | B |
| 135 | D |
| 136 | D |
| 137 | C |
| 138 | D |
| 139 | A |
| 140 | A |
| 141 | B |
| 142 | — |
| 143 | A |
| 144 | A |
| 145 | B |
| 146 | B |
| 147 | B |
| 148 | E |
| 149 | E |
| 150 | E |
| 151 | A |
| 152 | E |
| 153 | B |
| 154 | B |
| 155 | B |
| 156 | A |
| 157 | A |
| 158 | A |
| 159 | B |
| 160 | A |
| 161 | B |
| 162 | A |
| 163 | B |
| 164 | A |
| 165 | B |
| 166 | C |
| 167 | B |
| 168 | D |
| 169 | E |
| 170 | B |
| 171 | A |
| 172 | B |
| 173 | A |
| 174 | A |
| 175 | A |
| 176 | B |
| 177 | B |
| 178 | B |
| 179 | E |
| 180 | B |
| 181 | C |
| 182 | A |
| 183 | A |
| 184 | A |
| 185 | A |
| 186 | A |
| 187 | A |
| 188 | A |
| 189 | A |
| 190 | A |
| 191 | A |
| 192 | A |
| 193 | A |
| 194 | B |
| 195 | A |
| 196 | A |
| 197 | A |
| 198 | A |
| 199 | B |

TABLE XIII-continued

| Test Compound (Example No.) | 5-HT$_6$ Binding Ki (nM) |
|---|---|
| 200 | A |
| 201 | A |
| 202 | E |
| 203 | A |

For Table XIII
A = 0.01 nM-10 nM
B = 11 nM-25 nM
C = 26 nM-35 nM
D = 36 nM-45 nM
E = >45 nM

What is claimed is:

1. A compound of formula I

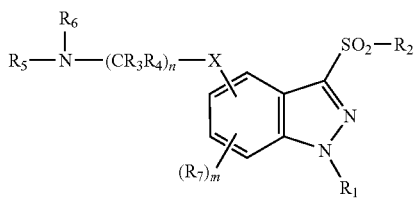

wherein
X is O or S;
n is an integer of 2, 3, 4, 5 or 6;
R$_1$ is H or an alkyl, cycloalkyl, aryl or heteroaryl group each optionally substituted;
R$_2$ is an optionally substituted cycloalkyl or aryl group;
R$_3$ and R$_4$ are each independently H, or an optionally substituted alkyl group;
R$_5$ and R$_6$ are each independently H, or an alkyl, alkenyl, alkynyl, or cycloalkyl, group each optionally substituted;
R$_7$ is H, halogen, CN, OR$_8$, CO$_2$R$_9$, CONR$_{10}$R$_{11}$, or an alkyl, alkenyl, alkynyl, cycloalkyl, cycloheteroalkyl, aryl or heteroaryl group each optionally substituted;
m is an integer of 1, 2 or 3;
R$_8$ is H, COR$_{12}$ or an alkyl, alkenyl, alkynyl, aryl or heteroaryl group each optionally substituted;
R$_9$ is H or a C$_1$-C$_6$alkyl, aryl or heteroaryl group each optionally substituted;
R$_{10}$ and R$_{11}$ are each independently H or an optionally substituted alkyl group; and
R$_{12}$ is an optionally substituted C$_1$-C$_6$alkyl, cycloalkyl, cycloheteroalkyl, aryl or heteroaryl group; or
a stereoisomer thereof or a pharmaceutically acceptable salt thereof.

2. The compound according to claim 1 wherein X is O.

3. The compound according to claim 1 wherein n is 2 or 3.

4. The compound according to claim 2 wherein R$_2$ is an optionally substituted aryl.

5. The compound according to claim 3 wherein X is O.

6. The compound according to claim 5 wherein R$_5$ and R$_6$ are each independently H or C$_1$-C$_4$ alkyl.

7. The compound according to claim 5 wherein R$_2$ is an optionally substituted naphthyl group.

8. The compound according to claim 7 wherein R$_2$ is naphthyl and n is 3.

9. The compound according to claim 1 selected from the group consisting of:
N,N-Dimethyl-3-{[3-(1-naphthylsulfonyl)-1H-indazol-5-yl]oxy}propan-1-amine;
N,N-Dimethyl-2-{[3-(phenylsulfonyl)-1H-indazol-5-yl]oxy}ethanamine;
N,N-Dimethyl-2-{[3-(1-naphthylsulfonyl)-1H-indazol-5-yl]oxy}ethanamine;
N-(2-{[3-(1-Naphthylsulfonyl)-1H-indazol-5-yl]oxy}ethyl)cyclopentanamine;
N-Ethyl-N-methyl-2-{[3-(1-naphthylsulfonyl)-1H-indazol-5-yl]oxy}ethanamine;
N-(2-{[3-(1-Naphthylsulfonyl)-1H-indazol-5-yl]oxy}ethyl)butan-1-amine;
N-Ethyl-2-{[3-(phenylsulfonyl)-1H-indazol-5-yl]oxy}ethanamine;
N-(2-{[3-(Phenylsulfonyl)-1H-indazol-5-yl]oxy}ethyl)propan-2-amine;
N-(2-{[3-(1-Naphthylsulfonyl)-1H-indazol-5-yl]oxy}ethyl)propan-2-amine;
N-Ethyl-2-{[3-(1-naphthylsulfonyl)-1H-indazol-5-yl]oxy}ethanamine;
N-Methyl-2-{[3-(1-naphthylsulfonyl)-1H-indazol-5-yl]oxy}ethanamine;
N,N-Diethyl-2-{[3-(1-naphthylsulfonyl)-1H-indazol-5-yl]oxy}ethanamine;
N-(2-{[3-(1-Naphthylsulfonyl)-1H-indazol-5-yl]oxy}ethyl)cyclopropanamine;
(2-{[1-(3-Chlorobenzyl)-3-(1-naphthylsulfonyl)-1H-indazol-7-yl]oxy}ethyl)amine;
N-(2-{[3-(Phenylsulfonyl)-1H-indazol-5-yl]oxy}ethyl)cyclopentanamine;
N-Methyl-2-{[3-(phenylsulfonyl)-1H-indazol-5-yl]oxy}ethanamine;
N-Methyl-2-{[1-methyl-3-(phenylsulfonyl)-1H-indazol-7-yl]oxy}ethanamine;
(2-{[1-(3-Chlorobenzyl)-3-(phenylsulfonyl)-1H-indazol-7-yl]oxy}ethyl)methylamine;
(2-{[1-(3-Chlorobenzyl)-3-(phenylsulfonyl)-1H-indazol-7-yl]oxy}ethyl)ethylamine;
N-Methyl-2-{[3-(phenylsulfonyl)-1H-indazol-7-yl]oxy}ethanamine;
(2-{[1-(3-Chlorobenzyl)-3-(1-naphthylsulfonyl)-1H-indazol-7-yl]oxy}ethyl)ethylamine;
(2-{[1-(3-Chlorobenzyl )-3-(1-naphthylsulfonyl)-1H-indazol-7-yl]oxy}ethyl)methylamine;
N-Ethyl-2-{[3-(phenylsulfonyl)-1H-indazol-7-yl]oxy}ethanamine;
N,N-Diethyl-2-{[3-(phenylsulfonyl)-1H-indazol-7-yl]oxy}ethanamine;
N-(2-{[3-(Phenylsulfonyl)-1H-indazol-7-yl]oxy}ethyl)butan-1-amine;
N,N-Diethyl-2-{[1-methyl-3-(1-naphthylsulfonyl)-1H-indazol-7-yl]oxy}ethanamine;
N-Ethyl-2-{[1-methyl-3-(1-naphthylsulfonyl)-1H-indazol-7-yl]oxy}ethanamine;
N-Ethyl-2-{[3-(1-naphthylsulfonyl)-1H-indazol-7-yl]oxy}ethanamine;
(2-{[3-(1-Naphthylsulfonyl)-1H-indazol-7-yl]oxy}ethyl)amine;
(2-{[1-(3-Chlorobenzyl)-5-fluoro-3-(1-naphthylsulfonyl)-1H-indazol-7-yl]oxy}ethyl)-dimethylamine;
(2-{[1-Benzyl-3-(1-naphthylsulfonyl)-1H-indazol-5-yl]oxy}ethyl)methylamine;
(2-{[1-Benzyl-3-(1-naphthylsulfonyl)-1H-indazol-5-yl]oxy}ethyl)dimethylamine;
(2-{[1-Benzyl-3-(1-naphthylsulfonyl)-1H-indazol-5-yl]oxy}ethyl)ethylamine;
N-Methyl-2-{[3-(1-naphthylsulfonyl)-1H-indazol-7-yl]oxy}ethanamine;
N,N-Dimethyl-2-{[3-(1-naphthylsulfonyl)-1H-indazol-7-yl]oxy}ethanamine;
N,N-Diethyl-2-{[5-fluoro-3-(1-naphthylsulfonyl)-1H-indazol-7-yl]oxy}ethanamine;

(2-{[5-Fluoro-3-(1-naphthylsulfonyl)-1H-indazol-7-yl]oxy}ethyl)dimethylamine;
N-Ethyl-2-{[5-fluoro-3-(1-naphthylsulfonyl)-1H-indazol-7-y]oxy}ethanamine;
(2-{[1-(3-Chlorobenzyl)-3-(1-naphthylsulfonyl)-1H-indazol-5-yl]oxy}ethyl)-dimethylamine;
N-Methyl-3-{[3-(1-naphthylsulfonyl)-1H-indazol-5-yl]oxy}propan-1-amine;
N-Ethyl-N-methyl-3-{[3-(1-naphthylsulfonyl)-1H-indazol-5-yl]oxy}propan-1-amine;
N,N-Dimethyl-3-{[3-(1-naphthylsulfonyl)-1H-indazol-5-yl]oxy}propan-1-amine;
N,N-Diethyl-3-{[3-(1-naphthylsulfonyl)-1H-indazol-5-yl]oxy}propan-1-amine;
N-(3-{[3-(1-Naphthylsulfonyl)-1H-indazol-5-yl]oxy}propyl)butan-1-amine;
(2-{[5-Methoxy-3-(1-naphthylsulfonyl)-1H-indazol-7-yl]oxy}ethyl)methylamine;
(2-{[5-Methoxy-3-(1-naphthylsulfonyl)-1H-indazol-7-yl]oxy}ethyl)dimethylamine;
(2-{[1-(3-Chlorobenzyl)-3-(1-naphthylsulfonyl)-1H-indazol -5-yl]oxy}ethyl)ethylamine;
(3-{[1-(3-Chlorobenzyl)-3-(1-naphthylsulfonyl)-1H-indazol-7-yl]oxy}propyl)-diethylamine;
N-Methyl-3-{[3-(1-naphthylsulfonyl)-1H-indazol-7-yl]oxy}propan-1-amine;
N,N-Diethyl-3-{[3-(1-naphthylsulfonyl)-1H-indazol-7-yl]oxy}propan-1-amine;
N-Methyl-2-{[1-methyl-3-(1-naphthylsulfonyl)-1H-indazol-5-yl]oxy}ethanamine;
N,N-Dimethyl-2-{[1-methyl-3-(1-naphthylsulfonyl)-1H-indazol-5-yl]oxy}ethanamine;
N-Ethyl-N-methyl-2-{[1-methyl-3-(1-naphthylsulfonyl)-1H-indazol-5-yl]oxy}ethanamine;
N-Ethyl-2-{[1-methyl-3-(1-naphthylsulfonyl)-1H-indazol-5-yl]oxy}ethanamine;
N,N-Diethyl-2-{[1-methyl-3-(1-naphthylsulfonyl)-1H-indazol-5-yl]oxy}ethanamine;
N-(2-{[1-Methyl-3-(1-naphthylsulfonyl)-1H-indazol-5-yl]oxy}ethyl)propan-2-amine;
(2-{[1-Methyl-3-(1-naphthylsulfonyl)-1H-indazol-7-yl]oxy}ethyl)amine;
N-Ethyl-3-{[3-(1-naphthylsulfonyl)-1H-indazol-5-yl]oxy}propan-1-amine;
N-Isopropyl-3-{[3-(1-naphthylsulfonyl)-1H-indazol-5-yl]oxy}propan-1-amine;
N-(3-{[3-(1-Naphthylsulfonyl)-1H-indazol-5-yl]oxy}propyl)cyclopentanamine;
N-(3-{[3-(1-Naphthylsulfonyl)-1H-indazol-5-yl]oxy}propyl)cyclopropanamine;
(3-{[3-(1-Naphthylsulfonyl)-1H-indazol-5-yl]oxy}propyl)amine;
N-Methyl-4-{[3-(1-naphthylsulfonyl)-1H-indazol-5-yl]oxy}butan-1-amine
N,N-Dimethyl-4-{[3-(1-naphthylsulfonyl)-1H-indazol-5-yl]oxy}butan-1-amine;
N-Ethyl-4-{[3-(1-naphthylsulfonyl)-1H-indazol-5-yl]oxy}butan-1-amine;
N,N-Diethyl-4-{[3-(1-naphthylsulfonyl)-1H-indazol-5-yl]oxy}butan-1-amine;
N-Methyl-4-{[3-(1-naphthylsulfonyl)-1H-indazol-5-yl]oxy}-N-propylbutan-1-amine;
(4-{[3-(1-Naphthylsulfonyl)-1H-indazol-5-yl]oxy}butyl)amine;
(2-{[5-Fluoro-3-(1-naphthylsulfonyl)-1H-indazol-7-yl]oxy}ethyl)methylamine;
(2-{[3-(1-Naphthylsulfonyl)-1H-indazol-5-yl]oxy}ethyl)amine;
2-{[5-Fluoro-3-(phenysulfonyl)-1H-indazol-7-yl]oxy}ethanamine;
2-{[3-(Phenylsulfonyl)-1H-indazol-7-yl]oxy}ethanamine;
N,N-Dimethyl-2-{[3-(1-naphthylsulfonyl)-1H-indazol-4-yl]oxy}ethanamine;
2-{[3-(1-Naphthylsulfonyl)-1H-indazol-4-yl]oxy}ethanamine;
N-Methyl-{[3-(1-naphthylsulfonyl)-1H-indazol-6-yl]oxy}ethanamine;
2-{[3-(1-Naphthylsulfonyl)-1H-indazol-6-yl]oxy}ethanamine;
a stereoisomer thereof; and
a pharmaceutically acceptable salt thereof.

10. A pharmaceutical composition which comprises a pharmaceutically acceptable carrier and an effective amount of a compound of formula I

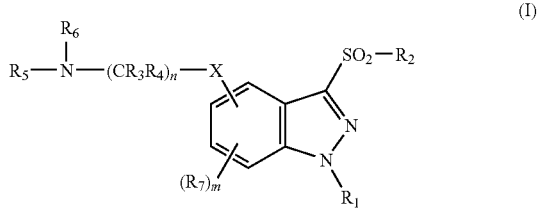

wherein
X is O;
n is an integer of 2, 3, 4, 5 or 6;
$R_1$ is H or an alkyl, cycloalkyl, aryl or heteroaryl group each optionally substituted;
$R_2$ is an optionally substituted cycloalkyl or aryl group
$R_3$ and $R_4$ are each independently H, or an optionally substituted alkyl group;
$R_5$ and $R_6$ are each independently H, or an alkyl, alkenyl, alkynyl, or cycloalkyl, group each optionally substituted,
$R_7$ is H, halogen, CN, $OR_8$, $CO_2R_9$, $CONR_{10}R_{11}$, or an alkyl, alkenyl, alkynyl, cycloalkyl, cycloheteroalkyl, aryl or heteroaryl group each optionally substituted;
m is an integer of 1, 2 or 3;
$R_8$ is H, $COR_{12}$ or an alkyl, alkenyl, alkynyl, aryl or heteroaryl group each optionally substituted;
$R_9$ is H or a $C_1$-$C_6$alkyl, aryl or heteroaryl group each optionally substituted;
$R_{10}$ and $R_{11}$ are each independently H or an optionally substituted alkyl group; and
$R_{12}$ is an optionally substituted $C_1$-$C_6$alkyl, cycloalkyl, cycloheteroalkyl, aryl or heteroaryl group; or a stereoisomer thereof or a pharmaceutically acceptable salt thereof.

11. The composition according to claim 10 having a formula I compound wherein X is O.

12. The composition according to claim 11 having a formula I compound wherein n is 2 or 3.

13. The composition according to claim 12 having a formula I compound wherein X is O; $R_2$ is an optionally substituted phenyl or naphthyl or group; and n is 3.

14. The composition according to claim 10 having a formula I compound selected from the group consisting of:
N,N-Dimethyl-3-{[3-(1-naphthylsulfonyl)-1H-indazol-5-yl]oxy}propan-1-amine;
N,N-Dimethyl-2-{[3-(phenylsulfonyl)-1H-indazol-5-yl]oxy}ethanamine;
N,N-Dimethyl-2-{[3-(1-naphthylsulfonyl)-1H-indazol-5-yl]oxy}ethanamine;
N-(2-{[3-(1-Naphthylsulfonyl)-1H-indazol-5-yl]oxy}ethyl)cyclopentanamine;

N-Ethyl-N-methyl-2-{[3-(1-naphthylsulfonyl)-1H-indazol-5-yl]oxy}ethanamine;
N-(2-{[3-(1-Naphthylsulfonyl)-1H-indazol-5-yl]oxy}ethyl)butan-1-amine;
N-Ethyl-2-{[3-(phenylsulfonyl)-1H-indazol-5-yl]oxy}ethanamine;
N-(2-{[3-(Phenylsulfonyl)-1H-indazol-5-yl]oxy}ethyl)propan-2-amine;
N-(2-{[3-(1-Naphthylsulfonyl)-1H-indazol-5-yl]oxy}ethyl)propan-2-amine;
N-Ethyl-2-{[3-(1-naphthylsulfonyl)-1H-indazol-5-yl]oxy}ethanamine;
N-Methyl-2-{[3-(1-naphthylsulfonyl)-1H-indazol-5-yl]oxy}ethanamine;
N,N-Diethyl-2-{[3-(1-naphthylsulfonyl)-1H-indazol-5-yl]oxy}ethanamine;
N-(2-{[3-(1-Naphthylsulfonyl)-1H-indazol-5-yl]oxy}ethyl)cyclopropanamine;
(2-{[1-(3-Chlorobenzyl)-3-(1-naphthylsulfonyl)-1H-indazol-7-yl]oxy}ethyl)amine;
N-(2-{[3-(Phenylsulfonyl)-1H-indazol-5-yl]oxy}ethyl)cyclopentanamine;
N-Methyl-2-{[3-(phenylsulfonyl)-1H-indazol-5-yl]oxy}ethanamine;
N-Methyl-2-{[1-methyl-3-(phenylsulfonyl)-1H-indazol-7-yl]oxy}ethanamine;
(2-{[1-(3-Chlorobenzyl)-3-(phenylsulfonyl)-1H-indazol-7-yl]oxy}ethyl)methylamine;
(2-{[1-(3-Chlorobenzyl)-3-(phenylsulfonyl)-1H-indazol-7-yl]oxy}ethyl)ethylamine;
N-Methyl-2-{[3-(phenylsulfonyl)-1H-indazol-7-yl]oxy}ethanamine;
(2-{[1-(3-Chlorobenzyl)-3-(1-naphthylsulfonyl)-1H-indazol-7-yl]oxy}ethyl)ethylamine;
(2-{[1-(3-Chlorobenzyl)-3-(1-naphthylsulfonyl)-1H-indazol-7-yl]oxy}ethyl)methylamine;
N-Ethyl-2-{[3-(phenylsulfonyl)-1H-indazol-7-yl]oxy}ethanamine;
N,N-Diethyl-2-{[3-(phenylsulfonyl)-1H-indazol-7-yl]oxy}ethanamine;
N-(2-{[3-(Phenylsulfonyl)-1H-indazol-7-yl]oxy}ethyl)butan-1-amine;
N,N-Diethyl-2-{[1-methyl-3-(1-naphthylsulfonyl)-1H-indazol-7-yl]oxy}ethanamine;
N-Ethyl-2-{[1-methyl-3-(1-naphthylsulfonyl)-1H-indazol-7-yl]oxy}ethanamine;
N-Ethyl-2-{[3-(1-naphthylsulfonyl)-1H-indazol-7-yl]oxy}ethanamine;
(2-{[3-(1-Naphthylsulfonyl)-1H-indazol-7-yl]oxy}ethyl)amine;
(2-{[1-(3-Chlorobenzyl)-5-fluoro-3-(1-naphthylsulfonyl)-1H-indazol-7-yl]oxy}ethyl)-dimethylamine;
(2-{[1-Benzyl-3-(1-naphthylsulfonyl)-1H-indazol-5-yl]oxy}ethyl)methylamine;
(2-{[1-Benzyl-3-(1-naphthylsulfonyl)-1H-indazol-5-yl]oxy}ethyl)dimethylamine;
(2-{[1-Benzyl-3-(1-naphthylsulfonyl)-1H-indazol-5-yl]oxy}ethyl)ethylamine;
N-Methyl-2-{[3-(1-naphthylsulfonyl)-1H-indazol-7-yl]oxy}ethanamine;
N,N-Dimethyl 2-{[3-(1-naphthylsulfonyl)-1H-indazol-7-yl]oxy}ethanamine;
N,N-Diethyl-2-{[5-fluoro-3-(1-naphthylsulfonyl)-1H-indazol-7-yl]oxy}ethanamine;
(2-{[5-Fluoro-3-(1-naphthylsulfonyl)-1H-indazol-7-yl]oxy}ethyldimethylamine;
N-Ethyl-2-{[5-fluoro-3-(1-naphthylsulfonyl)-1H-indazol-7-yl]oxy}ethanamine;
(2-{[1-(3-Chlorobenzyl)-3-(1-naphthylsulfonyl)-1H-indazol-5-yl]oxy}ethyl)-dimethylamine;
N-Methyl-3-{[3-(1-naphthylsulfonyl)-1H-indazol-5-yl]oxy}propan-1-amine;
N-Ethyl-N-methyl-3-{[3-(1-naphthylsulfonyl)-1H-indazol-5-yl]oxy}propan-1-amine;
N,N-Dimethyl-3-{[3-(1-naphthylsulfonyl)-1H-indazol)-5-yl]oxy}propan-1-amine;
N,N-Diethyl-3-{[3(1-naphthylsulfonyl)-1H-indazol-5-yl]oxy}propan-1-amine;
N-(3-{[3-(1-Naphthylsulfonyl)-1H-indazol-5-yl]oxy}propyl)butan-1-amine;
(2-{[5-Methoxy-3-(1-naphthylsulfonyl)-1H-indazol-7-yl]oxy}ethyl)methylamine;
(2-{[5-Methoxy-3-(1-naphthylsulfonyl)-1H-indazol-7-yl]oxy}ethyl)dimethylamine;
(2-{[1-(3-Chlorobenzyl)-3-(1-naphthylsulfonyl)-1H-indazol-5-yl]oxy}ethyl)ethylamine;
(3-{[1-(3-Chlorobenzyl)-3-(1-naphthylsulfonyl)-1H-indazol-7-yl]oxy}propyl)-diethylamine;
N-Methyl-3-{[3-(1-naphthylsulfonyl)-1H-indazol-7-yl]oxy}propan-1-amine;
N,N-Diethyl-3-{[3-(1-naphtylsulfonyl)-1H-indazol-7-yl]oxy}propan-1-amine;
N-Methyl-2-{[1-methyl-3-(1-naphtylsulfonyl)-1H-indazol-5-yl]oxy}ethanamine;
N,N-Dimethyl-2-{[1-methyl-3-(1-naphthylsulfonyl)-1H-indazol-5-yl]oxy}ethanamine;
N-Ethyl-N-methyl-2-{[1-methyl-3-(1-naphthylsulfonyl)-1H-indazol-5-yl]oxy}ethanamine;
N-Ethyl -2-{[1-methyl-3-(1-naphthylsulfonyl)-1H-indazol-5-yl]oxy}ethanamine;
N,N-Diethyl-2-{[1-methyl-3-(1-naphthylsulfonyl)-1H-indazol-5-yl]oxy}ethanamine;
N-(2-{[1-Methyl -3-(1-naphthylsulfonyl)-1H-indazol-5-yl]oxy}ethyl)propan-2-amine;
(2-{[1-Methyl-3-(1-naphthylsulfonyl)-1H-indazol-7-yl]oxy}ethyl)amine;
N-Ethyl-3-{[3-(1-naphthylsulfonyl)-1H-indazol-5-yl]oxy}propan-1-amine;
N-Isopropyl-3-{[3-(1-naphthylsulfonyl)-1H-indazol-5-yl]oxy}propan-1-amine;
N-(3-{[3-(1-Naphthylsulfonyl)-1H-indazol-5-yl]oxy}propyl)cyclopentanamine;
N-(3-{[3-(1-Naphthylsulfonyl)-1H-indazol-5-yl]oxy}propyl)cyclopropanamine;
(3-{[3-(1-Naphthylsulfonyl)-1H-indazol-5-yl]oxy}propyl)amine;
N-Methyl-4-{[3-(1-naphthylsulfonyl)-1H-indazol-5-yl]oxy}butan-1-amine
N,N-Dimethyl-4-{[3-(1-naphthylsulfonyl)-1H-indazol-5-yl]oxy}butan-1-amine;
N-Ethyl-4-{[3-(1-naphthylsulfonyl)-1H-indazol-5-yl]oxy}butan-1-amine;
N,N-Diethyl-4-{[3-(1-naphthylsulfonyl)-1H-indazol-5-yl]oxy}butan-1-amine;
N-Methyl-4-{[3-(1-naphthylsulfonyl)-1H-indazol-5-yl]oxy}-N-propylbutan-1-amine;
(4-{[3-(1-Naphthylsulfonyl)-1H-indazol-5-yl]oxy}butyl)amine;
(2-{[5-Fluoro-3-(1-naphthylsulfonyl)-1H-indazol-7-yl]oxy}ethyl)methylamine;
(2-{[3-(1-Naphthylsulfonyl)-1H-indazol-5-yl]oxy}ethyl)amine;
2-{[5-Fluoro-3-(phenylsulfonyl)-1H-indazol-7-yl]oxy}ethanamine;
2-{[3-(Phenylsulfonyl)-1H-indazol-7-yl]oxy}ethanamine;
N,N-Dimethyl-2-{[3-(1-naphthylsulfonyl)-1H-indazol-4-yl]oxy}ethanamine;
2-{[3-(1-Naphthylsulfonyl)-1H-indazol-4-yl]oxy}ethanamine;

N-Methyl-2-{[3-(1-naphthylsulfonyl)-1H-indazol-6-yl]oxy}ethanamine;
2-{[3-(1-Naphthylsulfonyl)-1H-indazol-6-yl]oxy}ethanamine;
a stereoisomer thereof; and
a pharmaceutically acceptable salt thereof.

15. The compound according to claim 1 selected from the group consisting of:
[2-(3-benzenesulfonyl-1H-indazol-5-yloxy)-ethyl]ethylmethylamine;
[2-(3-benzenesulfonyl-1H-indazol-5-yloxy)-ethyl]diethylamine;
[2-(3-benzenesulfonyl-1H-indazol-5-yloxy)-ethyl]isopropylamine;
[2-(3-benzenesulfonyl-1H-indazol-5-yloxy)-ethyl]butylamine;
[2-(3-benzenesulfonyl-1H-indazol-5-yloxy)-ethyl]cyclopropylamine;
dimethyl-{3-[3-(naphthalene-1-sulfonyl)-1H-indazol-5-yloxy]propyl}amine;
methyl-{3-[3-(naphthalene-1-sulfonyl)-1H-indazol-5-yloxy]propyl}amine;
butyl-{3-[3-(naphthalene-1-sulfonyl)-1H-indazol-5-yloxy]propyl}amine;
{2-[1-benzyl-3-(naphthalene-1-sulfonyl)-1H-indazol-5-yloxy]ethyl}isopropyamine;
{2-[1-benzyl-3-(naphthalene-1-sulfonyl)-1H-indazol-5-yloxy]-ethyl}diethylamine;
{2-[1-(3-chloro-benzyl)-3-(naphthalene-1-sulfonyl)-1H-indazol-5-yloxy]-ethyl}ethyl-methylamine;
{2-[1-(3-chloro-benzyl)-3-(naphthalene-1-sulfonyl)-1H-indazol-5-yloxy]-ethyl}diethylamine;
{2-[1-(3-chloro-benzyl)-3-(naphthalene-1-sulfonyl)-1H-indazol-5-yloxy]-ethyl}isopropylamine;
{2-[1-(3-chloro-benzyl)-3-(naphthalene-1-sulfonyl)-1H-indazol-5-yloxy]-ethyl}methylamine;
{2-[1-(3-chloro-benzyl)-3-(naphthalene-1-sulfonyl)-1H-indazol-7-yloxy]-ethyl}ethylamine;
{2-[1-(3-chloro-benzyl)-3-(naphthalene-1-sulfonyl)-1H-indazol-7-yloxy]-ethyl}diethylamine;
butyl-{2-[1-(3-chloro-benzyl)-3-(naphthalene-1-sulfonyl)-1H-indazol-7-yloxy]-ethyl}methylamine;
{2-[3-benzenesulfonyl-1-(3-chloro-benzyl)-1H-indazol-7-yloxy]-ethyl}diethylamine;
{2-[3-benzenesulfonyl-1-(3-chloro-benzyl)-1H-indazol-7-yloxy]-ethyl}butylamine;
dimethyl-{2-[1-methyl-3-(naphthalene-1-sulfonyl)-1H-indazol-7-yloxy]-ethyl}amine;
butyl-{2-[1-methyl-3-(naphthalene-1-sulfonyl)-1H-indazol-7-yloxy]-ethyl}amine;
[2-(3-benzenesulfonyl-1-methyl-1H-indazol-7-yloxy)-ethyl]ethylamine;
[2-(3-benzenesulfonyl-1-methyl-1H-indazol-7-yloxy)-ethyl]diethylamine;
(2-{[1-(3-chlorobenzyl)-5-fluoro-3-(1-naphthylsulfonyl)-1H-indazol-7-yl]oxy}ethyl)amine;
(2-{[1-(3-chlorobenzyl)-5-fluoro-3-(1-naphthylsulfonyl)-1H-indazol-7-yl]oxy}ethyl)methylamine hydrochloride;
{2-[1-(3-chloro-benzyl)-5-fluoro-3-(naphthalene-1-sulfonyl)-1H-indazol-7-yloxy]ethyl}ethylamine hydrochloride;
{2-[1-(3-chloro-benzyl)-5-fluoro-3-(naphthalene-1-sulfonyl)-1H-indazol-7-yloxy]ethyl}diethylamine hydrochloride;
{2-[5-fluoro-3-(naphthalene-1-sulfonyl)-1H-indazol-7-yloxy]-ethyl}methylamine hydrochloride;
{2-[1-(3-chlorobenzyl)-5-methoxy-3-(naphthalene-1-sulfonyl)-1H-indazol-7-yloxy]ethyl}methylamine hydrochloride;
{2-[1-(3-chlorobenzyl)-5-methoxy-3-(naphthalene-1-sulfonyl)-1H-indazol-7-yloxy]ethyl}ethylamine hydrochloride;
{2-[1-(3-chlorobenzyl)-5-methoxy-3-(naphthalene-1-sulfonyl)-1H-indazol-7-yloxy]ethyl}dimethylamine hydrochloride;
{3-[1-(3-chlorobenzyl)-5-methoxy-3-(naphthalene-1-sulfonyl)-1H-indazol-7-yloxy]propyl}methylamine hydrochloride;
{3-[1-(3-chlorobenzyl)-5-methoxy-3-(naphthalene-1-sulfonyl)-1H-indazol-7-yloxy]propyl}ethylamine hydrochloride;
{3-[1-(3-chlorobenzyl)-5-methoxy-3-(naphthalene-1-sulfonyl)-1H-indazol-7-yloxy]propyl}dimethylamine hydrochloride;
ethyl {3-[5-methoxy-3-(naphthalene-1-sulfonyl)-1H-indazol-7-yloxy]propyl}amine hydrochloride;
{3-[5-methoxy-3-(naphthalene-1-sulfonyl)-1H-indazol-7-yloxy]propyl}dimethylamine hydrochloride;
N-methyl-2-{[3-naphthylsulfonyl)-1H-indazol-4-yl]oxy}ethanamine hydrochloride;
dimethyl {2-[3-(naphthalene-1-sulfonyl)-1H-indazol-6-yloxy]ethyl}amine hydrochloride;
a stereoisomer thereof; and
a pharmaceutically acceptable salt thereof.

16. The composition according to claim 10 having a formula I compound selected from the group consisting of:
[2-(3-benzenesulfonyl-1H-indazol-5-yloxy)ethyl]ethylmethylamine;
[2-(3-benzenesulfonyl-1H-indazol-5-yloxy)ethyl]diethylamine;
[2-(3-benzenesulfonyl-1H-indazol-5-yloxy)ethyl]isopropylamine;
[2-(3-benzenesulfonyl-1H-indazol-5-yloxy)ethyl]butylamine;
[2-(3-benzenesulfonyl-1H-indazol-5-yloxy)ethyl]cyclopropylamine;
dimethyl-{3-[3-(naphthalene-1-sulfonyl)-1H-indazol-5-yloxy]propyl}amine;
methyl-{3-[3-(naphthalene-1-sulfonyl)-1H-indazol-5-yloxy]propyl}amine;
butyl-{3-[3-(naphthalene-1-sulfonyl)-1H-indazol-5-yloxy]propyl}amine;
{2-[1-benzyl-3-(naphthalene-1-sulfonyl)-1H-indazol-5-yloxy]ethyl}isopropyamine;
{2-[1-benzyl-3-(naphthalene-1-sulfonyl)-1H-indazol-5-yloxy]ethyl}diethylamine;
{2-[1-(3-chloro-benzyl)-3-(naphthalene-1-sulfonyl)-1H-indazol-5-yloxy]ethyl}ethyl-methylamine;
{2-[1-(3-chloro-benzyl)-3-(naphthalene-1-sulfonyl)-1H-indazol-5-yloxy]ethyl}diethylamine;
{2-[1-(3-chloro-benzyl)-3-(naphthalene-1-sulfonyl)-1H-indazol-5-yloxy]ethyl}isopropylamine;
{2-[1-(3-chloro-benzyl)-3-(naphthalene-1-sulfonyl)-1H-indazol-5-yloxy]ethyl}methylamine;
{2-[1-(3-chloro-benzyl)-3-(naphthalene-1-sulfonyl)-1H-indazol-7-yloxy]ethyl}ethylamine;
{2-[1-(3-chloro-benzyl)-3-(naphthalene-1-sulfonyl)-1H-indazol-7-yloxy]ethyl}diethylamine;
butyl-{2-[1-(3-chloro-benzyl)-3-(naphthalene-1-sulfonyl)-1H-indazol-7-yloxy]ethyl}methylamine;
{2-[3-benzenesulfonyl-1-(3-chloro-benzyl)-1H-indazol-7-yloxy]ethyl}diethylamine;
{2-[3-benzenesulfonyl-1-(3-chloro-benzyl)-1H-indazol-7-yloxy]ethyl}butylamine;
dimethyl-{2-[1-methyl-3-(naphthalene-1-sulfonyl)-1H-indazol-7-yloxy]ethyl}amine;
butyl-{2-[1-methyl-3-(naphthalene-1-sulfonyl)-1H-indazol-7-yloxy]ethyl}amine;

[2-(3-benzenesulfonyl-1-methyl-1H-indazol-7-yloxy)ethyl]ethylamine;

[2-(3-benzenesulfonyl-1-methyl-1H-indazol-7-yloxy)ethyl]diethylamine;

(2-{[1-(3-chlorobenzyl)-5-fluoro-3-(1-naphthylsulfonyl)-1H-indazol-7-yl]oxy}ethyl)amine;

(2-{[1-(3-chlorobenzyl)-5-fluoro-3-(1-naphthylsulfonyl)-1H-indazol-7-yl]oxy}ethyl)methylamine hydrochloride;

{2-[1-(3-chloro-benzyl)-5-fluoro-3-(naphthalene-1-sulfonyl)-1H-indazol-7-yloxy]ethyl}ethylamine hydrochloride;

{2-[1-(3-chloro-benzyl)-5-fluoro-3-(naphthalene-1-sulfonyl)-1H-indazol-7-yloxy]ethyl}diethylamine hydrochloride;

{2-[5-fluoro-3-(naphthalene-1-sulfonyl)-1H-indazol-7-yloxy]ethyl}methylamine hydrochloride;

{2-[1-(3-chlorobenzyl)-5-methoxy-3-(naphthalene-1-sulfonyl)-1H-indazol-7-yloxy]ethy}methylamine hydrochloride;

{2-[1-(3-chlorobenzyl)-5-methoxy-3-(naphthalene-1-sulfonyl)-1H-indazol-7-yloxy]ethyl}ethylamine hydrochloride;

{2-[1-(3-chlorobenzyl)-5-methoxy-3-(naphthalene-1-sulfonyl)-1H-indazol-7-yloxy]ethyl}dimethylamine hydrochloride;

{3-[1-(3-chlorobenzyl)-5-methoxy-3-(naphthalene-1-sulfonyl)-1H-indazol-7-yloxy]propyl}methylamine hydrochloride;

{3-[1-(3-chlorobenzyl)-5-methoxy-3-(naphthalene-1-sulfonyl)-1H-indazol-7-yloxy]propyl}ethylamine hydrochloride;

{3-[1-(3-chlorobenzyl)-5-methoxy-3-(naphthalene-1-sulfonyl)-1H-indazol-7-yloxy]propyl}dimethylamine hydrochloride;

ethyl {3-[5-methoxy-3-(naphthalene-1-sulfonyl)-1H-indazol-7-yloxy]propyl}amine hydrochloride;

{3-[5-methoxy-3-(naphthalene-1-sulfonyl)-1H-indazol-7-yloxy]propyl}dimethylamine hydrochloride;

N-methyl-2-{[3-naphthylsulfonyl)-1H-indazol-4-yl]oxy}ethanamine hydrochloride;

dimethyl {2-[3-(naphthalene-1-sulfonyl)-1H-indazol-6-yloxy]ethyl}amine hydrochloride;

a stereoisomer thereof; and a pharmaceutically acceptable salt thereof.

17. The compound according to claim 15, which is dimethyl-{3-[3-(naphthalene-1-sulfonyl)-1H-indazol-5-yloxy]propyl}amine or a pharmaceutically acceptable salt thereof.

18. The compound according to claim 17, which is dimethyl-{3-[3-(naphthalene-1-sulfonyl)-1H-indazol-5-yloxy]propyl}amine hydrochloride.

19. The compound according to claim 15, which is methyl-{3-[3-(naphthalene-1-sulfonyl)-1H-indazol-5-yloxy]propyl}amine or a pharmaceutically acceptable salt thereof.

20. The compound according to claim 19, which is methyl-{3-[3-(naphthalene-1-sulfonyl)-1H-indazol-5-yloxy]propyl}amine hydrochloride.

21. The composition according to claim 10 having a formula I compound, which is dimethyl-{3-[3-(naphthalene-1-sulfonyl)-1H-indazol-5-yloxy]-propyl}-amine or a pharmaceutically acceptable salt thereof.

22. The composition according to claim 10 having a formula I compound, which is methyl-{3-[3-(naphthalene-1-sulfonyl)-1H-indazol-5-yloxy]-propyl}-amine or a pharmaceutically acceptable salt thereof.

* * * * *

UNITED STATES PATENT AND TRADEMARK OFFICE
CERTIFICATE OF CORRECTION

PATENT NO. : 7,723,329 B2  Page 1 of 1
APPLICATION NO. : 11/504350
DATED : May 25, 2010
INVENTOR(S) : Hassan Mahmoud Elokdah et al.

It is certified that error appears in the above-identified patent and that said Letters Patent is hereby corrected as shown below:

In The Claims

In Claim 1, column 183, line 38, delete the "," after "cycloalkyl"

In Claim 9, column 185, line 4, change "zol-7-y]" to -- zol-7-yl] --

In Claim 9, column 186, line 7, change "N-Methyl-" to -- N-Methyl-2- --

In Claim 10, column 186, line 28, change "X is O;" to -- X is O or S; --

In Claim 10, column 186, line 32, add a --;-- after "group"

In Claim 10, column 186, lines 49-50, start "a stereoisomer thereof..." on a new line In Claim 14, column 187, line 63, change "oxy}ethyldimethylamine;" to -- oxy}ethyl)dimethylamine;--

In Claim 14, column 188, lines 5-6, change "(1-naphthylsulfonyl)-1H-indazol)-5-yl]oxy}propan-1-amine" to -- (1-naphthylsulfonyl)-1H-indazol-5-yl]oxy}propan-1-amine --

In Claim 14, column 188, line 20, change "naphtylsulfonyl" to -- naphthylsulfonyl --

In Claim 15, column 189, lines 30-31, change "1 H" to -- 1H--

In Claim 15, column 189, lines 45-46, change "1 H" to -- 1H --

Signed and Sealed this

Twenty-third Day of November, 2010

David J. Kappos
*Director of the United States Patent and Trademark Office*